United States Patent
Luzzio et al.

(10) Patent No.: US 10,508,101 B2
(45) Date of Patent: *Dec. 17, 2019

(54) PROTEIN KINASE C INHIBITORS AND METHODS OF THEIR USE

(71) Applicant: Novartis AG, Basel (CH)

(72) Inventors: Michael Joseph Luzzio, Noank, CT (US); Julien Papillon, Somerville, MA (US); Michael Scott Visser, Braintree, MA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/354,416

(22) Filed: Mar. 15, 2019

(65) Prior Publication Data

US 2019/0202809 A1    Jul. 4, 2019

Related U.S. Application Data

(63) Continuation of application No. 15/830,769, filed on Dec. 4, 2017, which is a continuation of application No. 15/237,880, filed on Aug. 16, 2016, now Pat. No. 9,845,309, which is a continuation of application No. 14/818,778, filed on Aug. 5, 2015, now Pat. No. 9,452,998.

(60) Provisional application No. 62/033,679, filed on Aug. 6, 2014.

(51) Int. Cl.

| | | |
|---|---|---|
| A61K 31/497 | (2006.01) |
| C07D 401/14 | (2006.01) |
| C07D 413/14 | (2006.01) |
| A61P 31/04 | (2006.01) |
| A61K 31/506 | (2006.01) |
| A61P 35/00 | (2006.01) |
| A61K 45/06 | (2006.01) |

(52) U.S. Cl.
CPC .......... C07D 401/14 (2013.01); A61K 31/497 (2013.01); A61K 31/506 (2013.01); A61K 45/06 (2013.01); A61P 31/04 (2018.01); A61P 35/00 (2018.01); C07D 413/14 (2013.01)

(58) Field of Classification Search
CPC .............. C07D 401/14; A61K 31/497
USPC ..................... 544/405; 514/255.05
See application file for complete search history.

(56) References Cited

U.S. PATENT DOCUMENTS

| | | |
|---|---|---|
| 8,460,743 B2 | 6/2013 | Mueller et al. |
| 8,592,455 B2 | 11/2013 | Burger et al. |
| 8,703,962 B2 | 4/2014 | Kyle et al. |
| 8,822,497 B2 | 9/2014 | Burger et al. |
| 8,829,193 B2 | 9/2014 | Burger et al. |
| 8,946,235 B2 | 2/2015 | Butterworth et al. |
| 9,452,998 B2 * | 9/2016 | Visser ................ C07D 401/14 |
| 9,845,309 B2 * | 12/2017 | Luzzio ................ C07D 401/14 |
| 2006/0052396 A1 | 3/2006 | Berg et al. |
| 2010/0120862 A1 | 5/2010 | Tafesse |
| 2012/0225062 A1 | 9/2012 | Burger et al. |
| 2013/0109682 A1 | 5/2013 | Burger et al. |
| 2016/0046605 A1 | 2/2016 | Visser et al. |
| 2016/0347737 A1 | 12/2016 | Luzzio et al. |
| 2018/0179181 A1 | 6/2018 | Luzzio et al. |

FOREIGN PATENT DOCUMENTS

| | | |
|---|---|---|
| AU | 2015298364 A1 | 2/2017 |
| AU | 2015298364 B2 | 8/2018 |
| CA | 2956996 A1 | 2/2016 |
| CN | 101679266 A | 3/2010 |
| CN | 101801958 A | 8/2010 |
| CN | 102317469 A | 1/2012 |
| CN | 102482265 A | 5/2012 |
| CN | 102821759 A | 12/2012 |
| CN | 103080106 A | 5/2013 |
| EP | 2178861 B1 | 8/2014 |
| EP | 3177608 A1 | 6/2017 |
| JP | 2010520228 A | 6/2010 |
| JP | 2012529512 A | 11/2012 |
| JP | 2013512281 A | 4/2013 |
| JP | 2013231049 A | 11/2013 |
| JP | 2014506917 A | 3/2014 |
| WO | WO-0155115 A1 | 8/2001 |
| WO | WO-03004472 A1 | 1/2003 |
| WO | WO-03004475 A1 | 1/2003 |
| WO | WO-2004055005 A1 | 7/2004 |
| WO | WO-2004096795 A2 | 11/2004 |
| WO | WO-2005079802 A1 | 9/2005 |
| WO | WO-2006018280 A2 | 2/2006 |
| WO | WO-2006045010 A2 | 4/2006 |
| WO | WO-2006048771 A1 | 5/2006 |
| WO | WO-2008002247 A1 | 1/2008 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Hayashi et al., "Protein Kinase Ctheta (PKCe): A key role in T cell life and death," Pharmac. Res. 55:537-544 (2007).*

Chapman et al., Cancer in Transplant Recipient, Cold Spring Harbor Perspectives in Medicine, (2013), 3:a015677, pp. 1-15.*

(Continued)

*Primary Examiner* — Deepak R Rao

(74) *Attorney, Agent, or Firm* — Schwegman Lundberg & Woessner, P.A.

(57) ABSTRACT

PKC inhibitors are disclosed. The PKC inhibitors are useful for treating PKC associated diseases, including certain cancers. The PKC inhibitors have improved efficacy at lower dosage amounts to achieve tumor regression, improved potency, PK profile, absorption, gastrointestinal tolerance and kinase selectivity.

23 Claims, 3 Drawing Sheets

Specification includes a Sequence Listing.

(56) References Cited

FOREIGN PATENT DOCUMENTS

| WO | WO-2008106692 A1 | 9/2008 |
|---|---|---|
| WO | WO-2009014637 A2 | 1/2009 |
| WO | WO-2009082346 A1 | 7/2009 |
| WO | WO-2010026124 A1 | 3/2010 |
| WO | WO-2010046780 A2 | 4/2010 |
| WO | WO-2010071837 A1 | 6/2010 |
| WO | WO-2010075380 A1 | 7/2010 |
| WO | WO-2011012661 A1 | 2/2011 |
| WO | WO-2011068898 A1 | 6/2011 |
| WO | WO-2012004217 A1 | 1/2012 |
| WO | WO-2012080729 A2 | 6/2012 |
| WO | WO-2012101064 A1 | 8/2012 |
| WO | WO-2012120415 A1 | 9/2012 |
| WO | WO-2012129562 A2 | 9/2012 |
| WO | WO-2013175388 A1 | 11/2013 |
| WO | WO-2014012511 A1 | 1/2014 |
| WO | WO-2014099880 A1 | 6/2014 |
| WO | WO-2014181287 A1 | 11/2014 |
| WO | WO-2016020864 A1 | 2/2016 |

OTHER PUBLICATIONS

"U.S. Appl. No. 14/818,778, Non Final Office Action dated Feb. 1, 2016", 18 pgs.
"U.S. Appl. No. 14/818,778, Notice of allowance dated May 20, 2016", 5 pgs.
"U.S. Appl. No. 14/818,778, Response filed Apr. 29, 2016 to Non Final Office Action dated Feb. 1, 2016", 7 pgs.
"U.S. Appl. No. 15/237,880, Advisory Action dated Jul. 27, 2017", 4 pgs.
"U.S. Appl. No. 15/237,880, Examiner Interview Summary dated Jun. 23, 2017", 3 pgs.
"U.S. Appl. No. 15/237,880, Final Office Action dated May 19, 2017", 17 pgs.
"U.S. Appl. No. 15/237,880, Non Final Office Action dated Nov. 3, 2016", 18 pgs.
"U.S. Appl. No. 15/237,880, Notice of allowance dated Aug. 11, 2017", 5 pgs.
"U.S. Appl. No. 15/237,880, Response filed Mar. 1, 2017 to Non Final Office Action dated Nov. 3, 2016", 11 pgs.
"U.S. Appl. No. 15/237,880, Response filed Jul. 12, 2017 to Final Office Action dated May 19, 2017", 14 pgs.
"U.S. Appl. No. 15/237,880, Response filed Jul. 28, 2017 to Advisory Action dated Jul. 27, 2017", 11 pgs.
"U.S. Appl. No. 15/830,769, Final Office Action dated Dec. 17, 2018", 16 pgs.
"U.S. Appl. No. 15/830,769, Non Final Office Action dated Apr. 3, 2018", 20 pgs.
"U.S. Appl. No. 15/830,769, Preliminary Amendment filed Mar. 14, 2018", 10 pgs.
"U.S. Appl. No. 15/830,769, Response filed Sep. 28, 2018 to Non Final Office Action dated Apr. 3, 2018", 13 pgs.
"Australian Application Serial No. 2015298364, First Examiner Report dated Aug. 18, 2017", 3 pgs.
"Australian Application Serial No. 2015298364, Response filed Jul. 30, 2018 to First Examiner dated Aug. 18, 2017", 22 pgs.
"Chile Application Serial No. 2017-00290, Office Action dated Mar. 4, 2019", w/o English Translation, 8 pgs.
"Chile Application Serial No. 2017-00290, Office Action dated Jul. 20, 2018", w/ English Translation, 16 pgs.
"Chile Application Serial No. 2017-00290, Response filed Jan. 17, 2019 to Office Action dated Jul. 20, 2018", w/ English Claims, 23 pgs.
"Chile Application Serial No. 2017-00290, Response filed May 29, 2019 to Office Action dated Mar. 4, 2019", w/o English Translation, 12 pgs.
"Chinese Application Serial No. 201580053955.6, Office Action dated Apr. 17, 2019", w/ English Translation, 15 pgs.
"Cuba Application Serial No. 2017-0010, Office Action dated Jan. 30, 2019", w/ English Translation, 6 pgs.

"Cuba Application Serial No. 2017-0010, Response filed Mar. 15, 2019 to Office Action dated Jan. 30, 2019", w/o English Translation, 10 pgs.
"Dominican Republic Application Serial No. P2017-0035, Office Action dated May 9, 2019", w/o English Translation, 3 pgs.
"Dominican Republic Application Serial No. P2017-0035, Office Action dated Jul. 17, 2018", w/ English Translation, 9 pgs.
"Dominican Republic Application Serial No. P2017-0035, Response filed Jan. 29, 2019 to Office Action dated Jul. 17, 2018", w/o English Translation, 9 pgs.
"Eurasian Application Serial No. 201790323, Office Action dated Nov. 21, 2018", w/ English Translation, 4 pgs.
"Eurasian Application Serial No. 201790323, Response filed Mar. 20, 2019 to Office Action dated Nov. 21 2018", w/ English Claims, 27 pgs.
"European Application Serial No. 15750138.8, Communication Pursuant to Article 94(3) EPC dated Feb. 7, 2018", 6 pgs.
"European Application Serial No. 15750138.8, Communication Pursuant to Article 94(3) EPC dated Oct. 17, 2018", 4 pgs.
"European Application Serial No. 15750138.8, Response filed Jun. 14, 2018 to Communication pursuant to Article 94(3) EPC dated Feb. 7, 2018", 5 pgs.
"European Application Serial No. 15750138.8, Response Filed Dec. 18, 2018 to Communication Pursuant to Article 94(3) EPC dated Oct. 17, 2018", 260 pgs.
"European Application Serial No. 19160124.4, Extended European Search Report dated Apr. 3, 2019", 8 pgs.
"Gulf Cooperation Council Application Serial No. 2015-29840, Examination Report dated Jan. 14, 2019", in English, 6 pgs.
"Gulf Cooperation Council Application Serial No. 2015-29840, Response filed Mar. 25, 2019 to Examination Report dated Jan. 14, 2019", w/o English Translation, 8 pgs.
"International Application Serial No. PCT/IB2015/055951, International Preliminary Report on Patentability dated Feb. 16, 2017", 9 pgs.
"International Application Serial No. PCT/IB2015/055951, International Search Report dated Sep. 11, 2015", 4 pgs.
"International Application Serial No. PCT/IB2015/055951, Written Opinion dated Sep. 11, 2015", 7 pgs.
"Israel Application Serial No. 250318, Office Action dated Mar. 17, 2019", w/ English List of Citations, 6 pgs.
"Japanese Application Serial No. 2017-506392, Notification of Reasons for Refusal dated Apr. 23, 2019", w/ English Translation, 6 pgs.
"Taiwanese Application Serial No. 104125461, Office Action dated Mar. 28, 2019", w/ English Translation, 7 pgs.
Ren, Ji-Xia, et al., "Discovery of Novel Pim-1 Kinase Inhibitors by a Hierarchical Multistage Virtual Screening Approach Based on SVM Model, Pharmacophore, and Molecular Docking", Journal of Chemical Information and Modeling. vol. 15, No. 6, (Jun. 27, 2011), 12 pgs.
Stewart, Jubilee R., et al., "Protein kinase C-alpha mediates epidermal growth factor receptor transactivation in human prostate cancer cells", Molecular Cancer Therapeutics, (2005), 8 pgs.
Xinqi, Wu, et al., "Protein kinase C inhibitor AEB071 targets ocular melanoma harboring GANQ mutations via effects on the PKC/Erkl/2 and PKC/NF-kB pathways", Therapeutic Discovery, (2012), 11 pgs.
U.S. Appl. No. 14/818,778, filed Aug. 5, 2015, Protein Kinase C Inhibitors and Methods of Their Use, U.S. Pat. No. 9,452,998.
U.S. Appl. No. 15/237,880, filed Aug. 16, 2016, Protein Kinase C Inhibitors and Methods of Their Use, U.S. Pat. No. 9,845,309.
U.S. Appl. No. 15/830,769, filed Dec. 4, 2017, Protein Kinase C Inhibitors and Methods of Their Use.
"Chinese Application Serial No. 201580053955.6, Response filed Aug. 2, 2019 to Office Action dated Apr. 17, 2019", w/ English Claims, 27 pgs.
"IDEAYA Biosciences Common Stock Prospectus", IDEAYA Biosciences, Inc., (May 22, 2019), 3 pgs.
"Israel Application Serial No. 250318, Response filed Jun. 2, 2019 to Office Action dated Jan. 23, 2019", w/ Amended Claims in English, 11 pgs.

(56) References Cited

OTHER PUBLICATIONS

"Taiwanese Application Serial No. 104125461, First Office Action dated Jul. 31, 2019", w/ English Translation, 5 pgs.
Abera, Mahlet B., et al., "Protein Kinase C-alpha Mediates Erlotinib Resistance in Lung Cancer Cells", Molecular Pharmacology, 87(5), (May 2015), 832-841.

* cited by examiner

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Phosphorylated-Ser

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Biotin
<220> FEATURE:
<221> NAME/KEY: MOD_RES
<222> LOCATION: (22)..(22)
<223> OTHER INFORMATION: Phosphorylated-Ser

<400> SEQUENCE: 2

Lys Tyr Arg Arg Ala Ala Val Pro Pro Ser Pro Ser Leu Ser Arg His
1               5                   10                  15

Ser Ser Pro His Gln Ser Glu Asp Glu Glu Glu
            20                  25
```

PROTEIN KINASE C INHIBITORS AND METHODS OF THEIR USE

RELATED APPLICATIONS

This application is a continuation of U.S. application Ser. No. 15/830,769 filed Dec. 4, 2017, which is a continuation of U.S. application Ser. No. 15/237,880 filed Aug. 16, 2016, now U.S. Pat. No. 9,845,309, which is a continuation of U.S. application Ser. No. 14/818,778 filed Aug. 5, 2015, now U.S. Pat. No. 9,452,998, which claims priority to U.S. Ser. No. 62/033,676, filed Aug. 6, 2014. The entire contents of all of these applications are incorporated herein by reference in their entireties.

FIELD OF THE INVENTION

The present invention relates to new compounds and their tautomers and stereoisomers, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Uveal melanoma is the most common primary intraocular malignant tumor in adults. Certain protein kinase inhibitors are described in International Publ. Nos. WO 02/38561 and WO 2008/106692. One protein kinase C (PKC) inhibitor, sotrastaurin, has been shown to have activity against certain PKC isotypes and has only recently been shown to selectively inhibit the growth of uveal melanoma cells harboring GNAQ mutations by targeting PKC/ERK1/2 and PKC/NF-κB pathways (see X. Wu, et al in Mol. Cancer Ther., Vol. 11, pages 1905-1914, 2012). A clinical trial studying the use of sotrastaurin to treat patients having uveal melanoma is in progress. However, there still remains a unmet need to provide next generation PKC inhibitors for treating uveal melanoma that have improved efficacy at lower dosage amounts to achieve tumor regression, improved potency, hERG activity, absorption, gastrointestinal tolerance and kinase selectivity.

Diffuse large B-cell lymphoma (DLBCL) represents the most common subtype of malignant lymphoma and is heterogeneous with respect to morphology, biology and clinical presentation. The PKC inhibitor, sotrastaurin (AEB071), has been shown to selectively inhibit growth of CD79-mutant DLBCL cells (see T. Naylor, et al in Cancer Res., Vol. 71(7), 2643-2653, 2011). In addition the study suggested that sotrastaurin showed significant synergy when combined with the mTor inhibitor everolimus (Afinitor™). A clinical trial studying the use of sotrastaurin to treat patients having DLBCL harboring the CD79 mutation is in progress. However, there still remains a unmet need to provide next generation PKC inhibitors for treating DLBCL that have improved efficacy at lower dosage amounts to achieve tumor regression, improved potency, PK profile, absorption, gastrointestinal tolerance and kinase selectivity.

SUMMARY

New compounds, their tautomers, stereoisomers, or pharmaceutically acceptable salts thereof or esters having a solubility enhancing moieties or prodrugs thereof are provided of the formula (I):

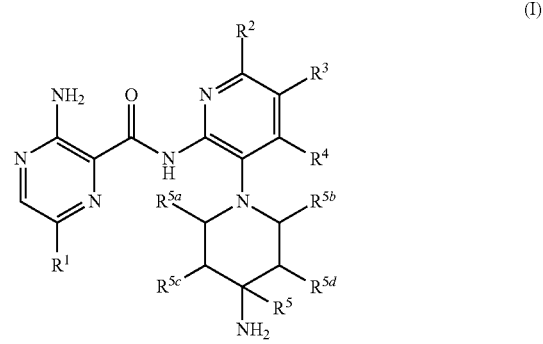

wherein:
$R^1$ is optionally substituted 6-10 membered aryl or 5-10 membered heteroaryl having 1 to 4 heteroatoms each independently selected from the group consisting of: O, N and S, said heteroaryl or aryl each being optionally substituted with 1 to 3 substituents each independently selected from the group consisting of: H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy;
$R^2$, $R^3$ and $R^4$ are each independently H, $^2$H, halo, hydroxy (—OH), $C_{1-3}$ alkoxy, $C_{1-3}$ haloalkyl or $C_{1-3}$ alkyl, optional substituted with one to two of hydroxyl, halo and $C_{1-3}$ haloalkoxy;
$R^5$ is H, $^2$H, $CH_3$, $CH_2F$, $CHF_2$, $CF_3$, $CH_2OH$, $C_{1-3}$ alkyl, $CH_2$—O—$C_{1-3}$ alkyl or $CH_2$—O—$C_{1-3}$ haloalkyl, said $C_{1-3}$ alkyl optionally substituted with H, F, OH, $C_{1-3}$ alkoxy and $C_{1-3}$ haloalkoxy;
$R^{5a}$ and $R^{5b}$ are each independently H, $^2$H, $C_{1-3}$ alkyl, said $C_{1-3}$ alkyl optionally substituted with F, OH, or $C_{1-3}$ alkoxy, or $R^{5a}$ and $R^{5b}$ are joined together forming a methylene or ethylene bridging group; and
$R^{5c}$ and $R^{5d}$ are each independently H, $^2$H, F, —OH, $C_{1-3}$ alkyl, said $C_{1-3}$ alkyl optionally substituted with F, OH, or $C_{1-3}$ alkoxy, or $R^{5c}$ and $R^{5d}$ are joined together forming a methylene, ethylene or —$CH_2$—O— bridging group.

In a separate embodiment, compounds, their tautomers, stereoisomers or pharmaceutically acceptable salts thereof or esters having a solubility enhancing moieties or prodrugs thereof are provided of the formula (Ia):

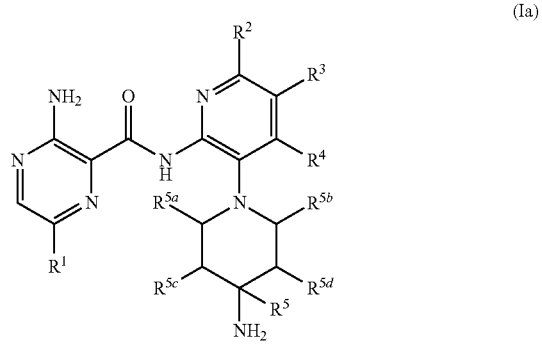

wherein:
R$^1$ is optionally substituted C$_{6-10}$ aryl, said aryl being optionally substituted with one to three substituents each independently selected from the group consisting of: H, $^2$H, halo, C$_{2-3}$ alkynyl, C$_{2-3}$ alkenyl, CN, C$_{1-3}$ alkyl, C$_{1-3}$ alkoxy, C$_{1-3}$ haloalkyl, C$_{1-3}$ haloalkoxy, C$_{3-7}$ cycloalkyl, CONH$_2$, CONHC$_{1-3}$ alkyl, CONHC$_{6-10}$ aryl, SONH$_2$, SONHC$_{1-3}$ alkyl, SONHC$_{6-10}$ aryl and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, C$_{1-3}$ alkyl, C$_{1-3}$ alkoxy, C$_{1-3}$ haloalkyl, and C$_{1-3}$ haloalkoxy;

R$^2$, R$^3$ and R$^4$ are each independently H, $^2$H, halo, hydroxy (—OH), C$_{1-3}$ alkoxy, C$_{1-3}$ haloalkyl or C$_{1-3}$ alkyl, optional substituted with one to two of hydroxy, halo and C$_{1-3}$ haloalkoxy;

R$^5$ is —H, $^2$H, CH$_3$, CH$_2$F, CHF$_2$, CF$_3$, CH$_2$OH, C$_{1-3}$ alkyl, CH$_2$—O—C$_{1-3}$ alkyl or CH$_2$—O—C$_{1-3}$ haloalkyl, said C$_{1-3}$ alkyl optionally substituted with H, F, OH, C$_{1-3}$ alkoxy and C$_{1-3}$ haloalkoxy;

R$^{5a}$ and R$^{5b}$ are each independently H, $^2$H, C$_{1-3}$ alkyl, or R$^{5a}$ and R$^{5b}$ are joined together forming a methylene or ethylene bridging group; and R$^{5c}$ and R$^{5d}$ are each independently H, F, C$_{1-3}$ alkyl, or C$_{1-3}$ alkoxy or R$^{5c}$ and R$^{5d}$ are joined together forming a methylene, ethylene or —CH$_2$—O— bridging group.

In a separate embodiment, compounds, their tautomers, stereoisomers, or pharmaceutically acceptable salts thereof or esters having a solubility enhancing moieties or prodrugs thereof are provided of the formula (II):

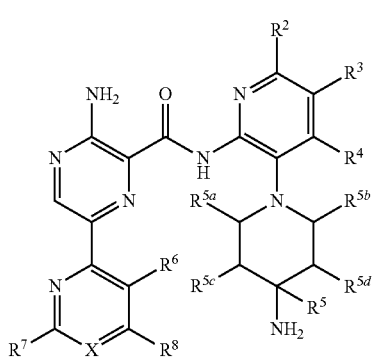

(II)

wherein:
X is N or CR;
R, R$^2$, R$^3$ and R$^4$ are each independently H, $^2$H, halo, hydroxy (—OH), C$_{1-3}$ alkoxy, C$_{1-3}$ haloalkyl or C$_{1-3}$ alkyl, optionally substituted with one to two of hydroxy, halo and C$_{1-3}$ haloalkoxy;

R$^5$ is —H, $^2$H, CH$_3$, CH$_2$F, CHF$_2$, CF$_3$, CH$_2$OH, C$_{1-3}$ alkyl, CH$_2$—O—C$_{1-3}$ alkyl or CH$_2$—O—C$_{1-3}$ haloalkyl, said C$_{1-3}$ alkyl optionally substituted with H, F, OH, C$_{1-3}$ alkoxy and C$_{1-3}$ haloalkoxy;

R$^{5a}$ and R$^{5b}$ are each independently H, $^2$H, C$_{1-3}$ alkyl, said C$_{1-3}$ alkyl optionally substituted with H, F, OH, C$_{1-3}$ alkoxy and C$_{1-3}$ haloalkoxy or R$^{5a}$ and R$^{5b}$ are joined together forming a methylene or ethylene bridging group;

R$^{5c}$ and R$^{5d}$ are each independently H, $^2$H, F, C$_{1-3}$ alkyl, or C$_{1-3}$ alkoxy or R$^{5c}$ and R$^{5d}$ are joined together forming a methylene, ethylene or —CH$_2$—O— bridging group; and R$^6$, R$^7$, R$^8$ and R$^9$ are each independently selected from H, $^2$H, halo, C$_{1-3}$ haloalkyl, C$_{1-3}$ alkoxy, C$_{1-3}$ haloalkoxy, C$_{3-7}$ cycloalkyl and 4-7 membered heterocyclyl, each optionally substituted with 1 to 3 substituents selected from H, halo, hydroxyl, C$_{2-3}$ alkynyl, C$_{2-3}$ alkenyl, CN, C$_{1-3}$ alkyl, C$_{1-3}$ alkoxy, C$_{1-3}$ haloalkyl, C$_{1-3}$ haloalkoxy and C$_{3-7}$ cycloalkyl; or wherein R$^6$ and R$^8$ optionally form a partially saturated carbobicyclic ring or heterobicyclic ring with the heteroaryl ring, said carbobicyclic ring or heterobicyclic ring optionally substituted with 1 to 3 groups selected from: H, $^2$H, halo, C$_{1-3}$ haloalkyl, C$_{1-3}$ alkoxy, C$_{1-3}$ haloalkoxy, C$_{3-7}$ cycloalkyl and 4-7 membered heterocyclyl having 1 to 3 heteroatoms selected from N, O and S.

In a separate embodiment, compounds, their tautomers, stereoisomers or pharmaceutically acceptable salts thereof or esters having a solubility enhancing moieties or prodrugs thereof are provided of the formula (III):

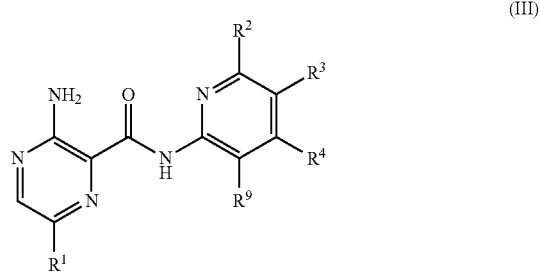

(III)

wherein:
R$^1$ is optionally substituted 6-10 membered aryl or 5-10 membered heteroaryl having 1 to 4 heteroatoms each independently selected from the group consisting of: O, N and S, said heteroaryl or aryl each being optionally substituted with 1 to 3 substituents each independently selected from the group consisting of: H, $^2$H, halo, C$_{2-3}$ alkynyl, C$_{2-3}$ alkenyl, CN, C$_{1-3}$ alkyl, C$_{1-3}$ alkoxy, C$_{1-3}$ haloalkyl, C$_{1-3}$ haloalkoxy, C$_{3-7}$ cycloalkyl, CONH$_2$, CONHC$_{1-3}$ alkyl, CONHC$_{6-10}$ aryl, SO$_2$NH$_2$, SO$_2$NHC$_{1-3}$ alkyl, SO$_2$NHC$_{6-10}$ aryl and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, C$_{1-3}$ alkyl, C$_{1-3}$ alkoxy, C$_{1-3}$ haloalkyl, and C$_{1-3}$ haloalkoxy;

R$^2$, R$^3$ and R$^4$ are each independently H, $^2$H, halo, hydroxy (—OH), C$_{1-3}$ alkoxy, C$_{1-3}$ haloalkyl or C$_{1-3}$ alkyl, each further optionally substituted with one to two of hydroxy, halo and C$_{1-3}$ haloalkoxy; and R$^9$ is independently H or 4-7 membered heterocyclyl or heterobicyclyl having 1 to 3 heteroatoms selected from N, O and S, SO, SO$_2$, said heterocycyl or heterobicylyl substituted with 1 to 4 substituents each independently selected from the group consisting of: H, $^2$H, amino (NH$_2$), halo, CN, C$_{1-3}$ alkyl, C$_{1-3}$ alkoxy, C$_{1-3}$ haloalkyl, C$_{1-3}$ haloalkoxy, C$_{3-7}$ cycloalkyl, C$_{2-3}$ alkynyl, C$_{2-3}$ alkenyl, COOC$_{1-3}$ alkyl, CONH$_2$, CONHC$_{1-3}$ alkyl, CONHC$_{6-10}$ aryl, SO$_2$NH$_2$, SO$_2$NHC$_{1-3}$ alkyl, SO$_2$NHC$_{6-10}$ aryl —O—(CH$_2$)-heterocyclyl (n=1-3), CO NH$_2$, said C$_{1-3}$ alkyl or —O—(CH$_2$)-heterocyclyl, said heterocylyl having 1 to 3 heteroatoms selected from N, O and S, SO, SO$_2$ each optionally substituted with 1 to 4 substituents selected from H, $NH_2$, OH, halo, $C_{1-3}$ alkoxy and $C_{1-3}$ haloalkoxy.

In other aspects, the present invention provides a pharmaceutical composition comprising: a compound of formula (I), (Ia), (II) or (III) or a pharmaceutically acceptable salt thereof and at least one pharmaceutically acceptable carrier.

In other aspects, the present invention provides a method for treating protein kinase C related disorders, specifically protein kinase C isoforms alpha and/or theta (PKCα/θ)), related disorders in a human or animal subject in recognized need of such treatment comprising administering to said subject an amount of a compound of formula (I), (II) or (III) or a pharmaceutically acceptable salt thereof effective to inhibit the PKCα/θ related activity in the subject.

The compounds of the invention are useful in the treatment of cancers, including for example melanoma, uveal melanoma, lymphoma, diffuse large B-cell lymphoma (DLBCL) and ibrutinib resistant cancers.

The compounds of the invention are also for treating immune related disorders, including but not limited to autoimmune diseases, allergic reaction and tissue transplant rejection, in a human or animal subject in recognized need of such treatment comprising administering to said subject an amount of a compound of formula (I), (Ia), (II) or (III) or a pharmaceutically acceptable salt thereof effective to reduce or prevent tumor growth in the subject.

The invention further provides compositions, methods of use, and methods of manufacture of a compound of formula (I), (Ia), (II) or (III), or a pharmaceutically acceptable salt thereof as described in the detailed description of the invention.

DETAILED DESCRIPTION

Figure 1:
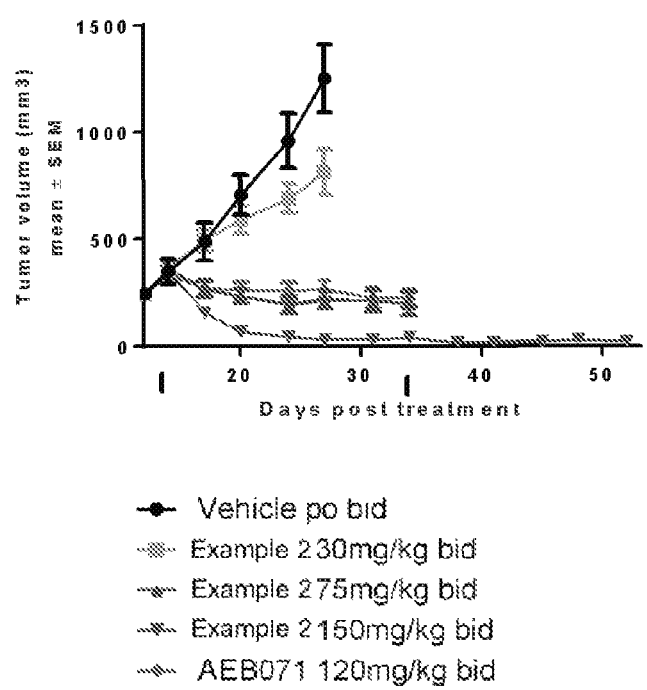
FIG. 1 summarizes that Example 2 decreases tumor proliferation in a 92.1 uveal melanoma xenografts in a dose dependent manner, as compared to sotrastaurin.
Figure 2:
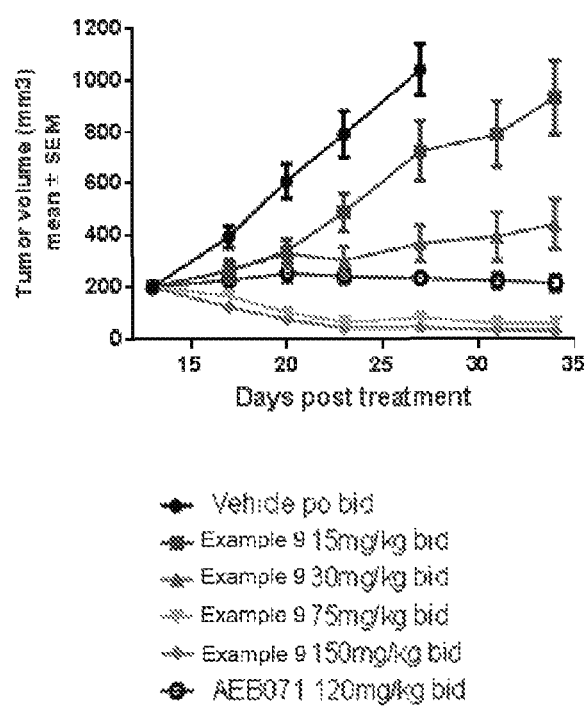
FIG. 2 summarizes that Example 9 decreases tumor proliferation in a 92.1 uveal melanoma xenografts in a dose dependent manner, as compared to sotrastaurin.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH$(CH_3)_2$, —CH$(CH_3)(CH_2CH_3)$, —CH$(CH_2CH_3)_2$, —C$(CH_3)_3$, —C$(CH_2CH_3)_3$, —CH$_2$CH$(CH_3)_2$, —CH$_2$CH$(CH_3)(CH_2CH_3)$, —CH$_2$CH$(CH_2CH_3)_2$, —CH$_2$C$(CH_3)_3$, —CH$_2$C$(CH_2CH_3)_3$, —CH$(CH_3)$—CH$(CH_3)$(CH$_2$CH$_3$), —CH$_2$CH$_2$CH$(CH_3)$(CH$_2$CH$_3$), —CH$_2$CH$_2$CH$(CH_3)_2$, —CH$_2$CH$_2$CH$(CH_2CH_3)_2$, —CH$_2$CH$_2$C$(CH_3)_3$, —CH$_2$CH$_2$C$(CH_2CH_3)_3$, —CH$(CH_3)$CH$_2$—CH$(CH_3)_2$, —CH$(CH_3)$CH$(CH_3)$CH$(CH_3)_2$, —CH$(CH_2CH_3)$CH$(CH_3)$CH$(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the term "$C_{1-12}$ alkyl group" includes primary alkyl groups, secondary alkyl groups, and tertiary alkyl groups. Alkyl groups include straight and branched chain alkyl groups and cyclic alkyl groups having 1 to 12 carbon atoms.

As used herein, "$C_{1-6}$ alkyl" includes both substituted or unsubstituted straight or branched chain alkyl groups having from 1 to 6 carbon atoms. Representative $C_{1-6}$ alkyl groups include, for example, methyl, ethyl, propyl, isopropyl, n-butyl, tert-butyl, neopentyl, tri-fluoromethyl, pentafluoroethyl and the like. $C_{1-6}$ alkyl groups may be substituted, such as with halo, hydroxy, amino, nitro and/or cyano groups, and the like. Representative $C_{1-3}$ haloalkyl and $C_{1-3}$ hydroxyalkyl include chloromethyl, tri chloromethyl, trifluoromethyl, fluoromethyl, fluoroethyl, chloroethyl, hydroxymethyl, hydroxyethyl, and the like. Other suitable substituted $C_{1-3}$ alkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

As used herein, "$C_{1-6}$ alkoxy" as used herein refers to the radical RO—, wherein R is $C_{1-6}$ alkyl. Representative examples of $C_{1-6}$ alkoxy groups include methoxy, ethoxy, t-butoxy, trifluoromethoxy and the like.

As used herein, the term "halogen" or "halo" refers to chloro, bromo, fluoro and iodo groups. "Haloalkyl" refers to a $C_{1-3}$ alkyl radical substituted with one or more halogen atoms. The term "haloalkoxy" refers to a $C_{1-3}$ alkoxy radical substituted with one or more halogen atoms. Hydroxy refers to the group —OH.

"Amino" refers herein to the group —$NH_2$. The term "$C_{1-3}$ alkylamino" refers herein to the group —NRR' where R and R' are each independently selected from hydrogen or a $C_{1-3}$ alkyl. The term "arylamino" refers herein to the group —NRR' where R is $C_{6-10}$ aryl, including phenyl, and R' is hydrogen, a $C_{1-3}$ alkyl, or $C_{6-10}$ aryl, including phenyl. The term "aralkylamino" refers herein to the group —NRR' where R is a aralkyl and R' is hydrogen, a $C_{1-3}$ alkyl, an aryl, including phenyl, or a aralkyl.

The term "alkoxyalkyl" refers to the group -alk$_1$-O-alk$_2$ where alk$_1$ is $C_{1-3}$ alkyl, and alk$_2$ is $C_{1-3}$ alkyl. The term "aryloxyalkyl" refers to the group —$C_{1-3}$ alkyl-O-aryl, wherein aryl is $C_{6-10}$ aryl, including phenyl. The term "aralkoxyalkyl" refers to the group -alkylenyl-O-aralkyl, where aralkyl is a lower aralkyl.

The term "aminocarbonyl" refers herein to the group —C(O)—$NH_2$. "Substituted aminocarbonyl" refers herein to the group —CO—NHR— or —C(O)—NRR' where R is $C_{1-3}$ alkyl or $C_{6-10}$ aryl and R' is hydrogen, $C_{1-3}$ alkyl or $C_{6-10}$ aryl. In some embodiments, R and R', together with the N atom attached to them may be taken together to form a "heterocycloalkylcarbonyl" group. The term "carboxyamido" also refers to the group —$CONH_2$. The term "substituted carboxyamide" refers herein to the group —CO—NHR— or —CO—NRR' where R is $C_{1-3}$ alkyl, $C_{6-10}$ aryl or and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy and R' is hydrogen, $C_{1-3}$ alkyl, $C_{6-10}$ aryl or and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy. The term "arylaminocarbonyl" refers herein to the group —C(O)—NRR' where R is an aryl and R' is hydrogen, $C_{1-3}$ alkyl or aryl. The term "aralkylaminocarbonyl" refers herein to the group —C(O)—NRR' where R is aralkyl and R' is hydrogen, $C_{1-3}$ alkyl, aryl, phenyl or aralkyl.

The term "aminosulfonyl" refers herein to the group —SO$_2$—NH$_2$. "Substituted aminosulfonyl" refers herein to the group —SO$_2$—NHR— or —SO$_2$—NRR' where R is $C_{1-3}$ alkyl or $C_{6-10}$ aryl and R' is hydrogen or a $C_{1-3}$ alkyl or $C_{6-10}$ aryl. The term "sulfonamido" refers to the group —SONH$_2$. The term "substituted sulfonamide" refers herein to the group —SO—NHR— or —SO—NRR' where R is $C_{1-3}$ alkyl, $C_{6-10}$ aryl or and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy and R' is hydrogen or a $C_{1-3}$ alkyl, $C_{6-10}$ aryl or and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy. The term "aralkylaminosulfonlyaryl" refers herein to the group -aryl-S(O)$_2$—NH-aralkyl.

The term "carbonyl" refers to the divalent group —C(O)—. "Carboxy" refers to —C(=O)—OH. "Alkoxycarbonyl" refers to ester —C(=O)—OR wherein R is $C_{1-3}$ alkyl. "Cycloalkyloxycarbonyl" refers to —C(=O)—OR wherein R is cycloalkyl. The term "aryloxycarbonyl" refers to —C(=O)—OR wherein R is aryl. The term "heterocyclyloxycarbonyl" refers to —C(=O)—OR wherein R is heterocyclyl.

The term "aralkoxycarbonyl" refers herein to the group —(C=O)—O-aralkyl, where the aralkyl is ara$C_{1-3}$ alkyl.

The term "sulfonyl" refers herein to the group —SO$_2$—. The term "sulfanyl" refers herein to the group —S—. "Alkylsulfonyl" refers to a substituted sulfonyl of the structure —SO$_2$R— in which R is $C_{1-3}$ alkyl. "Alkylsulfanyl" refers to a substituted sulfanyl of the structure —SR— in which R is $C_{1-3}$ alkyl. Thus, typical alkylsulfonyl and loweralkylsulfanyl groups employed in compounds of the present invention include, for example, methylsulfonyl and methylsulfanyl (i.e., where R is methyl), ethylsulfonyl and ethylsulfanyl (i.e., where R is ethyl), propylsulfonyl and propylsulfanyl (i.e., where R is propyl), and the like. The term "arylsulfonyl" refers herein to the group —SOO$_2$-aryl. The term "aralkylsulfonyl" refers herein to the group —SO$_2$-aralkyl, in which the aralkyl is ara$C_{1-3}$ alkyl. The term "sulfonamido" refers herein to —SO$_2$NH$_2$.

Alternatively, the term "amido" refers to —C(=O)NH$_2$ and "carbonylamino" refers to the divalent group —NH—(C=O)— in which the hydrogen atom of the amide nitrogen of the carbonylamino group can be replaced a $C_{1-3}$ alkyl, $C_{6-10}$ aryl, aralkyl or and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy. Such groups include moieties such as carbamate esters (—NH—C(O)—O—R) and amides —NH—C(O)—R, where R is a straight or branched chain $C_{1-3}$ alkyl, $C_{3-8}$ cycloalkyl, or $C_{6-10}$ aryl, including phenyl, aralkyl or and 4-7 membered heterocyclyl having 1 to 3 heteroatoms selected from N, O and S, said heterocyclyl optionally substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy.

The term "$C_{3-8}$ cycloalkyl" refers to a mono- or polycyclic, heterocyclic or carbocyclic $C_{3-8}$ alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperidinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures. The term "carbobicyclic or carbobicyclyl" refers to a saturated, orpartially unsaturated carbocyclic ring fused to another carbocyclic ring, aryl ring, heterocyclic ring or heteroaryl ring. The cycloalkyl group is unsubstituted or substituted.

The term "substituted heterocycle" or "heterocyclic group" or "heterocyclyl", as used herein, refers to any 3- or 4-membered ring containing a heteroatom selected from nitrogen, oxygen, and sulfur or a 5-, 6- or 7-membered ring containing from one to three heteroatoms selected from the group consisting of nitrogen, oxygen, or sulfur; wherein the 5-membered ring has 0-1 double bonds and the 6- and 7-membered rings have 0-1 double bonds or fused rings having 0-2 double bonds; wherein the nitrogen and sulfur atom maybe optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above and is referred to as a heterobicyclic ring or a heterobicyclyl group. The heterocylyl group is unsubstituted or substituted with 1 to 3 substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy.

The term "heterocycle" thus includes rings in which nitrogen is the heteroatom as well as partially and fully-saturated rings. Exemplary heterocycles include but are not limited to, for example: piperidinyl, piperazinyl, 1,2-oxazinane, 2-oxopiperazinyl, 2-oxopiperidinyl, N-methyl piperazinyl, and morpholinyl, each optionally substituted.

Heterocyclic moieties can be unsubstituted or monosubstituted or disubstituted with various substituents independently selected from hydroxy, halo, oxo (C=O), alkylimino (RN=, wherein R is a $C_{1-3}$ alkyl or $C_{1-3}$ alkoxy group), amino, $C_{1-3}$ alkylamino, $C_{1-3}$ dialkylamino, acylaminoalkyl, $C_{1-3}$ alkoxy, $C_{1-3}$ alkyl, cycloalkyl or $C_{1-3}$ haloalkyl.

The heterocyclic groups (heterocyclyl) may be attached at various positions as will be apparent to those having skill in the organic and medicinal chemistry arts in conjunction with the disclosure herein. Representative examples of heterocyclyl, heterobicyclyl and substituted heterocyclyl groups used in accordance with the invention are listed below:

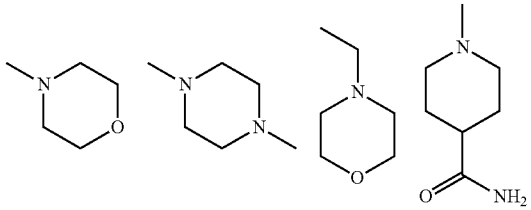

-continued

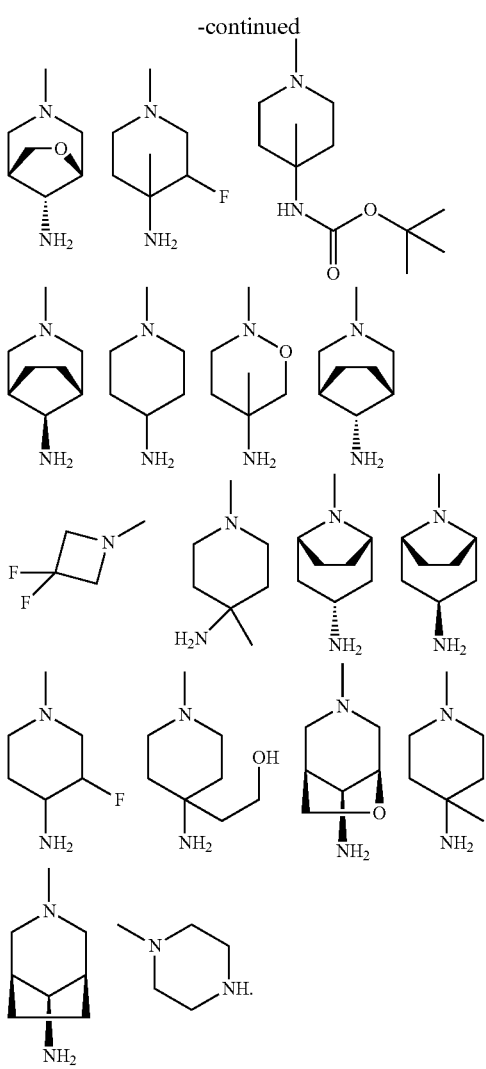

The term "$C_{6-10}$ aryl" refers to optionally substituted monocyclic and polycyclic aromatic groups having from 6 to 10 or 3 to 14 backbone carbon or hetero atoms, and includes both carbocyclic aryl groups and heterocyclic aryl groups. Carbocyclic aryl groups are $C_{6-10}$ aryl groups in which all ring atoms in the aromatic ring are carbon. Exemplary $C_{6-10}$ aryl moieties employed as substituents in compounds of the present invention include phenyl, naphthyl, isonaphthyl and the like.

"Aralkyl" refers to a $C_{1-3}$ alkyl or $C_{1-6}$ alkyl group substituted with an $C_{6-10}$ aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

The term "heteroaryl" refers to 5-10 membered carbocyclic ring system, including fused ring systems, having 1 to 4 heteroatoms each independently selected from the group consisting of: O, N and S. Said heteroaryl may be optionally substituted with one or two substituents. The term "heteroaryl" also refers herein to $C_{6-10}$ aryl groups having from 1 to 4 heteroatoms as ring atoms in an aromatic ring with the remainder of the ring atoms being carbon atoms. Exemplary substituents include, but are not limited to: halo, CN, $C_{1-3}$ alkyl, $C_{1-3}$ alkoxy, $C_{1-3}$ haloalkyl, $C_{1-3}$ haloalkoxy, $C_{3-7}$ cycloalkyl, and 4-7 membered heterocyclyl having 1 or 2 heteroatoms selected from N, O and S, said heterocyclyl optionally substituted with 1 to 3 substituents each independently selected from the group consisting of: halo, CN, $C_{1-3}$ alkyl, $C_{1-3}$ alkoxy, $C_{1-3}$ haloalkyl, and $C_{1-3}$ haloalkoxy Representative heteroaryl groups include, for example, those shown below. Representative heteroaryls include, for example, imidazolyl, pyridinyl (also referred to aspyridyl), pyrazinyl, azetidinyl, thiazolyl, triazolyl, benzimidazolyl, benzothiazolyl, thiazolyl, thiazolidinyl, isothiazolyl, isothiazolidinyl, indolyl, quinolinyl, isoquinolinyl, azetidinyl, N-methylazetidinyl, pyrimidinyl, pyridazinyl, oxazolyl, oxazolidinyl, isoxazolyl, isoazolidinyl, benzimidazolyl, benzothiazolyl, benzoxazolyl, furyl, thienyl, triazolyl, benzothienyl diazapinyl, pyrryl, pyrrolinyl, pyrrolidinyl, pyrazolyl, pyrazolinyl, pyrazolidinyl, imidazoyl, imidazolinyl, imidazolidinyl and benzoxazolyl. The heteroaryl is unsubstituted or substituted with 1 to 3 substituents each independently selected from the group consisting of: H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy.

The heteroaryl groups can be further substituted and may be attached at various positions as will be apparent to those having skill in the organic and medicinal chemistry arts in conjunction with the disclosure herein. Representative examples of heteroaryl and substituted heteroaryl groups used in accordance with the invention are listed below:

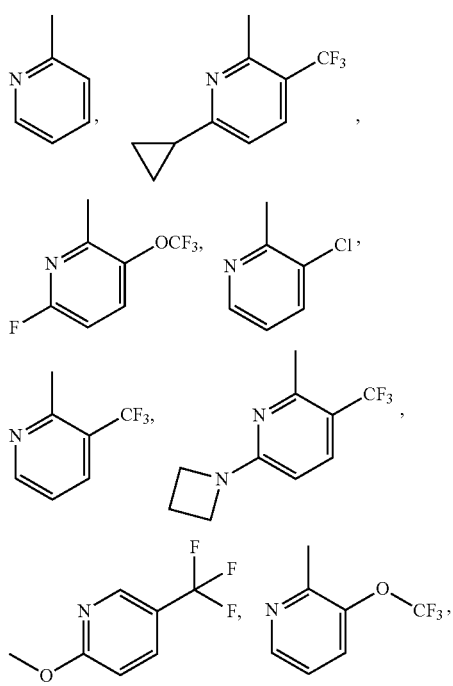

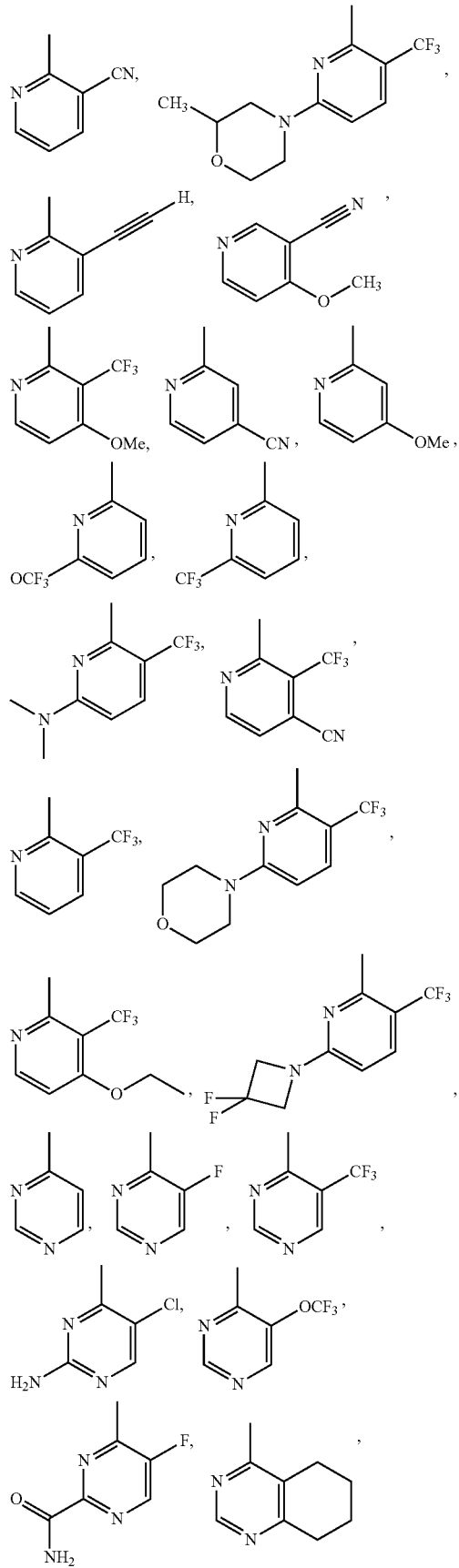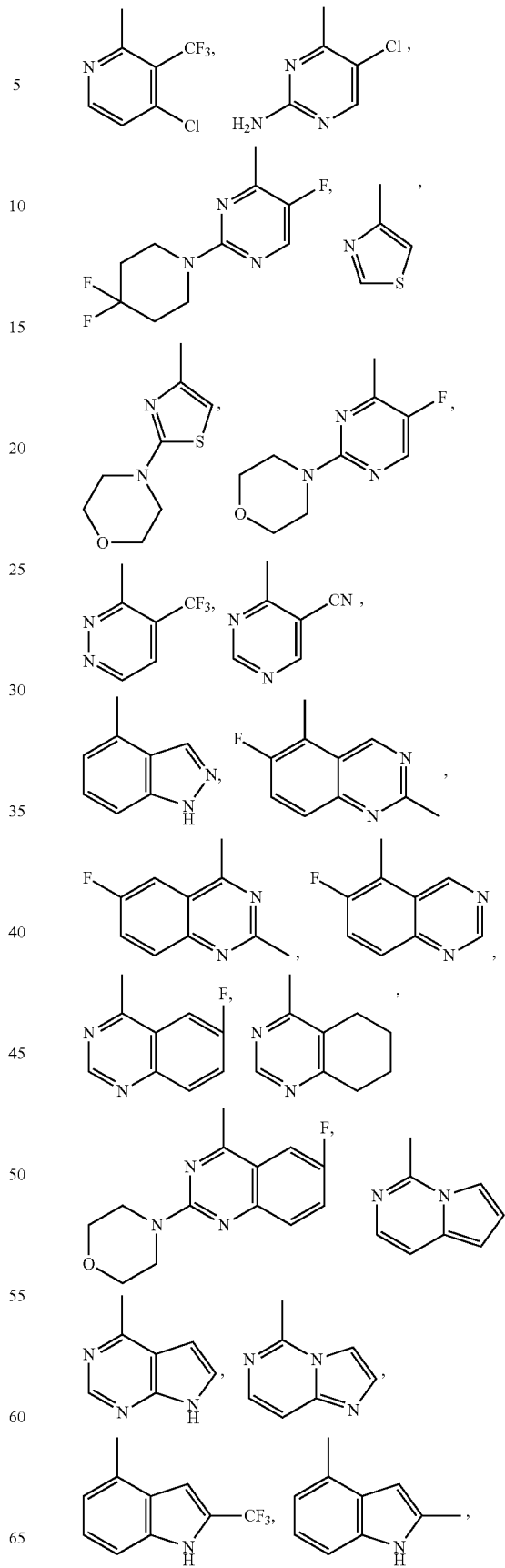

-continued

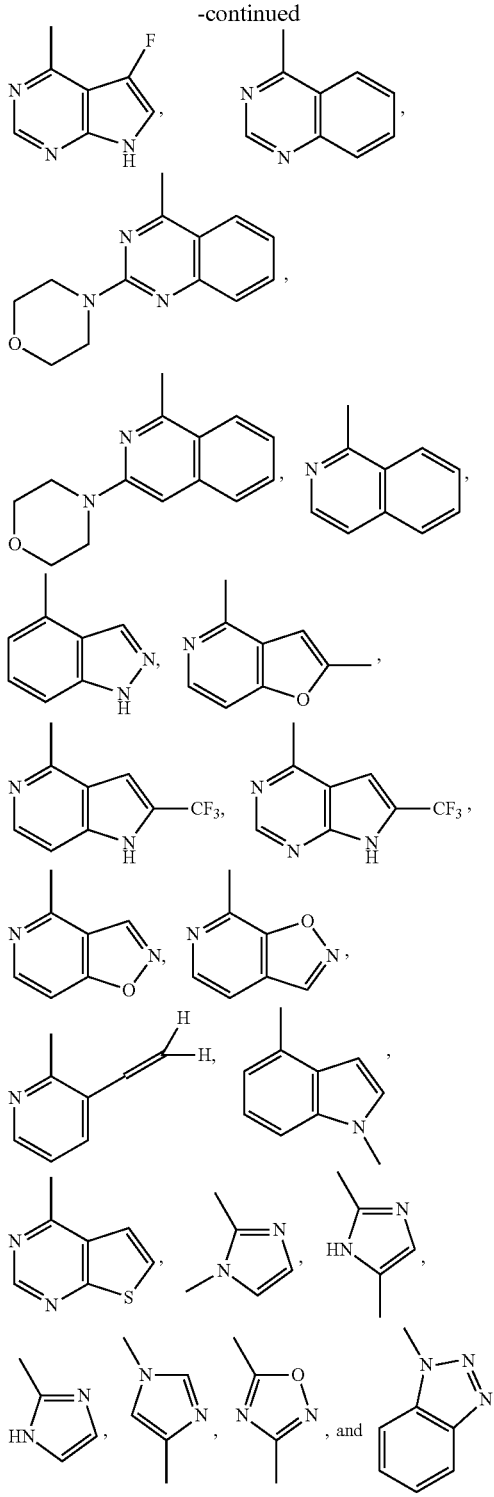

"Optionally substituted" or "substituted" refers to the replacement of one or more hydrogen atoms with a monovalent or divalent radical. Suitable substitution groups include, for example, H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy; and the like.

The substitution group can itself be substituted. The group substituted onto the substitution group can be carboxyl, halo; nitro, amino, cyano, hydroxy, $C_{1-3}$ alkyl, $C_{1-3}$ alkoxy, aminocarbonyl, —SR, thioamido, —$SO_3H$, —$SO_2R$ or $C_{3-8}$ cycloalkyl, where R is typically hydrogen, hydroxyl or $C_{1-3}$ alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

The term "$^2$H" refers to a heavy isotope of hydrogen that is also referred to as deuterium (D). It is understood that the above definitions are not intended to include impermissible substitution patterns (e.g., methyl substituted with five fluoro groups or a halogen atom substituted with another halogen atom). Such impermissible substitution patterns are well known to the skilled artisan.

The compounds of the invention, including the compounds of formulas (I), (Ia), (II) or (III) or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

In accordance with one aspect of the present invention, new compounds, their tautomers, stereoisomers, or pharmaceutically acceptable salts thereof or esters having a solubility enhancing moieties or prodrugs thereof are provided of the formula (I):

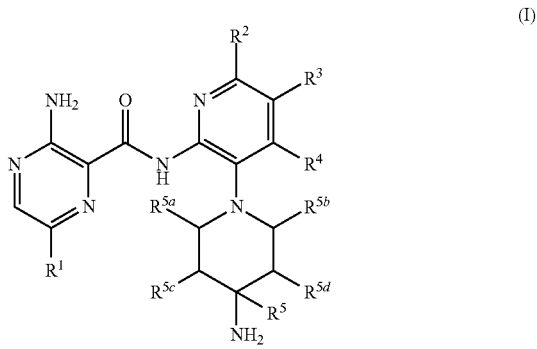

(I)

wherein:
$R^1$ is optionally substituted 6-10 membered aryl or 5-10 membered heteroaryl having 1 to 4 heteroatoms each independently selected from the group consisting of: O, N and S, said heteroaryl or aryl each being optionally substituted with 1 to 3 substituents each independently selected from the group consisting of: H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy;

$R^2$, $R^3$ and $R^4$ are each independently H, $^2$H, halo, hydroxy (—OH), $C_{1-3}$ alkoxy, $C_{1-3}$ haloalkyl or $C_{1-3}$ alkyl, optionally substituted with one to two of hydroxyl, halo and $C_{1-3}$ haloalkoxy;

$R^5$ is —H, $^2$H, $CH_3$, $CH_2F$, $CHF_2$, $CF_3$, $CH_2OH$, $C_{1-3}$ alkyl, $CH_2$—O—$C_{1-3}$ alkyl or $CH_2$—O—$C_{1-3}$ haloalkyl, said $C_{1-3}$ alkyl optionally substituted with H, F, OH, $C_{1-3}$ alkoxy and $C_{1-3}$ haloalkoxy;

$R^{5a}$ and $R^{5b}$ are each independently H, $^2$H, $C_{1-3}$ alkyl, said $C_{1-3}$ alkyl optionally substituted with H, F, OH, $C_{1-3}$ alkoxy and $C_{1-3}$ haloalkoxy, or $R^{5a}$ and $R^{5b}$ are joined together forming a methylene or ethylene bridging group; and $R^{5c}$ and $R^{5d}$ are each independently H, $^2$H, F, —OH, $C_{1-3}$ alkyl, said alkyl optionally substituted with F, OH, and alkoxy or $C_{1-3}$ alkoxy or $R^{5c}$ and $R^{5d}$ are joined together forming a methylene, ethylene or —$CH_2$—O— bridging group.

In one embodiment, new compounds, their tautomers, stereoisomers or pharmaceutically acceptable salts thereof or esters having a solubility enhancing moieties or prodrugs thereof are provided of the formula (I),
wherein:
$R^1$ is pyridinyl, pyrimidinyl, thiazolyl, indolyl, azaindolyl, imidazolyl, pyrazinyl, quinolinyl, azaquinolinyl, isoquinolinyl purinyl, benzothiazolyl, benzopyridyl, benzimidazolyl, phenyl or naphthyl, each unsubstituted or substituted with 1 to 3 substituents each independently selected from the group consisting of: H, $^2$H, halo, CN, $C_{1-3}$ alkyl, $C_{1-3}$ alkoxy, $C_{1-3}$ haloalkyl, $C_{1-3}$ haloalkoxy, $C_{3-7}$ cycloalkyl, morpholino, piperidinyl and piperazinyl;

$R^2$, $R^3$ and $R^4$ are each H;

$R^5$ is H, $^2$H, $CH_3$, $CH_2F$, $CHF_2$, $CF_3$, $CH_2OH$, $C_{1-3}$ alkyl, $CH_2$—O—$C_{1-3}$ alkyl, $CH_2$—O—$C_{1-3}$ alkyl or $CH_2$—O—$C_{1-3}$ haloalkyl;

$R^{5a}$ and $R^{5b}$ are each H, F, $C_{1-3}$ alkyl, $C_{1-3}$ alkoxy or $R^{5a}$ and $R^{5b}$ are joined together forming a methylene or ethylene bridging group; and $R^{5c}$ and $R^{5d}$ are each independently H, F, $C_{1-3}$ alkyl, or $C_{1-3}$ alkoxy or $R^{5c}$ and $R^{5d}$ are joined together forming a methylene, ethylene or —$CH_2$—O— bridging group.

In a separate embodiment, $R^{5a}$ and $R^{5d}$ are joined together forming a methylene, ethylene or —$CH_2$—O— bridging group, provided that the O atom of the —$CH_2$—O— bridging group is formed at $R^{5d}$. In a separate embodiment, if a bridging group is formed only one of $R^{5a}$ and $R^{5b}$, $R^{5c}$ and $R^{5d}$ or $R^{5a}$ and $R^{5d}$ forms a bridging group.

In another embodiment, new compounds, their tautomers, stereoisomers or pharmaceutically acceptable salts thereof or esters having a solubility enhancing moieties or prodrugs thereof are provided of the formula (I),
wherein:
$R^1$ is independently pyridinyl, pyrimidinyl, thiazolyl, indolyl, imidazolyl, pyrazinyl, quinolinyl, isoquinolinyl or phenyl, each unsubstituted or substituted with 1 to 3 substituents each independently selected from the group consisting of: H, $^2$H, halo, CN, acetylene, $C_{1-3}$ alkyl, $C_{1-3}$ alkoxy, $C_{1-3}$ haloalkyl, $C_{1-3}$ haloalkoxy, $C_{3-7}$ cycloalkyl, morpholino, piperidinyl and piperazinyl;

$R^2$, $R^3$ and $R^4$ are each H;

$R^5$ is independently H, $^2$H, $CH_3$, $CH_2F$, $CHF_2$, $CF_3$, $C_{1-3}$ alkyl, $CH_2OH$, $CH_2$—O—$C_{1-3}$ alkyl $CH_2$—O—$C_{1-3}$ haloalkyl;

$R^{5a}$ and $R^{5b}$ are each H; and $R^{5c}$ and $R^{5d}$ are each H.

In another embodiment, new compounds, their tautomers, stereoisomers or pharmaceutically acceptable salts thereof or esters having a solubility enhancing moieties or prodrugs thereof are provided of the formula (I),
wherein:
$R^1$ is pyridinyl or pyrimidinyl, substituted with 1 to 3 substituents each independently selected from the group consisting of: H, $^2$H, halo, CN, acetylene, $C_{1-3}$ alkyl, $C_{1-3}$ alkoxy, $C_{1-3}$ haloalkyl, $C_{1-3}$ haloalkoxy, $C_{3-7}$ cycloalkyl, morpholino, piperidinyl and piperazinyl;

$R^2$, $R^3$ and $R^4$ are each H;

$R^5$ is independently H, $CH_3$, $CH_2F$, $CHF_2$, $CF_3$, $CH_2OH$, $CH_2$—O—$C_{1-3}$ alkyl or $CH_2$—O—$C_{1-3}$ haloalkyl;

$R^{5a}$ and $R^{5b}$ are each H; and $R^{5c}$ and $R^{5d}$ are each H.

In another embodiment, a compound or a stereoisomer, tautomer, or a pharmaceutically acceptable salt thereof is selected from: 3-amino-N-(3-(4-aminopiperidin-1-yl)pyridin-2-yl)-6-(3-(trifluoromethyl)pyridin-2-yl)pyrazine-2-carboxamide, 3-amino-N-(3-(4-aminopiperidin-1-yl)pyridin-2-yl)-6-(3-(trifluoromethoxy) pyridin-2-yl)pyrazine-2-carboxamide, 3-amino-N-(3-(4-amino-4-(methoxymethyl)piperidin-1-yl)pyridin-2-yl)-6-(3-(trifluoromethyl)pyridin-2-yl)pyrazine-2-carboxamide, 3-amino-N-(3-(4-amino-4-methylpiperidin-1-yl)pyridin-2-yl)-6-(3 morpholinoisoquinolin-1-yl)pyrazine-2-carboxamide, 3-amino-N-(3-(4-amino-4-(hydroxymethyl)piperidin-1-yl)pyridin-2-yl)-6-(3-(trifluoromethyl)pyridin-2-yl)pyrazine-2-carboxamide, 3-amino-N-(3-(4-amino-4-(hydroxymethyl) piperidin-1-yl)pyridin-2-yl)-6-(3-(trifluoromethoxy) pyridin-2-yl)pyrazine-2-carboxamide, 3-amino-N-(3-(4-aminopiperidin-1-yl)pyridin-2-yl)-6-(6-morpholino-3-(trifluoromethyl)pyridin-2-yl)pyrazine-2-carboxamide, 3-amino-N-(3-(4-aminopiperidin-1-yl)pyridin-2-yl)-6-(2-morpholino thiazol-4-yl)pyrazine-2-carboxamide, 3-amino-N-(3-(4-amino -4-methylpiperidin-1-yl)pyridin-2-yl)-6-(3-(trifluoromethyl)pyridin-2-yl)pyrazine-2-carboxamide, 3-amino-N-(3-(4-amino-4-methylpiperidin-1-yl)pyridin-2-yl)-6-(3-(trifluoromethoxy)pyridin-2-yl)pyrazine-2-carboxamide, 3-amino-N-(3-(4-amino-4-methylpiperidin-1-yl) pyridin-2-yl)-6-(2-morpholino-5-(trifluoromethyl) pyrimidin-4-yl)pyrazine-2-carboxamide, 3-amino-N-(3-(4-amino -4-methylpiperidin-1-yl)pyridin-2-yl)-6-(6-fluoro-2-methylquinazolin-4-yl)pyrazine-2-carboxamide, 3-amino-N-(3-(4-amino-4-methylpiperidin-1-yl)pyridin-2-yl)-6-(4-methoxy-3-(trifluoromethyl)pyridin-2-yl)pyrazine-2-carboxamide, 3-amino-N-(3-(4-amino-4-methylpiperidin-1-yl)pyridin-2-yl)-6-(6-(3,3-difluoroazetidin-1-yl)-3-(trifluoromethyl)pyridin-2-yl)pyrazine-2-carboxamide, 3-amino-N-(3-(4-amino-4-methylpiperidin-1-yl)pyridin-2-yl)-6-(6-cyclopropyl-3-(trifluoromethyl)pyridin-2-yl)pyrazine-2-carboxamide, 3-amino-N-(3-(4-amino-4-methylpiperidin-1-yl)pyridin-2-yl)-6-(6-methoxy-3-(trifluoromethyl)pyridin-2-yl)pyrazine-2-carboxamide, 3-amino-N-(3-(4-amino-4-ethylpiperidin-1-yl)pyridin-2-yl)-6-(3-(trifluoromethyl)pyridin-2-yl)pyrazine-2-carboxamide, 3-amino-N-(3-(4-amino-4-methylpiperidin-1-yl)pyridin-2-yl)-6-(3-chloropyridin-2-yl)pyrazine-2-carboxamide, 3-amino-N-(3-(4-amino-4-methylpiperidin-1-yl)pyridin-2-yl)-6-(3-fluoropyridin-2-yl)pyrazine-2-carboxamide, 3-amino-N-(3-((1R,5 S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide, 3-amino-N-(3-(4-amino-4-methylpiperidin-1-yl)pyridin-2-yl)-6-(3-fluoro-4-methoxypyridin-2-yl)pyrazine-2-carboxamide, 3-amino-N-(3-(4-amino-4-(methoxymethyl)piperidin-1-yl)pyridin-2-yl)-6-(3-fluoropyridin-2-yl)pyrazine-2-carboxamide, 3-amino-N-(3-(4-amino-4-methylpiperidin-1-yl)pyridin-2-yl)-6-(6-cyano-3-fluoropyridin-2-yl)pyrazine-2-carboxamide, 3-amino-N-(3-(4-amino-4-methylpiperidin-1-yl)pyridin-2-yl)-6-(3-cyanopyridin-2-yl)pyrazine-2-carboxamide, 3-amino-N-(3-(4-amino-4-ethylpiperidin-1-yl)pyridin-2-yl)-6-(3-(trifluoromethoxy)pyridin-2-yl)pyrazine-2-carboxamide, 3-amino-N-(3-(4-amino-4-methylpiperidin-1-yl)pyridin-2-yl)-6-(3-cyano-4-methoxypyridin-2-yl)pyrazine-2-carboxamide, 3-amino-N-(3-(4-amino-4-(methoxymethyl)piperidin-1-yl)pyridin-2-yl)-6-(3-(trifluoromethoxy)pyridin-2-yl)pyrazine-2-carboxamide, 3-amino-N-(3-(4-amino-4-(2-hydroxyethyl)piperidin-1-yl)pyridin-2-yl)-6-(3-(trifluoromethyl)pyridin-2-yl)pyrazine-2-carboxamide, 3-amino-N-(3-((1S,5R,8S)-8-amino-6-oxa-3-azabicyclo[3.2.1]octan-3-yl)pyridin-2-yl)-6-(6-morpholino-3-(trifluoromethyl)pyridin-2-yl)pyrazine-2-carboxamide, 3-amino-N-(3-(4-aminopiperidin-1-yl)pyridin-2-yl)-6-(5,6,7,8-tetrahydroquinazolin-4-yl)pyrazine-2-carboxamide, 3-amino-N-(3-(4-aminopiperidin-1-yl)pyridin-2-yl)-6-(7H-pyrrolo[2,3-d]pyrimidin-4-yl)pyrazine-2-carboxamide, 3-amino-N-(3-(4-amino-4-(2-hydroxyethyl)piperidin-1-yl)pyridin-2-yl)-6-(3-fluoropyridin-2-yl)pyrazine-2-carboxamide, 3-amino-N-(3-(4-amino-4-methylpiperidin-1-yl)pyridin-2-yl)-6-(6-(dimethylamino)-3-(trifluoromethyl)pyridin-2-yl)pyrazine-2-carboxamide, 3-amino-N-(3-((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide, 3-amino-N-(3-(4-amino-4-methylpiperidin-1-yl)pyridin-2-yl)-6-(4-cyano-3-fluoropyridin-2-yl)pyrazine-2-carboxamide, 3-amino-N-(3-(4-amino-4-(2-methoxyethyl)piperidin-1-yl)pyridin-2-yl)-6-(3-(trifluoromethyl)pyridin-2-yl)pyrazine-2-carboxamide, 3-amino-N-(3-(4-amino-4-methylpiperidin-1-yl)pyridin-2-yl)-6-(6-morpholino-3-(trifluoromethyl)pyridin-2-yl)pyrazine-2-carboxamide, 3-amino-N-(3-(4-amino-4-methylpiperidin-1-yl)pyridin-2-yl)-6-(6-fluoroquinazolin-4-yl)pyrazine-2-carboxamide, 3-amino-N-(3-(4-aminopiperidin-1-yl)pyridin-2-yl)-6-(5-fluoro-7H-pyrrolo[2,3-d]pyrimidin-4-yl)pyrazine-2-carboxamide, 3-amino-N-(3-(4-aminopiperidin-1-yl)pyridin-2-yl)-6-(3-morpholinophenyl)pyrazine-2-carboxamide, 3-amino-N-(3-(4-aminopiperidin-1-yl)pyridin-2-yl)-6-(3,6-bis(trifluoromethyl)pyridin-2-yl)pyrazine-2-carboxamide, 3-amino-N-(3-(4-amino-4-methylpiperidin-1-yl)pyridin-2-yl)-6-(5-morpholino-2-(trifluoromethyl)phenyl)pyrazine-2-carboxamide, (±) 3-amino-N-(3-((cis)-4-amino-3-fluoropiperidin-1-yl)pyridin-2-yl)-6-(3-(trifluoromethoxy)pyridin-2-yl)pyrazine-2-carboxamide, 3-amino-N-(3-(4-aminopiperidin-1-yl)pyridin-2-yl)-6-(2-morpholinopyrimidin-4-yl)pyrazine-2-carboxamide, 3-amino-N-(3-(4-amino-4-methylpiperidin-1-yl)pyridin-2-yl)-6-(2-(3,6-dihydro -2H-pyran-4-yl)-5-(trifluoromethyl)pyrimidin-4-yl)pyrazine-2-carboxamide, 3-amino-N-(3-(4-amino-4-methylpiperidin-1-yl)pyridin-2-yl)-6-(2-morpholinoquinazolin-4-yl)pyrazine-2-carboxamide, 3-amino-N-(3-(4-aminopiperidin-1-yl)pyridin-2-yl)-6-(1-methyl-1H-indazol-4-yl)pyrazine-2-carboxamide, 3-amino-N-(3-(4-amino-4-methylpiperidin-1-yl)pyridin-2-yl)-6-(7-fluoroisoquinolin-1-yl)pyrazine-2-carboxamide, 3-amino-N-(3-(4-aminopiperidin-1-yl)pyridin-2-yl)-6-(3-fluoropyridin-2-yl)pyrazine-2-carboxamide, 3-amino-N-(3-(4-aminopiperidin-1-yl)pyridin-2-yl)-6-(6-morpholinopyridin-2-yl)pyrazine-2-carboxamide, 3-amino-N-(3-(4-aminopiperidin-1-yl)pyridin-2-yl)-6-(3-morpholinophenyl)pyrazine-2-carboxamide, 3-amino-N -(3-(4-amino-4-methylpiperidin-1-yl)pyridin-2-yl)-6-(7-chloroisoquinolin-1-yl)pyrazine-2-carboxamide, 3-amino-N-(3-(4-aminopiperidin-1-yl)pyridin-2-yl)-6-(6-(azetidin-1-yl)-3-(trifluoromethyl)pyridin-2-yl)pyrazine-2-carboxamide, 3-amino-N-(3-((3 S,4R)-4-amino-3-fluoropiperidin-1-yl)pyridin-2-yl)-6-(3-(trifluoromethoxy)pyridin-2-yl)pyrazine-2-carboxamide, 3-amino-N-(3-(4-aminopiperidin-1-yl)pyridin-2-yl)-6-(2-(trifluoromethyl)-1H-indol-4-yl)pyrazine-2-carboxamide, 3-amino-N-(3-(4-aminopiperidin-1-yl)pyridin-2-yl)-6-(5-morpholino-2-(trifluoromethyl)phenyl)pyrazine-2-carboxamide, 3-amino-N-(3-(4-aminopiperidin-1-yl)pyridin-2-yl)-6-(6-(dimethylamino)-3-(trifluoromethyl)pyridin-2-yl)pyrazine-2-carboxamide, 3-amino-N-(3-(4-amino-4-methylpiperidin-1-yl)pyridin-2-yl)-6-(2-(4,4-difluoropiperidin-1-yl)-5-fluoropyrimidin-4-yl)pyrazine-2-carboxamide, 3-amino-N-(3-(4-amino-4-ethylpiperidin-1-yl)pyridin-2-yl)-6-(3-fluoropyridin-2-yl)pyrazine-2-carboxamide, 3-amino-N-(3-(4-amino-4-methylpiperidin-1-yl)pyridin-2-yl)-6-(5-fluoro-2-morpholinopyrimidin -4-yl)pyrazine-2-carboxamide, 3-amino-N-(3-(4-aminopiperidin-1-yl)pyridin-2-yl)-6-(1-methyl -1H-indol-4-yl)pyrazine-2-carboxamide, 3-amino-N-(3-(4-aminopiperidin-1-yl)pyridin-2-yl)-6-(1H-indazol-4-yl)pyrazine-2-carboxamide, 3-amino-N-(3-(4-amino-4-methylpiperidin-1-yl)pyridin-2-yl)-6-(4-cyano-3-(trifluoromethyl)pyridin-2-yl)pyrazine-2-carboxamide, 3-amino -N-(3-(4-aminopiperidin-1-yl)pyridin-2-yl)-6-(6-fluoro-2-morpholinoquinazolin-4-yl)pyrazine-2-carboxamide, 3-amino-N-(3-(4-aminopiperidin-1-yl)pyridin-2-yl)-6-(2-methyl-1H-indol-4-yl)pyrazine-2-carboxamide, 3-amino-N-(3-(4-aminopiperidin-1-yl)pyridin-2-yl)-6-(6-morpholino-3-(trifluoromethyl)pyridin-2-yl)pyrazine-2-carboxamide, 3-amino-N-(3-(4-amino-4-methylpiperidin-1-yl)pyridin-2-yl)-6-(4-ethoxy-3-(trifluoromethyl)pyridin-2-yl)pyrazine-2-carboxamide, 4-(5-amino-6-((3-(4-amino-4-methylpiperidin-1-yl)pyridin-2-yl)carbamoyl)pyrazin-2-yl)-5-fluoropyrimidine-2-carboxamide, 3-amino-N-(3-(4-amino-4-methylpiperidin-1-yl)pyridin-2-yl)-6-(2-cyano-5-(trifluoromethyl)pyrimidin-4-yl)pyrazine-2-carboxamide, 3-amino-N-(3-(4-amino-4-methylpiperidin-1-yl)pyridin-2-yl)-6-(2-amino-5-chloropyrimidin-4-yl)pyrazine-2-carboxamide, 3-amino-N-(3-(4-aminopiperidin-1-yl)pyridin-2-yl)-6-(1H-indol-4-yl)pyrazine-2-carboxamide, 3-amino-N-(3-(4-aminopiperidin-1-yl)pyridin-2-yl)-6-(3-morpholinoisoquinolin-1-yl)pyrazine-2-carboxamide, 3-amino-N-(3-(4-aminopiperidin -1-yl)pyridin-2-yl)-6-(3-morpholino-5-(trifluoromethyl)phenyl)pyrazine-2-carboxamide, 3-amino-N-(3-(4-amino-4-methylpiperidin-1-yl)pyridin-2-yl)-6-(4-chloro-3-(trifluoromethyl)pyridin-2-yl)pyrazine-2-carboxamide, 3-amino-N-(3-(4-amino-4-methylpiperidin-1-yl)pyridin-2-yl)-6-(3-cyano-4-methoxypyridin-2-yl)pyrazine-2-carboxamide, 3-amino-N-(3-(4-aminopiperidin-1-yl)pyridin-2-yl)-6-(5-morpholino- 2-(trifluoromethyl)phenyl)pyrazine-2-carboxamide, 3-amino-N-(3-(4-aminopiperidin-1-yl)pyridine -2-yl)-6-(6-morpholino-3-(trifluoromethyl)pyridin-2-yl)pyrazine-2-carboxamide, 3-amino-N-(3-(4-aminopiperidin-1-yl)pyridin-2-yl)-6-(3-morpholinoisoquinolin-1-yl)pyrazine-2-carboxamide, 3-amino-N-(3-(4-aminopiperidin-1-yl)-6-methylpyridin-2-yl)-6-(3-(trifluoromethoxy)pyridin-2-yl)pyrazine-2-carboxamide, 3-amino-N-(3-(4-aminopiperidin-1-yl)-6-methylpyridin-2-yl)-6-(3-(trifluoromethyl)pyridin-2-yl)pyrazine-2-carboxamide, 3-amino-N-(3-(4-amino-3-methoxypiperidin-1-yl)pyridin-2-yl)-6-(3-(trifluoromethoxy)pyridin-2-yl)pyrazine-2-carboxamide, 3-amino-N-(3-(4-amino-4-methylpiperidin-1-yl)pyridin-2-yl)-6-(3-fluoro-4-methylpyridin-2-yl)pyrazine-2-carboxamide, 3-amino-N-(3-(4-amino-4-methylpiperidin-1-yl)pyridin-2-yl)-6-(4-ethoxy-3-fluoropyridin-2-yl)pyrazine-2-carboxamide, 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide and 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide.

In another embodiment, a compound or a stereoisomer, tautomer, or pharmaceutically acceptable salt thereof, is selected from:

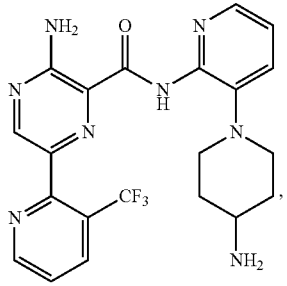

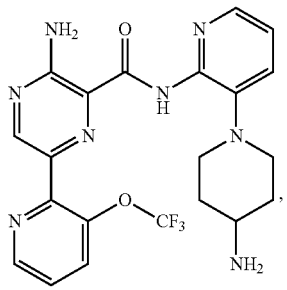

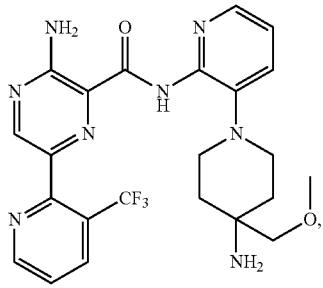

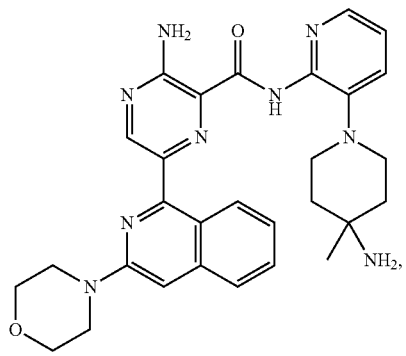

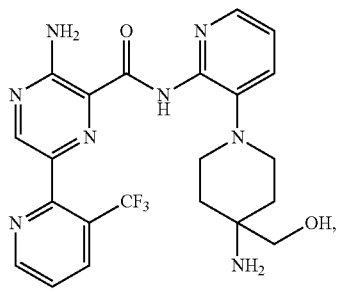

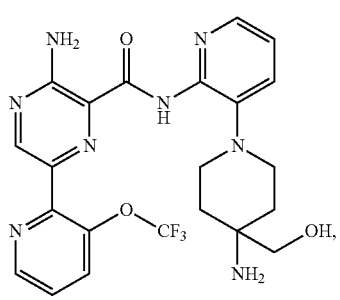

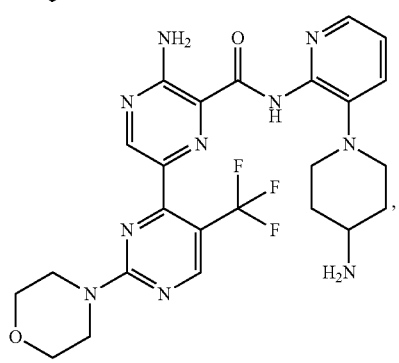

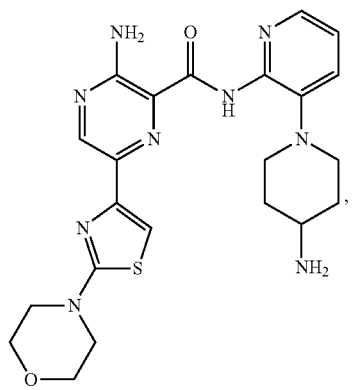

-continued
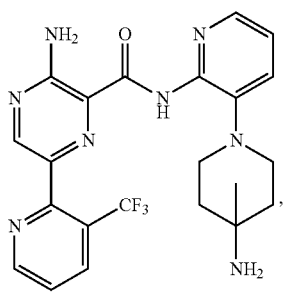
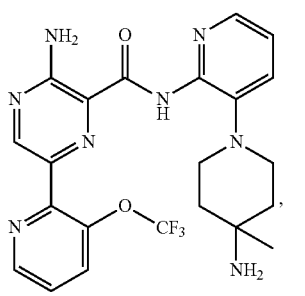
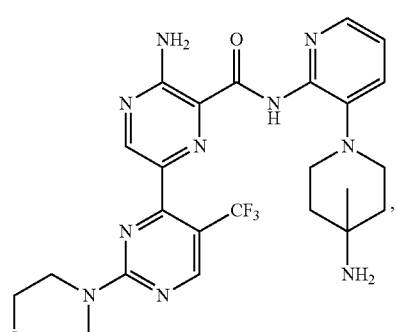
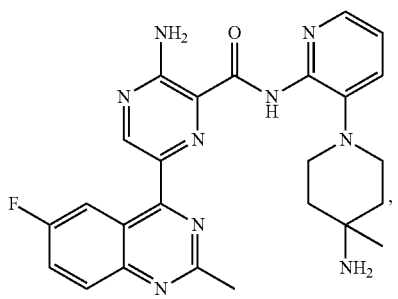
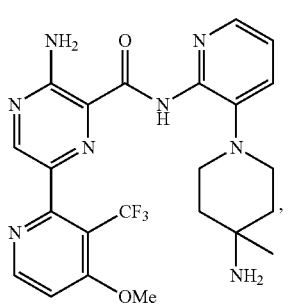
-continued
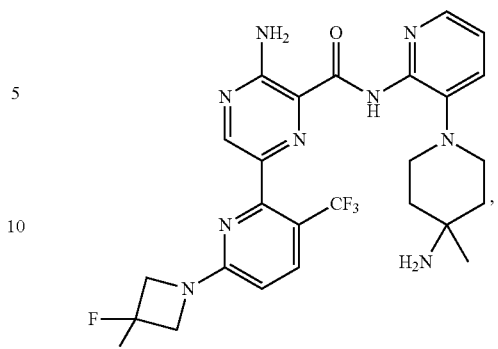
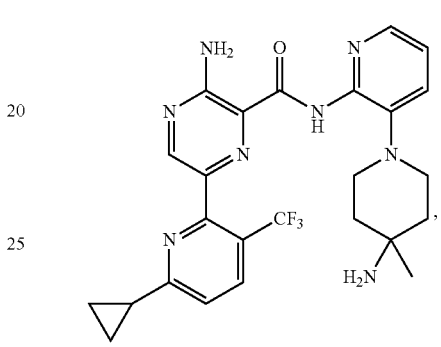
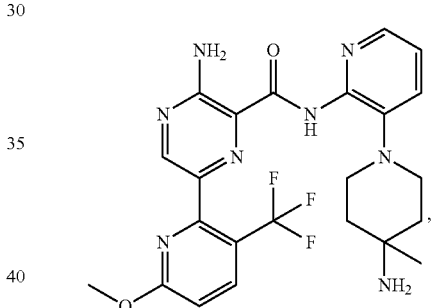
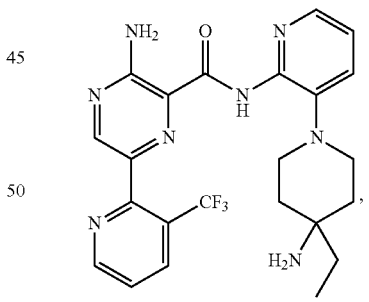
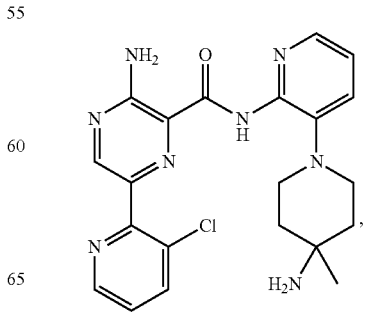

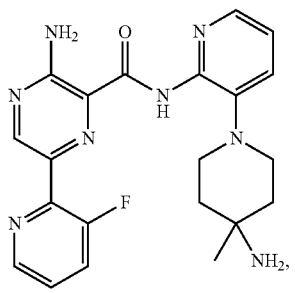
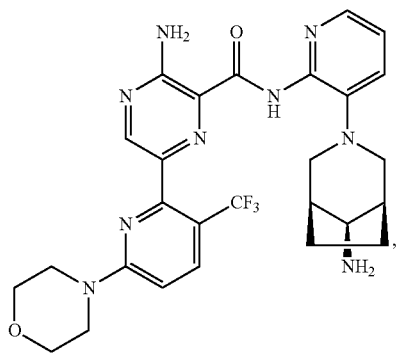
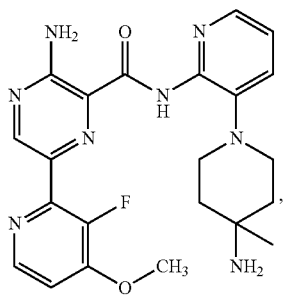
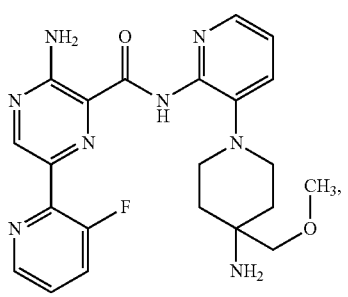
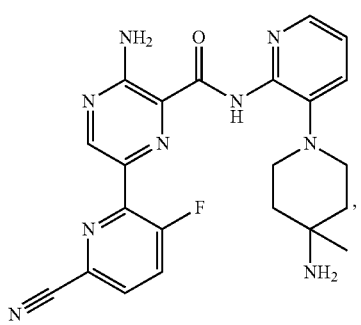
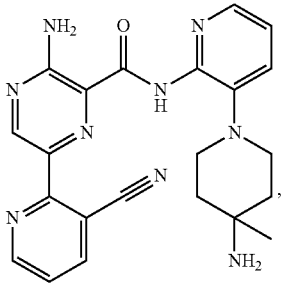
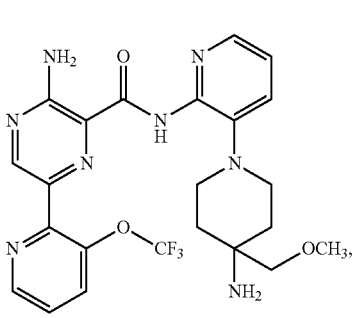
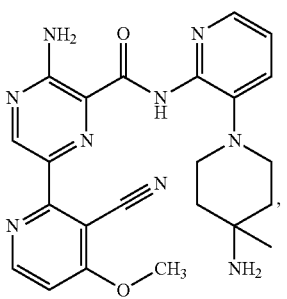
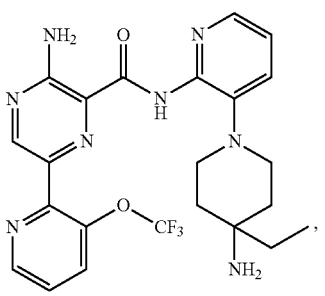
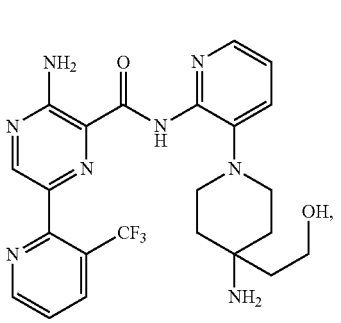

-continued
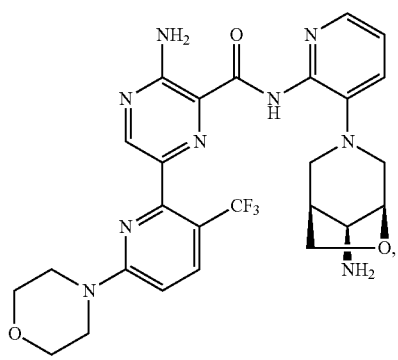
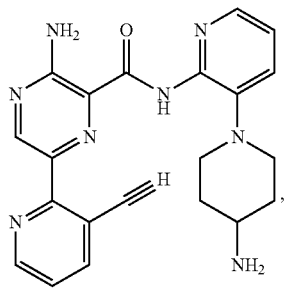
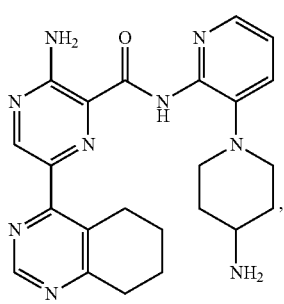
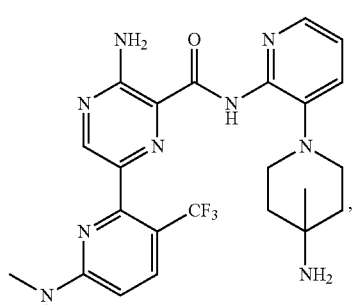
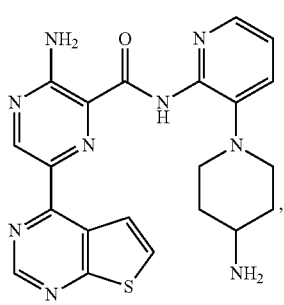
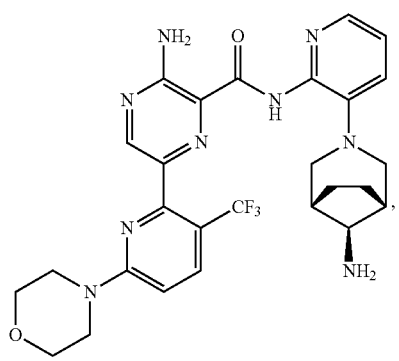
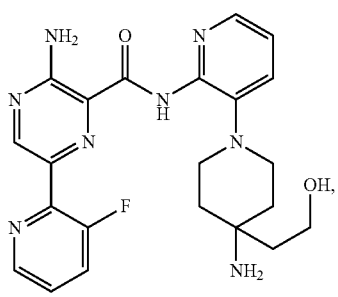
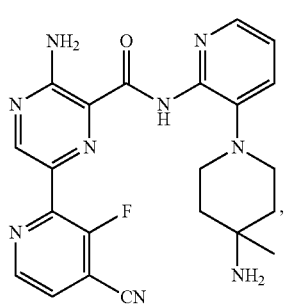
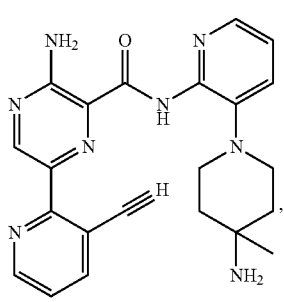
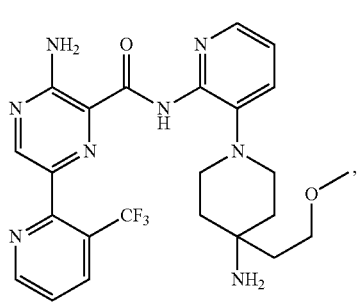

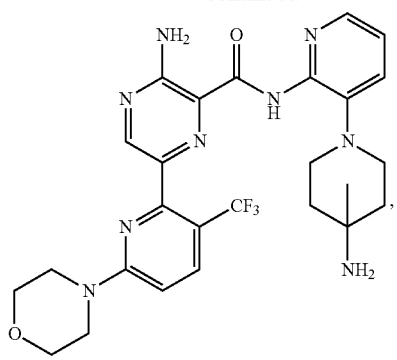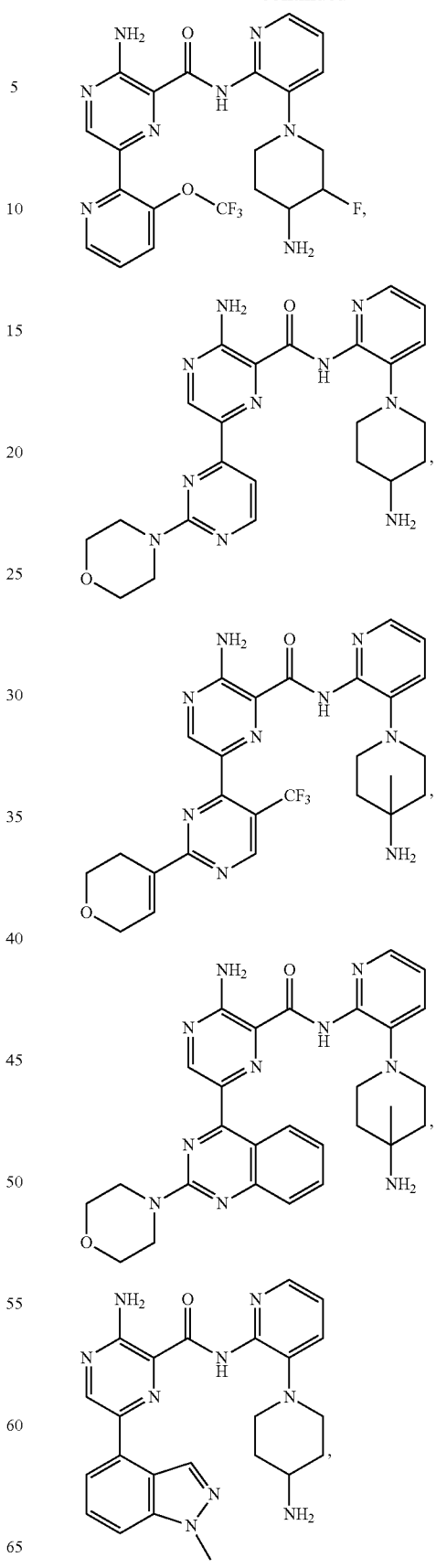

29
-continued
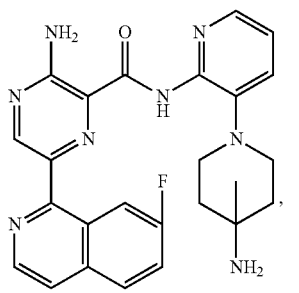
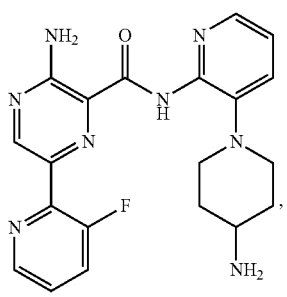
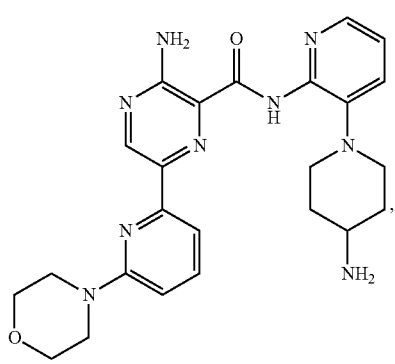
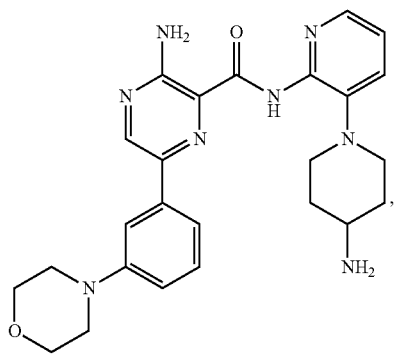
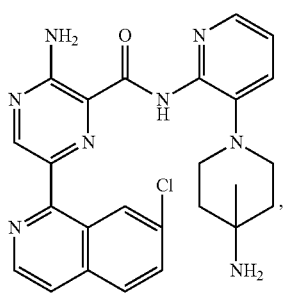
30
-continued
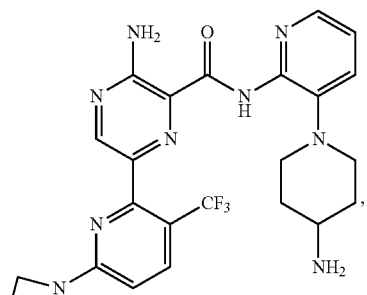
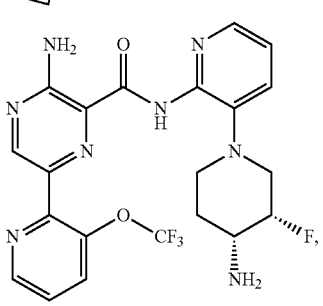
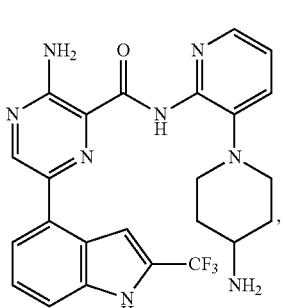
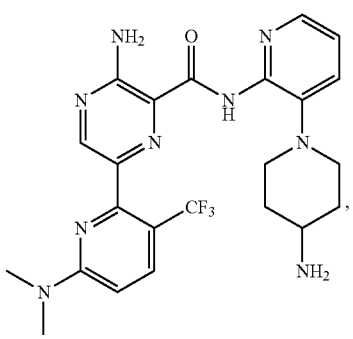
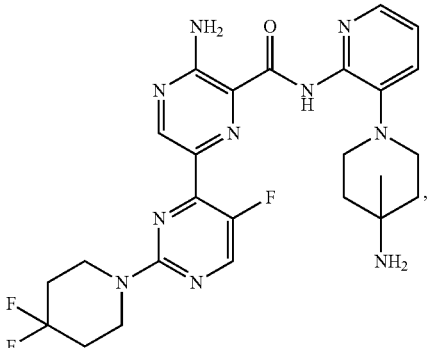

31
-continued
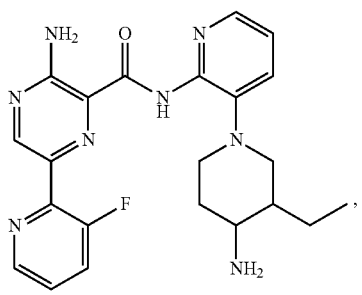
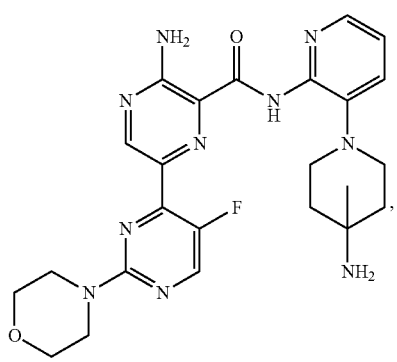
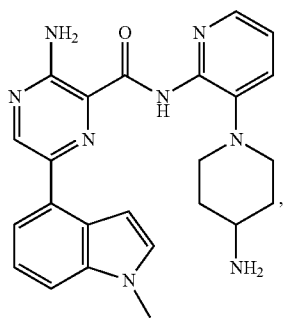
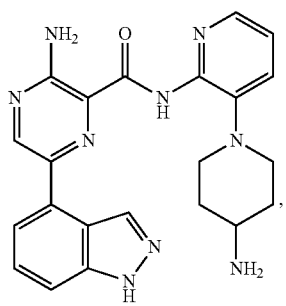
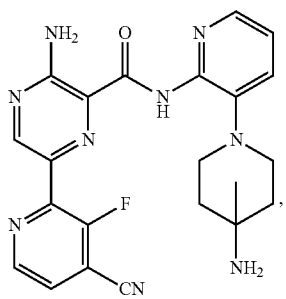
32
-continued
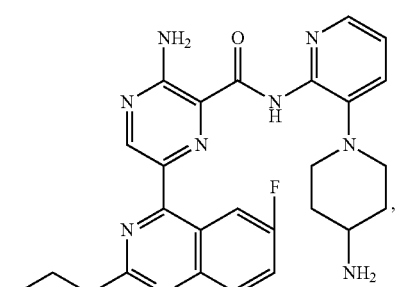
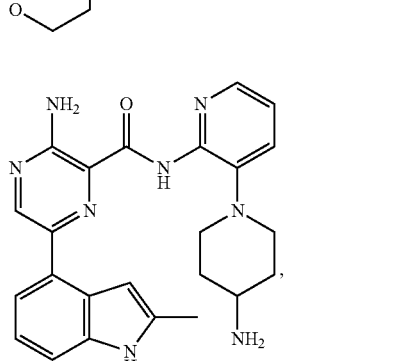
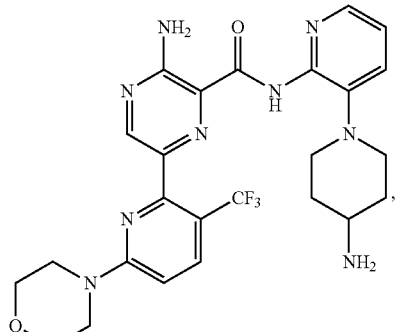
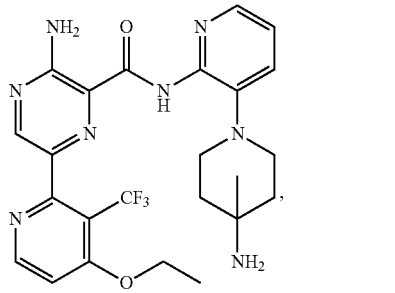
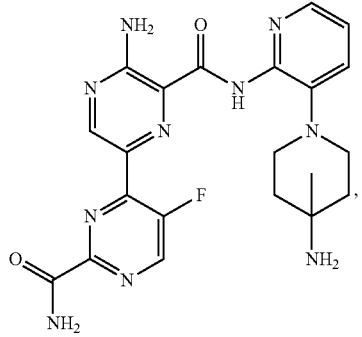

33
-continued
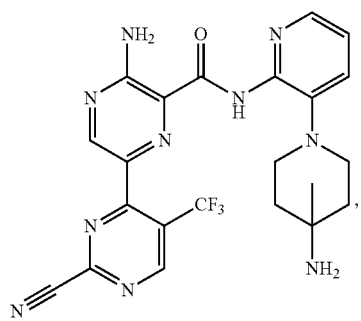
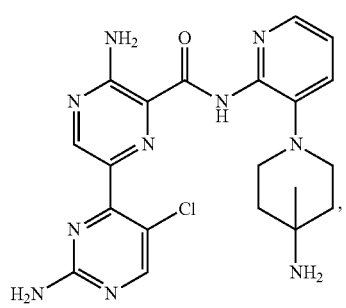
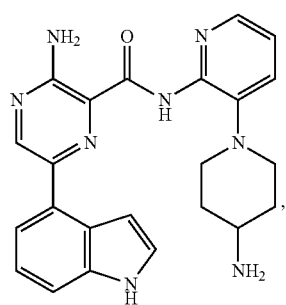
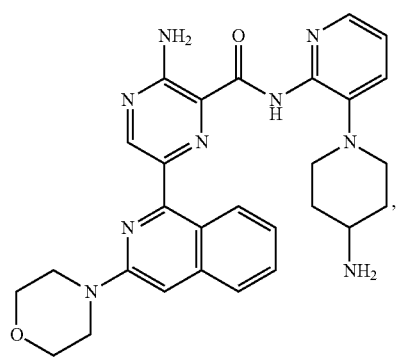
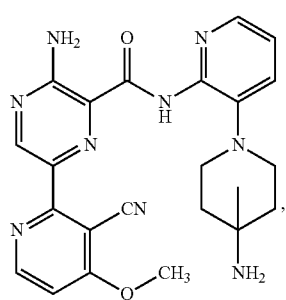
34
-continued
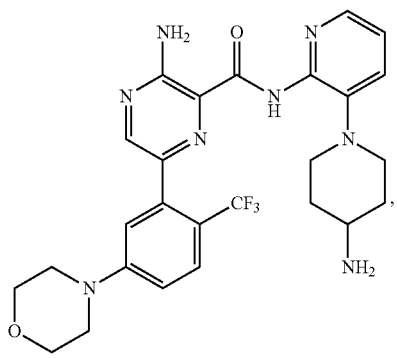
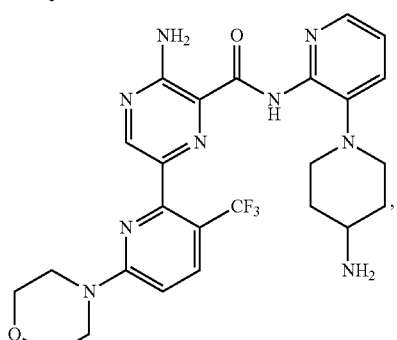
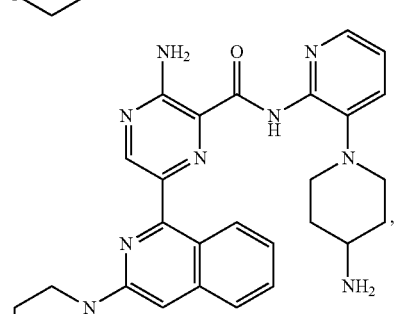
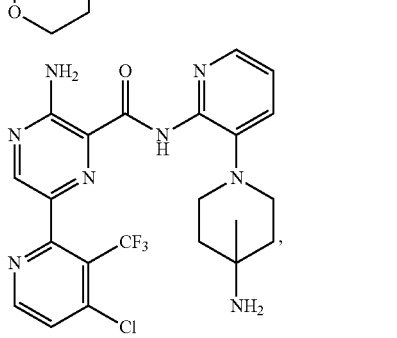
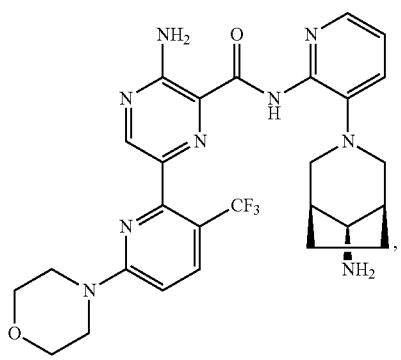

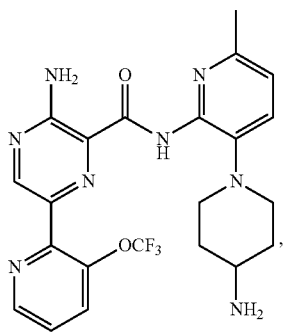

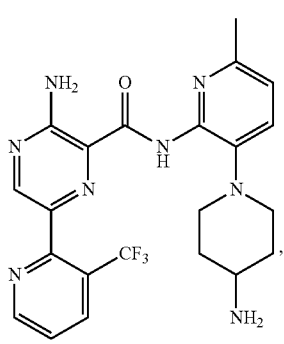

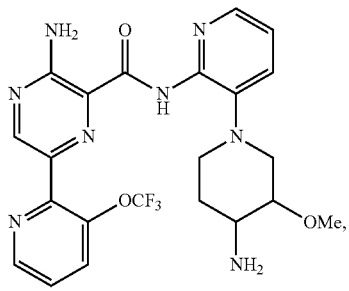

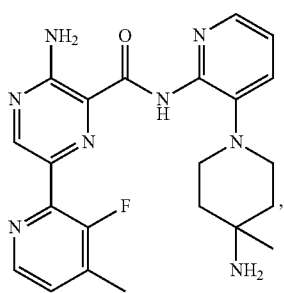

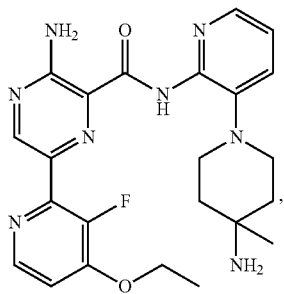

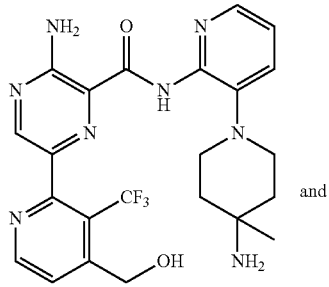

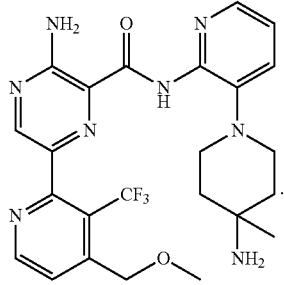

In a separate embodiment, compounds, their tautomers, stereoisomers, or pharmaceutically acceptable salts thereof or esters having a solubility enhancing moieties or prodrugs thereof are provided of the formula (Ia):

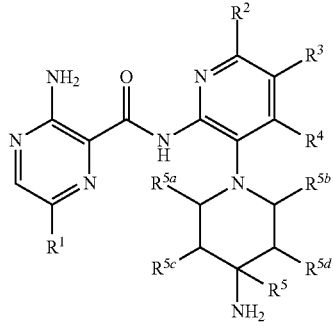

(Ia)

wherein:

$R^1$ is optionally substituted $C_{6-10}$ aryl, said aryl being optionally substituted with 1 to 3 substituents each independently selected from the group consisting of: H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy;

$R^2$, $R^3$ and $R^4$ are each independently H, $^2$H, halo, hydroxy (—OH), $C_{1-3}$ alkoxy, $C_{1-3}$ haloalkyl or $C_{1-3}$ alkyl, optionally substituted with one to two of hydroxyl, halo and $C_{1-3}$ haloalkoxy;

$R^5$ is independently H, $^2$H, $CH_3$, $CH_2F$, $CHF_2$, $CF_3$, $CH_2OH$, $C_{1-3}$ alkyl, $CH_2$—O—$C_{1-3}$ alkyl or $CH_2$—O—$C_{1-3}$ haloalkyl, said $C_{1-3}$ alkyl optionally substituted with H, F, OH, $C_{1-3}$ alkoxy and $C_{1-3}$ haloalkoxy;

$R^{5a}$ and $R^{5b}$ are each independently H, $^2$H, $C_{1-3}$ alkyl, said $C_{1-3}$ alkyl optionally substituted with H, F, OH, $C_{1-3}$ alkoxy and C$_{1-3}$ haloalkoxy, or R$^{5a}$ and R$^{5b}$ are joined together forming a methylene or ethylene bridging group; and R$^{5c}$ and R$^{5d}$ are each independently H, $^2$H, F, —OH, C$_{1-3}$ alkyl, said alkyl optionally substituted with F, OH, and alkoxy or C$_{1-3}$ alkoxy or R$^{5c}$ and R$^{5d}$ are joined together forming a methylene, ethylene or —CH$_2$—O— bridging group.

In a separate embodiment, R$^{5a}$ and R$^{5d}$ are each independently H, $^2$H, F, —OH, C$_{1-3}$ alkyl, said alkyl optionally substituted with F, OH, C$_{1-3}$ alkoxy or are joined together forming a methylene, ethylene or —CH$_2$—O— bridging group, provided that the oxygen atom of the bridging group is attached at R$^{5d}$.

In a separate embodiment, if a bridging group is formed only one of R$^{5a}$ and R$^{5b}$, R$^{5c}$ and R$^{5d}$ or R$^{5a}$ and R$^{5d}$ forms a bridging group.

In a separate embodiment, compounds, their tautomers, stereoisomers or pharmaceutically acceptable salts thereof or esters having a solubility enhancing moieties or prodrugs thereof are provided of the formula (Ia), wherein:

R$^1$ is phenyl, substituted with one to three substituents each independently selected from the group consisting of: halo, CF$_3$, CN, NH$_2$, NHCOC$_{1-3}$alkyl, acetylene, C$_{1-3}$ alkyl, C$_{1-3}$ alkoxy, C$_{1-3}$ haloalkyl, C$_{1-3}$ haloalkoxy, C$_{3-7}$ cycloalkyl, morpholino, piperinyl, piperazinyl, N-methylpiperazinyl, SO$_2$C$_{1-3}$ alkyl and COOCH$_3$;

R$^2$, R$^3$ and R$^4$ are each H;

R$^5$ is independently H, CH$_3$, CH$_2$F, CHF$_2$, CF$_3$, CH$_2$OH, CH$_2$—O—C$_{1-3}$ alkyl;

R$^{5a}$ and R$^{5b}$ are each H or R$^{5a}$ and R$^{5b}$ are joined together forming a methylene, ethylene or —CH$_2$—O— bridging group; and R$^{5c}$ and R$^{5d}$ are each independently H, F C$_{1-3}$ alkyl, or C$_{1-3}$ alkoxy or R$^{5c}$ and R$^{5d}$ are joined together forming a methylene, ethylene or —CH$_2$—O— bridging group.

In a separate embodiment, R$^{5a}$ and R$^{5d}$ are each independently H, $^2$H, F, —OH, C$_{1-3}$ alkyl, said alkyl optionally substituted with F, OH, and alkoxy or C$_{1-3}$ alkoxy or R$^{5c}$ and R$^{5d}$ are joined together forming a methylene, ethylene or —CH$_2$—O— bridging group.

In a separate embodiment, if a bridging group is formed only one of R$^{5a}$ and R$^{5b}$, R$^{5c}$ and R$^{5d}$ or R$^{5a}$ and R$^{5d}$ forms a bridging group.

In another embodiment, new compounds, their tautomers, stereoisomers or pharmaceutically acceptable salts thereof or esters having a solubility enhancing moieties or prodrugs thereof are provided of the formula (Ia), wherein:

R$^1$ is phenyl, substituted with one or two substituents each independently selected from the group consisting of: H, $^2$H, halo, CN, acetylene, C$_{1-3}$ alkyl, C$_{1-3}$ alkoxy, C$_{1-3}$ haloalkyl, C$_{1-3}$ haloalkoxy, C$_{3-7}$ cycloalkyl, morpholino, piperidinyl, piperazinyl and COOCH$_3$;

R$^2$, R$^3$ and R$^4$ are each H;

R$^5$ is independently H, CH$_3$, CH$_2$F, CHF$_2$, CF$_3$, CH$_2$OH, CH$_2$—O—C$_{1-3}$ alkyl;

R$^{5a}$ and R$^{5b}$ are each H or R$^{5a}$ and R$^{5b}$ are joined together forming a methylene or ethylene bridging group; and R$^{5c}$ and R$^{5d}$ are each independently H, F C$_{1-3}$ alkyl, C$_{1-3}$ alkoxy or R$^{5c}$ and R$^{5d}$ are joined together forming a methylene, ethylene or —CH$_2$—O— bridging group.

In another embodiment, a compound or a stereoisomer, tautomer, or pharmaceutically acceptable salt thereof, is selected from: 3-amino-N-(3-(4-aminopiperidin-1-yl)pyridin-2-yl)-6-(3-morpholino-5-(trifluoromethyl)phenyl)pyra-zine-2-carboxamide, 3-amino -N-(3-(4-aminopiperidin-1-yl)pyridin-2-yl)-6-(5-morpholino-2-(trifluoromethyl)phenyl)pyrazine -2-carboxamide, 3-amino-N-(3-(4-aminopiperidin-1-yl)pyridin-2-yl)-6-(3-morpholinophenyl)pyrazine-2-carboxamide, and 3-amino-N-(3-(4-aminopiperidin-1-yl)pyridine -2-yl)-6-(3-morpholinophenyl)pyrazine-2-carboxamide.

In another embodiment, a compound or a stereoisomer, tautomer, or a pharmaceutically acceptable salt thereof, is selected from:

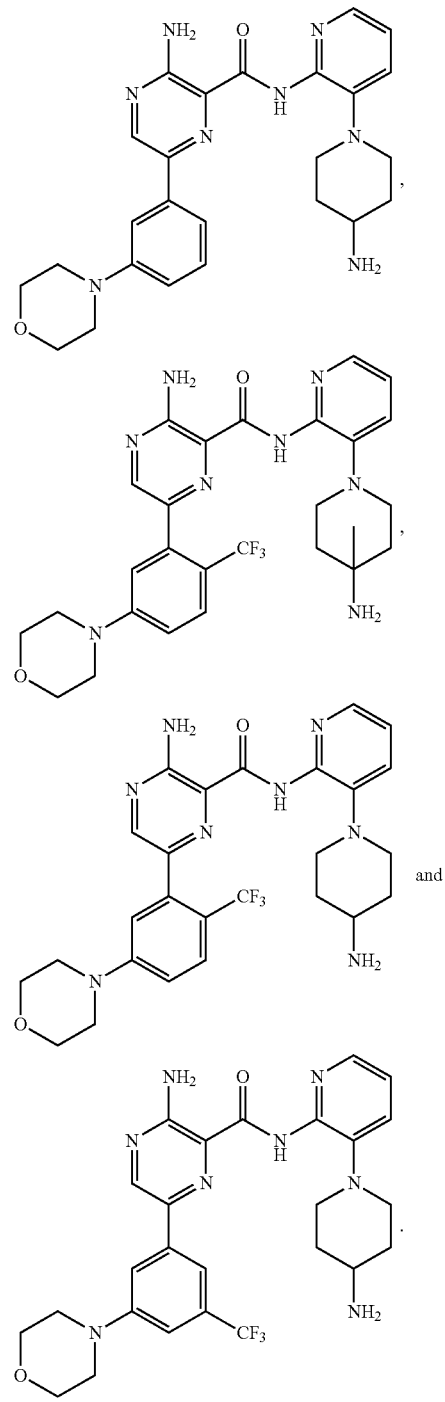

In a separate embodiment, compounds, their tautomers, stereoisomers or pharmaceutically acceptable salts thereof or esters having a solubility enhancing moieties or prodrugs thereof are provided of the formula (II):

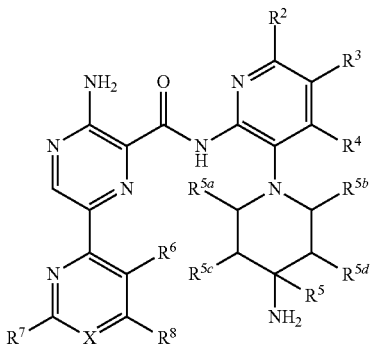

(II)

wherein:
X is N or CR;
R, $R^2$, $R^3$ and $R^4$ are each independently H, $^2$H, halo, hydroxy (—OH), $C_{1-3}$ alkoxy, $C_{1-3}$ haloalkyl $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl or $C_{1-3}$ alkyl, optionally substituted with one to two of hydroxyl, halo and $C_{1-3}$ haloalkoxy;
$R^5$ is —H, $^2$H, $CH_3$, $CH_2F$, $CHF_2$, $CF_3$, $CH_2OH$, $C_{1-3}$ alkyl, $CH_2$—O—$C_{1-3}$ alkyl or $CH_2$—O—$C_{1-3}$ haloalkyl, said $C_{1-3}$ alkyl optionally substituted with H, F, OH, $C_{1-3}$ alkoxy and $C_{1-3}$ haloalkoxy;
$R^{5a}$ and $R^{5b}$ are each independently H, $^2$H, $C_{1-3}$ alkyl, said $C_{1-3}$ alkyl optionally substituted with H, F, OH, $C_{1-3}$ alkoxy and $C_{1-3}$ haloalkoxy, or $R^{5a}$ and $R^{5b}$ are joined together forming a methylene or ethylene bridging group;
$R^{5c}$ and $R^{5d}$ are each independently H, $^2$H, F, —OH, $C_{1-3}$ alkyl, said alkyl optionally substituted with F, OH, and alkoxy or $C_{1-3}$ alkoxy or $R^{5c}$ and $R^{5d}$ are joined together forming a methylene, ethylene or —$CH_2$—O— bridging group; or
$R^{5a}$ and $R^{5d}$ are optionally joined together forming a methylene, ethylene or —$CH_2$—O— bridging group, provided that the O atom of the —$CH_2$—O— bridging group is bonded at $R^{5d}$; and
$R^6$, $R^8$ and $R^8$ are each independently selected from H, $^2$H, halo, $C_{1-3}$ haloalkyl, $C_{1-3}$ alkoxy, $C_{1-3}$ haloalkoxy, $C_{3-7}$ cycloalkyl and 4-7 membered heterocyclyl, optionally substituted with 1 to 3 substituents selected from H, halo, hydroxyl, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy and $C_{3-7}$ cycloalkyl; or
wherein $R^6$ and $R^8$ optionally forms a partially saturated carbobicyclic ring or heterobicyclic ring with the heteroaryl ring, said carbobicyclic ring or heterobicyclic ring optionally substituted with 1 to 3 groups selected from: H, $^2$H, halo, $C_{1-3}$ haloalkyl, $C_{1-3}$ alkoxy, $C_{1-3}$ haloalkoxy, $C_{3-7}$ cycloalkyl and 4-7 membered heterocyclyl.

In a separate embodiment, compounds, their tautomers, stereoisomers or pharmaceutically acceptable salts thereof or esters having a solubility enhancing moieties or prodrugs thereof are provided of the formula (II), wherein:
X is CR;
$R^2$, $R^3$ and $R^4$ are each H;
$R^5$ is independently H, $CH_3$, $CH_2F$, $CHF_2$, $CF_3$, $CH_2OH$, $CH_2$—O—$C_{1-3}$ alkyl
$R^{5a}$ and $R^{5b}$ are each H or $R^{5a}$ and $R^{5b}$ are joined together forming a methylene or ethylene bridging group;
$R^{5c}$ and $R^{5d}$ are each independently H, F, $C_{1-3}$ alkyl, or $C_{1-3}$ alkoxy or $R^{5c}$ and $R^{5d}$ are joined together forming a methylene, ethylene or —$CH_2$—O— bridging group; and
$R^6$ and $R^7$ are each independently selected from H, halo, $C_{1-3}$ haloalkyl, $C_{1-3}$ haloalkoxy, $C_{3-7}$ cycloalkyl, morpholino, piperinyl and piperazinyl.

In another embodiment, a compound or a pharmaceutically acceptable salt thereof is selected from:
3-amino-N-(3-(4-aminopiperidin-1-yl)pyridin-2-yl)-6-(3-(trifluoromethyl)pyridin-2-yl)pyrazine-2-carboxamide;
3-amino-N-(3-(4-aminopiperidin-1-yl)pyridin-2-yl)-6-(3-(trifluoromethoxy)pyridin-2-yl)pyrazine-2-carboxamide;
3-amino-N-(3-(4-amino-4-(methoxymethyl)piperidin-1-yl)pyridin-2-yl)-6-(3-(trifluoromethyl)pyridin-2-yl)pyrazine-2-carboxamide;
3-amino-N-(3-(4-amino-4-(hydroxymethyl)piperidin-1-yl)pyridin-2-yl)-6-(3-(trifluoromethyl)pyridin-2-yl)pyrazine-2-carboxamide;
3-amino-N-(3-(4-amino-4-(hydroxymethyl)piperidin-1-yl)pyridin-2-yl)-6-(3-(trifluoromethoxy)pyridin-2-yl)pyrazine-2-carboxamide;
3-amino-N-(3-(4-amino-4-methylpiperidin-1-yl)pyridin-2-yl)-6-(3-(trifluoromethyl)pyridin-2-yl)pyrazine-2-carboxamide;
3-amino-N-(3-(4-amino-4-methylpiperidin-1-yl)pyridin-2-yl)-6-(3-(trifluoromethoxy)pyridin-2-yl)pyrazine-2-carboxamide;
3-amino-N-(3-(4-amino-4-methylpiperidin-1-yl)pyridin-2-yl)-6-(4-methoxy-3-(trifluoromethyl)pyridin-2-yl)pyrazine-2-carboxamide;
3-amino-N-(3-(4-amino-4-ethylpiperidin-1-yl)pyridin-2-yl)-6-(3-(trifluoromethyl)pyridin-2-yl)pyrazine-2-carboxamide;
3-amino-N-(3-(4-amino-4-methylpiperidin-1-yl)pyridin-2-yl)-6-(3-chloropyridin-2-yl)pyrazine-2-carboxamide;
3-amino-N-(3-(4-amino-4-methylpiperidin-1-yl)pyridin-2-yl)-6-(3-fluoropyridin-2-yl)pyrazine-2-carboxamide;
3-amino-N-(3-(4-amino-4-methylpiperidin-1-yl)pyridin-2-yl)-6-(3-fluoro-4-methoxypyridin-2-yl)pyrazine-2-carboxamide;
3-amino-N-(3-(4-amino-4-(methoxymethyl)piperidin-1-yl)pyridin-2-yl)-6-(3-fluoropyridin-2-yl)pyrazine-2-carboxamide;
3-amino-N-(3-(4-amino-4-methylpiperidin-1-yl)pyridin-2-yl)-6-(3-cyanopyridin-2-yl)pyrazine-2-carboxamide;
3-amino-N-(3-(4-amino-4-ethylpiperidin-1-yl)pyridin-2-yl)-6-(3-(trifluoromethoxy)pyridin-2-yl)pyrazine-2-carboxamide;
3-amino-N-(3-(4-amino-4-methylpiperidin-1-yl)pyridin-2-yl)-6-(3-cyano-4-methoxypyridin-2-yl)pyrazine-2-carboxamide;
3-amino-N-(3-(4-amino-4-(methoxymethyl)piperidin-1-yl)pyridin-2-yl)-6-(3-(trifluoromethoxy)pyridin-2-yl)pyrazine-2-carboxamide;
3-amino-N-(3-(4-amino-4-(2-hydroxyethyl)piperidin-1-yl)pyridin-2-yl)-6-(3-(trifluoromethyl)pyridin-2-yl)pyrazine-2-carboxamide;
3-amino-N-(3-(4-amino-4-(2-hydroxyethyl)piperidin-1-yl)pyridin-2-yl)-6-(3-fluoropyridin-2-yl)pyrazine-2-carboxamide;

3-amino-N-(3-(4-amino-4-methylpiperidin-1-yl)pyridin-2-yl)-6-(4-cyano-3-fluoropyridin-2-yl)pyrazine-2-carboxamide;

3-amino-N-(3-(4-amino-4-(2-methoxyethyl)piperidin-1-yl)pyridin-2-yl)-6-(3-(trifluoromethyl)pyridin-2-yl)pyrazine-2-carboxamide;

(±)3-amino-N-(3-((cis)-4-amino-3-fluoropiperidin-1-yl)pyridin-2-yl)-6-(3-(trifluoromethoxy)pyridin-2-yl)pyrazine-2-carboxamide;

3-amino-N-(3-(4-aminopiperidin-1-yl)pyridin-2-yl)-6-(3-fluoropyridin-2-yl)pyrazine-2-carboxamide;

3-amino-N-(3-((3 S,4R)-4-amino-3-fluoropiperidin-1-yl)pyridin-2-yl)-6-(3-(trifluoromethoxy)pyridin-2-yl)pyrazine-2-carboxamide;

3-amino-N-(3-(4-amino-4-ethylpiperidin-1-yl)pyridin-2-yl)-6-(3-fluoropyridin-2-yl)pyrazine-2-carboxamide;

3-amino-N-(3-(4-amino-4-methylpiperidin-1-yl)pyridin-2-yl)-6-(4-cyano-3-(trifluoromethyl)pyridin-2-yl)pyrazine-2-carboxamide;

3-amino-N-(3-(4-amino-4-methylpiperidin-1-yl)pyridin-2-yl)-6-(4-ethoxy-3-(trifluoromethyl)pyridin-2-yl)pyrazine-2-carboxamide;

3-amino-N-(3-(4-amino-4-methylpiperidin-1-yl)pyridin-2-yl)-6-(4-chloro-3-(trifluoromethyl)pyridin-2-yl)pyrazine-2-carboxamide;

3-amino-N-(3-(4-amino-4-methylpiperidin-1-yl)pyridin-2-yl)-6-(3-cyano-4-methoxypyridin-2-yl)pyrazine-2-carboxamide;

3-amino-N-(3-(4-aminopiperidin-1-yl)-6-methylpyridin-2-yl)-6-(3-(trifluoromethoxy)pyridin-2-yl)pyrazine-2-carboxamide;

3-amino-N-(3-(4-aminopiperidin-1-yl)-6-methylpyridin-2-yl)-6-(3-(trifluoromethyl)pyridin-2-yl)pyrazine-2-carboxamide;

3-amino-N-(3-(4-amino-3-methoxypiperidin-1-yl)pyridin-2-yl)-6-(3-(trifluoromethoxy)pyridin-2-yl)pyrazine-2-carboxamide;

3-amino-N-(3-(4-amino-4-methylpiperidin-1-yl)pyridin-2-yl)-6-(3-fluoro-4-methylpyridin-2-yl)pyrazine-2-carboxamide;

3-amino-N-(3-(4-amino-4-methylpiperidin-1-yl)pyridin-2-yl)-6-(4-ethoxy-3-fluoropyridin-2-yl)pyrazine-2-carboxamide;

3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide; and 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide.

In another embodiment, a compound or a pharmaceutically acceptable salt thereof is selected from:

3-amino-N-(3-(4-amino-4-(ethoxymethyl)piperidin-1-yl)pyridin-2-yl)-6-(3-(trifluoromethyl)pyridin-2-yl)pyrazine-2-carboxamide;

3-amino-N-(3-(4-amino-4-(ethoxymethyl)piperidin-1-yl)pyridin-2-yl)-6-(3-(trifluoromethoxy)pyridin-2-yl)pyrazine-2-carboxamide;

3-amino-N-(3-(4-amino-4-((difluoromethoxy)methyl)piperidin-1-yl)pyridin-2-yl)-6-(3-(trifluoromethyl)pyridin-2-yl)pyrazine-2-carboxamide;

3-amino-N-(3-(4-amino-4-methylpiperidin-1-yl)pyridin-2-yl)-6-(3-cyano-4-isopropoxypyridin-2-yl)pyrazine-2-carboxamide;

3-amino-N-(3-(4-amino-4-methylpiperidin-1-yl)pyridin-2-yl)-6-(3-cyano-4-cyclopropoxypyridin-2-yl)pyrazine-2-carboxamide;

3-amino-N-(3-(4-amino-4-methylpiperidin-1-yl)pyridin-2-yl)-6-(4-(trifluoromethoxy)pyridin-2-yl)pyrazine-2-carboxamide;

3-amino-N-(3-(4-amino-4-(hydroxymethyl)piperidin-1-yl)pyridin-2-yl)-6-(3-cyano-4-methoxypyridin-2-yl)pyrazine-2-carboxamide;

3-amino-N-(3-(4-amino-4-(hydroxymethyl)piperidin-1-yl)pyridin-2-yl)-6-(3-cyanopyridin-2-yl)pyrazine-2-carboxamide;

3-amino-N-(3-(4-amino-4-methylpiperidin-1-yl)pyridin-2-yl)-6-(3-cyano-4-(trifluoromethoxy)pyridin-2-yl)pyrazine-2-carboxamide;

3-amino-N-(3-(4-amino-4-methylpiperidin-1-yl)pyridin-2-yl)-6-(3-cyano-4-phenoxypyridin-2-yl)pyrazine-2-carboxamide;

3-amino-N-(3-(4-amino-4-methylpiperidin-1-yl)pyridin-2-yl)-6-(5-methoxy-3-(trifluoromethyl)pyridin-2-yl)pyrazine-2-carboxamide;

3-amino-N-(3-(4-amino-3-fluoro-4-methylpiperidin-1-yl)pyridin-2-yl)-6-(3-(trifluoromethyl)pyridin-2-yl)pyrazine-2-carboxamide;

3-amino-N-(3-(4-amino-4-(cyanomethyl)piperidin-1-yl)pyridin-2-yl)-6-(3-(trifluoromethoxy)pyridin-2-yl)pyrazine-2-carboxamide;

3-amino-N-(3-(4-amino-4-(cyanomethyl)piperidin-1-yl)pyridin-2-yl)-6-(3-(trifluoromethyl)pyridin-2-yl)pyrazine-2-carboxamide;

3-amino-N-(3-(4-amino-3-fluoro-4-methylpiperidin-1-yl)pyridin-2-yl)-6-(3-(trifluoromethoxy)pyridin-2-yl)pyrazine-2-carboxamide;

3-amino-N-(3-((3 S, 4R)-4-amino-3-fluoro-4-methylpiperidin-1-yl)pyridin-2-yl)-6-(3-(trifluoromethoxy)pyridin-2-yl)pyrazine-2-carboxamide;

3-amino-N-(3-(4-amino-4-methylpiperidin-1-yl)pyridin-2-yl)-6-(3-cyano-4-ethoxypyridin-2-yl)pyrazine-2-carboxamide;

3-amino-N-(3-(4-amino-3-fluoro-4-(2-hydroxyethyl)piperidin-1-yl)pyridin-2-yl)-6-(3-(trifluoromethyl)pyridin-2-yl)pyrazine-2-carboxamide; and 3-amino-N-(3-(4-amino-4-(cyanomethyl)piperidin-1-yl)pyridin-2-yl)-6-(3-cyano-4-methoxypyridin-2-yl)pyrazine-2-carboxamide.

In another embodiment, a compound or a pharmaceutically acceptable salt thereof is selected from:

3-amino-N-(3-(4-amino-4-methylpiperidin-1-yl)pyridin-2-yl)-6-(3 morpholinoisoquinolin-1-yl)pyrazine-2-carboxamide;

3-amino-N-(3-(4-amino-4-methylpiperidin-1-yl)pyridin-2-yl)-6-(6-fluoro-2-methylquinazolin-4-yl)pyrazine-2-carboxamide;

3-amino-N-(3-(4-aminopiperidin-1-yl)pyridin-2-yl)-6-(5,6,7,8-tetrahydroquinazolin-4-yl)pyrazine-2-carboxamide;

3-amino-N-(3-(4-aminopiperidin-1-yl)pyridin-2-yl)-6-(7H-pyrrolo[2,3-d]pyrimidin-4-yl)pyrazine-2-carboxamide;

3-amino-N-(3-(4-amino-4-methylpiperidin-1-yl)pyridin-2-yl)-6-(6-fluoroquinazolin-4-yl)pyrazine-2-carboxamide;

3-amino-N-(3-(4-aminopiperidin-1-yl)pyridin-2-yl)-6-(5-fluoro-7H-pyrrolo[2,3-d]pyrimidin-4-yl)pyrazine-2-carboxamide;

3-amino-N-(3-(4-amino-4-methylpiperidin-1-yl)pyridin-2-yl)-6-(2-morpholinoquinazolin-4-yl)pyrazine-2-carboxamide;

3-amino-N-(3-(4-amino-4-methylpiperidin-1-yl)pyridin-2-yl)-6-(7-fluoroisoquinolin-1-yl)pyrazine-2-carboxamide;

3-amino-N-(3-(4-amino-4-methylpiperidin-1-yl)pyridin-2-yl)-6-(7-chloroisoquinolin-1-yl)pyrazine-2-carboxamide;

3-amino-N-(3-(4-aminopiperidin-1-yl)pyridin-2-yl)-6-(6-fluoro-2-morpholinoquinazolin-4-yl)pyrazine-2-carboxamide;

3-amino-N-(3-(4-aminopiperidin-1-yl)pyridin-2-yl)-6-(3-morpholinoisoquinolin-1-yl)pyrazine-2-carboxamide; and 3-amino-N-(3-(4-aminopiperidin-1-yl)pyridin-2-yl)-6-(3-morpholinoisoquinolin-1-yl)pyrazine-2-carboxamide.

In another embodiment a compound or a pharmaceutically acceptable salt thereof is selected from:

3-amino-N-(3-(4-amino-4-(hydroxymethyl)piperidin-1-yl)pyridin-2-yl)-6-(1-morpholinoisoquinolin-3-yl)pyrazine-2-carboxamide.

In another embodiment a compound or a pharmaceutically acceptable salt thereof is selected from:

3-amino-N-(3-(4-aminopiperidin-1-yl)pyridin-2-yl)-6-(3-(trifluoromethoxy)pyridin-2-yl)pyrazine-2-carboxamide;

3-amino-N-(3-(4-amino-4-methylpiperidin-1-yl)pyridin-2-yl)-6-(3-(trifluoromethyl)pyridin-2-yl)pyrazine-2-carboxamide; and 3-amino-N-(3-(4-amino-4-methylpiperidin-1-yl)pyridin-2-yl)-6-(3-(trifluoromethoxy)pyridin-2-yl)pyrazine-2-carboxamide.

In a separate embodiment, compounds, their tautomers, stereoisomers or pharmaceutically acceptable salts thereof or esters having a solubility enhancing moieties or prodrugs thereof are provided of the formula (III):

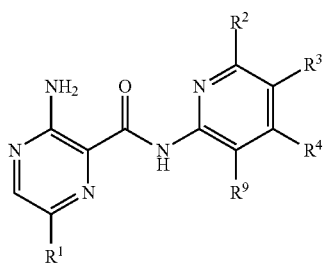

(III)

wherein:

$R^1$ is optionally substituted 6-10 membered aryl or 5-10 membered heteroaryl having 0 to 4 heteroatoms each independently selected from the group consisting of: O, N and S, said heteroaryl or aryl each being optionally substituted with 1 to 3 substituents each independently selected from the group consisting of: H, $^2$H, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^2$H, halo, CN, $C_{1-3}$ alkyl, $C_{1-3}$ alkoxy, $C_{1-3}$ haloalkyl, and $C_{1-3}$ haloalkoxy;

$R^2$, $R^3$ and $R^4$ are each independently H, $^2$H, halo, hydroxy (—OH), $C_{1-3}$ alkoxy, $C_{1-3}$ haloalkyl or $C_{1-3}$ alkyl, optional substituted with one to two of hydroxyl, halo and $C_{1-3}$ haloalkoxy; and $R^9$ is H or 4-7 membered heterocyclyl or heterobicyclyl having 1 or 2 heteroatoms selected from N, O and S, SO, $SO_2$, said heterocycyl or heterobicylyl substituted with 1 to 4 substituents each independently selected from the group consisting of: H, $^2$H, amino ($NH_2$), halo, CN, acetylene, $C_{1-3}$ alkyl, $C_{1-3}$ alkoxy, $C_{1-3}$ haloalkyl, $C_{1-3}$ haloalkoxy, $C_{3-7}$ cycloalkyl, $C_{2-3}$ alkynyl, $C_{2-3}$ alkenyl, $COOC_{1-3}$ alkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl, $SO(N)NHC_{1-3}$ alkyl, $SO(N)NHC_{6-10}$ aryl, —O—$(CH_2)$-heterocyclyl (n=1-3), CO $NH_2$, said $C_{1-3}$ alkyl or —O—$(CH_2)$-heterocyclyl, said heterocyclyl having 1 to 3 heteroatoms selected from N, O and S, SO, $SO_2$ each optionally substituted with 1 to 4 substituents selected from $NH_2$, OH, halo, $C_{1-3}$ alkoxy and $C_{1-3}$ haloalkoxy.

In one embodiment, $R^9$ is a substituted piperdinyl. In one embodiment, $R^9$ is a substituted piperdinyl selected from the structures:

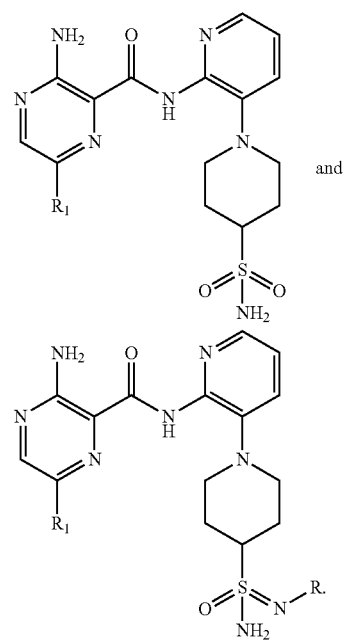

In a separate embodiment, $R^9$ is selected from piperidinyl, piperazinyl, 1,2-oxazinane, 2-oxopiperazinyl, 2-oxopiperidinyl and morpholinyl, optionally substituted.

As used herein, the term "pharmaceutically acceptable salts" refers to the nontoxic acid or alkaline earth metal salts of the compounds of Formulas (I), (Ia), (II) or (III). These salts can be prepared in situ during the final isolation and purification of the compounds of Formulas (I), (Ia), (II) or (III), or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, including the compounds of formulas (I), (Ia), (II) or (III) or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7): 765-767; Bagshawe K., *Drug Dev. Res.* 34:220-230 (1995); Bodor, N., Advances in Drug Res. 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formulas (I), (II) or (III) or their tautomers, prodrugs and stereoisomers, as well as the pharmaceutically acceptable salts, esters and prodrugs of any of them, are included within the invention.

In other aspects, the present invention provides a method for treating protein kinase C related disorders in a human or animal subject in recognized need of such treatment comprising administering to said subject an amount of a compound of formula (I), (Ia), (II) or (III) effective to PKC activity in the subject. PKC inhibitors useful in the practice of the present invention may inhibit several isoforms of the PKC, in particular they may selectively inhibit specific PKC isoforms (e.g., selective PKC inhibitors or isozyme-selective PKC inhibitors). The PKC inhibitors are able to selectively inhibit PKC isoforms which are selected from the classical PKC isoforms ($\alpha$, $\beta1$, $\beta2$, $\gamma$) and novel PKC isoforms ($\delta$, $\epsilon$, $\eta$, $\theta$) or atypical isoforms ($\zeta$, $\iota$), more preferably selected from the $\alpha$, $\beta$ ($\beta1$ and $\beta2$ isoforms) and $\theta$ PKC isoforms. Preferred PKC inhibitors are able to selectively inhibit PKC $\alpha$ and $\theta$ isoforms. Suitable PKC inhibitors include maleimide derivatives, such as compounds described in U.S. Pat. Nos. 5,545,636; 5,668,152; 5,672,681; 5,698,578; 5,710,145; 6,645,970; 7,220,774; 7,235,555; US Publication No. 2008/0318975; European Patent Nos. 0776895 B1; 0817627 B1; 1449529 B1; 1337527 B1; and PCT Publication Nos. WO03/082859; and WO07/006,533 Each of the references cited above are incorporated herein by reference. As used herein, the term "PKC inhibitor" refers to a protein kinase C inhibitor that may be pan (multi-subtype) or selective to one or more PKC isozymes. The term PKC generally refers to the entire family of isoforms: conventional isoforms; alpha, beta, and gamma, novel isoforms; delta, epsilon, eta, and theta, and atypical isoforms; zeta, and iota The term "selective PKC inhibitor" refers to a PKC inhibitor that possesses a selectivity of at least about 20 fold for one or more PKC isoforms as compared to the other PKC isoforms. Preferably, the selectivity is at least about 100 fold, more preferably at least about 500 fold, most preferably at least about 1,000 or at least about 2,000 fold The term "selective PKC alpha/theta inhibitor", "selective PKC $\alpha/\theta$ inhibitor" refers to a protein kinase C inhibitor that is more selective for the alpha and/or theta PKC isoform of PKC than the other disclosed isoforms of PKC. For example, PKC alpha or PKC alpha and theta, over the other named PKC isoforms of at least about 20 fold (preferably at least about 100, more preferably at least about 500, most preferably at least about 1,000 or at least about 2,000 fold).

Differential regulation of GSK3$\beta$ by protein kinase C isotopes was described by Goode, et al in the publication, J. Biol. Chem., Vol. 267, pp 16878-16882 (1992). More recently, dual regulation of GSK3$\alpha/\beta$ by protein kinase C isotope alpha and Akt was described to promote thrombin mediated Integrin $\alpha_{11b}/\beta_3$ activation and granule secretion in platelets by Moore, et al in the publication J. Biol. Chem., Vol. 288, pp 3918-3928 (2013).

In other aspects, the present invention provides a method for treating protein kinase related disorders, specifically protein kinase C, alpha, theta (PKCα/θ) related disorders related disorders in a human or animal subject in recognized need of such treatment comprising administering to said subject an amount of a compound of formula (I), (Ia), (II) or (III) effective to treat cancer or tumor growth associated with the PKCα/θ in the subject.

In other aspects, the present invention provides a method for treating immune related disorders, including but not limited to autoimmune diseases, allergic reaction and tissue transplant rejection, in a human or animal subject in recognized need of such treatment comprising administering to said subject an amount of a compound of formula (I), (II) or (III) effective to reduce or prevent tumor growth in the subject. In other aspects, the present invention provides a method for treating malignant solid tumors in a human or animal subject in recognized need of such treatment comprising administering to said subject an amount of a compound of formula (I), (II) or (III) effective to reduce or prevent tumor growth in the subject. In addition to a potential role in cancer treatment and myeloproliferative diseases, such inhibitor could be useful to control expansion of immune cells in other pathologic condition such as autoimmune diseases, allergic reactions and in organ transplantation rejection syndromes. Support that the invented selective PKC inhibitor of the present invention would be effective at treating immune related disorders is provided by the recent disclosure that sotrastaurin represents a new class of immunosuppressive agents affecting early T-Cell Activation (Evenou, et al, "The Journal of Pharmacology and Experimental Therapeutics," Vol. 330 pp. 792-801, 2009).

In other aspects, the present invention provides a method for treating cancer, tumors in a human or animal subject in recognized need of such treatment comprising administering to said subject an amount of a compound of formula (I), (Ia), (II) or (III) effective to reduce or prevent tumor growth in the subject. In other aspects, the present invention provides a method for treating malignant solid tumors in a human or animal subject in recognized need of such treatment comprising administering to said subject an amount of a compound of formula (I), (Ia), (II) or (III) effective to reduce or prevent tumor growth in the subject.

In other aspects, the present invention provides a method for treating uveal melanoma, including uveal melanoma harboring GNAQ or GNA11 mutations in a human or animal subject in recognized need of such treatment comprising administering to said subject an amount of a compound of formula (I), (Ia, (II) or (III) effective to reduce or prevent tumor growth in the subject.

In other aspects, the present invention provides a method for treating lymphoma, including diffuse large B-cell lymphoma (DLBCL), in a human or animal subject in recognized need of such treatment comprising administering to said subject an amount of a compound of formula (I), (Ia), (II) or (III) effective to reduce or prevent tumor growth in the subject.

In other aspects, the present invention provides a method for treating ibrutinib resistant cancers in a human or animal subject in recognized need of such treatment comprising administering to said subject an amount of a compound of formula (I), (Ia), (II) or (III) effective to reduce or prevent tumor growth in the subject. PKC is immediately downstream from Bruton's Tyrosine Kinase with regards to B-cell lymphomas and hematological cancers and provide support that the invented PKC inhbitiors would be effective at treating ibrutinib resistant cancers and diseases. Woyach, et al have described and identified certain specific mutations that may mediate ibrutinib resistance in the publication, J. New England Medicine, DOI: 10.1056/NEJMoa1400029, 2014.

In other aspects, the present invention provides a method for treating protein kinase related disorders, specifically protein kinase C, (PKCα/θ) related disorders in a human or animal subject in recognized need of such treatment comprising administering to said subject an amount of a compound of formula (I), (Ia), (II) or (III) effective to reduce or prevent tumor growth associated with the PKCα/θ related disorder in the subject. The term "a therapeutically effective amount" of a PKC inhibitor refers to an amount of the PKC inhibitor that will elicit a biological or medical response in a subject, for example, reduction or inhibition of an enzyme or the activity of a protein, and/or ameliorate symptoms, alleviate conditions, slow or delay disease progression, or prevent a disease, etc. In one non-limiting embodiment, the term "a therapeutically effective amount" refers to the amount of PKC inhibitor, that when administered to a subject, is effective to (1) at least partially alleviate, inhibit, prevent and/or ameliorate a condition, or a disorder or a disease mediated by or associated with the activity of PKC, such as for example B-cell lymphoma having chronic active B-cell receptor signalling (e.g., CD79 mutant diffuse-large B-cell lymphoma) or uveal melanoma harboring GNAQ or GNA11 mutations; and/or is effective to (2) at least partially reduce the size (tumor volume) or inhibit the further growth of tumors (solid or liquid). In another non-limiting embodiment, the term "a therapeutically effective amount" refers to the amount of the compound of the present invention that, when administered to a subject, cell, or a tissue, or a non-cellular biological material, or a medium, is effective to at least partially reduce or inhibit the growth of B-cell lymphoma having chronic active B-cell-receptor signaling (preferably, a CD79 mutant diffuse-large B-cell lymphoma) or uveal melanoma harboring (GNAQ or GNA11 mutations.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like In certain embodiments, the subject is a primate. In yet other embodiments, the subject is a human. As used herein, the term "inhibit", "inhibition" or "inhibiting" refers to the reduction or suppression of a given condition, symptom, or disorder, or disease, or a significant decrease in the baseline activity of a biological activity or process. As used herein, the term "treat", "treating" or "treatment" of any disease or disorder, refers (i) to ameliorating the disease or disorder (i.e., slowing or arresting or reducing the development of the disease or at least one of the clinical symptoms thereof (ii) to alleviating or ameliorating at least one physical parameter including those which may not be discernible by the patient; (iii) to modulating the disease or disorder, either physically, (e.g., stabilization of a discernible symptom), physiologically, {e.g., stabilization of a physical parameter), or both; or (iv) to preventing or delaying the onset or development or progression of the disease or disorder in general, the term "treating" or "treatment" describes the management and care of a patient for the purpose of combating the disease, condition, or disorder and includes the administration of a PKC inhibitor to prevent the onset of the symptoms or complications, alleviating the symptoms or complications, or eliminating the disease, condition or disorder.

In yet other aspects, the present invention provides methods for treating PKC related disorders, including cancers disclosed herein, in a human or animal subject in need of such treatment comprising administering to said subject an amount of a compound of formula (I), (Ia), (II) or (III) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formula (I), (II) or (III) are known to those skilled in the art.

In preferred embodiments, anticancer agents to be used in combination with compounds of the present invention comprise agents that induce or stimulate apoptosis. Agents that induce apoptosis include, but are not limited to, radiation (e.g., W); kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Ab1 kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol]; cellular signaling molecules; ceramides and cytokines; and staurosprine, and the like.

In yet other aspects, the present invention provides therapeutic compositions comprising at least one compound of formula (I), (Ia), (II) or (III) in combination with a pharmaceutically acceptable carrier, and optionally with one or more additional agents for the treatment of cancer, as are commonly employed in cancer therapy.

The term "cancer" refers to cancer diseases that can be beneficially treated by the inhibition of PKC, including, for example, solid cancers, such as carcinomas (e.g., of the lungs, pancreas, thyroid, ovarian, bladder, breast, prostate, or colon), melanomas, myeloid disorders (e.g., uveal melanoma, myeloid leukemia, multiple myeloma and erythroleukemia), adenomas (e.g., villous colon adenoma) and sarcomas (e.g., osteosarcoma).

"PKC inhibitor" is used herein to refer to a compound that exhibits an $IC_{50}$ with respect to PKCα/θ activity of less than about 100 nM as measured in the assays described hereinbelow. In some embodiments a PKC inhibitor has an $IC_{50}$ with respect to PKCα/θ activity of less than about 50 nM as measured in the assays described hereinbelow. In still other embodiments a PKC inhibitor has an $IC_{50}$ with respect to PKCα/θ activity of less than about 10 nM as measured in the assays described hereinbelow.

In another aspect, the present invention relates to methods of inhibiting at least one PKC isoform in a subject, or treating a biological condition mediated by the PKC isoform, including the PKC isoform signaling pathway, in a subject, comprising the step of administering a therapeutic composition comprising at least one compound of formula (I), (Ia), (II) or (III) effective to inhibit the PKC isoform (PKCα, PKCθ) or PKC isoform signaling pathway in the subject. The therapeutic compositions are useful for treating patients with a need for such inhibitors (e.g., those suffering from cancer mediated by abnormal PKC signaling).

In another aspect, the present invention relates to methods of inhibiting at least one serine/threonine kinase selected from PKCα or PKCθ in a subject, or treating a biological condition mediated by at least one of PKCα or PKCθ, comprising the step of administering a therapeutic composition comprising at least one compound of formula (I), (Ia), (II) or (III) effective to inhibit the kinase in the subject. The therapeutic compounds are useful for treating patients with a need for such inhibitors (e.g., those suffering from cancer mediated by abnormal PKC receptor signaling).

In another aspect, the present invention relates to methods of inhibiting the activity of PKCα or PKCθ in a subject, or treating a biological condition mediated by at least one of PKCα or PKCθ in a human or animal subject in need of such treatment, comprising the step of administering to the subject at least one compound of formula (I), (Ia) (II) or (III) in an amount effective to inhibit the kinase in the subject. The therapeutic compounds are useful for treating patients with a need for such inhibitors (e.g., those suffering from cancer mediated by abnormal serine/threonine kinase receptor signaling).

In other aspects, the present invention relates to the processes for preparing the compounds of Formulas (I), (Ia), (II) or (III), and to the synthetic intermediates useful in such processes, as described in detail below.

Synthetic Methods

Compounds of the invention (Formulas (I), (Ia), (II) or (III)) can be obtained through procedures known to the skilled in the art (Methods 1-6). For example, as shown in Scheme 1 (Method 1), 3-Amino-6-substituted-pyrazine-2-carboxylic acid can be prepared from its corresponding methyl 3-Amino-6-substituted-pyrazine-2-carboxylate starting from methyl 3-amino-6-bromopyrazine-2-carboxylate. A protected (1-(2-aminopyridin-3-yl)piperidin-4-yl) compound (e.g. tert-butyl (1-(2-aminopyridin-3-yl)piperidin-4-yl)carbamate), is then prepared starting from 3-fluoro-2-nitropyridine. The methyl 3-Amino-6-substituted-pyrazine-2-carboxylate is then reacted with a protected (1-(2-aminopyridin-3-yl)piperidin-4-yl) compound, then de-protected to yield a 3-amino-N-(3-(4-aminopiperidin-1-yl)pyridin-2-yl)-6-substituted -pyrazine-2-carboxamide of Formulas (I), (Ia), (II) or (III).

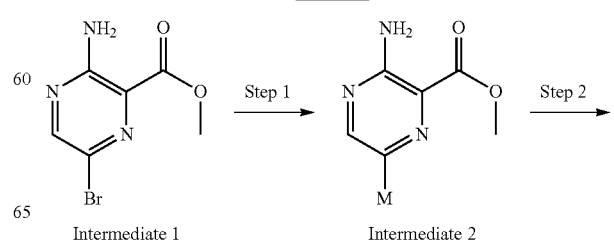

Scheme 1

Intermediate 1 → Step 1 → Intermediate 2 → Step 2

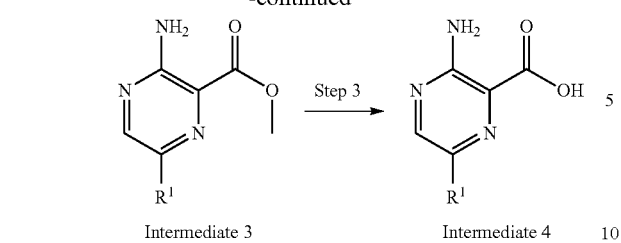

Intermediate 3 → Step 3 → Intermediate 4

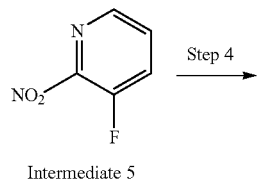

Intermediate 5 → Step 4

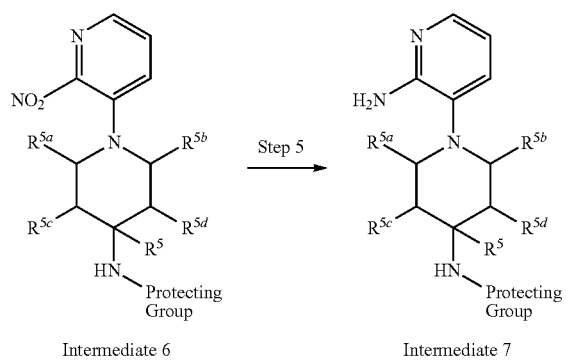

Intermediate 6 → Step 5 → Intermediate 7

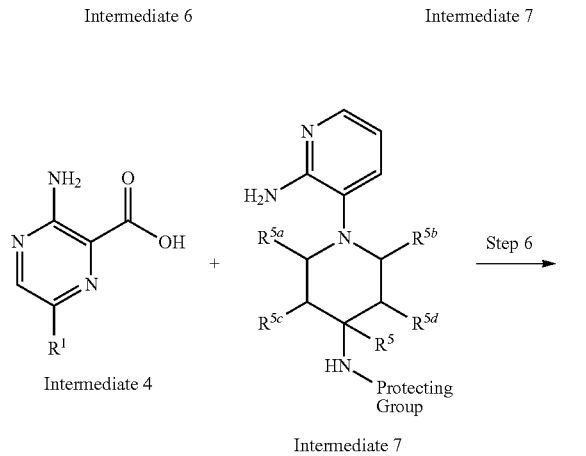

Intermediate 4 + Intermediate 7 → Step 6

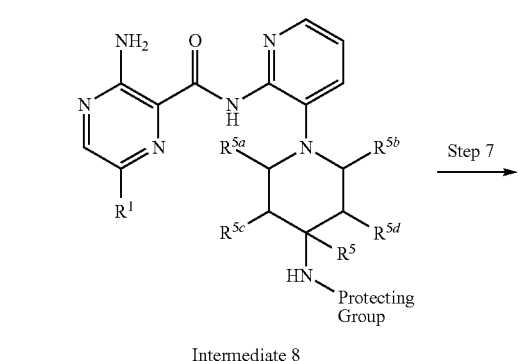

Intermediate 8

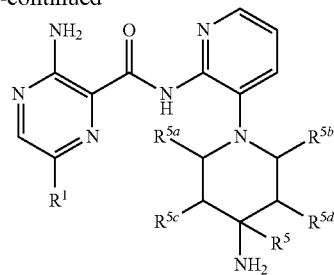

Compound of Formula I

Alternatively, 3-amino-N-(3-(4-amino-4-(methoxymethyl)piperidin-1-yl)pyridin-2-yl)-6-substituted-pyrazine-2-carboxamide of Formulas (I), (Ia), (II), or (III), can be prepared in one less synthetic step, as depicted in Method 2 (Scheme 2). For example, as shown in Scheme 2, 3-Amino-6-substituted-pyrazine-2-carboxylic acid can be prepared from its corresponding methyl 3-Amino-6-substituted-pyrazine-2-carboxylate starting from methyl 3-amino-6-bromopyrazine-2-carboxylate. A protected (1-(2-aminopyridin-3-yl)piperidin-4-yl) compound (e.g. tert-butyl (1-(2-aminopyridin-3-yl)piperidin-4-yl)carbamate), is then prepared starting from 3-fluoro-2-nitropyridine. The methyl 3-Amino-6-substituted-pyrazine-2-carboxylate is then reacted with a protected (1-(2-aminopyridin-3-yl)piperidin-4-yl) compound, then de-protected to yield a 3-amino-N-(3-(4-aminopiperidin-1-yl)pyridin-2-yl)-6-substituted-pyrazine-2-carboxamide of Formulas (I), (Ia), (II) or (III).

Scheme 2

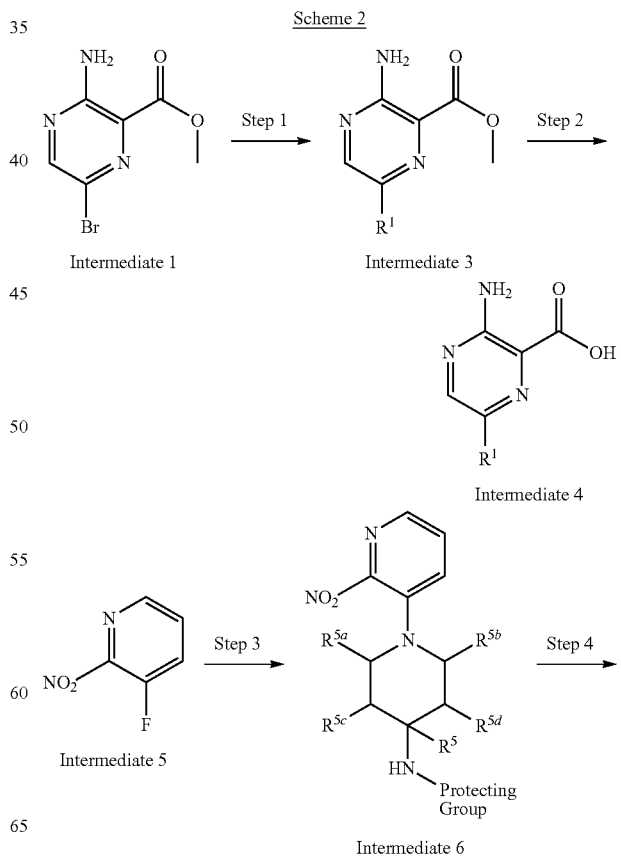

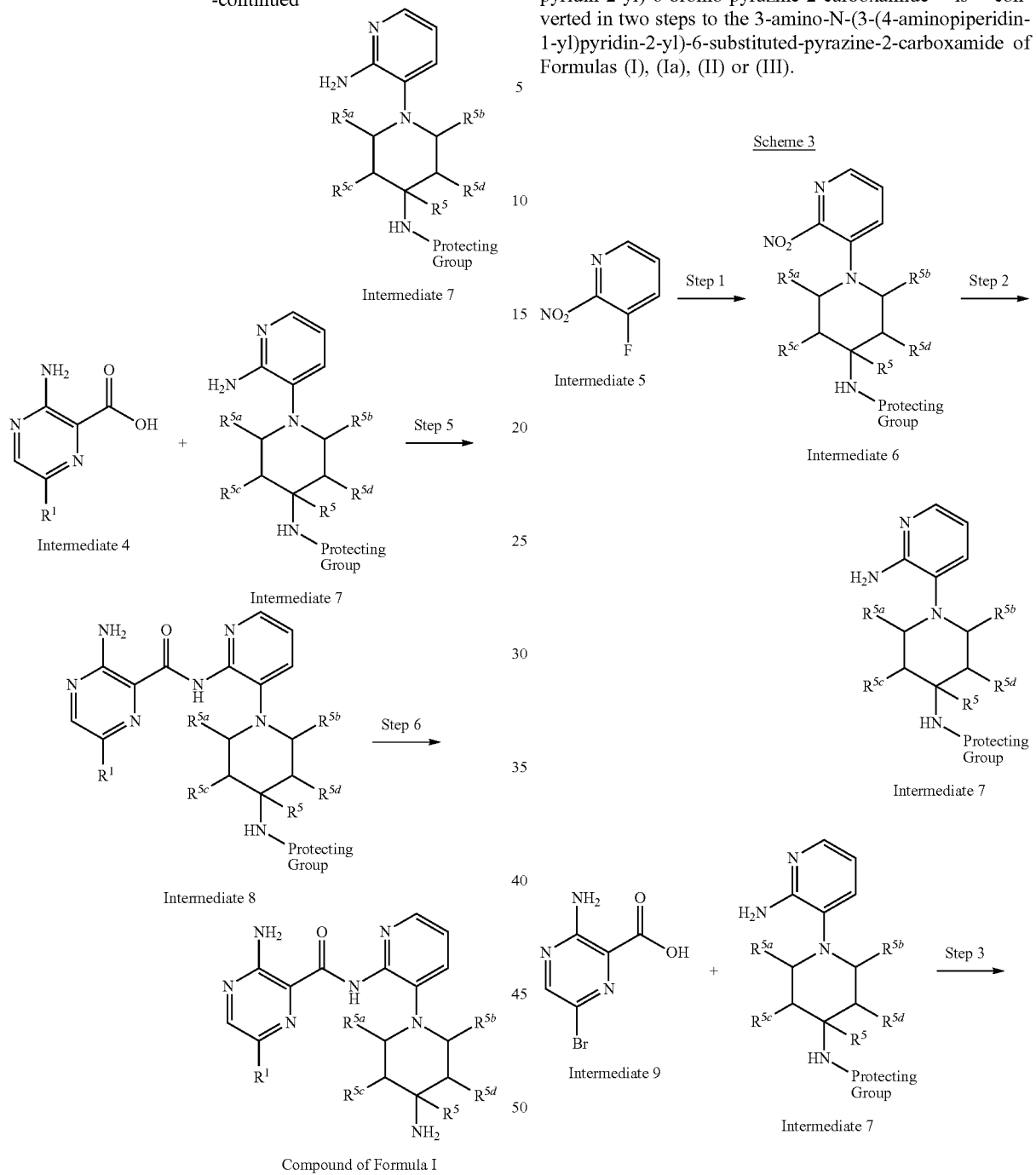

pyridin-2-yl)-6-bromo-pyrazine-2-carboxamide is converted in two steps to the 3-amino-N-(3-(4-aminopiperidin-1-yl)pyridin-2-yl)-6-substituted-pyrazine-2-carboxamide of Formulas (I), (Ia), (II) or (III).

In an alternative manner, 3-amino-N-(3-(4-amino-4-(methoxymethyl)piperidin-1-yl)pyridin-2-yl)-6-substituted-pyrazine-2-carboxamide of Formulas (I), (Ia), (II), or (III) can be obtained as depicted in Method 3 (Scheme 3). For example, starting from 3-fluoro-2-nitropyridine, a protected (1-(2-aminopyridin-3-yl)piperidin-4-yl) compound is prepared. The protected (1-(2-aminopyridin-3-yl)piperidin-4-yl) compound is then reacted with 3-amino-6-bromopyrazine-2-caboxylic acid or a protected acid (e.g. methyl 3-amino-6-bromopyrazine-2-carboxylate) to produce a 3-amino-N-(3-(4-amino-4-(methoxymethyl)piperidin -1-yl) pyridin-2-yl)-6-bromo-pyrazine-2-carboxamide. The 3-amino-N-(3-(4-amino-4-(methoxymethyl)piperidin-1-yl)

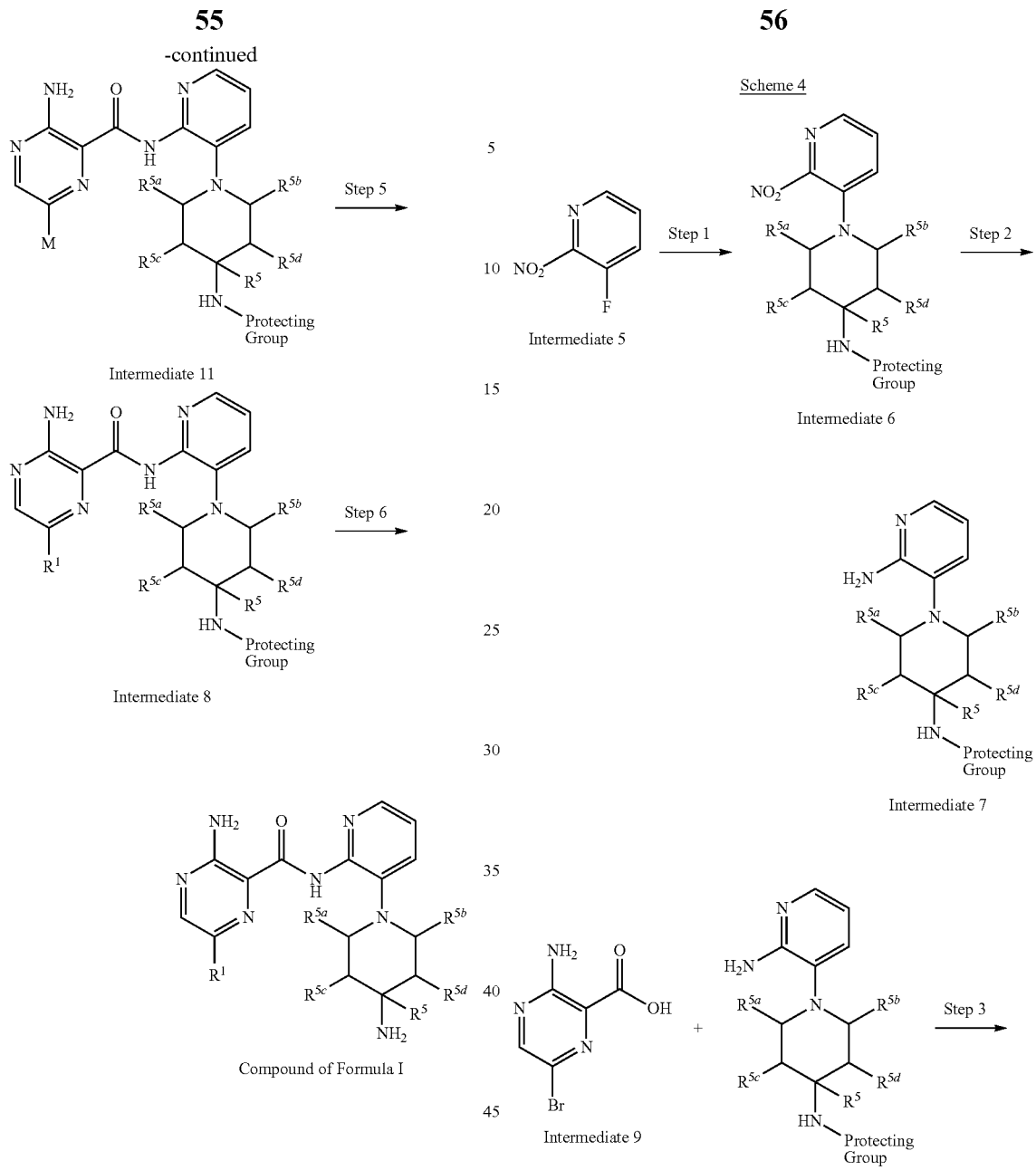

In an alternative manner, 3-amino-N-(3-(4-amino-4-(methoxymethyl)piperidin-1-yl)pyridin-2-yl)-6-substituted-pyrazine-2-carboxamide of Formulas (I), (Ia), (II), or (III) can be obtained as depicted in Method 4 (Scheme 4). For example, starting from 3-fluoro-2-nitropyridine, a protected (1-(2-aminopyridin-3-yl)piperidin-4-yl) compound is prepared. The protected (1-(2-aminopyridin-3-yl)piperidin-4-yl) compound is then reacted with 3-amino-6-bromopyrazine-2-caboxylic acid or a protected acid (e.g. methyl 3-amino-6-bromopyrazine-2-carboxylate) to produce a 3-amino-N-(3-(4-amino-4-(methoxymethyl)piperidin -1-yl) pyridin-2-yl)-6-bromo-pyrazine-2-carboxamide. The 3-amino-N-(3-(4-amino-4-(methoxymethyl)piperidin-1-yl) pyridin-2-yl)-6-bromo-pyrazine-2-carboxamide is converted in fewer steps to the 3-amino-N-(3-(4-aminopiperidin-1-yl)pyridin-2-yl)-6-substituted-pyrazine-2-carboxamide of Formulas (I), (Ia), (II) or (III).

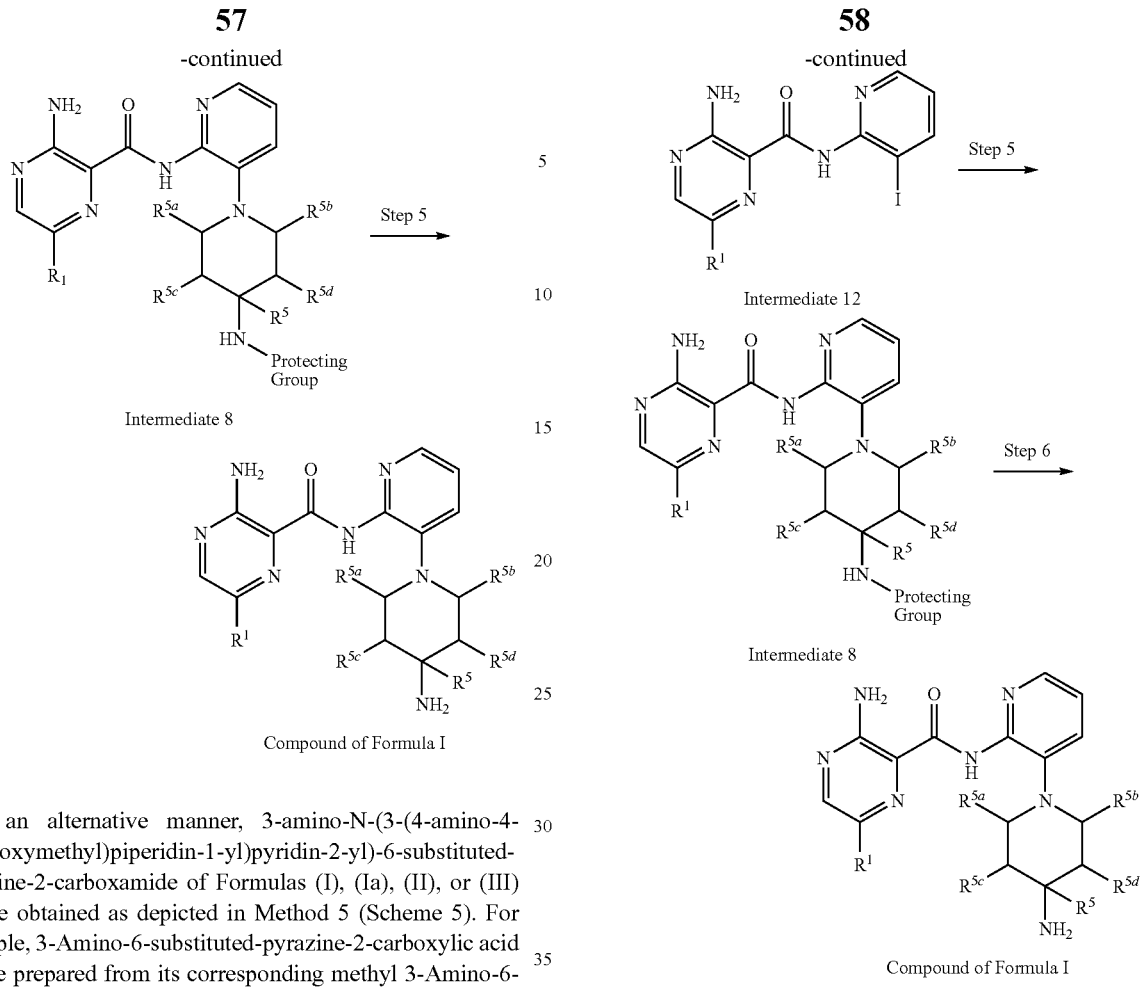

In an alternative manner, 3-amino-N-(3-(4-amino-4-(methoxymethyl)piperidin-1-yl)pyridin-2-yl)-6-substituted-pyrazine-2-carboxamide of Formulas (I), (Ia), (II), or (III) can be obtained as depicted in Method 5 (Scheme 5). For example, 3-Amino-6-substituted-pyrazine-2-carboxylic acid can be prepared from its corresponding methyl 3-Amino-6-substituted-pyrazine-2-carboxylate starting from methyl 3-amino-6-bromopyrazine-2-carboxylate. The 3-Amino-6-substituted-pyrazine-2-carboxylic acid is then reacted with 2-amino-3-iodo-pyridine to produce Intermediate 12, which is then converted to (1-(2-aminopyridin-3-yl)piperidin-4-yl) compound, then de-protected to yield a 3-amino-N-(3-(4-aminopiperidin-1-yl)pyridin-2-yl)-6-substituted-pyrazine-2-carboxamide of Formulas (I), (Ia), (II) or (III).

In yet another alternative manner, 3-amino-N-(3-(4-amino-4-(methoxymethyl)piperidin-1-yl)pyridin-2-yl)-6-substituted-pyrazine-2-carboxamide of Formulas (I), (Ia), (II), or (III), can be prepared in one less synthetic step as depicted in Method 6 (Scheme 6). For example, a 3-Amino-6-halo-substituted-pyrazine-2-carboxylic acid can be prepared from its corresponding methyl 3-Amino-6-substituted-pyrazine-2-carboxylate starting from methyl 3-amino-6-bromopyrazine-2-carboxylate in one less step. The 3-Amino-6-substituted-pyrazine-2-carboxylic acid is then reacted with 2-amino-3-iodo-pyridine to produce Intermediate 12, which is then converted to (1-(2-aminopyridin-3-yl)piperidin-4-yl) compound, then de-protected to yield a 3-amino-N-(3-(4-aminopiperidin-1-yl)pyridin-2-yl)-6-substituted-pyrazine-2-carboxamide of Formulas (I), (Ia), (II) or (III).

Scheme 5

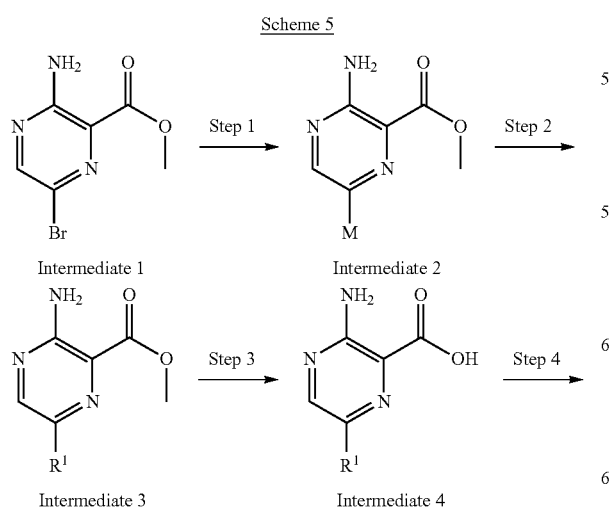

Scheme 6

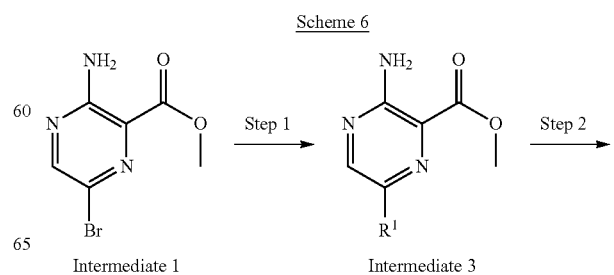

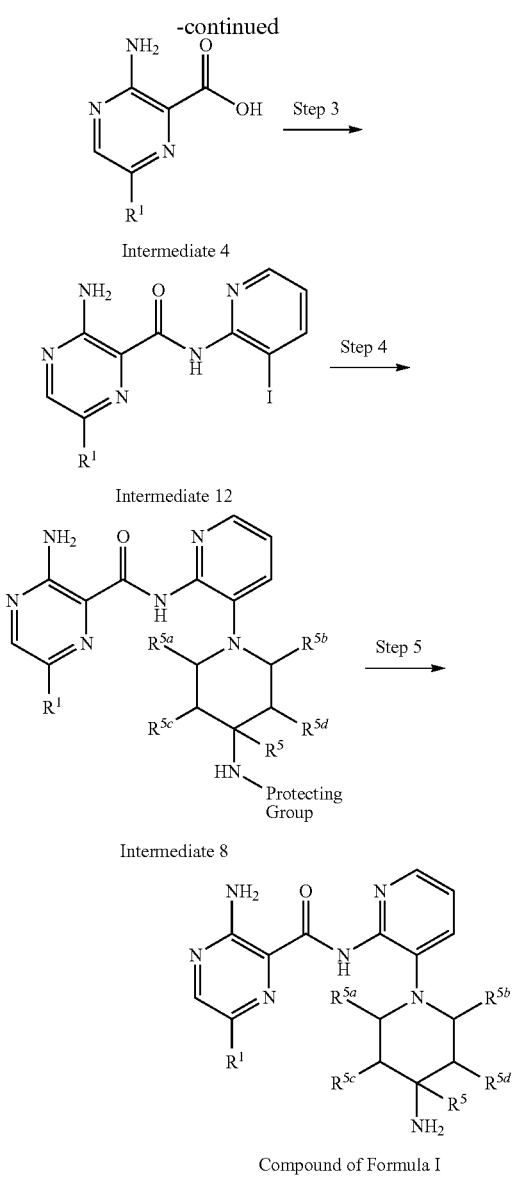

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit the disclosed PKC isoform activity by any of the assays described herein, by other PKC activity assays known to those having ordinary skill in the art or by detecting an inhibition or alleviation of symptoms of cancer.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Androgen receptor modulators are compounds which interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

Cytotoxic and/or cytostatic agents are compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine -platinum(II)]bis [diamine(chloro)platinum (II)]tetrachloride, diarizidinyl spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032). A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L -prolyl-L-proline-t-butyl-amide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo -benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo -[de]pyrano[3',4':b,7]-indolizino[1,2b]quinoline-10,13(9H, 15H)dione, lurtotecan, 7-[2-(N -isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N -[2-(dimethylamino)ethyl]-9-hydroxy-5,6-dimethyl-6H-pyrido[4,3-b] carbazole-1-carboxamide, asulacrine, (5a, 5aB, 8aa, 9b)-9-[2-[N-[2-(dimethylamino)ethyl]-N-methylamino] ethyl]-5-[4-hydrooxy-3,5-dimethoxyphenyl]-5,5a,6,8,8a, 9-hexahydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis [(2-aminoethyl)amino] benzo[g]isoquinoline-5,10-dione, 5-(3-aminopropylamino)-7,10-dihydroxy-2-(2-hydroxyethyl aminomethyl)-6H-pyrazolo[4,5,1'-de] acridin-6-one, N-[1-[2(diethyl amino)

ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy -7H-indeno[2,1-c]quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK-1), inhibitors of bub-1 and inhibitors of bub-R1. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E) -tetradecadienoyl]glycyl amino]-L-glycero-B-L-manno-heptopyranosyl] adenine, aplidine, ectein -ascidin, troxacitabine, 4-[2-amino-4-oxo4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo(7.4.1.0.0)-tetradeca -2,4,6-trien-9-yl acetic acid ester, swainsonine, lometrexol, dexrazoxane, methioninase, 2'-cyano -2'-deoxy-N4-palmitoyl-1-B-D-arabino furanosyl cytosine and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926 and 4,319, 039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342, 952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. In an embodiment, the HMG-CoA reductase inhibitor is selected from lovastatin and simvastatin.

Prenyl-protein transferase inhibitors are compounds which inhibit any one or any combination of the prenyl-protein transferase enzymes, including farnesyl-protein transferase (FPTase), geranylgeranyl -protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl -2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5 (S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl) -5-imidazolylmethyl]-5-[2-(ethanesulfonyl) methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N -(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl -4-(3-chlorobenzyl)-piperidine-1-ylmethyl]-2-methylimidazol-1-yl -methyl}benzonitrile, 4-{3-[4-(2-oxo-2H-pyridin-1-yl)benzyl]-3H-imidazol-4-ylmethyl}-benzonitrile, 4-{3-[4-(5-chloro-2-oxo-2H-[1,2']bipyridin-5'-ylmethyl]-3H-imidazol-4-yl -methyl}benzonitrile, 4-{3-[4-(2-oxo-2H-[1,2']bipyridin-5'-ylmethyl]-3H-imidazol4-yl -methyl}benzonitrile, 4-{3-(2-oxo-1-phenyl-1,2-dihydro-pyridin-4-ylmethyl)-3H-imidazol-4-ylmethyl}benzonitrile, 18,19-dihydro-19-oxo-5H, 17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano -12,14-etheno-6,10-metheno-22H-benzo[d]imidazo[4,3-k][1,6,9, 12]oxatriaza-cyclooctadecine-9-carbonitrile, 19,20-dihydro-19-oxo-5H, 17H-18,21-ethano-6,10:12,16-dimetheno-22H -imidazo[3,4-h][1,8,11,14] oxatriazacycloeicosine-9-carbonitrile, and (+−)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9): 1394-1401 (1999).

Angiogenesis inhibitors refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS 89:7384 (1992); *JNCI* 69:475 (1982); *Arch. Ophthalmol.* 108:573 (1990); *Anat. Rec.*, (238):68 (1994); *FEBS Letters* 372:83 (1995); *Clin, Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology,* 17:963-968 (October 1999); Kim et al., *Nature,* 362:841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The invention also encompasses combinations of the compounds of the invention with NSAIDs which are selective COX-2 inhibitors (generally defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the present invention include 3-phenyl-4-(4-(methylsulfonyl)phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862, 5-methoxy4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentanose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway are pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example, rapamycin, everolimus and Wyeth CCI-779). Such agents include small molecule inhibitor compounds and antibody antagonists.

Apoptosis inducing agents include activators of TNF receptor family members (including the TRAIL receptors).

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec™), nilotinib (Tasigna™), everolimus (Afinitor™), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, effecting the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al., *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formulas (I), (Ia), (II), (III) and (IV) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formulas (I), (Ia), (II), (III) and (IV) are used in combination with at least one additional agent, such as Gleevec™ or Tasigna™ in the treatment of hematological cancers, such as chronic myelogenous leukemia (CML), to reverse or prevent resistance to the at least one additional agent.

In another aspect, the present invention relates to methods of inhibiting at least one serine/threonine kinase in the Jak/Stat signaling pathway in a subject, or treating a biological condition mediated by a PKC signaling pathway in a subject, comprising administering a therapeutic composition comprising at least one compound of formula (I), (Ia), (II) or (III) effective to inhibit the activity of the at least one serine/threonine kinase in the PKC signaling pathway in the subject.

The therapeutic compositions in accordance with this aspect of the invention are useful for treating patients with a need for such inhibitors (e.g., those suffering from cancer mediated by abnormal PKC signaling). Cancer types mediated by abnormal PKC signaling include, for example, melanoma, uveal melanoma, lymphoma, diffuse large B-cell lymphoma (DLBCL) and ibrutinib resistant cancers, papillary cancer, thyroid cancer, ovarian cancer, colon cancer, pancreatic cancer, non-small cell lung cancer (NSCLC), hematological cancers, chronic myelogenous leukemia (CML), acute lymphoblastic leukemia (ALL), and acute myeloid leukemia.

In one embodiment, the invention provides a method of inhibiting PKCα, PKCθ and GSKβ in a human or animal subject. The method includes administering an effective amount of a compound, or a pharmaceutically acceptable salt thereof, of any of the embodiments of compounds of formula (I), (Ia), (II) or (III) to a subject in need thereof.

The present invention will be understood more readily by reference to the following examples, which are provided by way of illustration and are not intended to be limiting of the present invention.

Representative side chains for use in the compounds of the following examples may generally be prepared in accordance with the following procedures:

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18 −5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

The compounds and/or intermediates were characterized by LCMS. General conditions are as follows.

Low and High resolution Mass spectra were acquired on LC/MS systems using electrospray ionization methods from a range of instruments of the following configurations: Low resolution—Agilent 1100 HPLC-UV system equipped with Waters ZQ Mass Spectrometer and Schimadzu ELSD detectors; Low resolution—Waters AcQuity UPLC-UV system equipped with Waters SQ Mass Spectrometer and Thermo CAD detectors; High resolution—Waters AcQuity UPLC-UV system equipped with a Waters LCT Premier Mass Spectrometer. [M+H]$^+$ refers to the protonated molecular ion of the chemical species.

Analytical Instrument Methods

Low Resolution MS Methods

Agilent 1100 HPLC-UV with Waters ZQ Mass Spectrometer

Acidic Method: Column: Sunfire C18, 3×30 mm, 3.5 μm, temperature 40° C., 2 μL injection volume; Solvent A: 0.05% TFA in Water; Solvent B: Acetonitrile; Gradient: 5-95%.

Basic Method: Column: Xbridge C18, 3×30 mm, 3.5 μm, temperature 40° C., 2 μL injection volume; Solvent A: 5 mM NH$_4$OH in water; Solvent B: Acetonitrile; Gradient: 5-95%.

Low Resolution MS Method

Waters AcQuity equipped with Waters SQ Mass Spectrometer

Acidic Method: Column: Acquity UPLC BEH C18, 2.1× 50 mm, 1.7 μm, temperature 50° C., 1.5 μL injection volume; Solvent A: 0.05% TFA in Water; Solvent B: Acetonitrile; Gradient: 2-98% in 1.7 min.

Neutral Method: Column: Acquity BEH C18 1.7 μm 2.1×50 mm -50° C.; Solvent A: Water+3.75 mM Amm Ace+2% CAN; Solvent B: ACN+3.75 mM Amm Ace+ 5% Water; Gradient: 2 to 98% B in 1.7 min—flow 1 mL/min.

HRMS Method

Waters AcQuity UPLC-UV Equipped with Waters LCT Premier Mass Spectrometer

Acidic Method: Column: ACQUITY UPLC BEH C18, 130 Å, 1.7 um, 2.1 mm×50 mm—temp: 50° C.; Solvent A: WATER+0.1% Formic Acid; Solvent B: Acetonitrile+0.1% Formic Acid; Gradient: 2-98% Solvent B in 7.5 min; Scan speed: 0.2s, over range of 120-1100 Daltons Basic Method: Column: ACQUITY UPLC BEH C18, 130 Å, 1.7 um, 2.1 mm×50 mm—temp: 50° C.; Solvent A: Water+5 mM NH$_4$OH; Solvent B: 5 mM NH$_4$OH in Acetonitrile; Gradient 2-98% in 7.5 min; Scan speed: 0.2s, over range of 120-1100 Daltons Nuclear magnetic resonance (NMR) analysis was performed on a Bruker 400 MHz NMR spectrometer using ICON-NMR, under TopSpin program control. Spectra were measured at 298K, unless indicated otherwise and were referenced relative to the solvent chemical shift.

The purity of some of the compounds is assessed by elemental analysis (Desert Analytics, Tucson, Ariz.).

Melting points are determined on a Laboratory Devices Mel-Temp apparatus (Holliston, Mass.).

Preparative separations are carried out using

Waters 2545 HPLC System equipped with Waters PDA 2998 and/or Waters 3100 Mass Spectrometer detection.

Acidic UV triggered: Water/Acetonitrile with 0.1% TFA modifier, Flow rate 75 mL/min, 1.5 mL injection volume; Column: Waters Sunfire 30 mm ID x 50 mm, 5 μm particle.

Basic UV triggered: Water/Acetonitrile with 5 mM NH$_4$OH, Flow rate 75 mL/min, 1.5 mL injection volume; Column: Waters X-Bridge 30 mm ID x 50 mm, 5 μm particle Methods:

All methods run a focused gradient from the starting % acetonitrile to the final % acetonitrile over 3.5 minutes with a 10 second initial hold. After the gradient, all methods go to 95% acetonitrile over 30 seconds and hold there for 1.5 minutes before returning to the initial conditions. The Initial and Final conditions for each gradient are as follows:

Method 0: 5-12% Acetonitrile
Method 1: 7.5-20% Acetonitrile
Method 2: 10-30% Acetonitrile
Method 3: 15-40% Acetonitrile
Method 4: 25-50% Acetonitrile
Method 5: 35-60% Acetonitrile
Method 6: 45-70% Acetonitrile
Method 7: 55-80% Acetonitrile
Method 8: 65-95% Acetonitrile It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

Abbreviations

| | |
|---|---|
| DCM | dichloromethane |
| DIEA | diisopropylethylamine |
| DMA | dimethylacetamide |
| DMAP | 4-dimethylaminopyridine |
| DME | 1,2-dimethoxyethane |
| DMF | N,N-dimethylformamide |
| EtOAc | ethyl acetate |
| EtOH | Ethanol |
| MeCN | acetonitrile |
| MeOH | methanol |
| ACN | acetonitrile |
| BA | bioavailability |
| NBS | N-bromosuccinimide |
| NMP | N-methyl-2-pyrrolidone |
| RT or rt | room temperature |
| TDMSCl | tert-butyldimethylsilylchloride |
| TEA | triethylamine |
| THF | tetrahydrofuran |
| Ret. Time | Retention time |

MS Mass Spectra
HRMS High Resolution Mass Spectra
n-BuLi n-Butyllithium
DBAD Diisobutylazadicarboxylate
TFA Trifluoroacetic Acid
hr hour
g gram
L Liter
equiv equivalent
min minute
mmol millimole
NaHCO$_3$ sodium bicarbonate
N$_2$ nitrogen
MTBE methyl tertbutylether
mL milliliter
SiO$_2$ silica gel
NaH sodium hydride
TLC thin layer chromatography
KMnO$_4$ potassium permanganate NH4Cl ammonium chloride
HPLC High Performance Liquid Chromatography
AMRI Albany Molecular Research Inc
NH4OH Ammonium Hydroxide
DIAD Diisopropylazadicarboxylate
HCl hydrochloric acid
DCE dichloroethane
NH3 ammonia
HCOOH formic acid
Boc tert-butyl carboxylate
IPA isopropanol
mg milligram Example 1

3-amino-N-(3-(4-aminopiperidin-1-yl)pyridin-2-yl)-6-(3-(trifluoromethyl)pyridin-2-yl)pyrazine-2-carboxamide

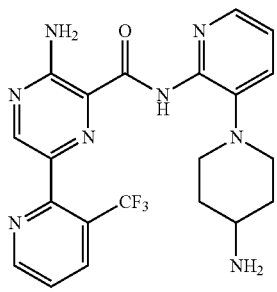

1) Synthesis of 3-Amino-6-(3-(trifluoromethyl)pyridin-2-yl)pyrazine-2-carboxylic Acid

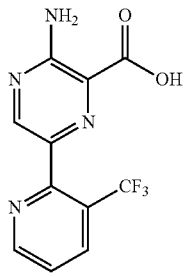

Step 1. Synthesis of methyl 3-amino-6-(trimethylstannyl)pyrazine-2-carboxylate

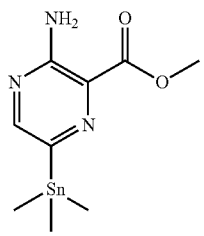

To a 500 mL two neck round-bottom flask equipped with a magnetic stirrer and a reflux condenser, methyl 3-amino-6-bromopyrazine-2-carboxylate (25 g, 108 mmol) and Pd(PPh3)4 (6.23 g, 5.39 mmol) were suspended in 1,2-dimethoxyethane (200 ml) at rt (room temperature) under an argon atmosphere. The mixture was degassed and flushed with Argon (two times) and hexamethylditin (29.0 mL, 140 mmol) was added via syringe through a rubber septum, the mixture was degassed and flushed with argon again, and heated to 90° C. for 2 h. The mixture was cooled to rt and concentrated in vacuo. Water (400 mL) and ethyl acetate (200 mL) were added, stirred for 20 minutes and filtered through celite. The filtrate was transferred to a separation funnel, the phases were separated and the organic phase was washed with brine, dried over sodium sulfate and the solvent was removed under reduced pressure. The residue was filtered over silica gel with heptane, then a solvent mixture of (ethyl acetate 1:9 heptane) and finally a solvent mixture (ethyl acetate 2:8 heptane) which gave methyl 3-amino-6-(trimethylstannyl)pyrazine-2-carboxylate (20.92 g) of a yellow solid.

LC-MS (Basic Method): ret.time=1.07 min, M+H=317.8.

Step 2. Synthesis of methyl 3-amino-6-(3-(trifluoromethyl)pyridin-2-yl)pyrazine-2-carboxylate

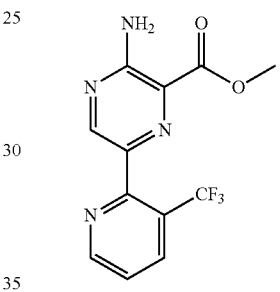

In a 500 mL round-bottom flask equipped with a magnetic stirrer and argon inlet, methyl 3-amino-6-(trimethyl stannyl) pyrazine-2-carboxylate (20.92 g, 55.0 mmol), 2-Bromo-3-(trifluoromethyl) pyridine (14.38 g, 60.5 mmol), Pd2(dba)3 (5.54 g, 6.05 mmol) and P(o-Tol)3 (3.79 g, 12.09 mmol) were dissolved in DMF (100 ml) at rt, followed by addition of NEt3 (10.72 ml, 77 mmol). The reaction mixture was heated to 110° C. under argon for 1 h. After cooling to rt, the reaction mixture was filtered through celite, washed with ethyl acetate and concentrated under reduced pressure. The residue was purified by silica gel chromatography using ethyl acetate heptane which gave methyl 3-amino-6-(3-(trifluoromethyl)pyridin-2-yl)pyrazine-2-carboxylate (7.8 g) as a yellow solid.

LC-MS (Basic Method): ret.time=0.93 min, M+H=299.0.

Step 3. Synthesis of 3-amino-6-(3-(trifluoromethyl)pyridin-2-yl)pyrazine-2-carboxylic Acid

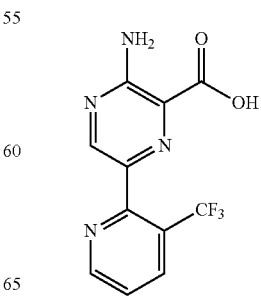

In a 250 mL round-bottom flask equipped with a magnetic stirrer, methyl 3-amino-6-(3-(trifluoromethyl)pyridin-2-yl)pyrazine-2-carboxylate (7.8 g, 23.80 mmol) was dissolved in dioxane (100 mL) at rt. LiOH monohydrate (2.008 g, 47.6 mmol) was dissolved in water (25 ml) and added at rt and stirred for 1 h. The suspension was diluted with water (50 mL) and extracted with ethyl acetate (3×100 mL), the organic layer was back extracted with water (2×50 mL). The aqueous layer was adjusted to pH 3 with conc. HCl and extracted with ethyl acetate (3×100 mL), the combined organic layers were dried over sodium sulfate, filtered and concentrated which gave 3-amino-6-(3-(trifluoromethyl)pyridin-2-yl)pyrazine-2-carboxylic acid (6.89 g) as a yellow powder. LC-MS (Basic method) M+H=284.9. $^1$H-NMR (DMSO-d6): δ (ppm)=13.04(s broad, 0.84 H), 8.92 (d, 1H, J=4.9 Hz), 8.71 (s, 1H), 8.33 (d, 1H, J=8.1 Hz), 7.70-7.67 (m, 3H).

2) Synthesis of 3-amino-N-(3-(4-aminopiperidin-1-yl)pyridin-2-yl)-6-(3-(trifluoromethyl) pyridin-2-yl) pyrazine-2-carboxamide

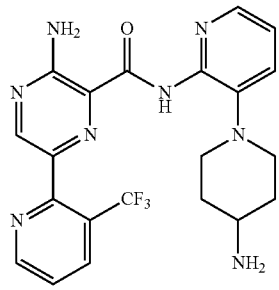

Step 1. tert-butyl (1-(2-nitropyridin-3-yl)piperidin-4-yl)carbamate

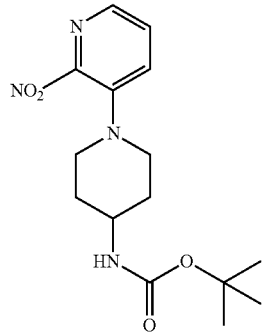 [SMILES: CC(C)(C)OC(=O)NC1CCN(c2cccnc2[N+](=O)[O-])CC1]

To a 100 mL round-bottom flask equipped with a magnetic stirrer and a nitrogen inlet, was added THF (20 mL), 3-fluoro-2-nitropyridine (1.524 g, 10.73 mmol), tert-butyl piperidin-4-ylcarbamate (2.256 grams, 11.26 mmol), N-ethyl-N-isopropylpropan-2-amine (3.47 g, 26.8 mmol). The mixture was heated to 70° C. for 24 hours. The mixture was cooled and concentrated to a thick residue. The residue was purified by silica gel chromatography using ethyl acetate-heptane which gave tert-butyl (1-(2-nitropyridin-3-yl)piperidin-4-yl)carbamate (3.24 g, 98% yield). LC-MS (Basic method): ret.time=1.30 min, M+H=323.3

Step 2. tert-butyl (1-(2-aminopyridin-3-yl)piperidin-4-yl)carbamate

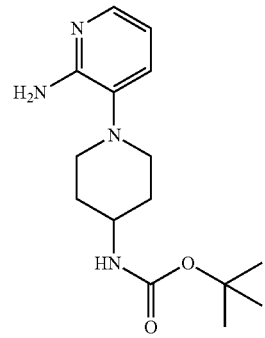

To a 250 mL round bottom flask equipped with a magnetic stirr bar purged with nitrogen was added tert-butyl (1-(2-nitropyridin-3-yl)piperidin-4-yl)carbamate (3.2 grams, 9.93 mmol), THF (75 ml) and Pd/C (1.1 g, 10% Pd on charcoal wet). The resultant mixture was stirred under an atmosphere of hydrogen until all tert-butyl (1-(2-aminopyridin-3-yl)piperidin-4-yl)carbamate was consumed. The reaction was then purged with nitrogen, magnesium sulfate was added and stirred. The mixture was then filtered through a pad of celite. The filter pad was washed with excess DMC. The filtrate was concentrated to a thick residue which solidified under vacuum. The solid was dried to a constant weight and used directly (2.9 grams, 99.9% yield).

LC-MS (Basic method): ret.time=1.04 min, M+H=293.

Step 3. Synthesis of tert-butyl (1-(2-(3-amino-6-(3-(trifluoromethyl)pyridin-2-yl)pyrazine-2-carboxamido)pyridin-3-yl)piperidin-4-yl)carbamate

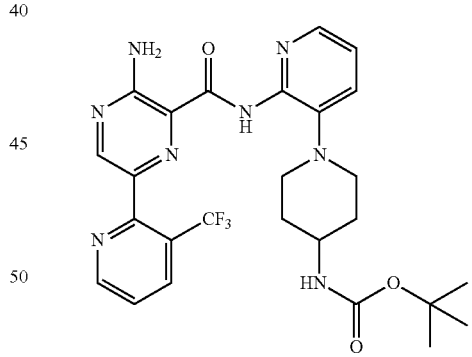

To a 25 ml flask was added 3-amino-6-(3-(trifluoromethyl)pyridin-2-yl)pyrazine-2-carboxylic acid (332 mg, 1.168 mmol), DMF (4 ml), 2-(3H-[1,2,3]triazolo[4,5-b]pyridin-3-yl)-1,1,3,3-tetramethylisouronium hexafluorophosphate(V) (454 mg, 1.194 mmol) and N-ethyl-N-isopropylpropan-2-amine (0.8 ml, 4.58 mmol). The mixture was allowed to stir for about 5 minutes followed by the addition of tert-butyl (1-(2-aminopyridin-3-yl)piperidin-4-yl)carbamate (311 mg, 1.064 mmol). The resultant mixture was allowed to stir over night. The residue was quenched with sat. NaCl solution (150 mL) and extracted with EtOAc (2×250 mL). The combined organic phases were dried over Na$_2$SO$_4$, filtrated and concentrated to a dark solid which was purified by silica gel chromatography using an ethyl acetate-heptane. LC-MS (Basic method): ret.time=1.22 min, M+H=559.

Step 4. Synthesis of 3-amino-N-(3-(4-aminopiperidin-1-yl)pyridin-2-yl)-6-(3-(trifluoromethyl)pyridin-2-yl)pyrazine-2-carboxamide

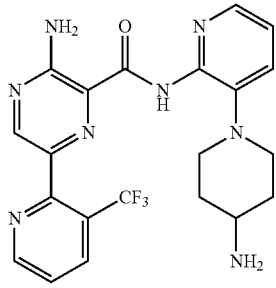

To a 100 mL flask was added a magnetic stirrer, tert-butyl (1-(2-(3-amino-6-(3-(trifluoromethyl)pyridin-2-yl)pyrazine-2-carboxamido)pyridin-3-yl)piperidin-4-yl)carbamate, and dichloromethane (10 mL). The mixture was stirred until all solids dissolved and then cooled in an ice water bath under nitrogen. To this mixture was added trifluoroacetic acid (10 mL). The ice bath was removed and the mixture was stirred for 3 hours at RT. The mixture was then concentrated and the residue was then co-evaporated with toluene (20 mL). The resultant residue was then mixed with brine (20 mL), saturated with NaHCO$_3$ and extracted with dichloromethane (3×50 mL). The combined organic phases were dried over Na$_2$SO$_4$, filtered and concentrated to a solid. The solid was dissolved in dichloromethane and precipitated with heptane. The solid was filtered and dried under vacuum to a constant weight which gave 3-amino-N-(3-(4-aminopiperidin-1-yl)pyridin-2-yl)-6-(3-(trifluoromethyl)pyridin-2-yl)pyrazine-2-carboxamide (223 mg) in 95% yield. LC-MS (Basic Method): ret.time=1.1 min, M+H=459 $^1$H NMR (400 MHz, Chloroform-d) δ 10.74 (s, 1H), 8.97-8.84 (m, 1H), 8.77 (s, 1H), 8.30 (dd, J=5.2, 1.9 Hz, 1H), 8.20 (dd, J=8.0, 1.6 Hz, 1H), 7.53 (dd, J=8.1, 4.8 Hz, 1H), 7.42 (dd, J=7.9, 1.7 Hz, 1H), 7.06 (dd, J=7.9, 4.9 Hz, 1H), 3.11 (dd, J=11.1, 4.9 Hz, 2H), 2.87-2.49 (m, 3H), 1.45-1.14 (m, 3H).

Example 2

3-amino-N-(3-(4-aminopiperidin-1-yl)pyridin-2-yl)-6-(3-(trifluoromethoxy) pyridin-2-yl)pyrazine-2-carboxamide

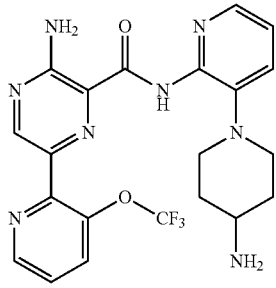

The 3-amino-N-(3-(4-aminopiperidin-1-yl)pyridin-2-yl)-6-(3-(trifluoromethoxy)pyridine -2-yl)pyrazine-2-carboxamide was prepared in a manner similar to Example 1 (Method 1) where 3-amino-6-(3-(trifluoromethoxy)pyridin-2-yl)pyrazine-2-carboxylic acid was used in place of 3-amino-6-(3-(trifluoromethyl)pyridin-2-yl)pyrazine-2-carboxylic acid which gave 3-amino-N-(3-(4-aminopiperidin-1-yl)pyridin-2-yl)-6-(3-(trifluoromethoxy)pyridin-2-yl)pyrazine-2-carboxamide (1.21 g) in 77% yield. LC-MS (Acidic Method): ret.time=1.12 min, M+H=475.2

$^1$H NMR (400 MHz, Methanol-d$_4$) δ 8.86 (s, 1H), 8.77 (dd, J=4.7, 1.4 Hz, 1H), 8.14 (dd, J=5.0, 1.6 Hz, 1H), 8.05 (dp, J=8.5, 1.4 Hz, 1H), 7.72-7.57 (m, 2H), 7.20 (dd, J=7.9, 4.9 Hz, 1H), 3.29 (s, 3H), 3.10 (dt, J=12.7, 4.0 Hz, 2H), 2.82-2.71 (m, 2H), 2.69-2.53 (m, 1H), 1.93-1.69 (m, 2H), 1.37 (dtd, J=13.9, 10.5, 3.6 Hz, 2H).

Example 3

3-amino-N-(3-(4-amino-4-(methoxymethyl)piperidin-1-yl)pyridin-2-yl)-6-(3-(trifluoromethyl)pyridin-2-yl)pyrazine-2-carboxamide

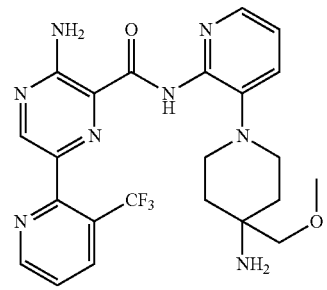 [SMILES: COCC1(N)CCN(c2cccnc2NC(=O)c2nc(-c3ncccc3C(F)(F)F)cnc2N)CC1]

Step 1: Synthesis of tert-butyl (4-(hydroxymethyl)-1-(2-nitropyridin-3-yl)piperidin-4-yl)carbamate

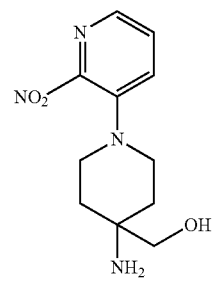 [SMILES: NC1(CO)CCN(c2cccnc2[N+](=O)[O-])CC1]

To a 25 ml pear shaped flask was added 3-fluoro-2-nitropyridine, (0.441 g, 3.1 mmol), tert-butyl (4-(hydroxymethyl)piperidin-4-yl)carbamate (0.65 g, 2.82 mmol), N-ethyl-N-isopropylpropan-2-amine, (0.839 g, 6.49 mmol) and tetrahydrofuran (10 mL) and a magnetic stirrer. The mixture was stirred under nitrogen and heated at 70° C. for 3 days. The mixture was then cooled and concentrated to a thick residue and chromatographed directly on silica gel (ethyl acetate-heptane) which gave tert-butyl (4-(hydroxymethyl)-1-(2-nitropyridin-3-yl)piperidin-4-yl)carbamate (0.668 g, 1.858 mmol) in 65.8% yield.

LC-MS (Basic method): ret.time=1.13 min, M+H=353.5.

Step 2: Synthesis of tert-butyl (4-(methoxymethyl)-1-(2-nitropyridin-3-yl)piperidin-4-yl)carbamate

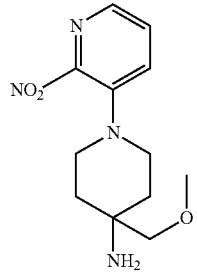 [SMILES: COCC1(N)CCN(c2cccnc2[N+](=O)[O-])CC1]

To a 25 mL pear shaped flask was added toluene (8 ml), dioxane (4 ml), tert-butyl (4-(hydroxymethyl)-1-(2-nitropyridin-3-yl)piperidin-4-yl)carbamate (0.546 g, 1.549 mmol), dimethyl sulfate (0.293 g, 2.324 mmol), sodium hydroxide (0.124 g, 1.549 mmol) and N,N,N-trimethyl-1, phenylmethanaminium chloride (0.288 g, 1.549 mmol). The resultant mixture was stirred for 18 hours. The reaction was diluted with 40 ml of ethyl acetate and stirred followed by the addition of a small amount (spoonful) of MgSO$_4$. The mixture was stirred for about 5 min., filtered and concentrated. The resultant residue was chromatographed on silica gel (ethyl acetate-heptane gradient 10-100%) which gave tert-butyl (4-(methoxymethyl)-1-(2-nitropyridin -3-yl)piperidin-4-yl)carbamate (0.556 g, 1.487 mmol) in 96% yield.

LC-MS (Basic Method): ret.time=1.44 min, M+H=367.4.

Step 3: Synthesis of tert-butyl (1-(2-aminopyridin-3-yl)-4-(methoxymethyl) piperidin-4-yl)carbamate

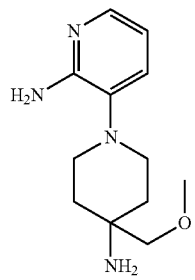

To a 100 mL round bottom flask was added tert-butyl (4-(methoxymethyl)-1-(2-nitropyridin-3-yl)piperidin-4-yl) carbamate (0.697 g, 1.902 mmol), ethyl acetate (20 mL) and 10% palladium on carbon wet (about 0.7 g). The flask was purged with hydrogen and stirred under a balloon of hydrogen for 16 hrs. To the resultant mixture was then added MgSO$_4$ (5 grams) and stirred. The mixture was then filtered through a pad of MgSO$_4$ under a cone of nitrogen. The filtrate was concentrated to dryness which gave tert-butyl (1-(2-aminopyridin-3-yl)-4-(methoxymethyl)piperidin-4-yl) carbamate (0.454 g, 1.322 mmol) in 98% yield.

LC-MS (Basic Method): ret.time=0.88 min, M+H=337.5.

Step 4: Synthesis of tert-butyl (1-(2-(3-amino-6-(3-(trifluoromethyl)pyridin-2-yl) pyrazine-2-carboxamido)pyridin-3-yl)-4-(methoxymethyl)piperidin-4-yl)carbamate

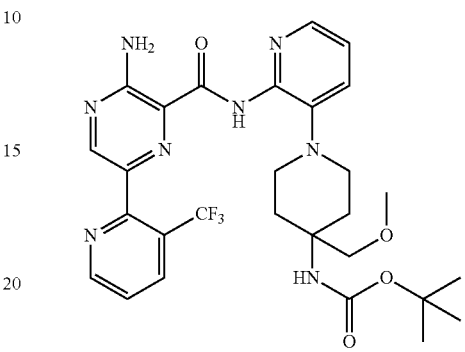

To a 25 mL flask was added 3-amino-6-(3-(trifluoromethyl)pyridin-2-yl)pyrazine-2-carboxylic acid (0.188 g, 0.66 mmoles), DMF (2 ml), 2-(1H-benzo[d][1,2,3]triazol-1-yl)-1,1,3,3-tetramethylisouronium hexafluorophosphate (HBTU), (0.25 g, 0.66 mmol) and N-ethyl-N-isopropylpropan-2-amine (0.18 ml, 0.99 mmol. The mixture was allowed to stir for about 60 minutes followed by the addition of tert-butyl (1-(2-aminopyridin-3-yl)-4-(methoxymethyl)piperidin-4-yl)carbamate (0.111 g, 0.33 mmol). The resultant mixture was allowed to stir for 18 hours and then concentrated to a thick residue. The residue was chromatographed directly on silica gel using ethyl acetate and heptane which gave tert-butyl (1-(2-(3-amino-6-(3-(trifluoromethyl)pyridin-2-yl)pyrazine-2-carboxamido)pyridin-3-yl)-4-(methoxymethyl)piperidin-4-yl)carbamate (0.432 g).

LC-MS (Basic method): ret.time=1.12 min, M+H=603.4.

Step 5: Synthesis of 3-amino-N-(3-(4-amino-4-(methoxymethyl)piperidin-1-yl) pyridine -2-yl)-6-(3-(trifluoromethyl)pyridin-2-yl)pyrazine-2-carboxamide

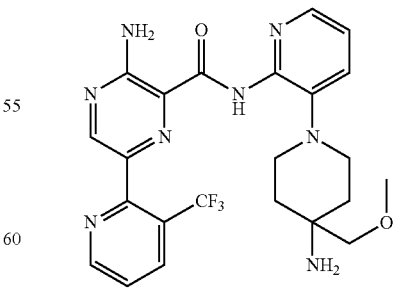

To a 100 ml flask was added a magnetic stirrer, tert-butyl (1-(2-(3-amino-6-(3-(trifluoromethyl)pyridin-2-yl)pyrazine-2-carboxamido)pyridin-3-yl)piperidin-4-yl)carbamate (0.199 g, 0.33 mmol) and dichloromethane (10 mL). The mixture was stirred until all solids dissolved and then cooled in an ice water bath under nitrogen. To this mixture was added trifluoroacetic acid (25 mL). The ice bath was removed and the mixture was stirred for 3 hours at room temperature. The mixture was then concentrated and the residue was then co-evaporated with toluene (30 mL) 3 times to a thick residue. The residue was purified by reverse phase HPLC (method 3) which gave 3-amino-N-(3-(4-amino-4-(methoxymethyl)piperidin-1-yl)pyridin-2-yl)-6-(3-(trifluoromethyl)pyridin-2-yl)pyrazine-2-carboxamide (0.142 g, 0.277 mmol) in 84% yield. LC-MS (Basic method): ret.time=1.04 min, M+H=503.2. $^1$H NMR (400 MHz, DMSO-d$_6$) δ 10.56 (s, 1H), 9.00 (dd, J=4.8, 1.5 Hz, 1H), 8.45 (dd, J=8.1, 1.4 Hz, 1H), 8.11 (dd, J=4.8, 1.6 Hz, 3H), 7.78 (dd, J=8.0, 4.8 Hz, 1H), 7.55 (dd, J=8.1, 1.8 Hz, 1H), 7.16 (dd, J=7.9, 4.8 Hz, 1H), 3.13 (s, 3H), 2.92 (dt, J=11.0, 7.1 Hz, 2H), 2.68 (dt, J=11.2, 3.4 Hz, 2H), 1.38-1.00 (m, 9H), 0.94-0.77 (m, 1H).

Example 4

3-amino-N-(3-(4-amino-4-methylpiperidin-1-yl)pyridin-2-yl)-6-(3 morpholinoisoquinolin-1-yl)pyrazine-2-carboxamide

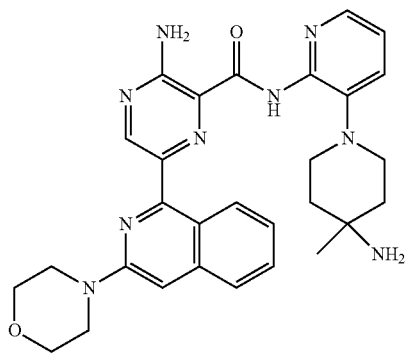 [SMILES: CC1(N)CCN(c2cccnc2NC(=O)c2nc(-c3nc(N4CCOCC4)cc4ccccc34)cnc2N)CC1]

Synthesis of 3-amino-6-(3-morpholinoisoquinolin-1-yl)pyrazine-2-carboxylic acid

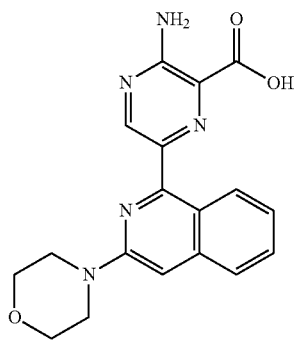 [SMILES: Nc1ncc(-c2nc(N3CCOCC3)cc3ccccc23)nc1C(=O)O]

Step 1. Synthesis of methyl 3-amino-6-(4,4,5,5-tetramethyl-1,3,2-dioxaborolan-2-yl)pyrazine-2-carboxylate

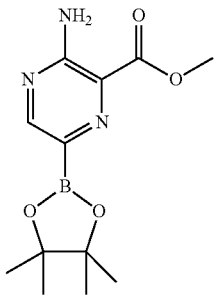

In a 500 mL round-bottom flask equipped with a magnetic stirrer, a solution of methyl 3-amino-6-bromopyrazine-2-carboxylate (10 g, 43.1 mmol), bis(pinacolato)diboron (13.68 g, 53.9 mmol), KOAc (7.61 g, 78 mmol) and PdCl$_2$(dppf) (79 mg, 0.108 mmol) in dioxane (200 mL) was degassed and flushed with nitrogen (two times), and then was heated at 80° C. for 3 hr. The reaction mixture was cooled to 25° C. and added 30 mL of DCM and filtered through celite. The filtrate was added 60 mL of heptane. The suspension was concentrated to ½ volume, and filtered. The solid was washed with heptane (3×20 mL) and dried under vacuum which gave methyl 3-amino-6-(4,4,5,5-tetramethyl-1,3,2-dioxaborolan-2-yl)pyrazine-2-carboxylate (12.85 g, 46.0 mmol).

LC-MS (acidic method)::ret.time=1.04 min, M+H=198.1

Step 2. Synthesis of methyl 3-amino-6-(3-morpholinoisoquinolin-1-yl)pyrazine-2-carboxylate

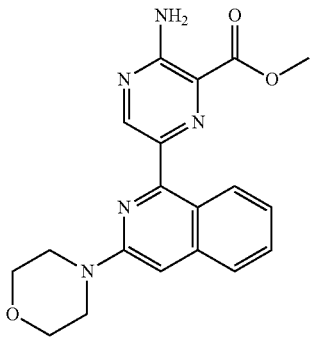 [SMILES: COC(=O)c1nc(-c2nc(N3CCOCC3)cc3ccccc23)cnc1N]

In a 15 mL round-bottom flask equipped with a magnetic stirrer, a solution of 4-(1-chloroisoquinolin-3-yl)morpholine (673 mg, 2.412 mmol), methyl 3-amino-6-(4,4,5,5-tetramethyl-1,3,2-dioxaborolan-2-yl)pyrazine-2-carboxylate (673 mg, 2.412 mmol), K$_3$PO$_4$ (3.02 ml, 3.02 mmol, 1M) and PdCl$_2$(dppf) (118 mg, 0.161 mmol) in dioxane (12 mL) was degassed and flushed with nitrogen (two times). The mixture was heated at 85° C. for 3 hr. The reaction was cooled to rt, and added water (100 mL) and extracted with EtOAc (3×50 mL), dried over Na$_2$SO$_4$ and concentrated. The crude product was purification by acidic HPLC column (Method 4) which gave methyl 3-amino-6-(3morpholinoisoquinolin-1-yl)pyrazine-2-carboxylate (460 mg, 1.259 mmol) in 62% yield.

LC-MS (acidic method)::ret.time=1.39 min, M+H=366.4.

Step 3. Synthesis of 3-amino-6-(3-morpholinoiso-quinolin-1-yl)pyrazine-2-carboxylic acid

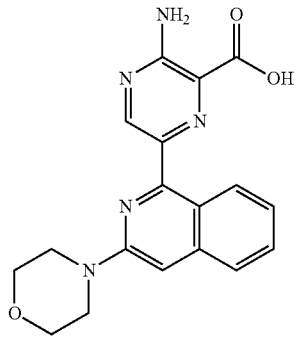 [SMILES: Nc1ncc(-c2nc(N3CCOCC3)cc3ccccc23)nc1C(=O)O]

In a 100 mL round-bottom flask equipped with a magnetic stirrer, a solution of methyl 3-amino-6-(3morpholinoisoquinolin-1-yl)pyrazine-2-carboxylate (460 mg, 1.259 mmol) in THF (4 mL) and MeOH (4.00 mL) was added LiOH.H$_2$O (3.15 mL, 6.29 mmol) in water (4 mL) and stirred for 25° C. for 2 hr. The reaction mixture was concentrated. Then was added 5 mL of water and acidified with 0.5N HCl to pH 5. The reaction mixture was filtered and washed with water (3×20 mL), and dried, which provided 3-amino-6-(3-morpholinoisoquinolin-1-yl)pyrazine-2-carboxylic acid (377 mg, 1.073 mmol) in 85% yield. LC-MS (acidic method):: ret.time=1.02 min, M+H=352.4.

Step 4. Synthesis 3-amino-N-(3-(4-methyl-4-pivalamidopiperidin-1-yl)pyridin-2-yl)-6-(3-morpholinoisoquinolin-1-yl)pyrazine-2-carboxamide

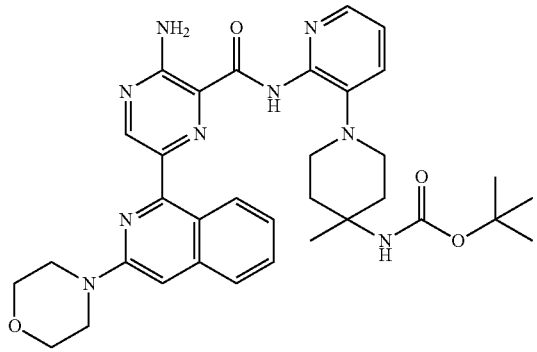 [SMILES: CC1(NC(=O)OC(C)(C)C)CCN(c2cccnc2NC(=O)c2nc(-c3nc(N4CCOCC4)cc4ccccc34)cnc2N)CC1]

In a 100 mL round-bottom flask equipped with a magnetic stirrer, a solution of 3-amino-6-(3-morpholinoisoquinolin-1-yl)pyrazine-2-carboxylic acid in DMF (3 mL) was added DIEA (0.149 mL, 0.854 mmol) and HATU (156 mg, 0.410 mmol), followed tert-butyl (1-(2-aminopyridin-3-yl)-4-methylpiperidin-4-yl)carbamate (105 mg, 0.342 mmol) and was stirred at 25° C. for 60 hr. The reaction mixture was added 80 mL of water and extracted with EtOAc (3×40 mL), dried over Na$_2$SO$_4$ and concentrated. The crude product was purified by basic HPLC (Method 3) which gave 3-amino-N-(3-(4-methyl-4-pivalamidopiperidin-1-yl)pyridin-2-yl)-6-(3-morpholinoisoquinolin-1-yl)pyrazine-2-carboxamide (108 mg, 0.169 mmol) in 49% yield.
LC-MS (acidic method)::ret.time=2.30 min, M+H=640.7.

Step 5. Synthesis 3-amino-N-(3-(4-amino-4-methyl-piperidin-1-yl)pyridin-2-yl)-6-(3-morpholinoisoquinolin-1-yl)pyrazine-2-carboxamide

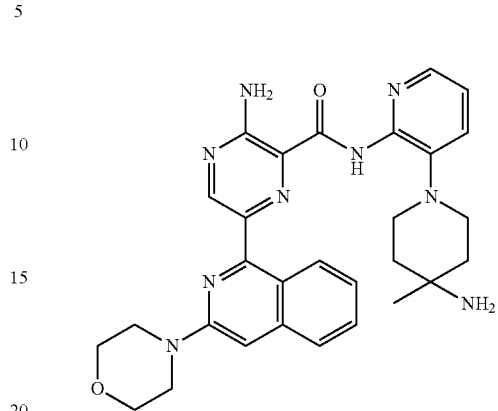

In a 100 mL round-bottom flask equipped with a magnetic stirrer, TFA (0.650 mL, 8.44 mmol) was cooled at −20° C., was added a solution of 3-amino-N-(3-(4-methyl-4-pivalamidopiperidin-1-yl)pyridin-2-yl)-6-(3-morpholinoisoquinolin-1-yl)pyrazine-2-carboxamide (108 mg, 0.169 mmol) in DCM (0.18 mL) slowly. The reaction mixture was stirred at 25° C. for 45 min. The reaction mixture was concentrated. The crude product was purified by basic HPLC (method 3) which gave 3-amino-N-(3-(4-amino-4-methylpiperidin-1-yl)pyridin-2-yl)-6-(3-morpholinoisoquinolin-1-yl)pyrazine-2-carboxamide (33 mg, 0.058 mmol) in 34% yield. LC-MS (acidic method)::ret.time=1.22 min, M+H=540.6. $^1$H NMR (METHANOL-d$_4$) d: 8.89 (s, 1H), 8.47 (d, J=8.5 Hz, 1H), 8.11 (dd, J=4.9, 1.6 Hz, 1H), 7.76 (d, J=8.5 Hz, 1H), 7.47-7.64 (m, 2H), 7.28 (ddd, J=8.5, 7.0, 1.1 Hz, 1H), 7.14 (dd, J=7.8, 5.0 Hz, 1H), 7.03 (s, 1H), 3.82-3.91 (m, 4H), 3.56-3.65 (m, 4H), 2.69-2.80 (m, 2H), 2.56-2.68 (m, 2H), 0.79-1.02 (m, 4H), 0.49 (br. s., 3H).

Example 5

3-amino-N-(3-(4-amino-4-(hydroxymethyl)piperidin-1-yl)pyridin-2-yl)-6-(3-(trifluoromethyl)pyridin-2-yl)pyrazine-2-carboxamide

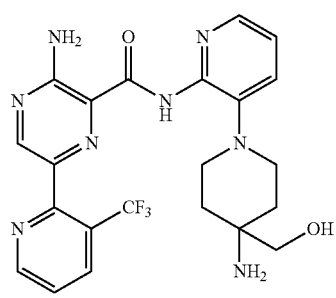 [SMILES: Nc1ncc(-c2ncccc2C(F)(F)F)nc1C(=O)Nc1ncccc1N1CCC(N)(CO)CC1]

Synthesis of tert-butyl (1-(2-aminopyridin-3-yl)-4-(((tert butyldimethylsilyl)oxy) methyl) piperidin-4-yl)carbamate

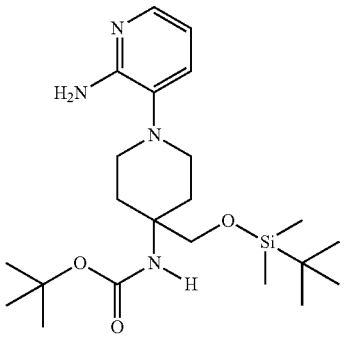 [SMILES: CC(C)(C)OC(=O)NC1(CO[Si](C)(C)C(C)(C)C)CCN(c2cccnc2N)CC1]

Step 1. Synthesis of tert-butyl (4-(hydroxymethyl)-1-(2-nitropyridin-3-yl)piperidin-4-yl)carbamate

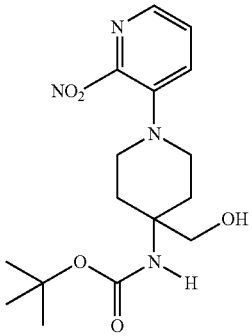 [SMILES: CC(C)(C)OC(=O)NC1(CO)CCN(c2cccnc2[N+](=O)[O-])CC1]

To a 25 mL round bottom flask was combined 3-fluoro-2-nitropyridine (0.441 g, 3.1 mmol), tert-butyl (4-(hydroxymethyl)piperidin-4-yl)carbamate (0.65 g, 2.82 mmol), N-ethyl-N-isopropylpropan-2-amine (1.2 mL) and THF (10 mL). The mixture was heated to 70° C. for 48 hrs. The mixture was cooled and concentrated to a thick residue. The residue was purified by silica gel chromatography using ethyl acetate and heptane which gave tert-butyl (4-(hydroxymethyl)-1-(2-nitropyridin-3-yl)piperidin-4-yl)carbamate (0.668 g) in 98% yield.

LC-MS (Basic method): ret.time=1.13 min, M+H=353.5.

Step 2. Synthesis of tert-butyl (4-(((tert-butyldimethylsilyl)oxy)methyl)-1-(2-nitropyridin-3-yl)piperidin-4-yl)carbamate

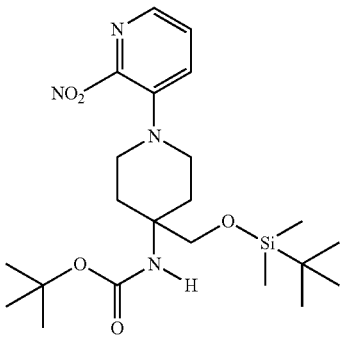 [SMILES: CC(C)(C)OC(=O)NC1(CO[Si](C)(C)C(C)(C)C)CCN(c2cccnc2[N+](=O)[O-])CC1]

To a 50 mL round bottom flask was combined tert-butyl (4-(hydroxymethyl)-1-(2-nitropyridin-3-yl)piperidin-4-yl)carbamate (1.08 g, 3.06 mmol), DMF (10 mL) and imidazole (0.459 g, 6.74 mmol) followed by tert-butylchlorodimethylsilane (0.554 g, 3.68 mmol). The mixture was allowed to stir until all alcohol was converted to the silyl ether. The mixture was then concentrated and chromatographed on silica gel using ethyl acetate and heptane which gave tert-butyl(4-(((tert-butyldimethylsilyl)oxy)methyl)-1-(2-nitropyridin-3-yl)piperidin-4-yl)carbamate (1.178 g) in 99% yield. LC-MS (Basic method): ret.time=1.84 min, M+H=467.3

Step 3. Synthesis of tert-butyl (1-(2-aminopyridin-3-yl)-4-(((tert butyldimethylsilyl)oxy) methyl) piperidin-4-yl)carbamate

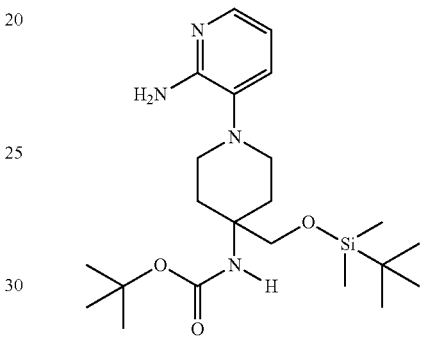

Starting with tert-butyl (4-(((tert-butyldimethylsilyl)oxy)methyl)-1-(2-nitropyridin-3-yl)piperidin-4-yl)carbamate (1.178 g), the nitro compound was treated with hydrogen and palladium as described in example 1 which gave tert-butyl (1-(2-aminopyridin-3-yl)-4-(((tert butyldimethylsilyl)oxy) methyl) piperidin-4-yl)carbamate (0.954 g) in 85% yield.

LC-MS (Basic method): ret.time=1.78 min, M+H=437.3

Step 4. Synthesis of tert-butyl (1-(2-(3-amino-6-(3-(trifluoromethyl)pyridin-2-yl)pyrazine-2-carboxamido)pyridin-3-yl)-4-(((tert-butyldimethylsilyl)oxy) methyl) piperidin-4-yl)carbamate

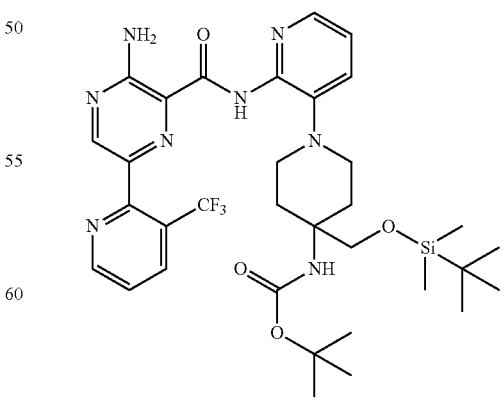

Starting with tert-butyl (1-(2-aminopyridin-3-yl)-4-(((tert butyldimethylsilyl)oxy) methyl) piperidin-4-yl)carbamate (0.2 g, 0.459 mmol), tert-butyl (1-(2-(3-amino-6-(3-(trifluoromethyl)pyridin-2-yl)pyrazine-2-carboxamido)pyridin-3-yl)-4-(((tert-butyldimethylsilyl)oxy)methyl)piperidin-4-yl)carbamate was prepared as described in example 1 and used directly.

Step 5. Synthesis of 3-amino-N-(3-(4-amino-4-(hydroxymethyl)piperidin-1-yl)pyridin-2-yl)-6-(3-(trifluoromethyl)pyridin-2-yl)pyrazine-2-carboxamide

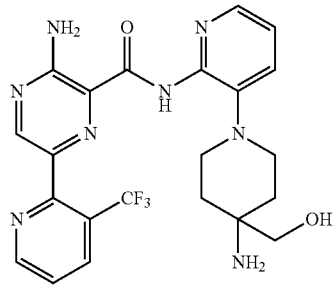 [SMILES: Nc1ncc(-c2ncccc2C(F)(F)F)nc1C(=O)Nc1ncccc1N1CCC(N)(CO)CC1]

The tert-butyl (1-(2-(3-amino-6-(3-(trifluoromethyl)pyridin-2-yl)pyrazine-2-carboxamido) pyridin-3-yl)-4-(((tert-butyldimethylsilyl)oxy)methyl) piperidin-4-yl)carbamate from step 4 was treated with trifluoroacetic acid in a manner as described in example 1 which gave 3-amino-N-(3-(4-amino-4-(hydroxymethyl)piperidin-1-yl)pyridin-2-yl)-6-(3-(trifluoromethyl)pyridin-2-yl)pyrazine-2-carboxamide (0.108 g, 0.217 mmol) in 21% yield. LC-MS (Basic method): ret.time=0.92 min, M+H=489.2. $^1$H NMR (400 MHz, DMSO-d$_6$) δ 10.55 (s, 1H), 8.97 (dd, J=4.8, 1.5 Hz, 1H), 8.77 (s, 1H), 8.39 (dd, J=8.2, 1.5 Hz, 1H), 8.26-7.65 (m, 4H), 7.56 (dd, J=8.2, 1.9 Hz, 1H), 7.16 (dd, J=7.9, 4.7 Hz, 1H), 4.34 (s, 1H), 3.23-3.07 (m, 3H), 2.91 (td, J=10.6, 4.2 Hz, 2H), 2.76-2.38 (m, 13H), 1.69-1.43 (m, 3H).

Example 6

3-amino-N-(3-(4-amino-4-(hydroxymethyl)piperidin-1-yl)pyridin-2-yl)-6-(3-(trifluoromethoxy)pyridin-2-yl)pyrazine-2-carboxamide

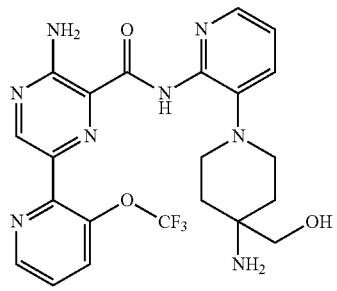 [SMILES: Nc1ncc(-c2ncccc2OC(F)(F)F)nc1C(=O)Nc1ncccc1N1CCC(N)(CO)CC1]

The 3-amino-N-(3-(4-amino-4-(hydroxymethyl)piperidin-1-yl)pyridin-2-yl)-6-(3-(trifluoromethoxy)pyridin-2-yl) pyrazine-2-carboxamide was prepared in a manner as described for Example 1, Method 1 (0.0865 g) in 85% yield. LC-MS (acidic method): ret.time=1.24 min, M+H=505.2. $^1$H NMR (DMSO-d6) δ: 10.75 (s, 1H), 8.92 (s, 1H), 8.77 (dd, J=4.6, 1.3 Hz, 1H), 8.11 (dd, J=4.8, 1.6 Hz, 1H), 8.08 (br s, 1H), 8.06 (dt, J=8.4, 1.4 Hz, 1H), 7.65 (dd, J=8.4, 4.6 Hz, 1H), 7.60 (dd, J=8.0, 1.7 Hz, 1H), 7.17 (dd, J=7.8, 4.8 Hz, 1H), 4.48 (s, 1H), 2.97 (td, J=11.3, 3.0 Hz, 2H), 2.75 (dq, J=7.6, 3.9 Hz, 4H), 1.77 (s, 2H), 1.47-1.16 (m, 4H).

Example 7

3-amino-N-(3-(4-aminopiperidin-1-yl)pyridin-2-yl)-6-(6-morpholino-3-(trifluoromethyl)pyridin-2-yl) pyrazine-2-carboxamide

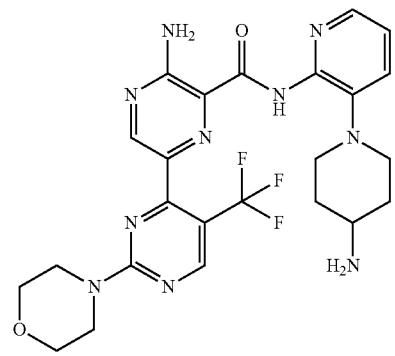 [SMILES: Nc1ncc(-c2nc(N3CCOCC3)ncc2C(F)(F)F)nc1C(=O)Nc1ncccc1N1CCC(N)CC1]

Synthesis of tert-butyl (1-(2-(3-amino-6-(4,4,5,5-tetramethyl-1,3,2-dioxaborolan-2-yl)pyrazine-2-carboxamido)pyridin-3-yl)piperidin-4-yl)carbamate

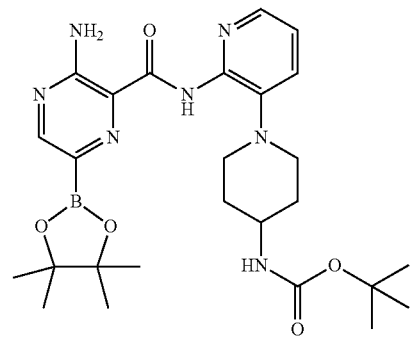 [SMILES: CC(C)(C)OC(=O)NC1CCN(c2cccnc2NC(=O)c2nc(B3OC(C)(C)C(C)(C)O3)cnc2N)CC1]

Step 1. Synthesis of tert-butyl (1-(2-(3-amino-6-bromopyrazine-2-carboxamido) pyridin-3-yl)piperidin-4-yl)carbamate

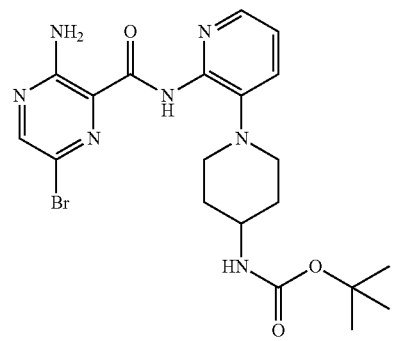 [SMILES: CC(C)(C)OC(=O)NC1CCN(c2cccnc2NC(=O)c2nc(Br)cnc2N)CC1]

In a 100 mL round-bottom flask equipped with a magnetic stirrer, a solution of 3-amino-6-bromopyrazine-2-carboxylic acid (1.044 g, 4.79 mmol), tert-butyl (1-(2-aminopyridin-3- yl)piperidin-4-yl)carbamate (1.4 g, 4.79 mmol), DIPEA (2.091 mL, 11.97 mmol) and HATU (2.185 g, 5.75 mmol) in DMF (15 mL) was stirred at 25° C. for 15 hr. The reaction mixture was quenched with 30 mL water and extracted with EtOAc (3×20 mL). The ethyl acetate wash was dried over $Na_2SO_4$ and concentrated. The crude product was purified by silica gel chromatography using ethyl acetate and heptane which gave 3-amino-N-(3-(4-aminopiperidin-1-yl)pyridin-2-yl)-6-bromopyrazine-2-carboxamide (1.76 g, 3.57 mmol) in 74% yield. LC-MS (acidic method)::ret.time=1.17 min, M+H=492.3.

Step 2. Synthesis of tert-butyl (1-(2-(3-amino-6-(4,4,5,5-tetramethyl-1,3,2-dioxaborolan-2-yl)pyrazine-2-carboxamido)pyridin-3-yl)piperidin-4-yl)carbamate

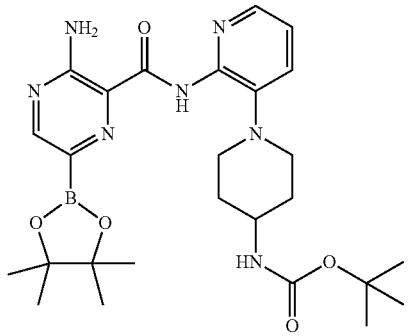 [SMILES: CC(C)(C)OC(=O)NC1CCN(c2cccnc2NC(=O)c2nc(B3OC(C)(C)C(C)(C)O3)cnc2N)CC1]

In a 15 seal round-bottom flask equipped with a magnetic stirrer, a solution of 3-amino-N-(3-(4-aminopiperidin-1-yl)pyridin-2-yl)-6-bromopyrazine-2-carboxamide (220 mg, 0.447 mmol), bis(pinacolato)diboron (142 mg, 0.559 mmol), KOAc (79 mg, 0.804 mmol) and PdCl2(dppf) (16.35 mg, 0.022 mmol) in dioxane (2.5 mL) was degassed and flushed with nitrogen (two times), and was heated at 80° C. for 3 h. The reaction mixture was cooled to rt, diluted with 30 mL of DCM and filtered through celite. The filtrate was then diluted with 60 mL of heptane, and then concentrated to ½ volume. The mixture was filtered, the solid was washed with heptane (3×20 mL) and dried under vacuum which gave tert-butyl (1-(2-(3-amino-6-(4,4,5,5-tetramethyl-1,3,2-dioxaborolan-2-yl)pyrazine-2-carboxamido)pyridin-3-yl)piperidin-4-yl)carbamate (173 mg, 0.321 mmol) in 71% yield. LC-MS (acidic method)::ret.time=0.91 min, M+H=458.4.

Step 3. Synthesis of tert-butyl (1-(2-(3-amino-6-(6-morpholino-3-(trifluoromethyl)pyridin-2-yl)pyrazine-2-carboxamido)pyridin-3-yl)piperidin-4-yl)carbamate

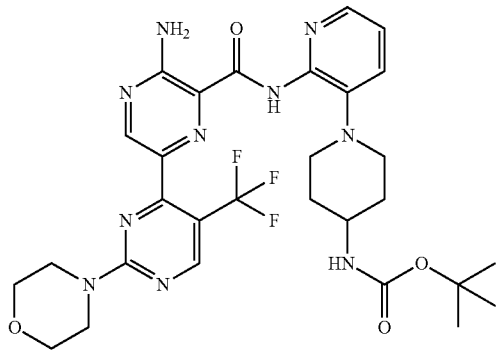 [SMILES: CC(C)(C)OC(=O)NC1CCN(c2cccnc2NC(=O)c2nc(-c3nc(N4CCOCC4)ncc3C(F)(F)F)cnc2N)CC1]

In a 15 mL round-bottom flask equipped with a magnetic stirrer, a solution of tert-butyl (1-(2-(3-amino-6-(6-morpholino-3-(trifluoromethyl)pyridin-2-yl)pyrazine-2-carboxamido)pyridin-3-yl)piperidin-4-yl)carbamate (316 mg, 0.497 mmol), 4-(6-chloro-5-(trifluoromethyl)pyridin-2-yl)morpholine (190 mg, 0.710 mmol), $K_3PO_4$ (1M) (0.923 ml, 0.923 mmol) and $PdCl_2$(dppf) (41.6 mg, 0.057 mmol). in dioxane (6 mL) was degassed and flushed with nitrogen (two times). After being stirred at 80° C. for 2 h., the reaction was cooled to rt. The reaction mixture was added to water (100 mL) and extracted with EtOAc (3×50 mL), then dried over $Na_2SO_4$ and concentrated. The crude product was purified by HPLC (acidic method 3) which gave tert-butyl (1-(2-(3-amino-6-(6-morpholino-3-(trifluoromethyl)pyridin-2-yl)pyrazine-2-carboxamido)pyridin-3-yl)piperidin-4-yl)carbamate (62 mg, 0.096 mmol) 13% yield.

LC-MS (acidic method): ret.time=1.18 min, M+H=645.7.

Step 4. Synthesis of 3-amino-N-(3-(4-aminopiperidin-1-yl)pyridin-2-yl)-6-(6-morpholino-3-(trifluoromethyl)pyridin-2-yl)pyrazine-2-carboxamide

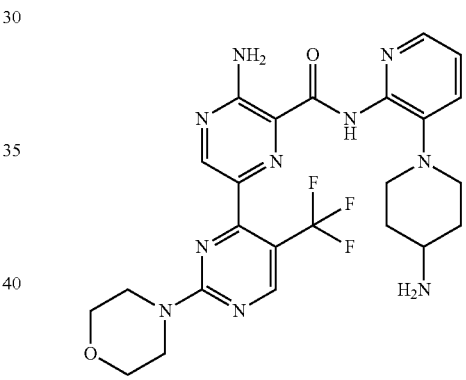

In a 100 mL round-bottom flask equipped with a magnetic stirrer, TFA (0.370 mL, 4.81 mmol) was cooled to −20° C., a solution of 3-amino-N-(3-(4-aminopiperidin-1-yl)pyridin-2-yl)-6-(6-morpholino-3-(trifluoromethyl)pyridin-2-yl)pyrazine-2-carboxamide (62 mg, 0.096 mmol) in DCM (2 mL) was added and was stirred at 25° C. for 45 min. The reaction mixture was concentrated. The crude product was purification by HPLC (basic method 3) which gave 3-amino-N-(3-(4-aminopiperidin-1-yl)pyridin-2-yl)-6-(6-morpholino-3-(trifluoromethyl)pyridin-2-yl)pyrazine-2-carboxamide (26.3 mg, 0.048 mmol) in 50% yield.

LC-MS (acidic method): ret.time=1.03 min, M+H=545.6 (M+H). $^1$H NMR (METHANOL-$d_4$) d: 8.89 (s, 1H), 8.76 (s, 1H), 8.12 (dd, J=4.9, 1.4 Hz, 1H), 7.63 (dd, J=8.0, 1.5 Hz, 1H), 7.20 (dd, J=7.9, 4.9 Hz, 1H), 3.89-4.02 (m, 4H), 3.78 (t, J=4.9 Hz, 4H), 3.07 (d, J=12.0 Hz, 2H), 2.52-2.79 (m, 3H), 1.79 (d, J=10.8 Hz, 2H), 1.18-1.44 (m, 2H).

Example 8

3-amino-N-(3-(4-aminopiperidin-1-yl)pyridin-2-yl)-6-(2-morpholino thiazol-4-yl)pyrazine-2-carboxamide

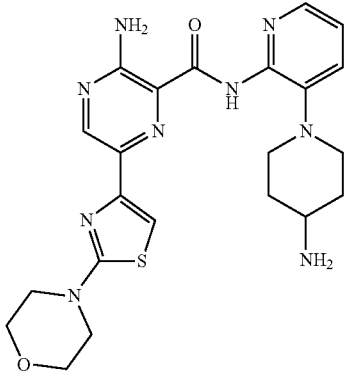 [SMILES: Nc1ncc(-c2csc(N3CCOCC3)n2)nc1C(=O)Nc1ncccc1N1CCC(N)CC1]

Step 1: Synthesis of tert-butyl (1-(2-(3-amino-6-(2-morpholinothiazol-4-yl) pyrazine-2-carboxamido)pyridin-3-yl)piperidin-4-yl)carbamate

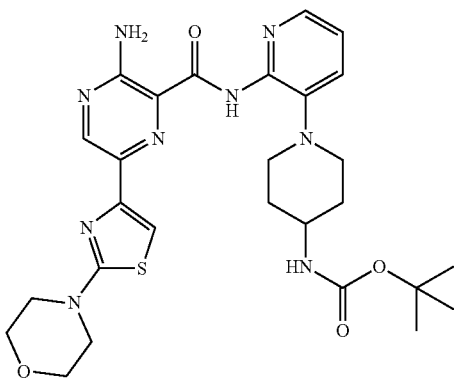 [SMILES: CC(C)(C)OC(=O)NC1CCN(c2cccnc2NC(=O)c2nc(-c3csc(N4CCOCC4)n3)cnc2N)CC1]

To a 25 mL round bottom flask was added (5-amino-6-((3-(4-(((tert-butoxycarbonyl)amino)piperidin-1-yl)pyridin-2-yl)carbamoyl)pyrazin-2-yl)boronic acid (0.36 g, 0.787 mmol), 4-(4-chlorothiazol-2-yl)morpholine (0.161 g, 0.787 mmol), Pd (dppe) dichloride (0.085 g, 0.116 mmol), potassium phosphate 1 M (1 mL) and a magnetic stirrer. The resultant mixture was degassed with nitrogen and then placed in an 80° C. preheated oil bath and heated for 2 hours. The reaction was removed from heat, cooled and then poured into 100 ml of dichloromethane. Magnesium sulfate was added to dry the reaction, followed by filtration and concentration to a thick residue. The residue was chromatographed on silica gel using ethyl acetate and heptane which gave tert-butyl (1-(2-(3-amino-6-(2-morpholinothiazol-4-yl)pyrazine-2-carboxamido)pyridin-3-yl)piperidin-4-yl)carbamate (0.187 g, 0.289 mmol) in 37% yield.

LC-MS (basic method): ret.time=1.30 min, M+H=582.5.

Step 2: Synthesis of 3-amino-N-(3-(4-aminopiperidin-1-yl)pyridin-2-yl)-6-(2-morpholinothiazol-4-yl)pyrazine-2-carboxamide

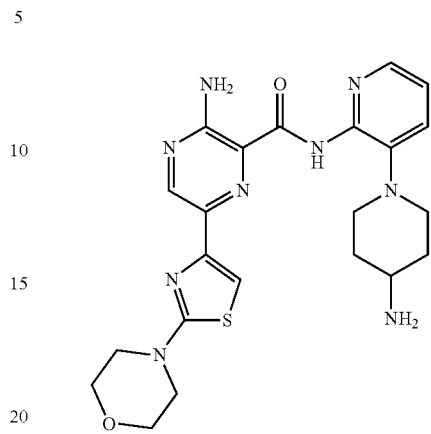

To a 100 mL flask was added a magnetic stirrer, tert-butyl (1-(2-(3-amino-6-(2-morpholinothiazol-4-yl)pyrazine-2-carboxamido)pyridin-3-yl)piperidin-4-yl)carbamate (0.113 g, 0.194 mmol) and dichloromethane (5 mL). The mixture was stirred until all solids dissolved and then cooled in an ice water bath under nitrogen. To this mixture was added trifluoroacetic acid (15 mL). The ice bath was removed and the mixture was stirred for 3 hours at room temperature. The mixture was then concentrated and the residue was then co-evaporated with toluene (30 mL) 3 times to a thick residue. The residue was purified by method 3, which gave 3-amino-N-(3-(4-aminopiperidin-1-yl)pyridin-2-yl)-6-(2-morpholinothiazol-4-yl)pyrazine-2-carboxamide (0.026 g, 0.052 mmol) in 27% yield.

LC-MS (Basic method): ret.time=1.16 min, M+H=482.6.
$^1$H NMR (400 MHz, Chloroform-d) δ 10.97 (s, 2H), 8.85 (s, 2H), 8.23 (d, J=4.8 Hz, 2H), 7.36 (d, J=8.0 Hz, 3H), 7.22 (d, J=18.0 Hz, 4H), 7.03-6.95 (m, 3H), 3.83-3.76 (m, 10H), 3.62 (s, OH), 3.53-3.45 (m, 10H), 3.08 (d, J=11.5 Hz, 5H), 2.74 (s, 2H), 2.66 (t, J=11.8 Hz, 6H), 1.89 (d, J=12.7 Hz, 5H), 1.54 (d, J=11.9 Hz, 6H), 1.46 (s, 8H), 1.18 (s, 5H).

Example 9

3-amino-N-(3-(4-amino-4-methylpiperidin-1-yl)pyridin-2-yl)-6-(3-(trifluoromethyl)pyridin-2-yl)pyrazine-2-carboxamide

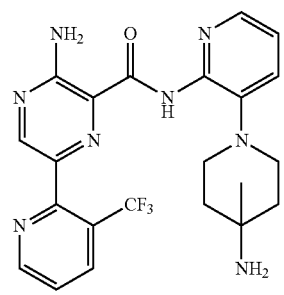

Step 1: Synthesis of tert-butyl (4-methyl-1-(2-nitro-pyridin-3-yl)piperidin-4-yl)carbamate

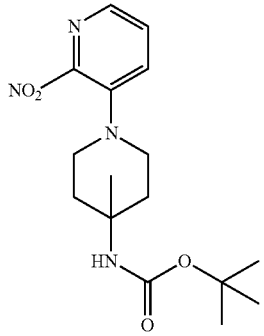

To a solution of 3-fluoro-2-nitropyridine (11.2 g, 81 mmol) in dioxane (200 mL) was added tert-butyl (4-methylpiperidin-4-yl)carbamate (26 g, 121 mmol). Huenig's Base (28.3 mL, 162 mmol) was added and the mixture was heated to 85° C. for 18 hrs. The reaction was cooled to RT and concentrated to give a brown solid. The solids were washed with 200 mL of 4:1 heptane:EtOAc. Slurry was concentrated to half volume and filtered to collect (26.2 g, 78 mmol, 96%) brown solid. LC-MS (Acidic Method): ret. time=1.46 min, M+H=337.4

Step 2: Synthesis of tert-butyl (4-methyl-1-(2-nitro-pyridin-3-yl)piperidin-4-yl)carbamate

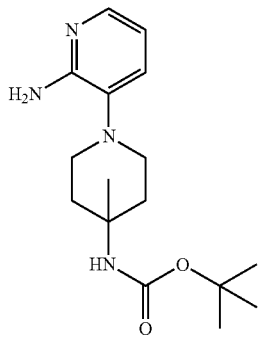

To a solution of tert-butyl (4-methyl-1-(2-nitropyridin-3-yl)piperidin-4-yl)carbamate (11.6 g, 37.2 mmol) in ethyl acetate (200 mL). 10% Pd—C (3.48 g) was added and stirred under H$_2$ balloon pressure at RT for 4 h. A small amount of MgSO$_4$ was added to the reaction and then the reaction mixture was filtered through a pad of cellite, then washed with ethyl acetate (100 mL) and the filtrate was concentrated to afford a brown solid (8.54 g, 27.9 mmol, 85%). LC-MS (Acidic Method): ret.time=0.91 min, M+H=307.4.

Step 3: Synthesis of tert-butyl (1-(2-(3-amino-6-(3-(trifluoromethyl)pyridin-2-yl)pyrazine-2-carboxamido)pyridin-3-yl)-4-methylpiperidin-4-yl)carbamate

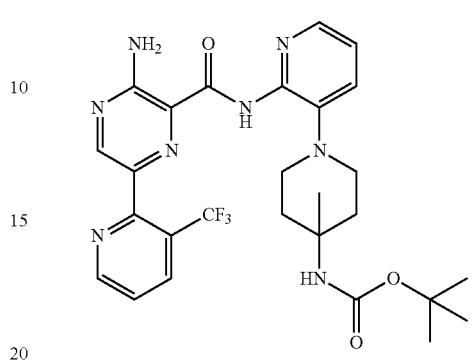

To a solution of 3-amino-6-(3-(trifluoromethyl)pyridin-2-yl)pyrazine-2-carboxylic acid in dimethyl formamide (125 mL) was added ((1H-benzo[d][1,2,3]triazol-1-yl) oxy) tris (dimethylamino) phosphonium hexafluorophosphate(V) (1.8 g, 4.24 mmol) and 4-methylmorpholine (1 mL, 9.79 mmol). Reaction stirred at RT for 40 minutes. Tert-butyl (1-(2-aminopyridin-3-yl)-4-methylpiperidin-4-yl) carbamate in dimethylformamide (25 mL) was added and reaction stirred for 16 hrs at RT. The reaction mixture was diluted with EtOAc and was washed with NaHCO$_3$(aq) (3×200 mL) and brine (1x 200 mL). The organic phase was dried with Na$_2$SO$_4$, filtered and concentrated. The crude product was taken up in acetonitrile (30 mL) and mixture was allowed to stand at RT for a period of time. Yellow solid collected by filtration (1.39 g, 74%). LC-MS (Acidic Method): ret. time=1.13 min, M+H=573.3.

Step 4: Synthesis of 3-amino-N-(3-(4-amino-4-methylpiperidin-1-yl)pyridin-2-yl)-6-(3-(trifluoromethyl)pyridin-2-yl)pyrazine-2-carboxamide

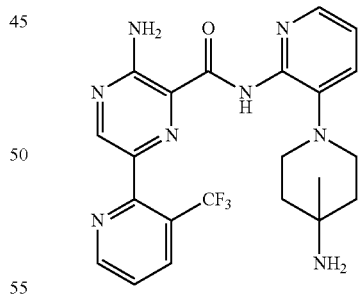

A solution of tert-butyl (1-(2-(3-amino-6-(3-(trifluoromethyl)pyridin-2-yl)pyrazine-2-carboxamido)pyridin-3-yl)-4-methylpiperidin-4-yl)carbamate (1.39 g, 2.06 mmol) in dichloromethane (10 mL) was cooled to 0° C. 2,2,2-trifluoroacetic acid (2.4 ml, 31 mmol) was added dropwise to the solution. The mixture was allowed to warm to 22° C. and stirred for 4 hrs. Reaction mixture was concentrated to remove DCM and excess TFA. A red oil was produced, which was taken up in 100 mL CHCl$_3$/IPA 3:1 and saturated aq. NaHCO$_3$ was added to neutralize the solution. The mixture was then stirred at 22° C. for 16 hrs. The mixture transferred to separatory funnel and aqueous layers were washed with CHCl₃/IPA 3:1 (3×100 mL). Combined organic phases were dried with Na₂SO₄, filtered and concentrated to afford a yellow solid. The crude product was recrystallized from acetonitrile. A yellow solid was collected by filtration (0.82 g, 83%). LC-MS (Acidic Method): ret.time=0.75 min, M+H=473.2. ¹H NMR (400 MHz, Methanol-d₄) δ 8.92 (dd, J=5.1, 1.4 Hz, 1H), 8.68 (s, 1H), 8.47-8.27 (m, 1H), 8.12 (dd, J=4.9, 1.6 Hz, 1H), 7.83-7.50 (m, 2H), 7.18 (dd, J=7.9, 4.9 Hz, 1H), 3.02-2.65 (m, 4H), 1.54-1.24 (m, 4H), 0.74 (s, 3H).

Example 10

3-amino-N-(3-(4-amino-4-methylpiperidin-1-yl)pyridin-2-yl)-6-(3-(trifluoromethoxy)pyridin-2-yl)pyrazine-2-carboxamide

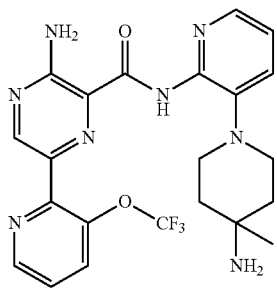 [SMILES: CC1(N)CCN(c2cccnc2NC(=O)c2nc(-c3ncccc3OC(F)(F)F)cnc2N)CC1]

The 3-amino-N-(3-(4-amino-4-methylpiperidin-1-yl)pyridin-2-yl)-6-(3-(trifluoromethoxy)pyridin-2-yl)pyrazine-2-carboxamide was prepared in a manner as described for Example 1, Method 1 (1.41 g) in 77% yield. LC-MS (acidic method): ret.time=1.0 min, M+H=489.1 ¹H NMR (400 MHz, Methanol-d₄) δ 8.81 (s, 1H), 8.73 (dd, J=4.7, 1.3 Hz, 1H), 8.13 (dd, J=4.9, 1.6 Hz, 1H), 8.01 (dp, J=8.4, 1.4 Hz, 1H), 7.75-7.54 (m, 2H), 7.19 (dd, J=7.9, 4.9 Hz, 1H), 3.04-2.74 (m, 4H), 1.67-1.35 (m, 4H), 0.82 (s, 3H).

Example 11

3-amino-N-(3-(4-amino-4-methylpiperidin-1-yl)pyridin-2-yl)-6-(2-morpholino-5-(trifluoromethyl)pyrimidin-4-yl)pyrazine-2-carboxamide

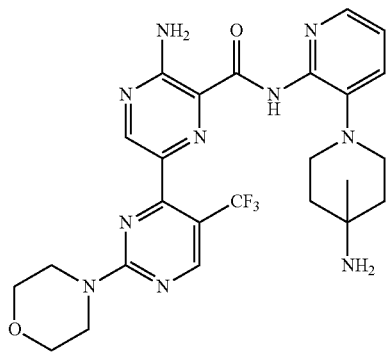

Step 1: Synthesis of 4-(4-chloro-5-(trifluoromethyl)pyrimidin-2-yl)morpholine

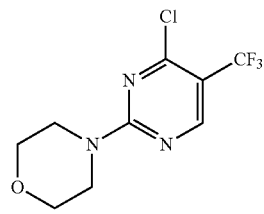 [SMILES: FC(F)(F)c1cnc(N2CCOCC2)nc1Cl]

To a round bottom flask was added morpholine (0.897 g, 10.3 mmol), and a solution of dichloroethane-tert-butanol (1:1, 30 mL) stirred under nitrogen and cooled in an ice water bath. To this mixture was added zinc chloride (5.45 g, 40 mmol) in one portion and stirred for 30 minutes followed by the addition of 2,4-dichloro-5-(trifluoromethyl)pyrimidine (2.17 g, 10 mmol). The resultant solution was stirred at ice water bath temperature followed by the fast dropwise addition of N-ethyl-N-isopropylpropan-2-amine. The reaction was kept stirred at ice water bath temperature for 2 hours and then allowed to warm to room temperature and stirred for an additional 18 hours. Poured reaction into 200 mL of DCM, stirred and filtered. The filtrate was concentrated and chromatographed on silica gel using ethyl acetate heptane which yielded 4-(4-chloro-5-(trifluoromethyl)pyrimidin-2-yl)morpholine (2.1 g, 7.61 mmol) in 76% yield. LC-MS (basic method): ret.time=1.40 min, M+H=268.4.

Step 2: Synthesis of tert-butyl (1-(2-(3-amino-6-(2-morpholino-5-(trifluoromethyl) pyrimidin-4-yl)pyrazine-2-carboxamido)pyridin-3-yl)-4-methylpiperidin-4-yl) carbamate

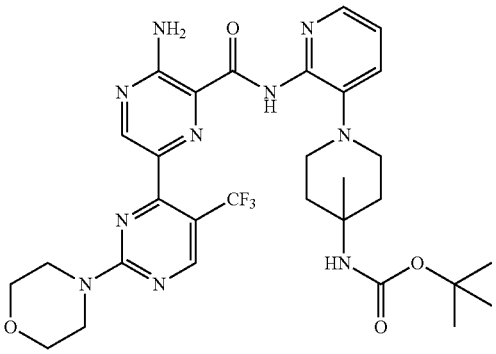

To a 10 mL screw cap vial was added 3-amino-6-(2-morpholino-5-(trifluoromethyl)pyrimidin-4-yl)pyrazine-2-carboxylic acid (0.104 g, 0.281 mmol), which was prepared in analogy to Example 4, DMF (2 ml), N-ethyl-N-isopropylpropan-2-amine (0.12 mL, 0.689 mmol) and 2-(1H-benzo[d][1,2,3]triazol-1-yl)-1,1,3,3-tetramethylisouronium hexafluorophosphate(V) (0.128 g, 0.337 mmol). The mixture was stirred for 1 hour. To the resultant mixture was added tert-butyl (1-(2-aminopyridin-3-yl)-4-methylpiperidin-4-yl)carbamate (0.095 g, 0.309 mmol) and was stirred for 20 hours. The reaction was concentrated and tert-butyl (1-(2-(3-amino-6-(2-morpholino-5-(trifluoromethyl)pyrimidin-4-yl)pyrazine-2-carboxamido)pyridin-3-yl)-4-methylpiperidin-4-yl)carbamate was obtained in 14% yield and used directly. LC-MS (basic method): ret.time=1.46 min, M+H=659.4.

Step 3: Synthesis of 3-amino-N-(3-(4-amino-4-methylpiperidin-1-yl)pyridin-2-yl)-6-(2-morpholino-5-(trifluoromethyl)pyrimidin-4-yl)pyrazine-2-carboxamide

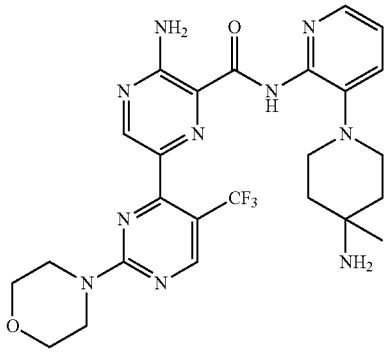 [SMILES: CC1(N)CCN(c2cccnc2NC(=O)c2nc(-c3nc(N4CCOCC4)ncc3C(F)(F)F)cnc2N)CC1]

To a 25 mL flask was added tert-butyl (1-(2-(3-amino-6-(2-morpholino-5-(trifluoromethyl)pyrimidin-4-yl)pyrazine-2-carboxamido)pyridin-3-yl)-4-methylpiperidin-4-yl)carbamate (0.185 g, 0.281 mmol) and dichloromethane (10 mL) which was then stirred and cooled in an ice water bath under nitrogen. To this resultant mixture was added trifluoroacetic acid (20 mL) and stirred and then allowed to warm to room temperature. The mixture was stirred for two and one half hours. The mixture was then concentrated and then coevaporated with toluene (30 mL). This coevaporation was done three times. The mixture was then chromatographed by HPLC method 4. The resultant solid was then triturated with hot water, allowed to cool. The solid material obtained was filtered and dried to a constant weight which gave 3-amino-N-(3-(4-amino-4-methylpiperidin-1-yl)pyridin-2-yl)-6-(2-morpholino-5-(trifluoromethyl)pyrimidin-4-yl)pyrazine-2-carboxamide (0.0104 g, 0.281 mmol) in 14% yield. LC-MS (basic method): ret.time=1.15 min, M+H=559.4. 1H NMR (400 MHz, Chloroform-d) δ 10.55 (s, 1H), 8.84 (s, 1H), 8.69 (s, 1H), 8.29 (dd, J=4.9, 1.6 Hz, 1H), 7.45 (dd, J=8.0, 1.7 Hz, 1H), 7.32 (s, 0H), 7.10 (dd, J=7.8, 4.8 Hz, 1H), 5.64 (d, J=81.5 Hz, 1H), 5.32 (s, 1H), 3.97 (t, J=4.8 Hz, 4H), 3.81 (t, J=4.7 Hz, 4H), 3.06-2.75 (m, 4H), 1.61 (ddd, J=13.5, 9.3, 4.0 Hz, 2H), 1.42 (dt, J=13.3, 3.9 Hz, 2H), 1.26 (s, 4H), 0.97 (s, 3H), 0.94-0.76 (m, 1H).

Example 12

3-amino-N-(3-(4-amino-4-methylpiperidin-1-yl)pyridin-2-yl)-6-(6-fluoro-2-methylquinazolin-4-yl)pyrazine-2-carboxamide

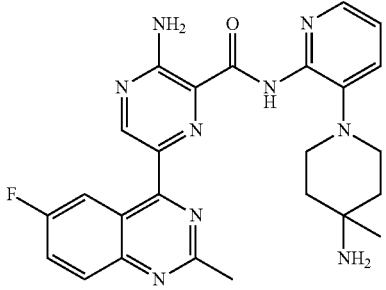 [SMILES: Cc1nc(-c2cnc(N)c(C(=O)Nc3ncccc3N3CCC(C)(N)CC3)n2)c2cc(F)ccc2n1]

Step 1: tert-butyl (1-(2-(3-amino-6-(6-fluoro-2-methylquinazolin-4-yl)pyrazine-2-carboxamido)pyridin-3-yl)-4-methylpiperidin-4-yl)carbamate

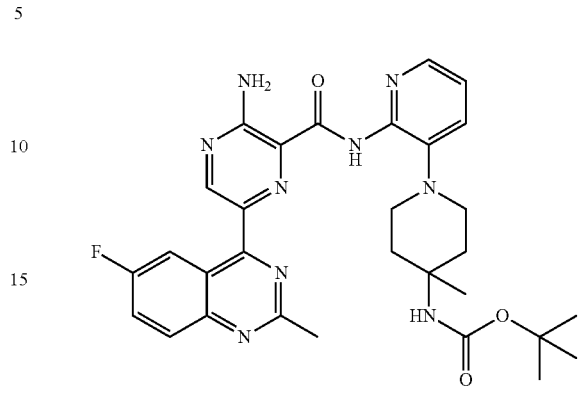

The mixture of tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate (293 mg, 0.529 mmol), (4-chloro-5-fluoro-7H-pyrrolo[2,3-d]pyrimidine (125 mg, 0.637 mmol) and K₃PO₄ (1591 μl, 1.591 mmol, 1M aq. solution) in dioxane (2 mL) was degassed with N₂ stream for 10 min. Then PdCl₂(dppf) (19.41 mg, 0.027 mmol) was added. The reaction mixture was degassed for 5 min and then was heated at 80° C. under N₂ atmosphere for 5 h. The reaction mixture was cooled to RT and filtered through Celite pad and washed with DCM. The filtrate was added water and DCM. The aqueous phase was further extracted with DCM 2×. The combined DCM phases were concentrated under vacuum. The residue was dissolved in MeOH and several drops of water, then filtered. The resulting solution was then separated with prep-HPLC (C-18 column, 25-50% ACN/H₂O w/0.1% TFA). The desired fractions were combined and then DCM and 2M Na₂CO₃ aq. Solution were further added to make aqueous phase pH 8. The aq. phase was extracted with DCM 2×. The combined DCM phases were evaporated to provide 141 mg (69% yield) as tert-butyl (1-(2-(3-amino-6-(6-fluoro-2-methylquinazolin-4-yl)pyrazine-2-carboxamido)pyridin-3-yl)-4-methylpiperidin-4-yl)carbamate. LC/MS: m/z M+H=588.6

Step 2: 3-amino-N-(3-(4-amino-4-methylpiperidin-1-yl)pyridin-2-yl)-6-(6-fluoro-2-methylquinazolin-4-yl)pyrazine-2-carboxamide

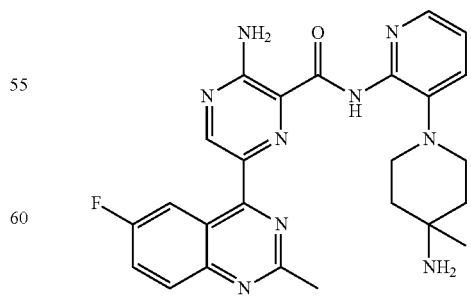

To a solution of TFA (336 μL, 4.36 mmol) in DCM (1 mL) at 0° C. was added tert-butyl (1-(2-(3-amino-6-(6-fluoro-2-methylquinazolin-4-yl)pyrazine-2-carboxamido)pyridin-3- yl)-4-methylpiperidin-4-yl)carbamate (128 mg, 0.218 mmol) in DCM (2 mL). The reaction mixture was concentrated under vacuum. The residue was diluted with DCM and water, and then 2N Na₂CO₃ was added to achieve pH 12 of the aqueous phase. The basic aqueous phase was extracted by DCM 3×. The combined organic phases were concentrated. The residue was dissolved in MeOH/MeCN and then separated by prep-HPLC(C-18 column, 10-30% ACN/H₂O w/0.1% TFA). The desired fractions were combined and 2N Na₂CO₃ was added to achieve pH 11. The resulting basic solution was extracted by DCM 3×. The combined DCM phases were concentrated under vacuum, which provided 74 mg (70% yield) 3-amino-N-(3-(4-amino-4-methylpiperidin-1-yl)pyridin-2-yl)-6-(6-fluoro-2-methylquinazolin-4-yl)pyrazine-2-carboxamide. LC/MS: m/z M+H=488.2 ¹H NMR (METHANOL-d₄) δ: 9.15 (s, 1H), 8.52 (dd, J=9.7, 2.9 Hz, 1H), 8.17 (dd, J=5.0, 1.5 Hz, 1H), 8.10 (dd, J=9.3, 5.3 Hz, 1H), 7.87 (ddd, J=9.2, 8.2, 2.9 Hz, 1H), 7.68 (dd, J=7.9, 1.6 Hz, 1H), 7.21 (dd, J=7.9, 4.9 Hz, 1H), 3.37 (s, 2H), 2.93 (s, 3H), 2.80-2.90 (m, 2H), 2.68-2.78 (m, 2H), 0.98-1.07 (m, 2H), 0.87-0.97 (m, 2H), 0.42 (s, 3H)

Example 13

3-amino-N-(3-(4-amino-4-methylpiperidin-1-yl) pyridin-2-yl)-6-(4-methoxy-3-(trifluoromethyl)pyridin-2-yl)pyrazine-2-carboxamide

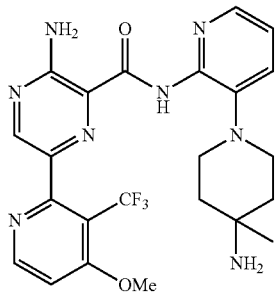

1) Synthesis of 3-amino-6-(4-methoxy-3-(trifluoromethyl)pyridin-2-yl)pyrazine-2-carboxylic acid

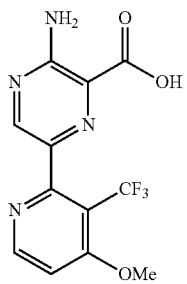 [SMILES: COc1ccnc(-c2cnc(N)c(C(=O)O)n2)c1C(F)(F)F]

Step 1. Synthesis of methyl 3-amino-6-(4,4,5,5-tetramethyl-1,3,2-dioxaborolan-2-yl)pyrazine-2-carboxylate

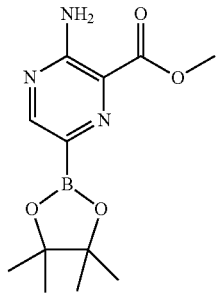

A mixture of methyl 3-amino-6-bromopyrazine-2-carboxylate (8.8 g, 38 mmol), 4,4,4',4',5,5,5',5'-octamethyl-2,2'-bi(1,3,2-dioxaborolane) (9.6 g, 38 mmol), and potassium acetate (11 g, 110 mmol) in dioxane (200 mL) was degassed and then added [1,1'-bis(diphenylphosphino)ferrocene]dichloropalladium(II) (1.4 g, 1.9 mmol). The resulting mixture was stirred and heated at 80° C. under nitrogen atmosphere for 15 h. Additional ore 4,4,4',4',5,5,5',5'-octamethyl-2,2'-bi (1,3,2-dioxaborolane) (1.9 g, 7.6 mmol) was added and the reaction mixture was heated for another 3 h. the reaction mixture was cooled to room temperature and the mixture was diluted with dichloromethane and filtered through a pad of diatomaceous earth. The filtrate was concentrated at reduced pressure and purified by silica gel chromatography with a gradient from 0%-10% methanol in dichloromethane to afford the desired product as brown solid (9.5 g, 90% yield). LC-MS (acidic method) ret.time=0.42 min, M+H=198.1 (LC-MS acidic method).

Step 2. Synthesis of 2-bromo-4-methoxy-3-(trifluoromethyl)pyridine

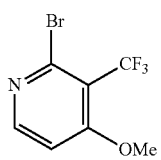

A mixture of 2-bromo-4-chloro-3-(trifluoromethyl)pyridine (200 mg, 0.768 mmol) and aqueous sodium hydroxide (6 N, 0.640 mL) in methanol (7 mL) was stirred at room temperature for 2 h. The mixture was extracted with ethyl acetate (3×10 mL) and the combined organic layers were dried over sodium sulfate, filtered and concentrated in vacuo to obtain 165 mg, 84% yield) of a white powder. LC-MS (acidic method): ret.time=1.11 min, M+H=257.9.

Step 3. Synthesis of methyl 3-amino-6-(4-methoxy-3-(trifluoromethyl)pyridin-2-yl)pyrazine-2-carboxylate

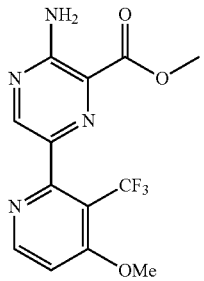

A solution of methyl 3-amino-6-(4,4,5,5-tetramethyl-1,3,2-dioxaborolan-2-yl)pyrazine-2-carboxylate (180 mg, 0.645 mmol), 2-bromo-4-methoxy-3-(trifluoromethyl)pyridine (165 mg, 0.645 mmol), and 1M potassium phosphate (0.838 mL, 0.838 mmol) in tetrahydrofuran (4 mL) was degassed under vacuum for 10 min, and then was added chloro(2-dicyclohexylphosphino-2',4',6'-triisopropyl-1,1'-biphenyl)[2-(2'-amino-1,1'-biphen-yl)palladium (II) (25 mg, 0.032 mmol). The mixture was heated at 50° C. under nitrogen atmosphere for 3 h. The reaction was cooled to room temperature and diluted with ethyl acetate. The aqueous layer was added sat. ammonium chloride and back extracted with more ethyl acetate. The combined organic solution was purified by silica gel chromatography with a gradient from 0%-100% ethyl acetate in heptane to afford the desired product as white solid (14 mg, 7% yield). LC-MS (Acidic method): ret.time=0.92 min, M+H=329.3.

Step 4. Synthesis of 3-amino-6-(4-methoxy-3-(trifluoromethyl)pyridin-2-yl)pyrazine-2-carboxylic acid

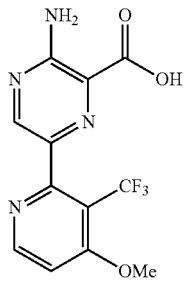

A mixture of methyl 3-amino-6-(4-methoxy-3-(trifluoromethyl)pyridin-2-yl)pyrazine-2-carboxylate (14 mg, 0.043 mmol) and aqueous sodium hydroxide (6 N, 0.071 mL, 0.43 mmol) in methanol (3 mL) was stirred at room temperature for 5 h. Then it was heated at 60° C. for 1 h. Adjust pH to 5 by using conc. HCl. The solution was concentrated in vacuo to obtain a white powder. It was used in the next step without further purification. LC-MS (acidic method): ret.time=0.81 min, M+H=315.0.

2) Synthesis of 3-amino-N-(3-(4-amino-4-methylpiperidin-1-yl)pyridin-2-yl)-6-(4-methoxy-3-(trifluoromethyl)pyridin-2-yl)pyrazine-2-carboxamide

Step 1. Synthesis of tert-butyl (4-methyl-1-(2-nitropyridin-3-yl)piperidin-4-yl)carbamate

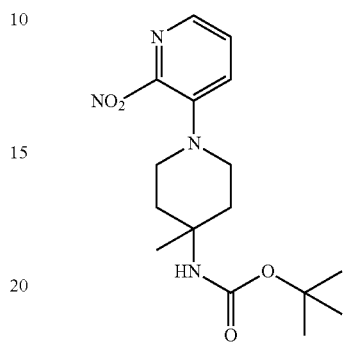

A mixture of 3-fluoro-2-nitropyridine (550 mg, 3.87 mmol), tert-butyl (4-methylpiperidin-4-yl)carbamate (871 mg, 4.06 mmol), and triethylamine (1.61 ml, 11.6 mmol) in dioxane (10 mL) was heated to 100° C. for 6 h. The mixture was cooled and concentrated to a thick residue. The residue was diluted with water and extracted with dichloromethane (3×20 mL). The combined organic layer was purified by silica gel chromatography with a gradient from 0%-100% ethyl acetate in heptane to afford the desired product as yellow solid (1.3 g, 100% yield). LC-MS (Basic Method): ret.time=1.28 min, M+H=337.2.

Step 2. Synthesis of tert-butyl (1-(2-aminopyridin-3-yl)-4-methylpiperidin-4-yl)carbamate

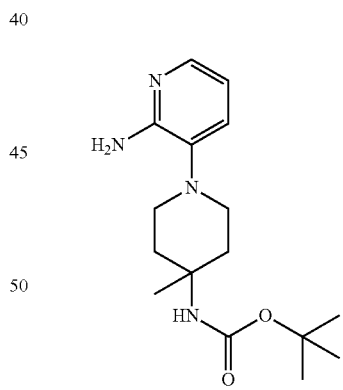

To a solution of tert-butyl (4-methyl-1-(2-nitropyridin-3-yl)piperidin-4-yl)carbamate (550 mg, 1.64 mmol) in ethanol (10 mL) was added Pd/C (17 mg, 10% Pd on charcoal wet). The resultant mixture was stirred under an atmosphere of hydrogen until all tert-butyl (4-methyl-1-(2-nitropyridin-3-yl)piperidin-4-yl)carbamate was consumed. The reaction was then purged with nitrogen. The mixture was then filtered through a pad of celite. The filter pad was washed with excess DMC. The filtrate was concentrated to a thick residue which solidified under vacuum. The solid was dried to a constant weight and used directly (500 mg, 100% yield). LC-MS (Basic Method): ret.time=0.78 min, M+H=308.3.

Step 3. Synthesis of tert-butyl (1-(2-(3-amino-6-(4-methoxy-3-(trifluoromethyl)pyridin-2-yl)pyrazine-2-carboxamido)pyridin-3-yl)-4-methylpiperidin-4-yl) carbamate

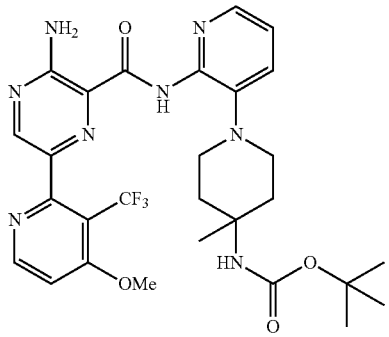 [SMILES: COc1ccnc(-c2cnc(N)c(C(=O)Nc3ncccc3N3CCC(C)(NC(=O)OC(C)(C)C)CC3)n2)c1C(F)(F)F]

A mixture of 3-amino-6-(4-methoxy-3-(trifluoromethyl)pyridin-2-yl)pyrazine-2-carboxylic acid (14 mg, 0.043 mmol), tert-butyl (1-(2-aminopyridin-3-yl)-4-methylpiperidin-4-yl)carbamate (13 mg, 0.043 mmol), N-ethyl-N-isopropylpropan-2-amine (0.019 mL, 0.11 mmol), and (1-cyano-2-ethoxy-2-oxoethylidenaminooxy)dimethylaminomorpholino-carbenium hexafluorophosphate (COMU) (44 mg, 0.10 mmol) in dimethylformamide (0.4 ml) was stirred under nitrogen atmosphere at room temperature for 60 h. The residue was concentrated to a dark solid which was purified by HPLC (Sunfire 30×50 mm 5 μm column ACN/H2O w/0.1% TFA 75 mL/min., 0.5 mL injection) to afford a yellow solid (25 mg, 81% yield). LC-MS (Basic Method): ret.time=1.18 min, M+H=603.2.

Step 4. Synthesis of 3-amino-N-(3-(4-amino-4-methylpiperidin-1-yl)pyridin-2-yl)-6-(4-methoxy-3-(trifluoromethyl)pyridin-2-yl)pyrazine-2-carboxamide

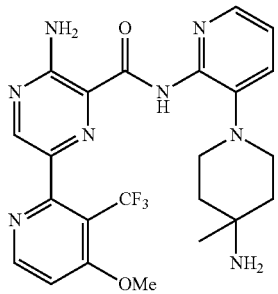 [SMILES: COc1ccnc(-c2cnc(N)c(C(=O)Nc3ncccc3N3CCC(C)(N)CC3)n2)c1C(F)(F)F]

A mixture of tert-butyl (1-(2-(3-amino-6-(4-methoxy-3-(trifluoromethyl)pyridin-2-yl)pyrazine-2-carboxamido)pyridin-3-yl)-4-methylpiperidin-4-yl)carbamate (25 mg, 0.041 mmol) and trifluoroacetic acid (0.32 mL, 4.2 mmol) in dichloromethane (2 mL) was stirred at room temperature for 12 h. The resultant residue was concentrated to a dark gum which was purified by HPLC (X-Bridge 30×50 mm 5 um column ACN/H$_2$O w/5 mM NH$_4$OH 75 mL/min. at 5 mL injection) to afford a yellow solid (5 mg, 23% yield). LC-MS (Basic method): ret.time=0.79 min, M+H=502.9. $^1$H NMR (400 MHz, METHANOL-d$_4$) δ ppm 8.70 (d, J=5.77 Hz, 1 H) 8.53 (s, 1 H) 8.11 (dd, J=5.02, 1.51 Hz, 1 H) 7.67 (dd, J=7.91, 1.63 Hz, 1 H) 7.40 (d, J=5.77 Hz, 1 H) 7.16 (dd, J=7.91, 4.89 Hz, 1 H) 4.08 (s, 3 H) 2.85-3.00 (m, 2 H) 2.72-2.85 (m, 2 H) 1.28-1.50 (m, 4 H) 0.81 (s, 3 H).

Example 14

3-amino-N-(3-(4-amino-4-methylpiperidin-1-yl)pyridin-2-yl)-6-(6-(3,3-difluoroazetidin-1-yl)-3-(trifluoromethyl)pyridin-2-yl)pyrazine-2-carboxamide

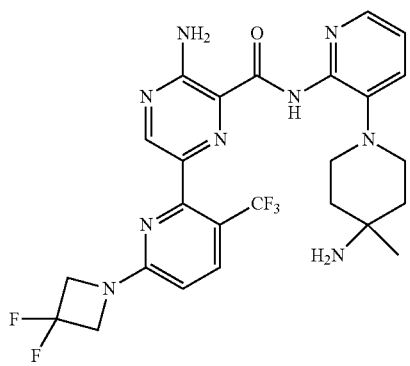 [SMILES: CC1(N)CCN(c2cccnc2NC(=O)c2nc(-c3nc(N4CC(F)(F)C4)ccc3C(F)(F)F)cnc2N)CC1]

Step 1. Synthesis of tert-butyl (1-(2-(3-amino-6-bromopyrazine-2-carboxamido)pyridin-3-yl)-4-methylpiperidin-4-yl)carbamate

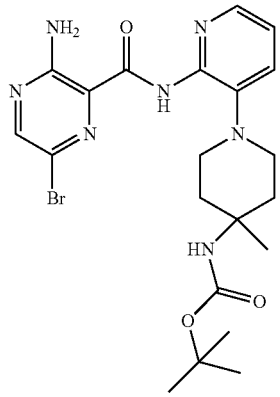 [SMILES: CC1(NC(=O)OC(C)(C)C)CCN(c2cccnc2NC(=O)c2nc(Br)cnc2N)CC1]

In a 100 mL round bottom flask equipped with a magnetic stirrer HBTU (2.23 gm, 5.87 mmol), 3-amino-6-bromopyrazine-2-carboxylic acid (1.17 gm, 5.39 mmol), and N-ethyl-N-isopropylpropan-2-amine (1.28 mL, 7.34 mmol) were allowed to stir in DMF (15 ml) for 15 minutes whereupon tert-butyl (1-(2-aminopyridin-3-yl)-4-methylpiperidin-4-yl)carbamate (1.5 gm, 4.9 mmol) was added in one portion. Reaction was allowed to stir for 16 hr. Reaction was then poured into DMF and extracted thrice with 50 mL ethyl acetate. Organic extracts were combined and dried with brine followed by anhydrous sodium sulfate. The residue was purified by silica gel using gradient chromotography ethanol—ethyl acetate 0-10% which yielded pure tert-butyl (1-(2-(3-amino-6-bromopyrazine-2-carboxamido)pyridin-3-yl)-4-methylpiperidin-4-yl)carbamate (1.86 gm, 67.5%

Step 2. Synthesis of tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate

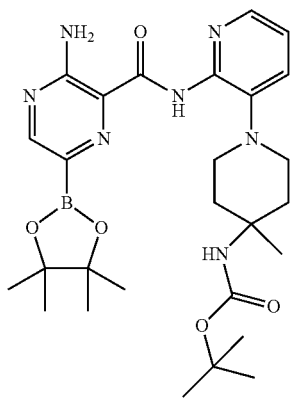 [SMILES: CC1(NC(=O)OC(C)(C)C)CCN(c2cccnc2NC(=O)c2nc(B3OC(C)(C)C(C)(C)O3)cnc2N)CC1]

In a 100 mL round-bottom flask equipped with a magnetic stirrer tert-butyl (1-(2-(3-amino-6-bromopyrazine-2-carboxamido)pyridin-3-yl)-4-methylpiperidin-4-yl)carbamate (1.9 gm, 3.7 mmol), bis(pinacolato)diboron (1 gm, 4 mmol) and potassium acetate (0.54 gm, 5.5 mmol) were suspended in dioxane (15 mL). The formed suspension was bubbled with nitrogen gas for minutes to remove dissolved oxygen. 1,1'-Bis(diphenylphosphino)ferrocene]dichloropalladium (II) (0.13 gm, 0.18 mmol) was then added and the reaction heated to 90° C. in an oil bath. After 3 hr volatiles were removed and the residue suspended in ethyl acetate which was washed with water to remove excess potassium acetate. The residue was dissolved into dichloromethane and triturated with heptane until solids formed which were filtered and washed with further portions of heptane to yield tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate (1.32 gm, 46% yield) as a brown powder of sufficient purity for further transformations. LC-MS (Acidic method): ret.time=0.91 min, M+H=554.4.

Step 3. Synthesis of 2-chloro-6-(3,3-difluoroazetidin-1-yl)-3-(trifluoromethyl)pyridine

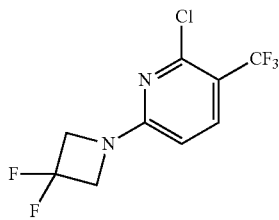 [SMILES: FC1(F)CN(c2ccc(C(F)(F)F)c(Cl)n2)C1]

In a 100 ml round bottom flask 2,6-dichloro-3-(trifluoromethyl)pyridine (1.25 gm, 5.79 mmol) was dissolved into DMF (30 mL) along with 3,3-difluoroazetidine (0.75 gm, 5.79 mmol) and N-ethyl-N-isopropylpropan-2-amine (1.5 ml, 8.7 mmol). After 16 hr the reaction was cooled, poured into water and extracted three times with 50 mL ethyl acetate. The combined organic layers were dried with brine and anhydrous sodium sulfate. Volatiles were removed and the residue purified by silica gel using gradient chromotography of 0-60% ethyl acetate in heptane to yield pure 2-chloro-6-(3,3-difluoroazetidin-1-yl)-3-(trifluoromethyl)pyridine (935 mg, 53% yield). LC-MS (Acidic method): ret.time=1.56 min, M+H=273.3.

Step 4. Synthesis of tert-butyl (1-(2-(3-amino-6-(6-(3,3-difluoroazetidin-1-yl)-3-(trifluoromethyl)pyridin-2-yl)pyrazine-2-carboxamido)pyridin-3-yl)-4-methylpiperidin-4-yl)carbamate

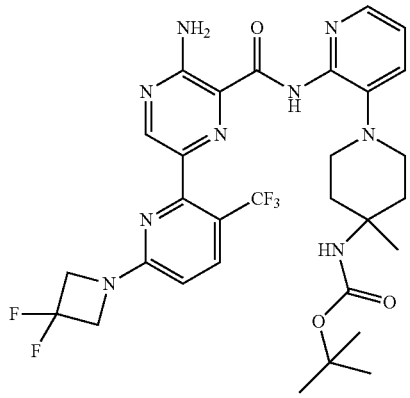 [SMILES: CC1(NC(=O)OC(C)(C)C)CCN(c2cccnc2NC(=O)c2nc(-c3nc(N4CC(F)(F)C4)ccc3C(F)(F)F)cnc2N)CC1]

In a 10 ml round bottom flask tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate (159 mg, 0.23 mmol) was combined with 2-chloro-6-(3,3-difluoroazetidin-1-yl)-3-(trifluoromethyl)pyridine (50 mg, 0.183 mmol) and dissolved into THF along with 1M aqueous tripotassium phosphate (0.3 ml, 0.3 mmol). Suspension was degassed by evacuating and purging with nitrogen three times then stirring under nitrogen for 15 minutes. 1,1'-Bis(diphenylphosphino)ferrocene]dichloropalladium (II) was added and then the reaction mixture was heated with a pre-heated oil bath to 50 C for 16 hr. The reaction volatiles were removed and the residue dissolved into DCM and filtered through celite. Volatiles were then removed and the residue purified by silica gel using gradient chromotography of 0-60% ethyl acetate in heptane to obtain pure desired tert-butyl (1-(2-(3-amino-6-(6-(3,3-difluoroazetidin-1-yl)-3-(trifluoromethyl)pyridin-2-yl)pyrazine-2-carboxamido)pyridin-3-yl)-4-methylpiperidin-4-yl)carbamate (70 mg, 54% yield). LC-MS (Acidic method): ret.time=1.27 min, M+H=664.7.

Step 5. Synthesis of 3-amino-N-(3-(4-amino-4-methylpiperidin-1-yl)pyridin-2-yl)-6-(6-(3,3-difluoroazetidin-1-yl)-3-(trifluoromethyl)pyridin-2-yl)pyrazine-2-carboxamide

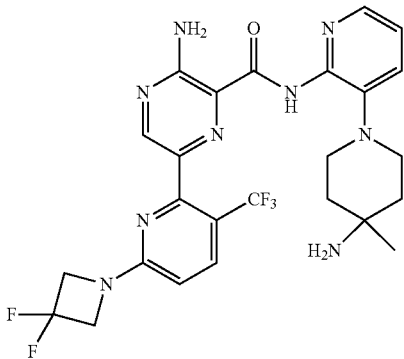 [SMILES: CC1(N)CCN(c2cccnc2NC(=O)c2nc(-c3nc(N4CC(F)(F)C4)ccc3C(F)(F)F)cnc2N)CC1]

Into a 10 mL round bottom flask tert-butyl (1-(2-(3-amino-6-(6-(3,3-difluoroazetidin-1-yl)-3-(trifluoromethyl)pyridin-2-yl)pyrazine-2-carboxamido)pyridin-3-yl)-4-methylpiperidin-4-yl)carbamate was dissolved into 1.5 mL dichloromethane and treated with 2,2,2-trifluoroacetic acid (0.2 ml, 2.2 mmol). After 16 hours the reaction was treated with saturated sodium bicarbonate solution until pH 9 was reached. A solid precipitate formed and slowly redissolved. The organic layer was separated then dried with brine, anhydrous sodium sulfate and then evaporated. The residue was purified by silica gel using gradient chromotography of 0-10% ethanol in ethylacetate to yield pure 3-amino-N-(3-(4-amino-4-methylpiperidin-1-yl)pyridin-2-yl)-6-(6-(3,3-difluoroazetidin-1-yl)-3-(trifluoromethyl)pyridin-2-yl)pyrazine-2-carboxamide (49 mg, 78% yield). LC-MS (Acidic method): ret.time=0.88 min, M+H=564.2. $^1$H NMR (400 MHz, Methanol-$d_4$) δ 8.64 (s, 1H), 8.11 (dd, J=5.0, 1.5 Hz, 1H), 8.03 (d, J=8.8 Hz, 1H), 7.65 (dd, J=7.9, 1.6 Hz, 1H), 7.17 (dd, J=7.9, 4.9 Hz, 1H), 6.72 (d, J=8.6 Hz, 1H), 4.51 (t, J=12.0 Hz, 4H), 2.99-2.74 (m, 4H), 1.52-1.33 (m, 4H), 0.81 (s, 3H).

Example 15

3-amino-N-(3-(4-amino-4-methylpiperidin-1-yl)pyridin-2-yl)-6-(6-cyclopropyl-3-(trifluoromethyl)pyridin-2-yl)pyrazine-2-carboxamide

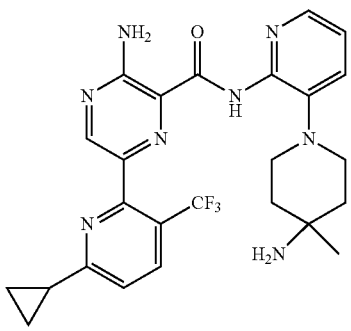 [SMILES: CC1(N)CCN(c2cccnc2NC(=O)c2nc(-c3nc(C4CC4)ccc3C(F)(F)F)cnc2N)CC1]

Step 1. Synthesis of 2-chloro-6-cyclopropyl-3-(trifluoromethyl)pyridine

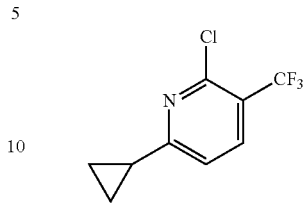

To a 100 mL round-bottom flask was added toluene (20 mL), 2,6-dichloro-3-(trifluoromethyl)pyridine (3 g, 13.8 mmol), cyclopropylboronic acid (1.3 g, 15.3 mmol), tricyclohexyl phosphine (0.39 g, 1.4 mmol), tribasic potassium phosphate (3.2 g, 15.3 mmol) and water (1 mL). Suspension was degassed by evacuating and purging with nitrogen three times then stirring under nitrogen for 15 minutes. Diacetoxypalladium (0.16 g, 0.7 mmol) was added and then the reaction mixture was heated with a pre-heated oil bath to 100° C. for 16 hours. After this time the reaction volatiles were removed, the residue dissolved into DCM, filtered and then purified by silica gel using gradient chromotography of 0-60% ethyl acetate in heptane to obtain the pure desired product 2-chloro-6-cyclopropyl-3-(trifluoromethyl)pyridine (2 gm, 59% yield). LC-MS (Acidic method): ret.time=1.61 min, M+H=222.2

Step 2. Synthesis tert-butyl (1-(2-(3-amino-6-(6-cyclopropyl-3-(trifluoromethyl) pyridin-2-yl)pyrazine-2-carboxamido)pyridin-3-yl)-4-methylpiperidin-4-yl) carbamate

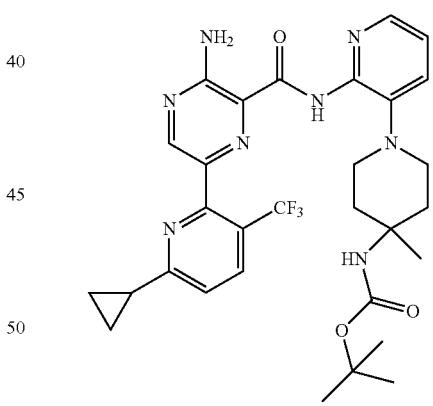

To a 10 mL round bottom flask equipped with a magnetic stirrer and purged with nitrogen was added 2-chloro-6-cyclopropyl-3-(trifluoromethyl)pyridine (50 mg, 0.23 mmol), dioxane (2 ml), tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate (156 mg, 0.23 mmol) and 1M aqueous tribasic potassium phosphate (0.29 mL, 0.29 mmol). The resultant mixture was stirred under an atmosphere of nitrogen in an oil bath at 90° C. until all 2-chloro-6-cyclopropyl-3-(trifluoromethyl)pyridine was consumed (16 hr). The mixture was then cooled and filtered through a pad of celite. The filter pad was washed with excess methylene chloride. The combined filtrates were concentrated to a thick residue and purified by silica gel using gradient chromatography of 0-75% ethyl acetate in heptane to yield (50 mg, 34% yield). LC-MS (Acidic method): ret.time=1.31 min, M+H=613.2.

Step 3. Synthesis of 3-amino-N-(3-(4-amino-4-methylpiperidin-1-yl)pyridin-2-yl)-6-(6-cyclopropyl-3-(trifluoromethyl)pyridin-2-yl)pyrazine-2-carboxamide

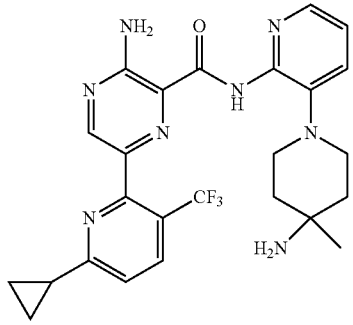 [SMILES: CC1(N)CCN(c2cccnc2NC(=O)c2nc(-c3nc(C4CC4)ccc3C(F)(F)F)cnc2N)CC1]

To a 10 mL flask was added tert-butyl (1-(2-(3-amino-6-(6-cyclopropyl-3-(trifluoromethyl)pyridin-2-yl)pyrazine-2-carboxamido)pyridin-3-yl)-4-methylpiperidin-4-yl)carbamate, dichloromethane (2 mL) and 2,2,2-trifluoroacetic acid (0.1 mL, 1.2 mmol). After 16 hrs the reaction was treated with excess saturated aqueous sodium bicarbonate solution until pH 9 was reached. The organic layer was separated, then dried with brine and anhydrous sodium sulfate. The impure final compound was purified by silica gel using gradient chromatography of 0-10% ethanol in ethyl acetate to yield pure 3-amino-N-(3-(4-amino-4-methylpiperidin-1-yl)pyridin-2-yl)-6-(6-cyclopropyl-3-(trifluoromethyl)pyridin-2-yl)pyrazine-2-carboxamide (41 mg, 93% yield). LC-MS (Acidic method): ret.time=1.22 min, M+H=513.2. $^1$H NMR (400 MHz, Methanol-$d_4$) δ 8.63 (s, 1H), 8.14-8.09 (m, 2H), 7.64 (dd, J=8.0, 1.6 Hz, 1H), 7.49 (d, J=8.2 Hz, 1H), 7.17 (dd, J=7.9, 4.9 Hz, 1H), 2.97-2.73 (m, 4H), 2.26 (ddd, J=7.7, 4.5, 2.5 Hz, 1H), 1.45-1.31 (m, 4H), 1.17-1.12 (m, 4H), 0.75 (s, 3H).

Example 16

3-amino-N-(3-(4-amino-4-methylpiperidin-1-yl)pyridin-2-yl)-6-(6-methoxy-3-(trifluoromethyl)pyridin-2-yl)pyrazine-2-carboxamide

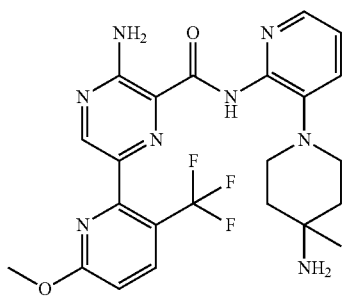

Step 1. Synthesis of tert-butyl (1-(2-(3-amino-6-(6-methoxy-3-(trifluoromethyl)pyridin-2-yl)pyrazine-2-carboxamido)pyridin-3-yl)-4-methylpiperidin-4-yl)carbamate

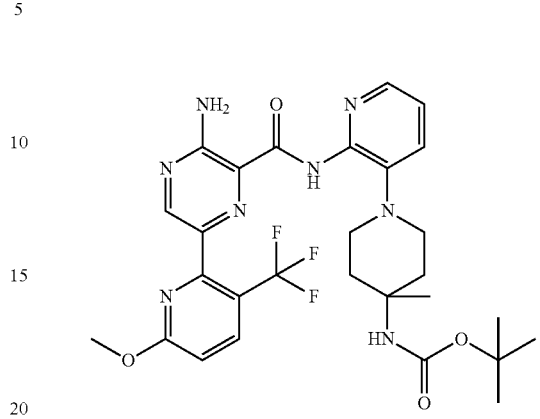

In a 40 mL vial equipped with a magnetic stirrer, 2-chloro-6-methoxy-3-(trifluoromethyl)pyridine (J. Heterocyclic Chem., 28, 971 (1991)) (40 mg, 0.190 mmol), tert-butyl (1-(2-(3-amino-6-(4,4,5,5-tetramethyl-1,3,2-dioxaborolan-2-yl)pyrazine-2-carboxamido)pyridin-3-yl)-4-methylpiperidin-4-yl)carbamate (100 mg, 0.181 mmol), PdCl$_2$(dppf) (6.61 mg, 0.09 mmol) and potassium phosphate (1M, 0.271 mL) were suspended in 1,4-dioxane (2 ml), degassed with N$_2$ for 10 min. and heated to 90° C. for 4 h. The mixture was cooled to rt and EtOAc (20 mL) was added, filtered through Celite washing with EtOAc 920 ml), concentrated in vacuo. The solid was purified by reverse-phase high-pressure liquid chromatography using a method with a 35-60% ACN 3.5 min gradient through an X-Bridge 30×50 mm 5 um column ACN/H$_2$O w 5 mM NH$_4$OH 75 mL/min., 5 mL injection 3 times which gave 50 mg (yellow solid). LC-MS (Acidic method): ret.time=1.17 min, M+H=603.7

Step 2. Synthesis of 3-amino-N-(3-(4-amino-4-methylpiperidin-1-yl)pyridin-2-yl)-6-(6-methoxy-3-(trifluoromethyl)pyridin-2-yl)pyrazine-2-carboxamide

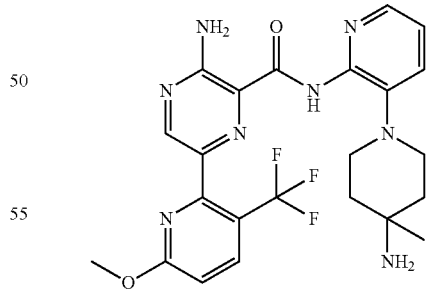

In a 40 mL vial equipped with a magnetic stirrer, was added 2,2,2-trifluoroacetic acid (64 mL, 0.830 mmol) to a solution of tert-butyl (1-(2-(3-amino-6-(6-methoxy-3-(trifluoromethyl)pyridin-2-yl)pyrazine-2-carboxamido)pyridin-3-yl)-4-methylpiperidin-4-yl)carbamate (50 mg, 0.083 mmol) in dichloromethane (5 mL) and allowed to stir for 30 min. at ambient temperature. The reaction was concentrated in vacuo and neutralized to afford 40 mg of the title compound. LC-MS (Acidic method): ret.time=0.83 min, M+H=503.5. $^1$H NMR (400 MHz, Methanol-$d_4$) δ 8.77 (s, 1H), 8.24-8.10 (m, 2H), 7.67 (dd, J=8.0, 1.6 Hz, 1H), 7.21 (dd, J=7.9, 4.9 Hz, 1H), 7.03 (d, J=8.8 Hz, 1H), 4.08 (s, 3H), 3.37 (s, 1H), 2.94 (ddd, J=12.6, 9.9, 3.1 Hz, 2H), 2.84 (dt, J=12.0, 4.6 Hz, 2H), 1.51 (ddd, J=13.6, 9.8, 4.1 Hz, 2H), 1.39 (dt, J=13.3, 3.8 Hz, 2H), 0.82 (s, 3H).

Example 17

3-amino-N-(3-(4-amino-4-ethylpiperidin-1-yl)pyridin-2-yl)-6-(3-(trifluoromethyl)pyridin-2-yl)pyrazine-2-carboxamide

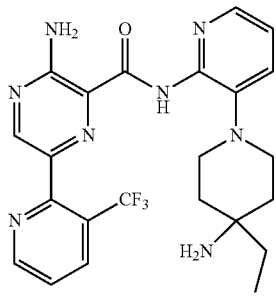 [SMILES: CCC1(N)CCN(c2cccnc2NC(=O)c2nc(-c3ncccc3C(F)(F)F)cnc2N)CC1]

Step 1. Synthesis of tert-butyl (4-ethyl-1-(2-nitropyridin-3-yl)piperidin-4-yl)carbamate

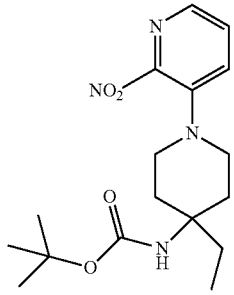 [SMILES: CCC1(NC(=O)OC(C)(C)C)CCN(c2cccnc2[N+](=O)[O-])CC1]

To a microwave vial equipped with a magnetic stirrer was added 3-fluoro-2-nitropyridine (205 mg, 1.44 mmol), tert-butyl piperidin-4-ylcarbamate (329 mg, 1.443 mmol), N-ethyl-N-isopropylpropan-2-amine (559 mg, 4.33 mmol) in ethanol (10 mL). The mixture was heated in a Biotage microwave reactor at 100° C. for 30 minutes. The mixture was cooled and concentrated to a thick residue. The residue was purified by silica gel chromatography (using methanol/dichloromethane as eluent) to give tert-butyl (4-ethyl-1-(2-nitropyridin-3-yl)piperidin-4-yl)carbamate (337 mg, 67% yield). LC-MS (Basic method): ret.time=1.45 min, M+H=351.0

$^1$H NMR (400 MHz, DMSO-$d_6$) δ 8.04 (dd, J=4.4, 1.3 Hz, 1H), 7.89 (dd, J=8.3, 1.4 Hz, 1H), 7.63 (dd, J=8.3, 4.4 Hz, 1H), 6.52 (s, 1H), 3.02-2.91 (m, 4H), 2.18-2.06 (m, 2H), 1.62 (q, J=7.4 Hz, 2H), 1.43-1.31 (m, 11H), 0.75 (t, J=7.4 Hz, 3H).

Step 2. Synthesis of tert-butyl (1-(2-aminopyridin-3-yl)-4-ethylpiperidin-4-yl)carbamate

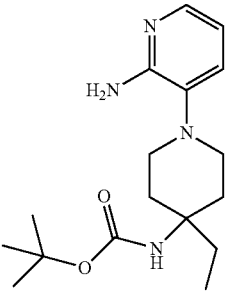 [SMILES: CCC1(NC(=O)OC(C)(C)C)CCN(c2cccnc2N)CC1]

To a round bottom flask equipped with a magnetic stirrer and purged with nitrogen was added tert-butyl (4-ethyl-1-(2-nitropyridin-3-yl)piperidin-4-yl)carbamate (337 mg, 0.96 mmol), ethanol (10 mL) and Pd/C (41 mg, 10% Pd on charcoal wet). The resultant mixture was stirred under an atmosphere of hydrogen until all tert-butyl (4-ethyl-1-(2-nitropyridin-3-yl)piperidin-4-yl)carbamate was consumed. The reaction was filtered through a pad of celite, then rinsed with methanol and ethyl acetate. The filtrate was concentrated in vacuo, then the obtained residue was dissolved in dichloromethane and filtered through a short pad of magnesium sulfate. The filtrate was concentrated to obtain tert-butyl (1-(2-aminopyridin-3-yl)-4-ethylpiperidin-4-yl)carbamate, as a white solid (268 mg, 87% yield). LC-MS (Basic method): ret.time=1.32 min, M+H=321.1.

Step 3. Synthesis of tert-butyl (1-(2-(3-amino-6-(3-(trifluoromethyl)pyridin-2-yl)pyrazine-2-carboxamido)pyridin-3-yl)-4-ethylpiperidin-4-yl)carbamate

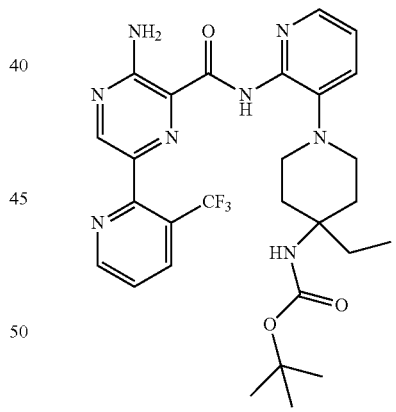

To a 20 mL scintillation vial equipped with a magnetic stirrer was added 3-amino-6-(3-(trifluoromethyl)pyridin-2-yl)pyrazine-2-carboxylic acid (61 mg, 0.22 mmol), 2-(1H-Benzotriazole-1-yl)-1,1,3,3-tetramethylaminium hexafluorophosphate (120 mg, 0.32 mmol), N-ethyl-N-isopropylpropan-2-amine (73 mg, 0.56 mmol) in DMF (2 mL). The mixture was allowed to stir for 5 minutes at rt followed by the addition of tert-butyl (1-(2-aminopyridin-3-yl)-4-ethylpiperidin-4-yl)carbamate (60 mg, 0.187 mmol). The resultant mixture was allowed to stir overnight at rt, after which it was filtered. The filtrate was concentrated, then the residue was purified by reverse-phase HPLC (35-60% ACN 3.5 min gradient, X-Bridge 30×50 mm 5 μm column ACN/H₂O w/5 mm NH4OH, 75 mL/min., 4 injections at 1.5 mL/injection) to obtain tert-butyl (1-(2-(3-amino-6-(3-(trifluoromethyl)pyridin-2-yl)pyrazine-2-carboxamido)pyridin-3-yl)-4-ethylpiperidin-4-yl)carbamate (81 mg, 66% yield). LC-MS (Basic method): ret.time=1.42 min, M+H=587.0.

Step 4. Synthesis of 3-amino-N-(3-(4-amino-4-ethylpiperidin-1-yl)pyridin-2-yl)-6-(3-(trifluoromethyl)pyridin-2-yl)pyrazine-2-carboxamide

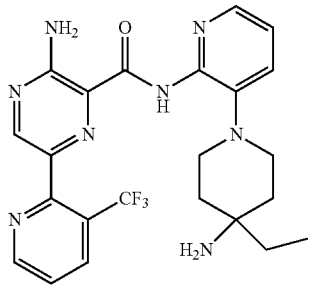 [SMILES: CCC1(N)CCN(c2cccnc2NC(=O)c2nc(-c3ncccc3C(F)(F)F)cnc2N)CC1]

To a 20 mL scintillation vial equipped with a magnetic stir bar was added tert-butyl (1-(2-(3-amino-6-(3-(trifluoromethyl)pyridin-2-yl)pyrazine-2-carboxamido)pyridin-3-yl)-4-ethylpiperidin-4-yl)carbamate (81 mg, 0.14 mmol) and 1,4-dioxane (1 ml). A 4N HCl/1,4-dioxane solution (0.69 mL, 2.76 mmol) was then added in a dropwise fashion. The resultant mixture was stirred at rt for 3 hours, at which point all tert-butyl (1-(2-(3-amino-6-(3-(trifluoromethyl)pyridin-2-yl)pyrazine-2-carboxamido)pyridin-3-yl)-4-ethylpiperidin-4-yl)carbamate was consumed. Acetonitrile was added to reaction mixture, then solid was filtered and rinsed with additional acetonitrile. The obtained solid was dried on a lyophilizer to obtain 3-amino-N-(3-(4-amino-4-ethylpiperidin-1-yl)pyridin-2-yl)-6-(3-(trifluoromethyl)pyridin-2-yl)pyrazine-2-carboxamide (57 mg, 77% yield), as its hydrochloride salt. LC-MS (Acidic method): ret.time=0.83 min, M+H=487.2. ¹H NMR (400 MHz, DMSO-d6) δ 10.59 (s, 1H), 8.98 (dd, J=4.9, 1.5 Hz, 1H), 8.81 (s, 1H), 8.44 (dd, J=8.1, 1.5 Hz, 1H), 8.20 (dd, J=5.1, 1.5 Hz, 1H), 8.08 (s, 5H), 7.81-7.71 (m, 2H), 7.33 (dd, J=7.9, 5.1 Hz, 1H), 3.17-3.07 (m, 2H), 2.93-2.84 (m, 2H), 1.68-1.58 (m, 2H), 1.35-1.26 (m, 2H), 1.06 (q, J=7.5 Hz, 2H), 0.53 (t, J=7.5 Hz, 3H).

Example 18

3-amino-N-(3-(4-amino-4-methylpiperidin-1-yl)pyridin-2-yl)-6-(3-chloropyridin-2-yl)pyrazine-2-carboxamide

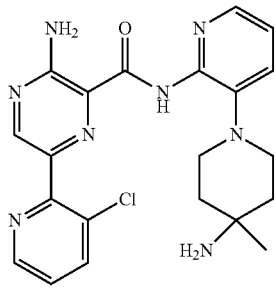 [SMILES: CC1(N)CCN(c2cccnc2NC(=O)c2nc(-c3ncccc3Cl)cnc2N)CC1]

Step 1. Synthesis of methyl 3-amino-6-(3-chloropyridin-2-yl)pyrazine-2-carboxylate

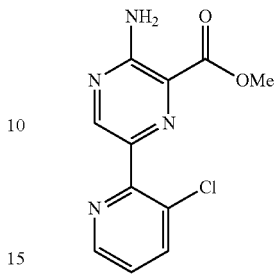

In a round-bottom flask equipped with a magnetic stirrer and nitrogen inlet was charged methyl 3-amino-6-(4,4,5,5-tetramethyl-1,3,2-dioxaborolan-2-yl)pyrazine-2-carboxylate (906 mg, 3.25 mmol), 2-bromo-3-chloropyridine (500 mg, 2.6 mmol), PdCl₂(dppf) DCM (149 mg, 0.18 mmol), potassium phosphate (3.6 ml, 3.6 mmol, 1M aq.) and THF (10 ml). The reaction was degassed with nitrogen for 5 minutes, then mixture was heated to 55° C. under nitrogen for 16 h. After cooling to rt, reaction mixture was diluted with ethyl acetate, then layers were allowed to separate. Organic layer was dried with sodium sulfate, dried and concentrated. The obtained residue was purified by silica gel chromatography (using gradient ethyl acetate/heptane 30-70% as eluent) to obtain methyl 3-amino-6-(3-chloropyridin-2-yl)pyrazine-2-carboxylate (191 mg). Due to low purity of product, it was therefore repurified by reverse-phase HPLC (15-40% ACN 3.5 min. gradient, X-Bridge 30×50 mm 5 μm column ACN/H₂O w/5 mm NH₄OH, 75 mL/min., 2 injections at 1.5 mL/injection) to obtain methyl 3-amino-6-(3-chloropyridin-2-yl)pyrazine-2-carboxylate (91 mg, 13% yield). LC-MS (Basic method): ret.time=0.92 min, M+H=265.0.

Step 2. Synthesis of methyl 3-amino-6-(3-chloropyridin-2-yl)pyrazine-2-carboxylate

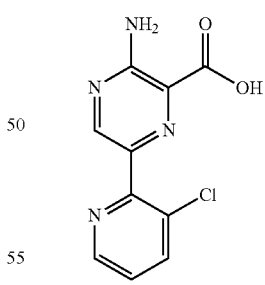

In a round-bottom flask equipped with a magnetic stirrer, methyl 3-amino-6-(3-chloropyridin-2-yl)pyrazine-2-carboxylate (91 mg, 0.34 mMoles) was dissolved in methanol (4 ml) at rt. Lithium hydroxide (0.52 mL, 1.03 mmol, 2N aq.) and added at rt and stirred for 16 h. Volatiles were removed in vacuo, then the aqueous residue was acidified with 2N aq. HCl until pH 2 was attained.

The obtained precipitate was filtered and rinsed with water, then dried on lyophilizer to afford methyl 3-amino-6-(3-chloropyridin-2-yl)pyrazine-2-carboxylate (77 mg, 89% yield), as a pale yellow solid. LC-MS (Acidic method): ret.time=0.68 min, M+H=251.4.

Step 3. Synthesis of tert-butyl (1-(2-(3-amino-6-(3-chloropyridin-2-yl)pyrazine-2-carboxamido)pyridin-3-yl)-4-methylpiperidin-4-yl)carbamate

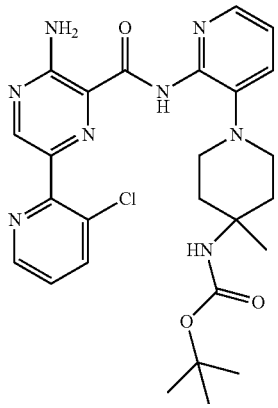 [SMILES: CC1(NC(=O)OC(C)(C)C)CCN(c2cccnc2NC(=O)c2nc(-c3ncccc3Cl)cnc2N)CC1]

To a 20 mL scintillation vial equipped with a magnetic stir bar was added methyl 3-amino-6-(3-chloropyridin-2-yl)pyrazine-2-carboxylate (38 mg, 0.15 mmol), 2-(1H-Benzotriazole-1-yl)-1,1,3,3-tetramethylaminium hexafluorophosphate (84 mg, 0.22 mmol), N-ethyl-N-isopropylpropan-2-amine (51 mg, 0.39 mmol) in DMF (1.5 mL). The mixture was allowed to stir for 5 minutes at rt followed by the addition of tert-butyl (1-(2-aminopyridin-3-yl)-4-methylpiperidin-4-yl)carbamate (40 mg, 0.13 mmol). The resultant mixture was allowed to stir overnight at rt, after which it was filtered. The filtrate was concentrated, then the residue was purified by reverse-phase HPLC (35-60% ACN 3.5 min gradient, X-Bridge 30×50 mm 5 μm column ACN/H$_2$O w/5 mL NH$_4$OH, 75 mL/min., 3 injections at 1.5 mL/injection) to obtain tert-butyl (1-(2-(3-amino-6-(3-chloropyridin-2-yl)pyrazine-2-carboxamido)pyridin-3-yl)-4-methylpiperidin-4-yl)carbamate (46 mg, 65% yield), LC-MS (Basic method): ret.time=1.35 min, M+H=538.9.

Step 4. Synthesis of 3-amino-N-(3-(4-amino-4-methylpiperidin-1-yl)pyridin-2-yl)-6-(3-chloropyridin-2-yl)pyrazine-2-carboxamide

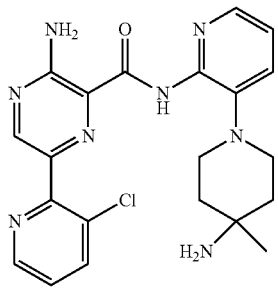 [SMILES: CC1(N)CCN(c2cccnc2NC(=O)c2nc(-c3ncccc3Cl)cnc2N)CC1]

To a 20 mL scintillation vial equipped with a magnetic stir bar was added tert-butyl (1-(2-(3-amino-6-(3-chloropyridin-2-yl)pyrazine-2-carboxamido)pyridin-3-yl)-4-methylpiperidin-4-yl)carbamate (46 mg, 0.085 mmol) and dichlorometh-ane (1 mL). Trifluoroacetic acid (146 mg, 1.28 mmol) was then added in a dropwise fashion. The resultant mixture was stirred at rt for 16 hours, at which point all tert-butyl (1-(2-(3-amino-6-(3-(trifluoromethyl)pyridin-2-yl)pyrazine-2-carboxamido)pyridin-3-yl)-4-ethylpiperidin-4-yl)carbamate was consumed. Reaction mixture was concentrated, then dichloromethane and 2N aqueous sodium carbonate solution were added to the obtained residue in two phases. The organic and aqueous phases (layers) were separated. Organic layer was washed once with additional 2N aqueous sodium carbonate solution, then dried with sodium sulfate, filtered and concentrated. Crude mixture was purified by reverse-phase HPLC (25-50% ACN 3.5 min gradient, X-Bridge 30×50 mm 5 μm column ACN/H$_2$O w/5 mm NH$_4$OH, 75 mL/min., 2 injections at 1.5 mLinjection) to obtain 3-amino-N-(3-(4-amino-4-methylpiperidin-1-yl)pyridin-2-yl)-6-(3-chloropyridin-2-yl)pyrazine-2-carboxamide (25 mg, 67% yield), LC-MS (Acidic method): ret. time=0.75 min, M+H=439.0. $^1$H NMR (400 MHz, DMSO-d$_6$) δ 10.82 (s, 1H), 8.77 (s, 1H), 8.67 (dd, J=4.7, 1.5 Hz, 1H), 8.14-8.06 (m, 2H), 7.59 (dd, J=7.9, 1.7 Hz, 1H), 7.52 (dd, J=8.2, 4.6 Hz, 1H), 7.15 (dd, J=7.9, 4.8 Hz, 1H), 2.97-2.88 (m, 2H), 2.77-2.67 (m, 2H), 1.46-1.22 (m, 6H), 0.71 (s, 3H).

Example 19

3-amino-N-(3-(4-amino-4-methylpiperidin-1-yl)pyridin-2-yl)-6-(3-fluoropyridin-2-yl)pyrazine-2-carboxamide

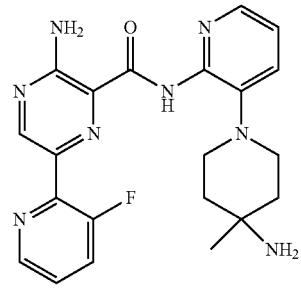 [SMILES: CC1(N)CCN(c2cccnc2NC(=O)c2nc(-c3ncccc3F)cnc2N)CC1]

Synthesis of 3-Amino-6-(3-Fluoropyridin-2-yl)pyrazine-2-carboxylic Acid

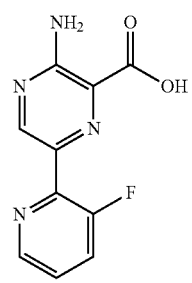 [SMILES: Nc1ncc(-c2ncccc2F)nc1C(=O)O]

Step 1. Synthesis of methyl 3-amino-6-(3-fluoro-pyridin-2-yl)pyrazine-2-carboxylate

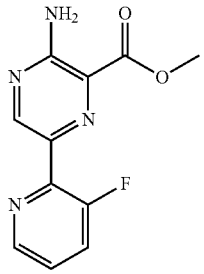 [SMILES: COC(=O)c1nc(-c2ncccc2F)cnc1N]

A microwave vial equipped with a stirring bar was charged with methyl 3-amino-6-(4,4,5,5-tetramethyl-1,3,2-dioxaborolan-2-yl)pyrazine-2-carboxylate (515 mg, ~80%, 1.847 mmol), PdCl$_2$(dppf)-DCM (81 mg, 0.099 mmol), 2-bromo-3-fluoropyridine (250 mg, 1.421 mmol), cesium carbonate (741 mg, 2.273 mmol) and dioxane (24 mL). Mixture was degassed for 5 minutes, then reaction was heated in a microwave reactor at 110° C. for 45 minutes. After cooling to rt, the reaction mixture was filtered through celite, washed with EtOAc (35 mL) and concentrated under reduced pressure. The residue was then diluted with MeOH (25 mL) which led to precipitation of a brown solid. Filtration of this solid gave 250 mg of methyl 3-amino-6-(3-fluoropyridin-2-yl)pyrazine-2-carboxylate. LC-MS (Method 3, Basic): ret.time=0.84 min, M+H=249.0.

Step 2. Synthesis of 3-amino-6-(3-fluoropyridin-2-yl)pyrazine-2-carboxylic Acid

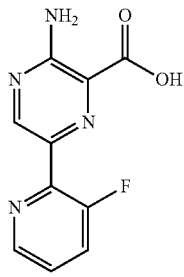

In a 40 ml vial methyl 3-amino-6-(3-fluoropyridin-2-yl)pyrazine-2-carboxylate (950 mg, 3.83 mmol) was partially dissolved in methanol (5 mL). To this mixture LiOH (860 mg, 11.48 mmol) in water (0.5 mL) was added and the mixture stirred for 3 h at room temperature. A solid precipitated during the reaction and was filtered which gave 1.13 g of 3-amino-6-(3-fluoropyridin-2-yl)pyrazine-2-carboxylic acid. LC-MS (Acidic method): ret.time=0.70 min, M+H=235.2.

Step 3: Synthesis of tert-butyl (1-(2-(3-amino-6-(3-fluoropyridin-2-yl)pyrazine-2-carboxamido)pyridin-3-yl)-4-methylpiperidin-4-yl)carbamate

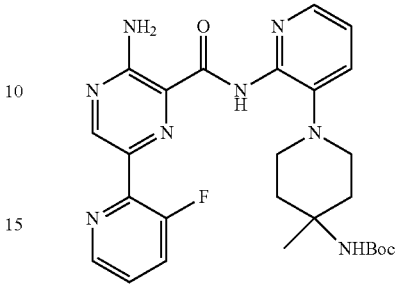

To a solution of 3-amino-6-(3-fluoropyridin-2-yl)pyrazine-2-carboxylic acid (500 mg, 2.135 mmol) in DCM/DMA (2:1, 4 ml/2 ml) was added tert-butyl (1-(2-aminopyridin-3-yl)-4-methylpiperidin-4-yl)carbamate (654 mg, 2.135 mmol), HBTU (1619 mg, 4.27 mmol) and DIPEA (1.492 mL, 8.54 mmol). The reaction was stirred at rt for 16 h, then quenched with water. The reaction was then diluted with DCM (25 mL) and washed with water (15 mL) and brine (15 mL). The organic layer was then separated, dried over MgSO$_4$ and evaporated to give a brownish solid which was then purified via basic HPLC which afforded 424.5 mg of tert-butyl (1-(2-(3-amino-6-(3-fluoropyridin-2-yl)pyrazine-2-carboxamido)pyridin-3-yl)-4-methylpiperidin-4-yl)carbamate. LC-MS (Basic Method): ret.time=1.32 min, M+H=523.3.

4) Synthesis of 3-amino-N-(3-(4-amino-4-methylpiperidin-1-yl)pyridin-2-yl)-6-(3-fluoropyridin-2-yl)pyrazine-2-carboxamide

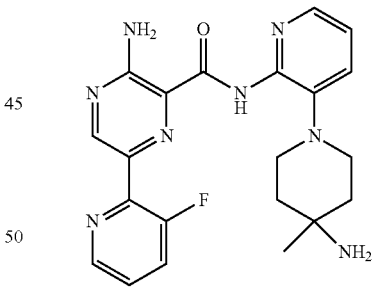

In a 40 mL vial tert-butyl (1-(2-(3-amino-6-(3-fluoropyridin-2-yl)pyrazine-2-carboxamido)pyridin-3-yl)-4-methylpiperidin-4-yl)carbamate (424.5 mg, 0.812 mmol) was dissolved in DCM (2.5 ml). To this mixture was added HCl/dioxane (2031 µL, 8.12 mmol) slowly. During the addition an orange solid was formed. The reaction was left to stir for 18 h before the precipitate was filtered. The obtained solid was then diluted with NaHCO$_3$(10 mL), and extracted with DCM (2×15 mL). The organic layers were combined, dried over MgSO$_4$ and evaporated to give 170 mg of 3-amino-N-(3-(4-amino-4-methylpiperidin-1-yl)pyridin-2-yl)-6-(3-fluoropyridin-2-yl)pyrazine-2-carboxamide. LC-MS (Basic method): ret.time=0.98 min, M+H=423.3. $^1$H NMR (400 MHz, DMSO-d$_6$) δ 10.81 (s, 1H), 8.94 (s, 1H), 8.58 (dd, J=4.3, 1.8 Hz, 1H), 8.11 (dd, J=4.8, 1.6 Hz, 2H), 7.90 (ddd, J=11.3, 8.4, 1.3 Hz, 2H), 7.65-7.52 (m, 2H), 7.16 (dd, J=7.8, 4.8 Hz, 1H), 3.57 (s, 1H), 2.96 (td, J=11.0, 2.7 Hz, 2H), 2.74 (dt, J=11.6, 4.2 Hz, 2H), 1.50 (ddd, J=13.7, 10.3, 3.8 Hz, 2H), 1.39-1.26 (m, 4H), 0.79 (s, 3H).

Example 20

3-amino-N-(3-(((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide

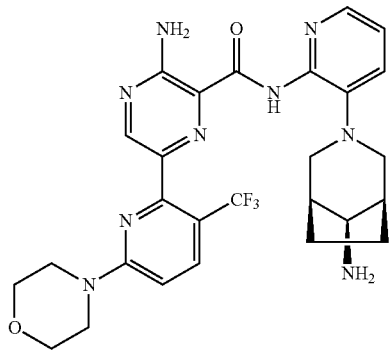 [SMILES: Nc1ncc(-c2nc(N3CCOCC3)ccc2C(F)(F)F)nc1C(=O)Nc1ncccc1N1C[C@H]2CC[C@@H](C1)[C@@H]2N]

Step 1: Synthesis of tert-butyl ((1R,5S,8s)-3-(2-nitropyridin-3-yl)-3-azabicyclo[3.2.1]octan-8-yl)carbamate

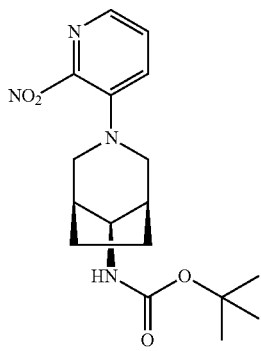 [SMILES: CC(C)(C)OC(=O)N[C@@H]1[C@@H]2CC[C@H]1CN(c1cccnc1[N+](=O)[O-])C2]

To a 25 mL pear shaped flask was added 3-fluoro-2-nitropyridine, (0.56 g, 3.94 mmol), tert-butyl (1R,5S,8s)-3-azabicyclo[3.2.1]octan-8-ylcarbamate (0.849 g, 3.75 mmol), N-ethyl-N-isopropylpropan-2-amine, (1.11 g, 8.59 mmol) and tetrahydrofuran (14 mL) and a magnetic stirrer. The mixture was stirred under nitrogen and heated at 70° C. for 1 day. The mixture was then cooled and concentrated to a thick residue and chromatographed directly on silica gel (ethyl acetate-heptane) which gave tert-butyl ((1R,5 S,8s)-3-(2-nitropyridin-3-yl)-3-azabicyclo[3.2.1]octan-8-yl)carbamate (0.993 g, 2.71 mmol) in 72% yield. LC-MS (Basic method): ret.time=1.41 min, M+H=349.6.

Step 2: Synthesis of tert-butyl ((1R,5S,8s)-3-(2-aminopyridin-3-yl)-3-azabicyclo[3.2.1]octan-8-yl)carbamate

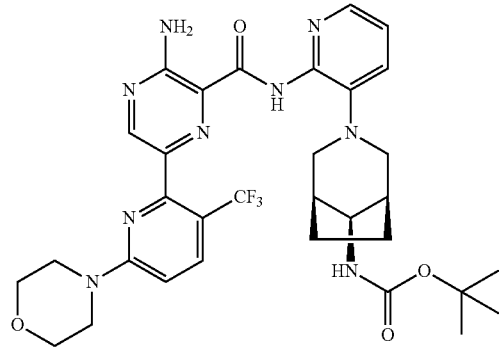 [SMILES: CC(C)(C)OC(=O)N[C@@H]1[C@@H]2CC[C@H]1CN(c1cccnc1NC(=O)c1nc(-c3nc(N4CCOCC4)ccc3C(F)(F)F)cnc1N)C2]

To a 100 mL round bottom flask was added tert-butyl ((1R,5S,8s)-3-(2-nitropyridin-3-yl)-3-azabicyclo[3.2.1]octan-8-yl)carbamate (0.99 g, 2.84 mmol), ethyl acetate (50 mL) and 10% palladium on carbon wet (1 g). The flask was purged with hydrogen and stirred under a balloon of hydrogen for 16 hrs. To the resultant mixture was then added MgSO$_4$ (5 grams) and stirred. The mixture was then filtered through a pad of MgSO$_4$ under a cone of nitrogen. The filtrate was concentrated to dryness which gave tert-butyl ((1R,5S,8s)-3-(2-aminopyridin-3-yl)-3-azabicyclo[3.2.1]octan-8-yl)carbamate (2.52 g, 1.322 mmol) in 98% yield. LC-MS (Basic method): ret.time=1.00 min, M+H=319.5.

Step 3: Synthesis of tert-butyl ((1R,5S,8s)-3-(2-(3-amino-6-(6-morpholino-3-(trifluoromethyl)pyridin-2-yl)pyrazine-2-carboxamido)pyridin-3-yl)-3-azabicyclo[3.2.1]octan-8-yl)carbamate To a 10 mL screw cap vial was added 3-amino-6-(6-morpholino-3-(trifluoromethyl)pyridin-2-yl)pyrazine-2-carboxylic acid (0.257 g, 0.696 mmol) which was prepared in analogy as in Example 1 (Method 1), DMF (2.5 mL), N-ethyl-N-isopropylpropan-2-amine (0.334 g, 0.2.58 mmol) and 2-(3H-[1,2,3]triazolo[4,5-b]pyridin-3-yl)-1,1,3,3-tetramethylisouronium hexafluorophosphate(V) (0.421 g, 1.107 mmol). The mixture was allowed to stir for 15 minutes. To the resultant mixture was added tert-butyl ((1R,5S,8s)-3-(2-aminopyridin-3-yl)-3-azabicyclo[3.2.1]octan-8-yl)carbamate (0.235 g, 0.738 mmol) and allowed to stir for 18 hours. The reaction was concentrated and was purified by silica gel chromatography using ethyl acetate and heptane which gave tert-butyl ((1R,5S,8s)-3-(2-(3- amino-6-(6-morpholino-3-(trifluoromethyl)pyridin-2-yl)pyrazine-2-carboxamido)pyridin-3-yl)-3-azabicyclo[3.2.1]octan-8-yl)carbamate (0.494 g, 0.556 mmol) in 80% yield. LC-MS (Basic method): ret.time=1.28 min, M+H=670.8.

Step 4: Synthesis of 3-amino-N-(3-((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide

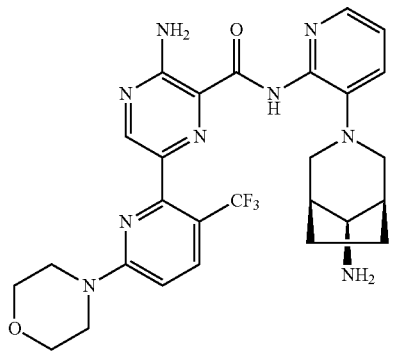 [SMILES: Nc1ncc(-c2nc(N3CCOCC3)ccc2C(F)(F)F)nc1C(=O)Nc1ncccc1N1C[C@H]2CC[C@@H](C1)[C@@H]2N]

To a 100 mL flask was added a magnetic stirrer, tert-butyl ((1R,5S,8s)-3-(2-(3-amino-6-(6-morpholino-3-(trifluoromethyl)pyridin-2-yl)pyrazine-2-carboxamido)pyridin-3-yl)-3-azabicyclo[3.2.1]octan-8-yl)carbamate (0.61 g, 0.923 mmol) and dichloromethane (10 mL). The mixture was stirred until all solids dissolved and then cooled in an ice water bath under nitrogen. To this mixture was added trifluoroacetic acid (25 mL). The ice bath was removed and the mixture was stirred for 2.5 hours at room temperature. The mixture was then concentrated and the residue was then co-evaporated with toluene (30 mL) 3 times to a thick residue. The residue was purified by a reverse phase HPLC method which gave 3-amino-N-(3-((1R,5S,8s)-8-amino-3-azabicyclo[3.2.1] octan-3-yl)pyridin-2-yl)-6-(6-morpholino-3-(trifluoromethyl)pyridin-2-yl)pyrazine-2-carboxamide (0.084 g, 0.277 mmol) in 15% yield. LC-MS (Basic method): ret.time=1.12 min, M+H=570.6. $^1$H NMR (400 MHz, Chloroform-d) δ 10.48 (s, 3H), 8.56 (s, 3H), 8.22 (d, J=4.8 Hz, 3H), 7.77 (d, J=9.0 Hz, 3H), 7.37 (d, J=7.9 Hz, 3H), 6.99 (dd, J=8.0, 4.8 Hz, 3H), 6.58 (d, J=9.0 Hz, 3H), 3.90-3.67 (m, 12H), 3.59 (t, J=4.8 Hz, 12H), 3.06-2.74 (m, 9H), 2.66 (d, J=10.7 Hz, 6H), 1.83 (s, 6H), 1.20 (d, J=12.5 Hz, 16H).

Example 21

3-amino-N-(3-(4-amino-4-methylpiperidin-1-yl)pyridin-2-yl)-6-(3-fluoro-4-methoxypyridin-2-yl)pyrazine-2-carboxamide

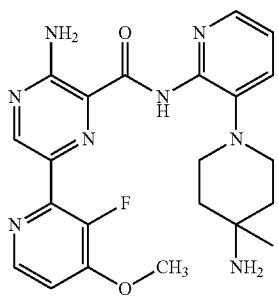 [SMILES: COc1ccnc(-c2cnc(N)c(C(=O)Nc3ncccc3N3CCC(C)(N)CC3)n2)c1F]

The 3-amino-N-(3-(4-amino-4-methylpiperidin-1-yl)pyridin-2-yl)-6-(3-fluoro-4-methoxypyridin-2-yl)pyrazine-2-carboxamide was prepared in a manner as described for Example 1, Method 1 (0.185 g) in 56% yield. LC-MS (Acidic method): ret.time=1.11 min, M+H=453.2

1H NMR (400 MHz, DMSO-d6) δ 10.83 (s, 1H), 8.91 (s, 1H), 8.41 (d, J=5.5 Hz, 1H), 8.11 (dd, J=4.8, 1.6 Hz, 1H), 7.62 (dd, J=7.9, 1.7 Hz, 1H), 7.33 (t, J=5.8 Hz, 1H), 7.16 (dd, J=7.8, 4.8 Hz, 1H), 3.97 (s, 3H), 2.95 (dd, J=12.2, 9.5 Hz, 2H), 2.82-2.66 (m, 2H), 1.53 (ddd, J=13.7, 10.4, 3.9 Hz, 2H), 1.44-1.13 (m, 4H), 0.82 (s, 3H).

Example 22

3-amino-N-(3-(4-amino-4-(methoxymethyl)piperidin-1-yl)pyridin-2-yl)-6-(3-fluoropyridin-2-yl)pyrazine-2-carboxamide

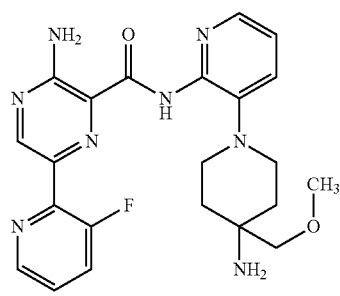 [SMILES: COCC1(N)CCN(c2cccnc2NC(=O)c2nc(-c3ncccc3F)cnc2N)CC1]

The 3-amino-N-(3-(4-amino-4-(methoxymethyl)piperidin-1-yl)pyridin-2-yl)-6-(3-fluoropyridin-2-yl)pyrazine-2-carboxamide was prepared in a similar manner as described for Example 1, Method 1 (0.01 g) in 58% yield. LC-MS (basic method): ret.time=2.11 min, M+H=452.2. $^1$H NMR (400 MHz, Methanol-d4) δ 8.91 (d, J=1.2 Hz, 1H), 8.57 (dt, J=4.6, 1.5 Hz, 1H), 8.13 (dd, J=5.0, 1.6 Hz, 1H), 7.83 (ddd, J=10.9, 8.4, 1.3 Hz, 1H), 7.70 (dd, J=7.9, 1.6 Hz, 1H), 7.57 (ddd, J=8.3, 4.6, 3.8 Hz, 1H), 7.20 (dd, J=7.9, 4.9 Hz, 1H), 3.48 (q, J=7.0 Hz, 7H), 3.23 (s, 19H), 3.06-2.84 (m, 6H), 1.66 (ddd, J=14.8, 11.1, 4.3 Hz, 2H), 1.52 (dt, J=13.1, 3.0 Hz, 2H), 1.18 (t, J=7.0 Hz, 10H).

Example 23

3-amino-N-(3-(4-amino-4-methylpiperidin-1-yl)pyridin-2-yl)-6-(6-cyano-3-fluoropyridin-2-yl)pyrazine-2-carboxamide

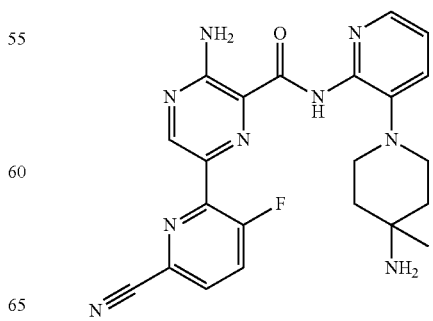

The 3-amino-N-(3-(4-amino-4-methylpiperidin-1-yl)pyridin-2-yl)-6-(6-cyano-3-fluoropyridin-2-yl)pyrazine-2-carboxamide was prepared in a similar manner as described for Example 7, Method 2 (0.016 g) in 78% yield. LC-MS (Acidic method): ret.time=0.72 min, M+H=448.3 ¹H NMR (400 MHz, DMSO-d₆) δ ppm 0.79 (s, 3 H) 1.29-1.38 (m, 2 H) 1.39-1.52 (m, 2 H) 2.73 (d, J=11.80 Hz, 2 H) 2.96 (t, J=9.79 Hz, 2 H) 3.17 (d, J=3.51 Hz, 3 H) 4.12 (d, J=4.27 Hz, 1 H) 7.17 (dd, J=7.78, 4.77 Hz, 1 H) 7.62 (dd, J=7.78, 1.51 Hz, 1 H) 8.11 (dd, J=4.77, 1.51 Hz, 1 H) 8.18-8.29 (m, 2 H) 8.93 (s, 1 H) 10.70 (s, 1 H).

Example 24

3-amino-N-(3-(4-amino-4-methylpiperidin-1-yl)pyridin-2-yl)-6-(3-cyanopyridin-2-yl)pyrazine-2-carboxamide

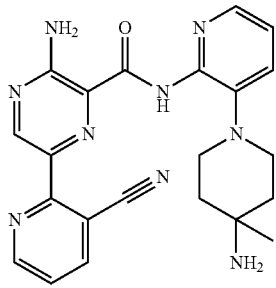 [SMILES: CC1(N)CCN(c2cccnc2NC(=O)c2nc(-c3ncccc3C#N)cnc2N)CC1]

The 3-amino-N-(3-(4-amino-4-methylpiperidin-1-yl)pyridin-2-yl)-6-(3-cyanopyridin-2-yl)pyrazine-2-carboxamide was prepared in a similar manner as described for Example 1, Method 1 (0.109 g) in 69% yield. LC-MS (Basic method): ret.time=1.92 min, M+H=429.2.

¹H NMR (400 MHz, DMSO-d₆) δ 10.56 (s, 1H), 9.18 (s, 1H), 8.95 (dd, J=4.8, 1.7 Hz, 1H), 8.52 (dd, J=8.0, 1.7 Hz, 1H), 8.29 (s, 1H), 8.26-8.15 (m, 5H), 7.87-7.60 (m, 3H), 7.35 (dd, J=7.9, 5.0 Hz, 1H), 3.20-3.02 (m, 3H), 2.97-2.79 (m, 3H), 2.01-1.73 (m, 3H), 1.64 (ddd, J=13.5, 9.2, 4.1 Hz, 2H), 1.36 (s, 1H), 1.05 (s, 3H).

Example 25

3-amino-N-(3-(4-amino-4-ethylpiperidin-1-yl)pyridin-2-yl)-6-(3-(trifluoromethoxy)pyridin-2-yl)pyrazine-2-carboxamide

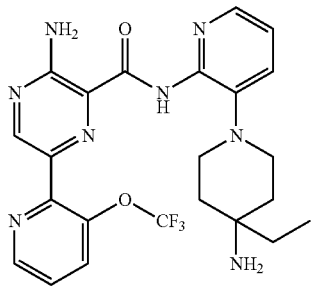 [SMILES: CCC1(N)CCN(c2cccnc2NC(=O)c2nc(-c3ncccc3OC(F)(F)F)cnc2N)CC1]

The 3-amino-N-(3-(4-amino-4-ethylpiperidin-1-yl)pyridin-2-yl)-6-(3-(trifluoromethoxy) pyridin-2-yl)pyrazine-2-carboxamide was prepared in a similar manner as described for Example 1, Method 1 (3.15 g) in 83% yield. LC-MS (Basic method): ret.time=1.02 min, M+H=503.2.

1H NMR (400 MHz, DMSO-d6) δ 10.80 (s, 1H), 8.84 (s, 1H), 8.76 (dd, J=4.7, 1.3 Hz, 1H), 8.16 (br s, 1H), 8.10 (dd, J=4.8, 1.6 Hz, 1H), 8.07 (dt, J=8.4, 1.4 Hz, 1H), 7.96 (br s, 1H), 7.65 (dd, J=8.4, 4.6 Hz, 1H), 7.59 (dd, J=7.9, 1.6 Hz, 1H), 7.16 (dd, J=7.8, 4.8 Hz, 1H), 2.95 (td, J=11.5, 2.9 Hz, 2H), 2.75-2.68 (m, 2H), 1.35-1.18 (m, 4H), 1.07 (s, 2H), 0.81 (q, J=7.4 Hz, 2H), 0.56 (t, J=7.4 Hz, 3H).

Example 26

3-amino-N-(3-(4-amino-4-methylpiperidin-1-yl)pyridin-2-yl)-6-(3-cyano-4-methoxypyridin-2-yl)pyrazine-2-carboxamide

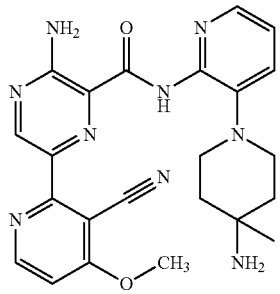 [SMILES: COc1ccnc(-c2cnc(N)c(C(=O)Nc3ncccc3N3CCC(C)(N)CC3)n2)c1C#N]

The 3-amino-N-(3-(4-amino-4-methylpiperidin-1-yl)pyridin-2-yl)-6-(3-cyano-4-methoxypyridin-2-yl)pyrazine-2-carboxamide was prepared in a similar manner as described for Example 7, Method 2 (0.018 g) in 49% yield. LC-MS (Acidic method): ret.time=0.69 min, M+H=460.2.
¹H NMR (400 MHz, METHANOL-d₄) δ ppm 0.92 (s, 4 H) 1.56 (d, J=13.05 Hz, 2 H) 1.65-1.80 (m, 2 H) 2.90-2.98 (m, 2 H) 2.98-3.07 (m, 2 H) 4.13 (s, 3 H) 7.24 (dd, J=8.03, 5.02 Hz, 1 H) 7.31 (d, J=6.02 Hz, 1 H) 7.71 (dd, J=7.91, 1.38 Hz, 1 H) 8.14 (dd, J=4.89, 1.38 Hz, 1 H) 8.74 (d, J=6.02 Hz, 1 H) 9.11 (s, 1 H).

Example 27

3-amino-N-(3-(4-amino-4-(methoxymethyl)piperidin-1-yl)pyridin-2-yl)-6-(3-(trifluoromethoxy)pyridin-2-yl)pyrazine-2-carboxamide

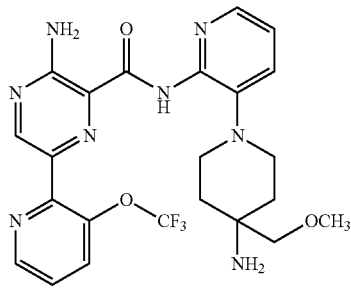 [SMILES: COCC1(N)CCN(c2cccnc2NC(=O)c2nc(-c3ncccc3OC(F)(F)F)cnc2N)CC1]

123

The 3-amino-N-(3-(4-amino-4-(methoxymethyl)piperidin-1-yl)pyridin-2-yl)-6-(3-(trifluoromethoxy) pyridin-2-yl)pyrazine-2-carboxamide was prepared in a similar manner as described for Example 1, Method 1 (0.018 g) in 49% yield. LC-MS (Acidic method): ret.time=0.79 min, M+H=519.2.

1H NMR (400 MHz, DMSO-d6) δ 10.78 (s, 1H), 8.89 (s, 1H), 8.79 (dd, J=4.6, 1.3 Hz, 1H), 8.17 (s, 1H), 8.14-8.06 (m, 2H), 7.98 (s, 1H), 7.69 (dd, J=8.3, 4.6 Hz, 1H), 7.59 (dd, J=8.0, 1.7 Hz, 1H), 7.16 (dd, J=7.9, 4.8 Hz, 1H), 3.09 (s, 3H), 2.97 (d, J=11.6, 2.7 Hz, 2H), 2.73 (dt, J=11.4, 3.7 Hz, 2H), 2.61 (s, 2H), 1.37 (dt, J=11.9, 6.5 Hz, 3H), 1.31-1.21 (m, 2H).

Example 28

3-amino-N-(3-(4-amino-4-(2-hydroxyethyl)piperidin-1-yl)pyridin-2-yl)-6-(3-(trifluoromethyl)pyridin-2-yl)pyrazine-2-carboxamide

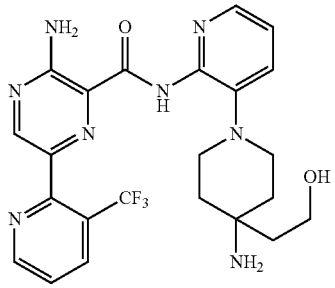 [SMILES: Nc1ncc(-c2ncccc2C(F)(F)F)nc1C(=O)Nc1ncccc1N1CCC(N)(CCO)CC1]

The 3-amino-N-(3-(4-amino-4-(2-hydroxyethyl)piperidin-1-yl)pyridin-2-yl)-6-(3-(trifluoromethyl)pyridin-2-yl)pyrazine-2-carboxamide was prepared in a similar manner as described for Example 1, Method 1 (0.039 g) in 38% yield. LC-MS (Basic method): ret.time=0.96 min, M+H=503.2. $^1$H NMR (400 MHz, DMSO-d6) δ 10.61 (s, 1H), 8.95 (dd, J=4.9, 1.5 Hz, 1H), 8.76 (s, 1H), 8.40 (dd, J=8.1, 1.5 Hz, 1H), 8.22-8.06 (m, 2H), 7.97 (br s, 1H), 7.71 (dd, J=8.0, 4.8 Hz, 1H), 7.56 (dd, J=7.9, 1.7 Hz, 1H), 7.16 (dd, J=7.9, 4.8 Hz, 1H), 4.77 (s, 1H), 3.29 (t, J=6.6 Hz, 2H), 2.94-2.83 (m, 2H), 2.71-2.63 (m, 2H), 1.39 (s, 2H), 1.27-1.13 (m, 4H), 0.92 (t, J=6.6 Hz, 2H).

Example 29

3-amino-N-(3-((1S,5R,8S)-8-amino-6-oxa-3-azabicyclo[3.2.1]octan-3-yl)pyridin-2-yl)-6-(6-morpholino-3-(trifluoromethyl)pyridin-2-yl)pyrazine-2-carboxamide

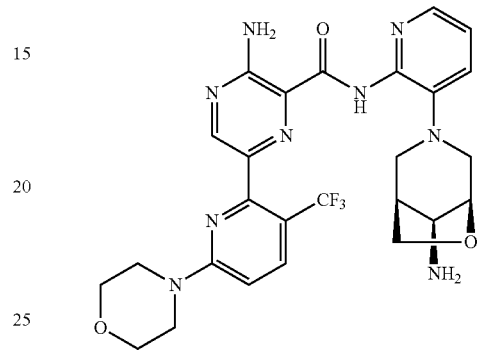

The 3-amino-N-(3-((1S,5R,8S)-8-amino-6-oxa-3-azabicyclo[3.2.1]octan-3-yl)pyridin-2-yl)-6-(6-morpholino-3-(trifluoromethyl)pyridin-2-yl)pyrazine-2-carboxamide was prepared in a similar manner as described for Example 1 (0.069 g) in 14% yield. LC-MS (basic method): ret. time=1.69 min, M+H=572.6. $^1$H NMR (400 MHz, Chloroform-d) δ 10.35 (s, 1H), 8.64 (s, 1H), 8.22 (d, J=4.8 Hz, 1H), 7.80 (d, J=8.9 Hz, 1H), 7.44 (d, J=7.9 Hz, 1H), 7.00 (dd, J=7.9, 4.8 Hz, 1H), 6.59 (d, J=9.0 Hz, 1H), 3.99 (d, J=8.3 Hz, 1H), 3.87 (d, J=4.2 Hz, 1H), 3.85-3.67 (m, 4H), 3.69-3.54 (m, 4H), 3.29 (dd, J=8.2, 4.8 Hz, 1H), 3.21-2.93 (m, 3H), 2.81 (dd, J=27.2, 11.4 Hz, 2H).

Examples 30-85

Examples 30-85, prepared by the synthetic methods (Methods 1-6) disclosed above, are summarized in Table 1

TABLE 1

| Compound Name | Structure | Synthetic Method | MS (M + H) |
|---|---|---|---|
| 30 3-amino-N-(3-(4-aminopiperidin-1-yl)pyridin-2-yl)-6-(5,6,7,8-tetrahydroquinazolin-4-yl)pyrazine-2-carboxamide | | Method 1 | 446.2 |

TABLE 1-continued

| Compound Name | Structure | Synthetic Method | MS (M + H) |
|---|---|---|---|
| 31 3-amino-N-(3-(4-aminopiperidin-1-yl)pyridin-2-yl)-6-(thieno[2,3-d]pyrimidin-4-yl)pyrazine-2-carboxamide | | Method 3 | 448.2 |
| 32 3-amino-N-(3-(4-amino-4-(2-hydroxyethyl)piperidin-1-yl)pyridin-2-yl)-6-(3-fluoropyridin-2-yl)pyrazine-2-carboxamide | | Method 1 | 453.2 |
| 33 3-amino-N-(3-(4-amino-4-methylpiperidin-1-yl)pyridin-2-yl)-6-(6-(dimethylamino)-3-(trifluoromethyl)pyridin-2-yl)pyrazine-2-carboxamide | | Method 1 | 516.2 |
| 34 3-amino-N-(3-((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide | | Method 1 | 570.6 |

TABLE 1-continued

| | Compound Name | Structure | Synthetic Method | MS (M + H) |
|---|---|---|---|---|
| 35 | 3-amino-N-(3-(4-amino-4-methylpiperidin-1-yl)pyridin-2-yl)-6-(4-cyano-3-fluoropyridin-2-yl)pyrazine-2-carboxamide | 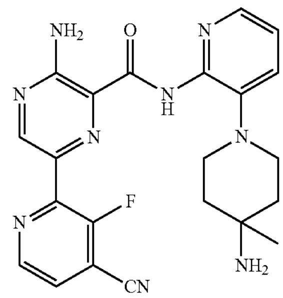 [SMILES: CC1(N)CCN(c2cccnc2NC(=O)c2nc(-c3nccc(C#N)c3F)cnc2N)CC1] | Method 3 | 448.2 |
| 36 | 3-amino-N-(3-(4-amino-4-(2-methoxyethyl)piperidin-1-yl)pyridin-2-yl)-6-(3-(trifluoromethyl)pyridin-2-yl)pyrazine-2-carboxamide | 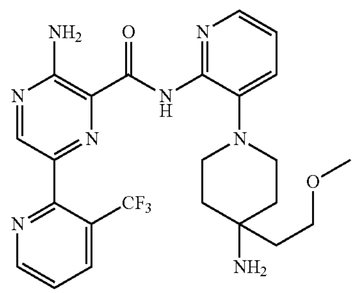 [SMILES: COCCC1(N)CCN(c2cccnc2NC(=O)c2nc(-c3ncccc3C(F)(F)F)cnc2N)CC1] | Method 1 | 517.2 |
| 37 | 3-amino-N-(3-(4-amino-4-methylpiperidin-1-yl)pyridin-2-yl)-6-(6-morpholino-3-(trifluoromethyl)pyridin-2-yl)pyrazine-2-carboxamide | 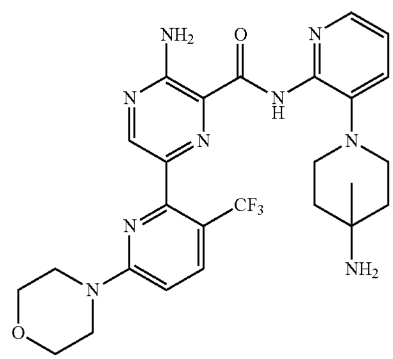 | Method 1 | 558.6 |
| 38 | 3-amino-N-(3-(4-amino-4-methylpiperidin-1-yl)pyridin-2-yl)-6-(6-fluoroquinazolin-4-yl)pyrazine-2-carboxamide | 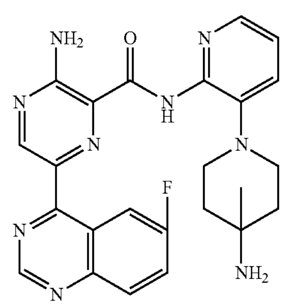 | Method 3 | 474.2 |
| 39 | 3-amion-N-(3-(4-aminopiperidin-1-yl)pyridin-2-yl)-6-(5-fluoro-7H-pyrrolo[2,3-d]pyrimidin-4-yl)pyrazine-2-carboxamide | 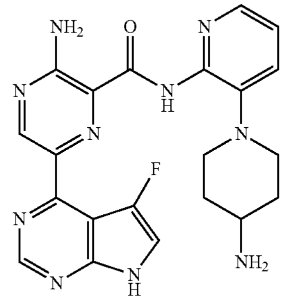 [SMILES: Nc1ncc(-c2ncnc3[nH]cc(F)c23)nc1C(=O)Nc1ncccc1N1CCC(N)CC1] | Method 3 | 449.2 |

TABLE 1-continued

| | Compound Name | Structure | Synthetic Method | MS (M + H) |
|---|---|---|---|---|
| 40 | 3-amino-N-(3-(4-aminopiperidin-1-yl)pyridin-2-yl)-6-(3-morpholinophenyl)pyrazine-2-carboxamide | 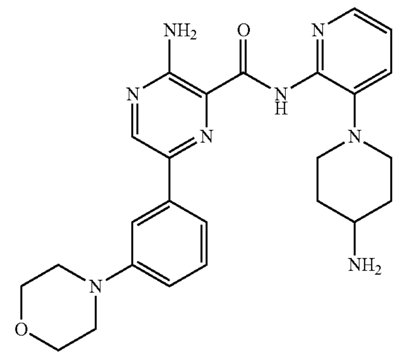 [SMILES: Nc1ncc(-c2cccc(N3CCOCC3)c2)nc1C(=O)Nc1ncccc1N1CCC(N)CC1] | Method 2 | 474.4 |
| 41 | 3-amino-N-(3-(4-aminopiperidin-1-yl)pyridin-2-yl)-6-(3,6-bis(trifluoromethyl)pyridin-2-yl)pyrazine-2-carboxamide | 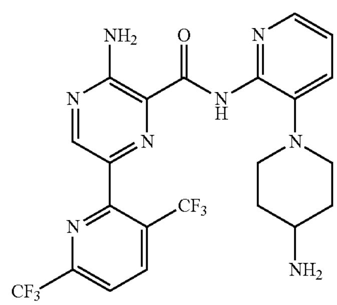 [SMILES: Nc1ncc(-c2nc(C(F)(F)F)ccc2C(F)(F)F)nc1C(=O)Nc1ncccc1N1CCC(N)CC1] | Method 1 | 527.2 |
| 42 | 3-amino-N-(3-(4-amino-4-methylpiperidin-1-yl)pyridin-2-yl)-6-(5-morpholino-2-(trifluoromethyl)phenyl)pyrazine-2-carboxamide | 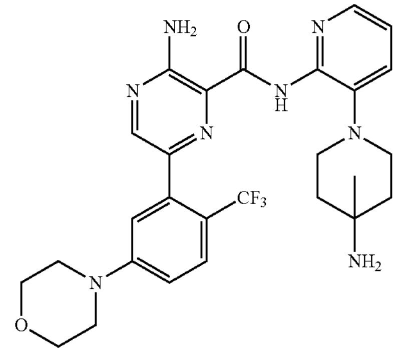 | Method 1 | 557.6 |
| 43 | (±) 3-amino-N-(3-((cis)-4-amino-3-fluoropiperidin-1-yl)pyridin-2-yl)-6-(3-(trifluoromethoxy)pyridin-2-yl)pyrazine-2-carboxamide | 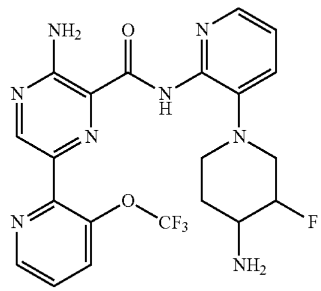 [SMILES: Nc1ncc(-c2ncccc2OC(F)(F)F)nc1C(=O)Nc1ncccc1N1CCC(N)C(F)C1] | Method 1 | 493.9 |

TABLE 1-continued

| Compound Name | Structure | Synthetic Method | MS (M + H) |
|---|---|---|---|
| 44 3-amino-N-(3-(4-aminopiperidin-1-yl)pyridin-2-yl)-6-(2-morpholinopyrimidin-4-yl)pyrazine-2-carboxamide | | Method 1 | 477.3 |
| 45 3-amino-N-(3-(4-amino-4-methylpiperidin-1-yl)pyridin-2-yl)-6-(2-(3,6-dihydro-2H-pyran-4-yl)-5-(trifluoromethyl)pyrimidin-4-yl)pyrazine-2-carboxamide | | Method 1 | 555.2 |
| 46 3-amino-N-(3-(4-amino-4-methylpiperidin-1-yl)pyridin-2-yl)-6-(2-morpholinoquinazolin-4-yl)pyrazine-2-carboxamide | | Method 3 | 541.3 |
| 47 3-amino-N-(3-(4-aminopiperidin-1-yl)pyridin-2-yl)-6-(1-methyl-1H-indazol-4-yl)pyrazine-2-carboxamide | | Method 3 | 444.5 |

TABLE 1-continued

| | Compound Name | Structure | Synthetic Method | MS (M + H) |
|---|---|---|---|---|
| 48 | 3-amino-N-(3-(4-amino-4-methylpiperidin-1-yl)pyridin-2-yl)-6-(7-fluoroisoquinolin-1-yl)pyrazine-2-carboxamide | 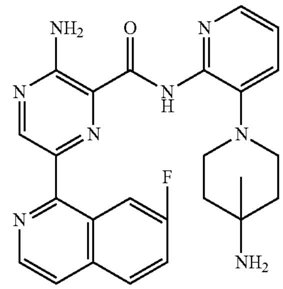 | Method 3 | 473.2 |
| 49 | 3-amino-N-(3-(4-aminopiperidin-1-yl)pyridin-2-yl)-6-(3-fluoropyridin-2-yl)pyrazine-2-carboxamide | 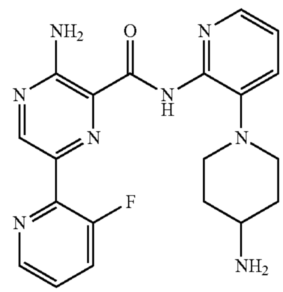 [SMILES: Nc1ncc(-c2ncccc2F)nc1C(=O)Nc1ncccc1N1CCC(N)CC1] | Method 1 | 409.2 |
| 50 | 3-amino-N-(3-(4-aminopiperidin-1-yl)pyridin-2-yl)-6-(6-morpholinopyridin-2-yl)pyrazine-2-carboxamide | 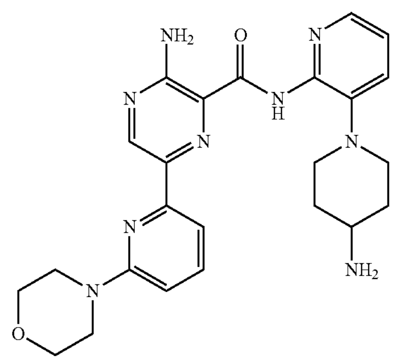 [SMILES: Nc1ncc(-c2cccc(N3CCOCC3)n2)nc1C(=O)Nc1ncccc1N1CCC(N)CC1] | Method 1 | 476.6 |
| 51 | 3-amino-N-(3-(4-aminopiperidin-1-yl)pyridin-2-yl)-6-(3-morpholinophenyl)pyrazine-2-carboxamide | 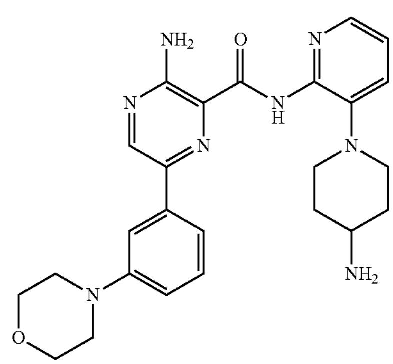 [SMILES: Nc1ncc(-c2cccc(N3CCOCC3)c2)nc1C(=O)Nc1ncccc1N1CCC(N)CC1] | Method 2 | 475.6 |

TABLE 1-continued

| | Compound Name | Structure | Synthetic Method | MS (M + H) |
|---|---|---|---|---|
| 52 | 3-amino-N-(3-(4-amino-4-methylpiperidin-1-yl)pyridin-2-yl)-6-(7-chloroisoquinolin-1-yl)pyrazine-2-carboxamide | 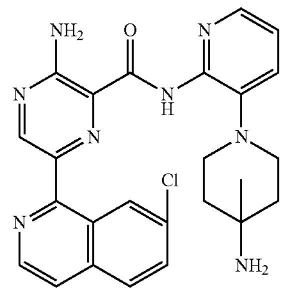 | Method 3 | 490.2 |
| 53 | 3-amino-N-(3-(4-aminopiperidin-1-yl)pyridin-2-yl)-6-(6-(azetidin-1-yl)-3-(trifluoromethyl)pyridin-2-yl)pyrazine-2-carboxamide | 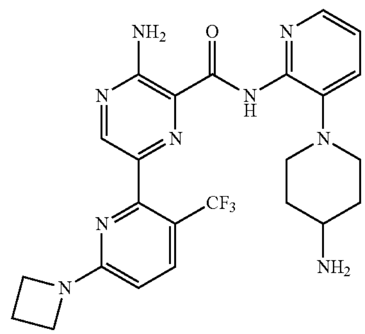 [SMILES: Nc1ncc(-c2nc(N3CCC3)ccc2C(F)(F)F)nc1C(=O)Nc1ncccc1N1CCC(N)CC1] | Method 1 | 514.5 |
| 54 | 3-amino-N-(3-((3S,4R)-4-amino-3-fluoropiperidin-1-yl)pyridin-2-yl)-6-(3-(trifluoromethoxy)pyridin-2-yl)pyrazine-2-carboxamide | 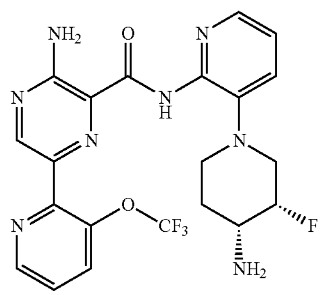 [SMILES: Nc1ncc(-c2ncccc2OC(F)(F)F)nc1C(=O)Nc1ncccc1N1CC[C@@H](N)[C@@H](F)C1] | Method 1 | 493.2 |
| 55 | 3-amino-N-(3-(4-aminopiperidin-1-yl)pyridin-2-yl)-6-(2-(trifluoromethyl)-1H-indol-4-yl)pyrazine-2-carboxamide | 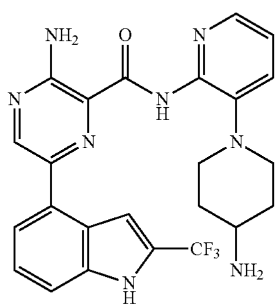 [SMILES: Nc1ncc(-c2cccc3[nH]c(C(F)(F)F)cc23)nc1C(=O)Nc1ncccc1N1CCC(N)CC1] | Method 3 | 497.5 |
| 56 | 3-amino-N-(3-(4-aminopiperidin-1-yl)pyridin-2-yl)-6-(5-morpholino-2-(trifluoromethyl)phenyl)pyrazine-2-carboxamide | 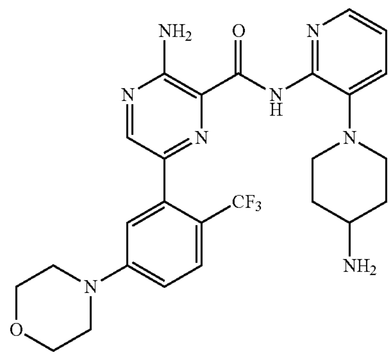 [SMILES: Nc1ncc(-c2cc(N3CCOCC3)ccc2C(F)(F)F)nc1C(=O)Nc1ncccc1N1CCC(N)CC1] | Method 1 | 543.6 |

TABLE 1-continued

| Compound Name | Structure | Synthetic Method | MS (M + H) |
|---|---|---|---|
| 57 3-amino-N-(3-(4-aminopiperidin-1-yl)pyridin-2-yl)-6-(6-(dimethylamino)-3-(trifluoromethyl)pyridin-2-yl)pyrazine-2-carboxamide | | Method 3 | 502.4 |
| 58 3-amino-N-(3-(4-amino-4-methylpiperidin-1-yl)pyridin-2-yl)-6-(2-(4,4-difluoropiperidin-1-yl)-5-fluoropyrimidin-4-yl)pyrazine-2-carboxamide | | Method 3 | 543.3 |
| 59 3-amino-N-(3-(4-amino-4-ethylpiperidin-1-yl)pyridin-2-yl)-6-(3-fluoropyridin-2-yl)pyrazine-2-carboxamide | | Method 1 | 437.2 |
| 60 3-amino-N-(3-(4-amino-4-methylpiperidin-1-yl)pyridin-2-yl)-6-(5-fluoro-2-morpholinopyrimidin-4-yl)pyrazine-2-carboxamide | | Method 3 | 509.3 |

TABLE 1-continued

| | Compound Name | Structure | Synthetic Method | MS (M + H) |
|---|---|---|---|---|
| 61 | 3-amino-N-(3-(4-aminoopiperidin-1-yl)pyridin-2-yl)-6-(1-methyl-1H-indol-4-yl)pyrazine-2-carboxamide | 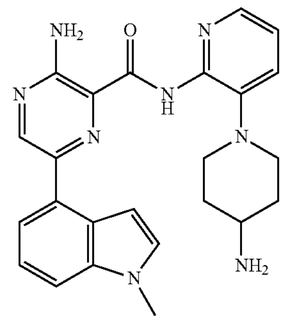 [SMILES: Cn1ccc2c(-c3cnc(N)c(C(=O)Nc4ncccc4N4CCC(N)CC4)n3)cccc21] | Method 3 | 443.6 |
| 62 | 3-amino-N-(3-(4-aminopiperidin-1-yl)pyridin-2-yl)-6-(1H-indazol-4-yl)pyrazine-2-carboxamide | 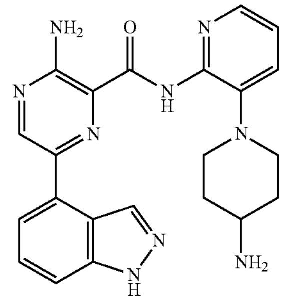 [SMILES: Nc1ncc(-c2cccc3[nH]ncc23)nc1C(=O)Nc1ncccc1N1CCC(N)CC1] | Method 3 | 430.4 |
| 63 | 3-amino-N-(3-(4-amino-4-methylpiperidin-1-yl)pyridin-2-yl)-6-(4-cyano-3-(trifluoromethyl)pyridin-2-yl)pyrazine-2-carboxamide | 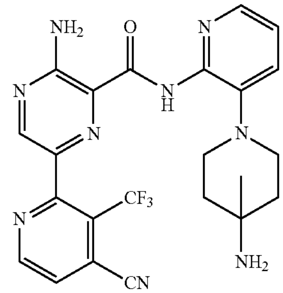 | Method 1 | 498.2 |
| 64 | 3-amino-N-(3-(4-aminopiperidin-1-yl)pyridin-2-yl)-6-(6-fluoro-2-morpholinoquinazolin-4-yl)pyrazine-2-carboxamide | 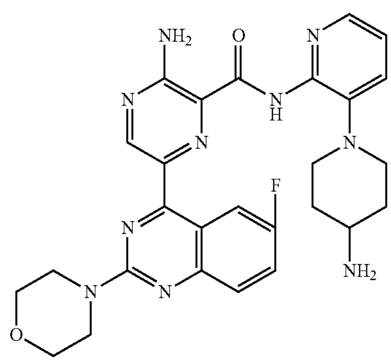 [SMILES: Nc1ncc(-c2nc(N3CCOCC3)nc3ccc(F)cc23)nc1C(=O)Nc1ncccc1N1CCC(N)CC1] | Method 3 | 559.3 |
| 65 | 3-amino-N-(3-(4-aminopiperidin-1-yl)pyridin-2-yl)-6-(2-methyl-1H-indol-4-yl)pyrazine-2-carboxamide | 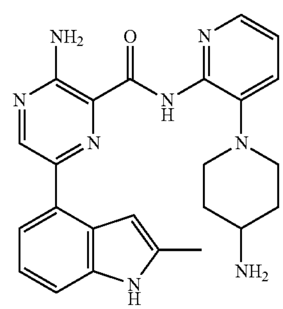 [SMILES: Cc1cc2c(-c3cnc(N)c(C(=O)Nc4ncccc4N4CCC(N)CC4)n3)cccc2[nH]1] | Method 3 | 443.6 |

TABLE 1-continued

| | Compound Name | Structure | Synthetic Method | MS (M + H) |
|---|---|---|---|---|
| 66 | 3-amino-N-(3-(4-aminopiperidin-1-yl)pyridin-2-yl)-6-(6-morpholino-3-(trifluoromethyl)pyridin-2-yl)pyrazine-2-carboxamide | | Method 3 | 544.5 |
| 67 | 3-amino-N-(3-(4-amino-4-methylpiperidin-1-yl)pyridin-2-yl)-6-(4-ethoxy-3-(trifluoromethyl)pyridin-2-yl)pyrazine-2-carboxamide | | Method 1 | 517.2 |
| 68 | 4-(5-amino-6-((3-(4-amino-4-methylpiperidin-1-yl)pyridin-2-yl)carbamoyl)pyrazin-2-yl)-5-fluoropyrimidine-2-carboxamide | | Method 3 | 466.3 |
| 69 | 3-amino-N-(3-(4-amino-4-methylpiperidin-1-yl)pyridin-2-yl)-6-(2-cyano-5-(trifluoromethyl)pyrimidin-4-yl)pyrazine-2-carboxamide | | Method 3 | 498.2 |

TABLE 1-continued

| Compound Name | Structure | Synthetic Method | MS (M + H) |
|---|---|---|---|
| 70 3-amino-N-(3-(4-amino-4-methylpiperidin-1-yl)pyridin-2-yl)-6-(2-amino-5-chloropyrimidin-4-yl)pyrazine-2-carboxamide | | Method 3 | 455.2 |
| 71 3-amino-N-(3-(4-aminopiperidin-1-yl)pyridin-2-yl)-6-(1H-indol-4-yl)pyrazine-2-carboxamide | | Method 2 | 429.2 |
| 72 3-amino-N-(3-(4-aminopiperidin-1-yl)pyridin-2-yl)-6-(3-morpholinoisoquinolin-1-yl)pyrazine-2-carboxamide | | Method 3 | 526.3 |
| 73 3-amino-N-(3-(4-aminopiperidin-1-yl)pyridin-2-yl)-6-(3-morpholino-5-(trifluoromethyl)phenyl)pyrazine-2-carboxamide | | Method 3 | 543.2 |

TABLE 1-continued

| Compound Name | Structure | Synthetic Method | MS (M + H) |
|---|---|---|---|
| 74 3-amino-N-(3-(4-amino-4-methylpiperidin-1-yl)pyridin-2-yl)-6-(4-chloro-3-(trifluoromethyl)pyridin-2-yl)pyrazine-2-carboxamide | | Method 1 | 507.2 |
| 75 3-amino-N-(3-(4-amino-4-methylpiperidin-1-yl)pyridin-2-yl)-6-(3-cyano-4-methoxypyridin-2-yl)pyrazine-2-carboxamide | | Method 3 | 60.5 |
| 76 3-amino-N-(3-(4-aminopiperidin-1-yl)pyridin-2-yl)-6-(5-morpholino-2-(trifluoromethyl)phenyl)pyrazine-2-carboxamide | | Method 1 | 543.5 |
| 77 3-amino-N-(3-(4-aminopiperidin-1-yl)pyridin-2-yl)-6-(6-morpholino-3-(trifluoromethyl)pyridin-2-yl)pyrazine-2-carboxamide | | Method 1 | 544.4 |

TABLE 1-continued

| Compound Name | Structure | Synthetic Method | MS (M + H) |
|---|---|---|---|
| 78 3-amino-N-(3-(4-aminopiperidin-1-yl)pyridin-2-yl)-6-(3-morpholinoisoquinolin-1-yl)pyrazine-2-carboxamide | | Method 3 | 526.6 |

Example 79

3-amino-N-(3-(4-aminopiperidin-1-yl)-6-methylpyridin-2-yl)-6-(3-(trifluoromethoxy)pyridin-2-yl)pyrazine-2-carboxamide

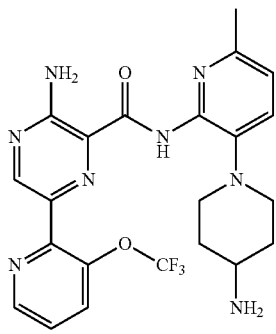 [SMILES: Cc1ccc(N2CCC(N)CC2)c(NC(=O)c2nc(-c3ncccc3OC(F)(F)F)cnc2N)n1]

Step 1: Synthesis of 6-methyl-2-nitropyridin-3-yl trifluoromethanesulfonate

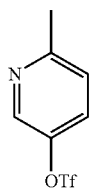

To a solution of 3-hydroxy-6-methyl-2-nitropyridine (1.0 g, 6.5 mmol) in DCM (24 mL) at 0° C. under N2 was added triethylamine (1.35 mL, 9.73 mmol) and followed by triflicanhydride (1.32 mL, 7.79 mmol). The mixture was stirred for 1 hours at 0° C. and then quenched with water. The organic layer was separated, washed with water and dried over MgSO4. After filtration and concentration at reduced pressure, the crude mixture was purified by flash chromatography on silica gel column eluting with 0-70% EtOAc/Heptane to afford the desired product as yellow oil (1.8 g, 98% yield). LC-MS (Acidic Method): ret.time=1.21 min, M+H=287.0. $^1$H NMR (400 MHz, CDCl$_3$) δ ppm 7.81 (d, 2 H) 7.59 (d, 1 H) 2.70 (s, 3 H).

Step 2. Synthesis of tert-butyl (1-(6-methyl-2-nitropyridin-3-yl)piperidin-4-yl)carbamate

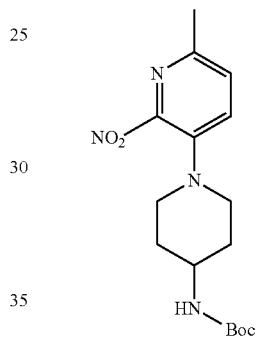

A mixture of 6-methyl-2-nitropyridin-3-yl trifluoromethanesulfonate (0.70 g, 2.45 mmol), tert-butyl piperidin-4-ylcarbamate (1.23 g, 6.11 mmol), and triethylamine (0.85 ml, 6.11 mmol) in acetonitrile (20 ml) was refluxed for 8 h. The reaction was cooled to room temperature and concentration at reduced pressure. The crude mixture was quenched with water and extracted with DCM. The crude organic layer was purified by flash chromatography on silica gel (0-100% EtOAc/Heptane) to afford quantitative yield of the desired product as yellow solid. LC-MS (Acidic Method): ret. time=1.27 min, M+H=337.2.

Synthesis of 3-amino-N-(3-(4-aminopiperidin-1-yl)-6-methylpyridin-2-yl)-6-(3-(trifluoromethoxy)pyridin-2-yl)pyrazine-2-carboxamide

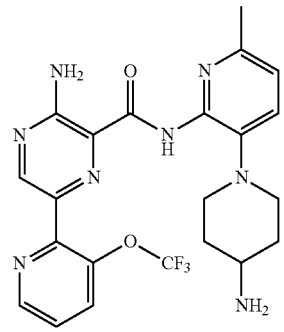 [SMILES: Cc1ccc(N2CCC(N)CC2)c(NC(=O)c2nc(-c3ncccc3OC(F)(F)F)cnc2N)n1]

The 3-amino-N-(3-(4-aminopiperidin-1-yl)-6-methyl-pyridin-2-yl)-6-(3-(trifluoromethoxy)pyridin-2-yl)pyrazine-2-carboxamide was prepared in a manner as described for Example 1, Method 1 (94 mg) in 16% yield. LC-MS (acidic method): ret.time=0.66 min, M+H=489.3. $^1$H NMR (400 MHz, Methanol-$d_4$) δ 8.85 (s, 1H), 8.73 (dd, J=4.7, 1.4 Hz, 1H), 8.00 (dt, J=8.4, 1.4 Hz, 1H), 7.61 (dd, J=8.4, 4.7 Hz, 1H), 7.53 (d, J=8.1 Hz, 1H), 7.05 (d, J=8.0 Hz, 1H), 3.05 (dt, J=12.4, 3.6 Hz, 2H), 2.76-2.60 (m, 3H), 2.50 (s, 3H), 1.85-1.75 (m, 2H), 1.42-1.29 (m, 2H).

Example 80

3-amino-N-(3-(4-aminopiperidin-1-yl)-6-methylpyridin-2-yl)-6-(3-(trifluoromethyl)pyridin-2-yl)pyrazine-2-carboxamide

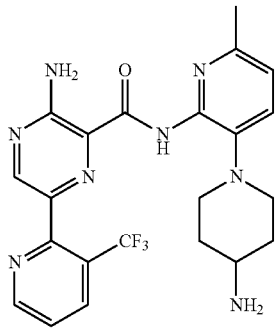 [SMILES: Cc1ccc(N2CCC(N)CC2)c(NC(=O)c2nc(-c3ncccc3C(F)(F)F)cnc2N)n1]

The 3-amino-N-(3-(4-aminopiperidin-1-yl)-6-methyl-pyridin-2-yl)-6-(3-(trifluoromethyl)pyridin-2-yl)pyrazine-2-carboxamide was prepared in a manner as described for Example 1, Method 1 (105 mg) in 18% yield. LC-MS (acidic method): ret.time=0.64 min, M+H=473.3. $^1$H NMR (400 MHz, Methanol-d4) δ 8.92 (dd, J=4.8, 1.5 Hz, 1H), 8.74 (s, 1H), 8.37 (dd, J=8.1, 1.5 Hz, 1H), 7.83-7.62 (m, 1H), 7.49 (d, J=8.0 Hz, 1H), 7.03 (d, J=8.0 Hz, 1H), 3.31 (p, J=1.6 Hz, 1H), 2.97 (dt, J=12.4, 3.6 Hz, 2H), 2.64 (td, J=11.5, 2.4 Hz, 2H), 2.55 (br s, 1H), 2.49 (s, 3H), 1.70 (dq, J=15.0, 3.1 Hz, 2H), 1.37-0.98 (m, 2H).

Example 81

3-amino-N-(3-(4-amino-3-methoxypiperidin-1-yl)pyridin-2-yl)-6-(3-(trifluoromethoxy)pyridin-2-yl)pyrazine-2-carboxamide

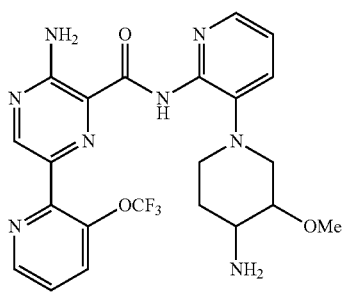 [SMILES: COC1CN(c2cccnc2NC(=O)c2nc(-c3ncccc3OC(F)(F)F)cnc2N)CCC1N]

Step 1: Synthesis of benzyl 7-oxa-3-azabicyclo[4.1.0]heptane-3-carboxylate

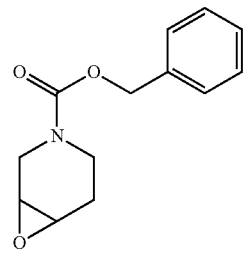 [SMILES: O=C(OCc1ccccc1)N1CCC2OC2C1]

To a solution of benzyl 5,6-dihydropyridine-1(2H)-carboxylate (3.8 g, 17 mmol) in DCM (60 ml) at −15° C. was added 3-chlorobenzoperoxoic acid (4.7 g, 70% pure, 19 mmol). The mixture was stirred at room temperature for 12 h and then washed with sodium bicarbonate solution. The organic layer was dried over sodium sulfate, filtered, and concentration at reduced pressure. The crude mixture was purified by flash chromatography on silica gel (30% EtOAc/Heptane) to afford the desired product as a colorless oil. LC-MS (Acidic Method): ret.time=1.08 min, M+H=234.3.

Step 2. Synthesis of benzyl 4-(bis(2,4-dimethoxybenzyl)amino)-3-hydroxypiperidine-1-carboxylate

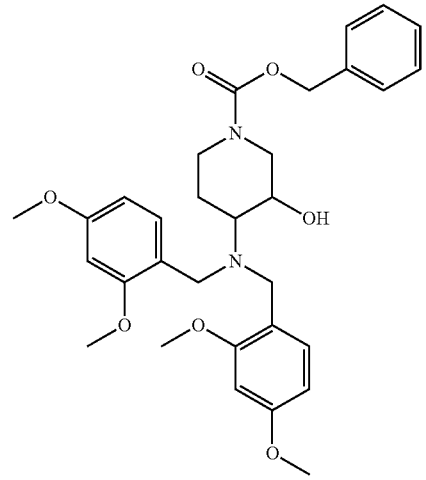 [SMILES: COc1ccc(CN(Cc2ccc(OC)cc2OC)C2CCN(C(=O)OCc3ccccc3)CC2O)c(OC)c1]

A suspension of dried lithium bromide (5.2 g, 60 mmol) in acetonitrile (15 ml) was stirred at 60° C. until a clear solution was formed. Benzyl 7-oxa-3-azabicyclo[4.1.0]heptane-3-carboxylate (8 g, 34 mmol) in acetonitrile (35 ml) was added, followed by bis(2,4-dimethoxybenzyl)amine (12 g, 38 mmol), and acetonitrile (50 ml). The mixture was stirred at 60° C. for 46 h. The reaction was cooled to room temperature and concentration at reduced pressure. The crude mixture was quenched with water and extracted with DCM. Aqueous layer was further extracted with DCM twice. The combined organic layer was purified by flash chromatography on silica gel (0-100% EtOAc/Heptane) to give two products with same M+H 551.0. The desired product came out first as colorless oil. LC-MS (Acidic Method): ret.time=1.18 min, M+H=551.0.

151

Step 3. Synthesis of benzyl 4-(bis(2,4-dimethoxybenzyl)amino)-3-methoxypiperidine-1-carboxylate

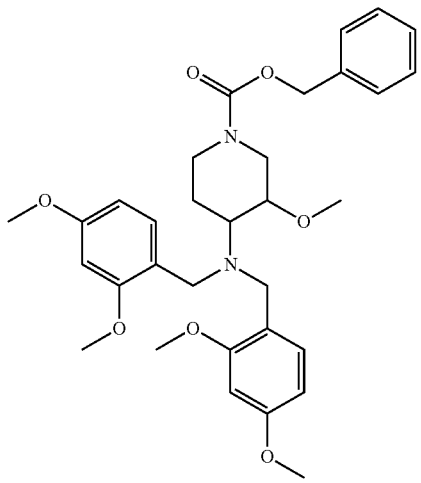 [SMILES: COc1ccc(CN(Cc2ccc(OC)cc2OC)C2CCN(C(=O)OCc3ccccc3)CC2OC)c(OC)c1]

To a solution of benzyl 4-(bis(2,4-dimethoxybenzyl)amino)-3-hydroxypiperidine-1-carboxylate (5.0 g, 9.1 mmol) in THF (100 ml) was added sodium hydride (0.55 g, 60% pure, 14 mmol) at 0° C. under nitrogen atmosphere. Iodomethane (2.1 ml, 33 mmol) was added. The mixture was stirred at room temperature for 12 h. The crude mixture was quenched with saturated aqueous ammonium chloride and extracted with EtOAc. Aqeuous layer was further extracted with EtOAc twice. The combined organic layer was washed with brine and purified by flash chromatography on silica gel (0-50% EtOAc/Heptane) to give the desired product. LC-MS (Acidic Method): ret.time=1.14 min, M+H=565.0.

Step 4. Synthesis of N,N-bis(2,4-dimethoxybenzyl)-3-methoxypiperidin-4-amine

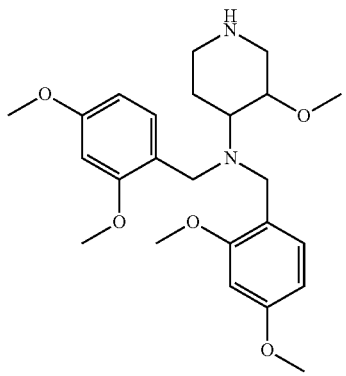

A mixture of benzyl 4-(bis(2,4-dimethoxybenzyl)amino)-3-methoxypiperidine-1-carboxylate (4.8 g, 8.4 mmol), palladium on carbon (0.45 g, 10% pure, 0.42 mmol) in ethanol (100 ml) was stirred under hydrogen balloon for 2.5 h. Filtered and concentrated to give the desired product as colorless oil. It was used in the next step without further purification. LC-MS (Acidic Method): ret.time=0.68 min, M+H=431.3.

152

Synthesis of 3-amino-N-(3-(4-amino-3-methoxypiperidin-1-yl)pyridin-2-yl)-6-(3-(trifluoromethoxy)pyridin-2-yl)pyrazine-2-carboxamide

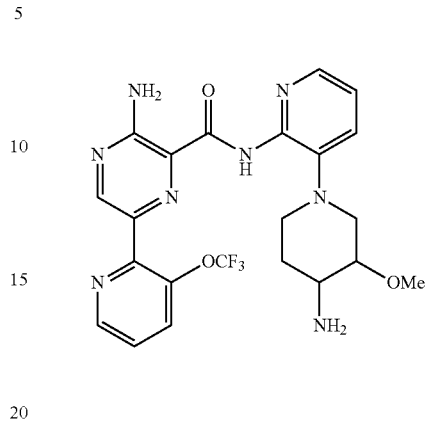

The 3-amino-N-(3-(4-amino-3-methoxypiperidin-1-yl)pyridin-2-yl)-6-(3-(trifluoromethoxy)pyridin-2-yl)pyrazine-2-carboxamide was prepared in a manner as described for Example 1, Method 1 (43 mg) in 75% yield. LC-MS (acidic method): ret.time=0.71 min, M+H=505.3. $^1$H NMR (400 MHz, Chloroform-d) δ 10.96 (s, 1H), 8.88 (s, 1H), 8.82 (dd, J=4.5, 1.4 Hz, 1H), 8.34 (dd, J=4.9, 1.6 Hz, 1H), 7.81 (dt, J=8.3, 1.4 Hz, 1H), 7.52-7.41 (m, 2H), 7.09 (dd, J=7.9, 4.8 Hz, 1H), 3.51 (s, 1H), 3.41 (ddd, J=11.0, 4.5, 2.1 Hz, 1H), 3.22 (s, 3H), 3.14-2.94 (m, 2H), 2.70 (td, J=12.0, 2.5 Hz, 1H), 2.56 (ddd, J=11.6, 9.1, 4.6 Hz, 1H), 2.41 (t, J=10.5 Hz, 1H), 1.90-1.79 (m, 1H).

Example 82

3-amino-N-(3-(4-amino-4-methylpiperidin-1-yl)pyridin-2-yl)-6-(3-fluoro-4-methylpyridin-2-yl)pyrazine-2-carboxamide

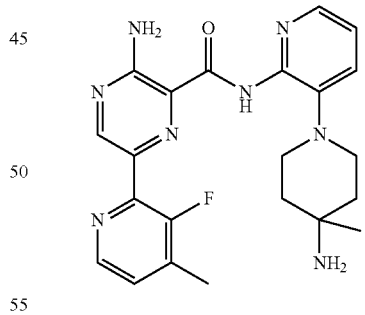

The 3-amino-N-(3-(4-amino-4-methylpiperidin-1-yl)pyridin-2-yl)-6-(3-fluoro-4-methylpyridin-2-yl)pyrazine-2-carboxamide was prepared in a manner as described for Example 1, Method 1 (8.6 mg) in 7.5% yield. LC-MS (acidic method): ret.time=1.04 min, M+H=437.1

$^1$H NMR (400 MHz, Methanol-d4) δ 8.83 (d, J=1.3 Hz, 1H), 8.39 (d, J=4.8 Hz, 1H), 8.12 (dd, J=5.0, 1.6 Hz, 1H), 7.68 (dd, J=7.9, 1.6 Hz, 1H), 7.40 (td, J=5.2, 0.9 Hz, 1H), 7.18 (dd, J=7.9, 4.9 Hz, 1H), 3.10-2.77 (m, 4H), 2.45 (d, J=1.9 Hz, 3H), 1.81-1.40 (m, 4H), 0.87 (s, 3H).

Example 83

3-amino-N-(3-(4-amino-4-methylpiperidin-1-yl)pyridin-2-yl)-6-(4-ethoxy-3-fluoropyridin-2-yl)pyrazine-2-carboxamide

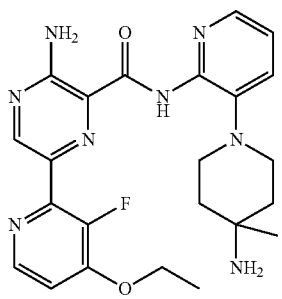 [SMILES: CCOc1ccnc(-c2cnc(N)c(C(=O)Nc3ncccc3N3CCC(C)(N)CC3)n2)c1F]

Step 1: Synthesis of 2-bromo-4-ethoxy-3-fluoropyridine

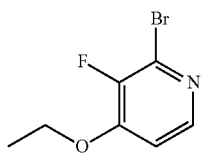

A mixture of 2-bromo-3-fluoropyridin-4-ol (0.20 g, 1.0 mmol), iodoethane (0.22 ml, 2.1 mmol), and potassium carbonate (0.29 g, 2.1 mmol) in acetone (7 mL) was refluxed for 4 h. The reaction mixture was concentration at reduced pressure and purified by flash chromatography on silica gel column eluting with 0-100% EtOAc/Heptane to afford the desired product as white solid (0.19 g, 83% yield). LC-MS (Acidic Method): ret.time=1.07 min, M+H=221.6.

Synthesis of 3-amino-N-(3-(4-amino-4-methylpiperidin-1-yl)pyridin-2-yl)-6-(4-ethoxy-3-fluoropyridin-2-yl)pyrazine-2-carboxamide

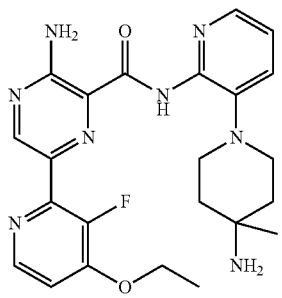

The 3-amino-N-(3-(4-amino-4-methylpiperidin-1-yl)pyridin-2-yl)-6-(4-ethoxy-3-fluoropyridin-2-yl)pyrazine-2-carboxamide was prepared in a manner as described for Example 1, Method 1 (57 mg) in 91% yield. LC-MS (acidic method): ret.time=1.06 min, M+H=467.2

$^1$H NMR (400 MHz, Methanol-d4) δ 8.86 (d, J=0.8 Hz, 1H), 8.35 (d, J=5.5 Hz, 1H), 8.12 (dd, J=4.9, 1.6 Hz, 1H), 7.70 (dd, J=7.9, 1.6 Hz, 1H), 7.30-7.14 (m, 2H), 4.28 (q, J=7.0 Hz, 2H), 3.05-2.83 (m, 4H), 1.73 (ddd, J=13.2, 9.2, 3.9 Hz, 2H), 1.64-1.53 (m, 2H), 1.51 (t, J=7.0 Hz, 3H), 0.98 (s, 3H).

Example 84

3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide

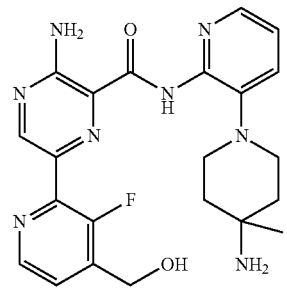 [SMILES: CC1(N)CCN(c2cccnc2NC(=O)c2nc(-c3nccc(CO)c3F)cnc2N)CC1]

Step 1: Synthesis of (2-chloro-3-(trifluoromethyl)pyridin-4-yl)methanol

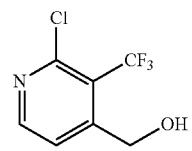

To a solution of 2-chloro-3-(trifluromethyl)isonicotinaldehyde (0.97 g, 4.6 mmol) in MeOH (10 mL) at 0° C. was added sodium borohydride (0.23 g, 6.0 mmol). The mixture was stirred at room temperature for 20 minutes. It was then concentrated and partitioned between DCM and water. The organic layer was washed with brine, dried over magnesium sulfate, filtered, and concentrated to give a yellow solid. (0.91 g, 93% yield). LC-MS (Acidic Method): ret.time=0.90 min, M+H=212.0.

Synthesis of 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide

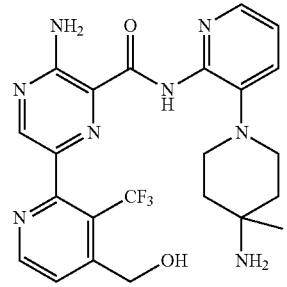 [SMILES: CC1(N)CCN(c2cccnc2NC(=O)c2nc(-c3nccc(CO)c3C(F)(F)F)cnc2N)CC1]

The 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide was prepared in a manner as described for Example 7, method 3 (36 mg) in 94% yield. LC-MS (acidic method): ret.time=0.62 min, M+H=503.1. ¹H NMR (400 MHz, DMSO-d6) δ 10.64 (s, 1H), 8.89 (d, J=5.1 Hz, 1H), 8.68 (s, 1H), 8.10 (dd, J=4.8, 1.6 Hz, 1H), 7.90 (d, J=5.1 Hz, 1H), 7.57 (dd, J=7.9, 1.7 Hz, 1H), 7.14 (dd, J=7.9, 4.8 Hz, 1H), 4.79 (s, 2H), 4.10-4.04 (br, 1H), 2.88 (ddd, J=12.4, 7.5, 5.2 Hz, 2H), 2.64 (dt, J=11.4, 4.5 Hz, 2H), 1.23-1.11 (m, 4H), 0.65 (s, 3H).

Example 85

3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide

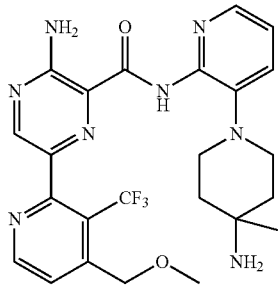 [SMILES: COCc1ccnc(-c2cnc(N)c(C(=O)Nc3ncccc3N3CCC(C)(N)CC3)n2)c1C(F)(F)F]

Step 1: Synthesis of 2-chloro-4-(methoxymethyl)-3-(trifluoromethyl)pyridine

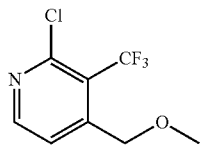

To a solution of 2-chloro-3-(trifluromethyl)pyridin-4-yl)methanol (0.15 mg, 0.69 mmol) in THF (5 mL) was added potassium tert-butoxide (0.10 g, 0.89 mmol). The mixture was stirred at room temperature for 10 minutes. It was then added methyl iodide (0.22 ml, 3.4 mmol) and stirred at room temperature for 17 h. Added more potassium tert-butoxide (0.10 g, 0.89 mmol) and stirred at room temperature for another 12 h. The mixture was then filtered and washed with EtOAc. The combined organic layer was purified by flash chromatography on silica gel column eluting with 0-30% EtOAc/Heptane to afford the desired product as colorless oil (25 mg, 16% yield). LC-MS (Acidic Method): ret.time=1.16 min, M+H=226.0.

Synthesis of 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide

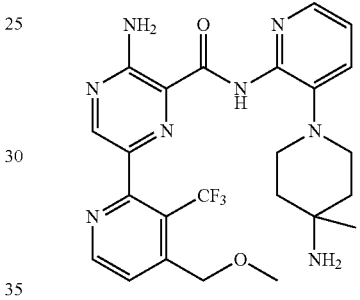

The 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide was prepared in a manner as described for Example 7, method 3 (7.5 mg) in 13% yield. LC-MS (acidic method): ret.time=1.11 min, M+H=517.1. ¹H NMR (400 MHz, Methanol-d4) δ 8.84 (d, J=5.1 Hz, 1H), 8.61 (s, 1H), 8.11 (dd, J=5.0, 1.6 Hz, 1H), 7.88 (dd, J=5.0, 1.1 Hz, 1H), 7.66 (dd, J=7.9, 1.7 Hz, 1H), 7.16 (dd, J=7.9, 4.9 Hz, 1H), 4.80-4.74 (m, 2H), 3.56 (s, 3H), 3.03-2.69 (m, 4H), 1.46-1.25 (m, 4H), 0.76 (s, 3H).

| 79 | 3-amino-N-(3-(4-aminopiperidin-1-yl)-6-methylpyridin-2-yl)-6-(3-(trifluoromethoxy)pyridin-2-yl)pyrazine-2-carboxamide | 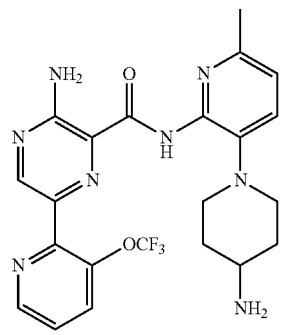 | Method 1 | 489.3 |

| | | | | |
|---|---|---|---|---|
| 80 | 3-amino-N-(3-(4-aminopiperidin-1-yl)-6-methylpyridin-2-yl)-6-(3-(trifluoromethyl)pyridin-2-yl)pyrazine-2-carboxamide | 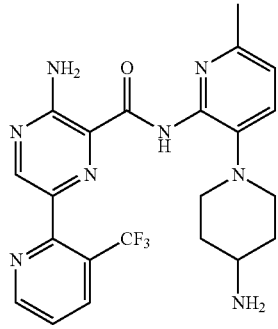 [SMILES: Cc1ccc(N2CCC(N)CC2)c(NC(=O)c2nc(-c3ncccc3C(F)(F)F)cnc2N)n1] | Method 1 | 473.3 |
| 81 | 3-amino-N-(3-(4-amino-3-methoxypiperidin-1-yl)pyridin-2-yl)-6-(3-(trifluoromethoxy)pyridin-2-yl)pyrazine-2-carboxamide | 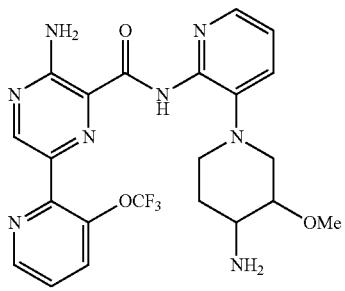 [SMILES: COC1CN(c2cccnc2NC(=O)c2nc(-c3ncccc3OC(F)(F)F)cnc2N)CCC1N] | Method 1 | 505.3 |
| 82 | 3-amino-N-(3-(4-amino-4-methylpiperidin-1-yl)pyridin-2-yl)-6-(3-fluoro-4-methylpyridin-2-yl)pyrazine-2-carboxamide | 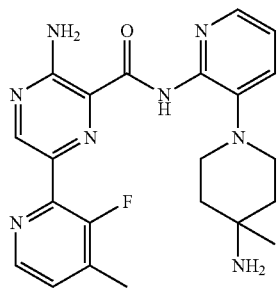 [SMILES: Cc1ccnc(-c2cnc(N)c(C(=O)Nc3ncccc3N3CCC(C)(N)CC3)n2)c1F] | Method 1 | 437.1 |
| 83 | 3-amino-N-(3-(4-amino-4-methylpiperidin-1-yl)pyridin-2-yl)-6-(4-ethoxy-3-fluoropyridin-2-yl)pyrazine-2-carboxamide | 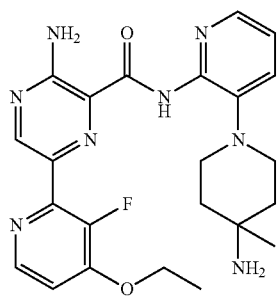 [SMILES: CCOc1ccnc(-c2cnc(N)c(C(=O)Nc3ncccc3N3CCC(C)(N)CC3)n2)c1F] | Method 1 | 467.2 |
| 84 | 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide | 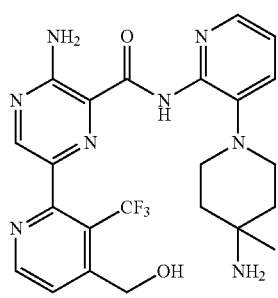 [SMILES: CC1(N)CCN(c2cccnc2NC(=O)c2nc(-c3nccc(CO)c3C(F)(F)F)cnc2N)CC1] | Method 3 | 503.1 |

| | Compound Name | Structure | Synthetic Method | MS (M + H) |
|---|---|---|---|---|
| 85 | 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide | 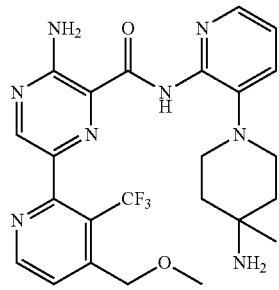 [SMILES: COCc1ccnc(-c2cnc(N)c(C(=O)Nc3ncccc3N3CCC(C)(N)CC3)n2)c1C(F)(F)F] | Method 3 | 517.1 |

The following compounds can be prepared according to the synthetic methods (Methods 1-6) described herein.

| | Compound Name | Structure | Synthetic Method | MS (M + H) |
|---|---|---|---|---|
| 86 | 3-amino-N-(3-(4-amino-4-methylpiperidin-1-yl)pyridin-2-yl)-6-(6-cyano-3-fluoropyridin-2-yl)pyrazine-2-carboxamide | 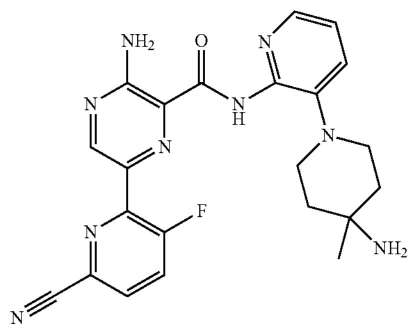 [SMILES: CC1(N)CCN(c2cccnc2NC(=O)c2nc(-c3nc(C#N)ccc3F)cnc2N)CC1] | Method 3 | 448.1 |
| 87 | 3-amino-N-(3-(4-amino-4-methylpiperidin-1-yl)pyridin-2-yl)-6-(6-(2-methylmorpholino)-3-(trifluoromethyl)pyridin-2-yl)pyrazine-2-carboxamide | 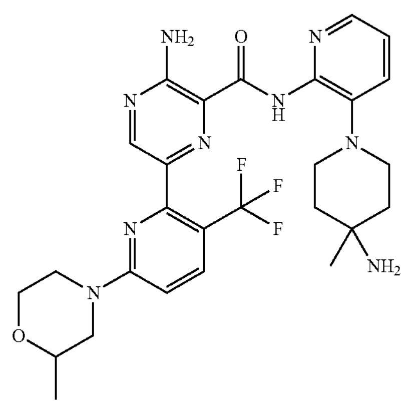 [SMILES: CC1CN(c2ccc(C(F)(F)F)c(-c3cnc(N)c(C(=O)Nc4ncccc4N4CCC(C)(N)CC4)n3)n2)CCO1] | Method 3 | 572.4 |
| 88 | 3-amino-N-(3-(4-amino-4-(ethoxymethyl)piperidin-1-yl)pyridin-2-yl)-6-(3-(trifluoromethyl)pyridin-2-yl)pyrazine-2-carboxamide | 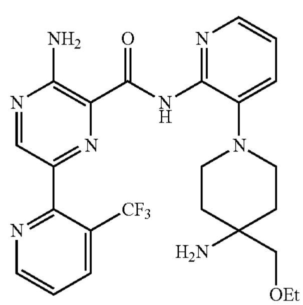 [SMILES: CCOCC1(N)CCN(c2cccnc2NC(=O)c2nc(-c3ncccc3C(F)(F)F)cnc2N)CC1] | Method 1 | 517.3 |

-continued

| | Compound Name | Structure | Synthetic Method | MS (M + H) |
|---|---|---|---|---|
| 89 | 3-amino-N-(3-(4-amino-4-(ethoxymethyl)piperidin-1-yl)pyridin-2-yl)-6-(3-(trifluoromethoxy)pyridin-2-yl)pyrazine-2-carboxamide | 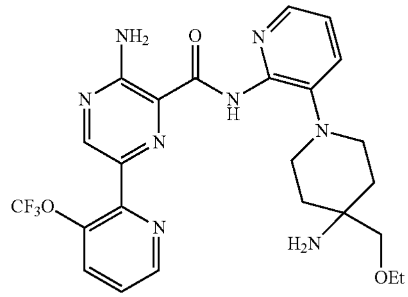 | Method 1 | 531.4 |
| 90 | 3-amino-N-(3-(4-amino-4-((difluoromethoxy)methyl)piperidin-1-yl)pyridin-2-yl)-6-(3-(trifluoromethyl)pyridin-2-yl)pyrazine-2-carboxamide | 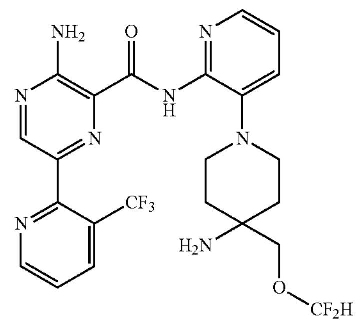 [SMILES: Nc1ncc(-c2ncccc2C(F)(F)F)nc1C(=O)Nc1ncccc1N1CCC(N)(COC(F)F)CC1] | Method 1 | 539.2 |
| 91 | 3-amino-N-(3-(4-amino-4-((difluoromethoxy)methyl)piperidin-1-yl)pyridin-2-yl)-6-(3-(trifluoromethoxy)pyridin-2-yl)pyrazine-2-carboxamide | 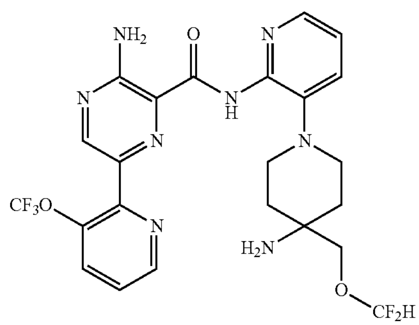 | Method 1 | 555.3 |
| 92 | 3-amino-N-(3-(4-amino-4-(hydroxymethyl)piperidin-1-yl)pyridin-2-yl)-6-(1-morpholinoisoquinolin-3-yl)pyrazine-2-carboxamide | 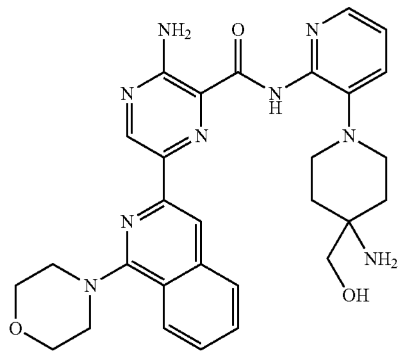 [SMILES: Nc1ncc(-c2cc3ccccc3c(N3CCOCC3)n2)nc1C(=O)Nc1ncccc1N1CCC(N)(CO)CC1] | Method 1 | 556.2 |

-continued

| | Compound Name | Structure | Synthetic Method | MS (M + H) |
|---|---|---|---|---|
| 93 | 3-amino-N-(3-(4-amino-4-(hydroxymethyl)piperidin-1-yl)pyridin-2-yl)-6-(6-morpholino-3-(trifluoromethyl)pyridin-2-yl)pyrazine-2-carboxamide | 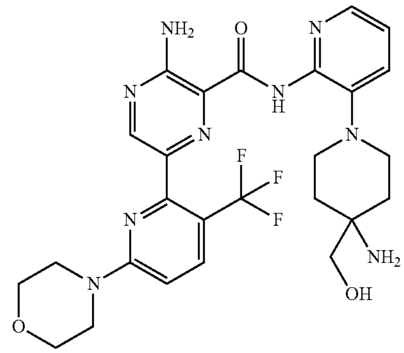 [SMILES: Nc1ncc(-c2nc(N3CCOCC3)ccc2C(F)(F)F)nc1C(=O)Nc1ncccc1N1CCC(N)(CO)CC1] | Method 1 | 574.7 |
| 94 | 3-amino-N-(3-(4-amino-4-methylpiperidin-1-yl)pyridin-2-yl)-6-(3-cyano-4-isopropoxypyridin-2-yl)pyrazine-2-carboxamide | 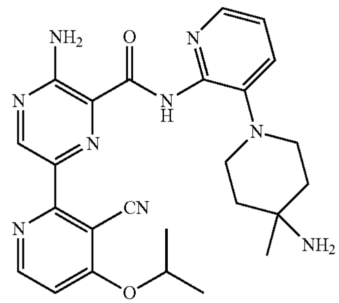 [SMILES: CC(C)Oc1ccnc(-c2cnc(N)c(C(=O)Nc3ncccc3N3CCC(C)(N)CC3)n2)c1C#N] | Method 3 | 488.2 |
| 95 | 3-amino-N-(3-(4-amino-4-methylpiperidin-1-yl)pyridin-2-yl)-6-(3-cyano-4-cyclopropoxypyridin-2-yl)pyrazine-2-carboxamide | 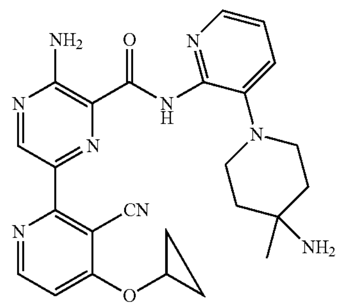 [SMILES: CC1(N)CCN(c2cccnc2NC(=O)c2nc(-c3nccc(OC4CC4)c3C#N)cnc2N)CC1] | Method 3 | 486.2 |
| 96 | 3-amino-N-(3-(4-amino-4-methylpiperidin-1-yl)pyridin-2-yl)-6-(4-(trifluoromethoxy)pyridin-2-yl)pyrazine-2-carboxamide | 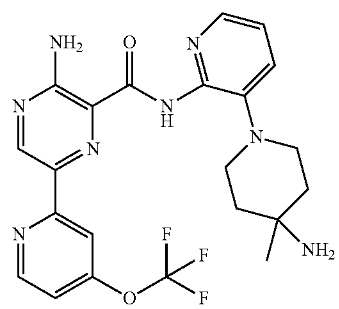 [SMILES: CC1(N)CCN(c2cccnc2NC(=O)c2nc(-c3cc(OC(F)(F)F)ccn3)cnc2N)CC1] | Method 3 | 489.2 |
| 97 | 3-amino-N-(3-(4-amino-4-(hydroxymethyl)piperidin-1-yl)pyridin-2-yl)-6-(3-cyano-4-methoxypyridin-2-yl)pyrazine-2-carboxamide | 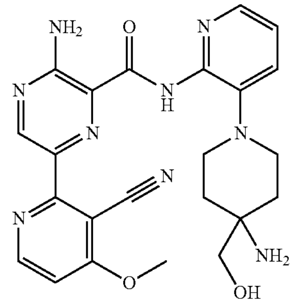 [SMILES: COc1ccnc(-c2cnc(N)c(C(=O)Nc3ncccc3N3CCC(N)(CO)CC3)n2)c1C#N] | Method 1 | 474.7 |

| | Compound Name | Structure | Synthetic Method | MS (M + H) |
|---|---|---|---|---|
| 98 | 3-amino-N-(3-(4-amino-4-(hydroxymethyl)piperidin-1-yl)pyridin-2-yl)-6-(3-cyanopyridin-2-yl)pyrazine-2-carboxamide | 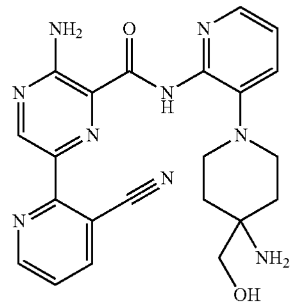 [SMILES: N#Cc1cccnc1-c1cnc(N)c(C(=O)Nc2ncccc2N2CCC(N)(CO)CC2)n1] | Method 1 | 474.7 |
| 99 | 3-amino-N-(3-(4-amino-4-methylpiperidin-1-yl)pyridin-2-yl)-6-(3-cyano-4-(trifluoromethoxy)pyridin-2-yl)pyrazine-2-carboxamide | 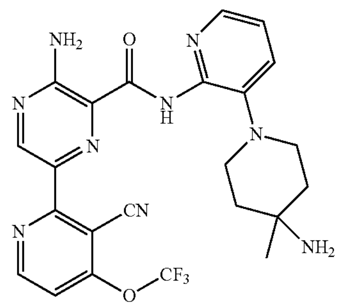 [SMILES: CC1(N)CCN(c2cccnc2NC(=O)c2nc(-c3nccc(OC(F)(F)F)c3C#N)cnc2N)CC1] | Method 3 | 514.2 |
| 100 | 3-amino-N-(3-(4-amino-4-methylpiperidin-1-yl)pyridin-2-yl)-6-(3-cyano-4-phenoxypyridin-2-yl)pyrazine-2-carboxamide | 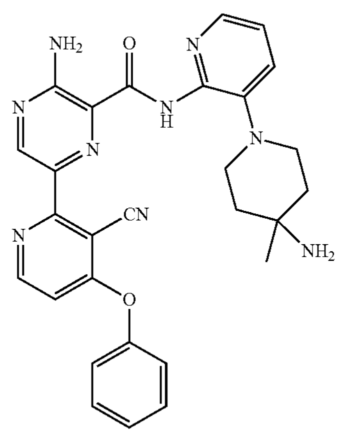 [SMILES: CC1(N)CCN(c2cccnc2NC(=O)c2nc(-c3nccc(Oc4ccccc4)c3C#N)cnc2N)CC1] | Method 3 | 523.0 |
| 101 | 3-amino-N-(3-(4-amino-4-methylpiperidin-1-yl)pyridin-2-yl)-6-(5-methoxy-3-(trifluoromethyl)pyridin-2-yl)pyrazine-2-carboxamide | 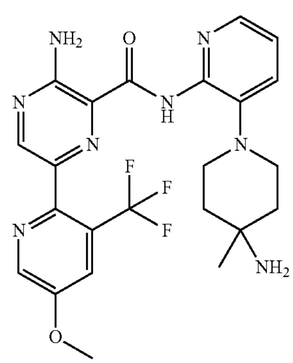 [SMILES: COc1cnc(-c2cnc(N)c(C(=O)Nc3ncccc3N3CCC(C)(N)CC3)n2)c(C(F)(F)F)c1] | Method 1 | 503.2 |

| | Compound Name | Structure | Synthetic Method | MS (M + H) |
|---|---|---|---|---|
| 102 | 3-amino-N-(3-(4-amino-3-fluoro-4-methylpiperidin-1-yl)pyridin-2-yl)-6-(3-(trifluoromethyl)pyridin-2-yl)pyrazine-2-carboxamide | 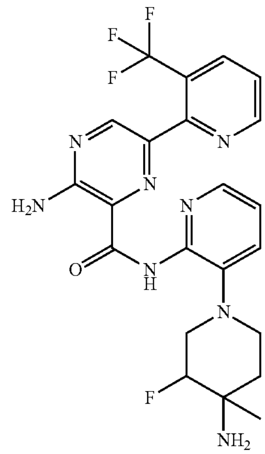 [SMILES: CC1(N)CCN(c2cccnc2NC(=O)c2nc(-c3ncccc3C(F)(F)F)cnc2N)CC1F] | Method 1 | 491.0 |
| 103 | 3-amino-N-(3-(4-amino-4-methylpiperidin-1-yl)pyridin-2-yl)-6-(6-(3-hydroxyazetidin-1-yl)-3-(trifluoromethyl)pyridin-2-yl)pyrazine-2-carboxamide | 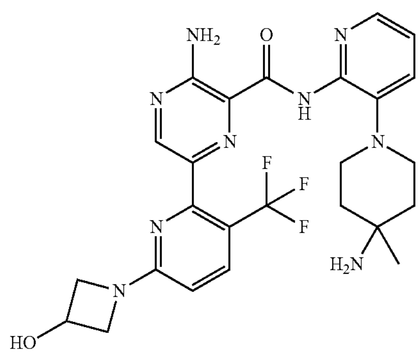 [SMILES: CC1(N)CCN(c2cccnc2NC(=O)c2nc(-c3nc(N4CC(O)C4)ccc3C(F)(F)F)cnc2N)CC1] | Method 4 | 544.2 |
| 104 | 3-amino-N-(3-(4-amino-4-(cyanomethyl)piperidin-1-yl)pyridin-2-yl)-6-(3-(trifluoromethoxy)pyridin-2-yl)pyrazine-2-carboxamide | 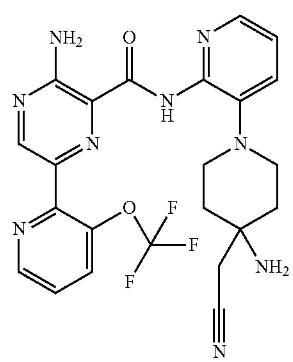 [SMILES: N#CCC1(N)CCN(c2cccnc2NC(=O)c2nc(-c3ncccc3OC(F)(F)F)cnc2N)CC1] | Method 2 | 514.1 |
| 105 | 3-amino-N-(3-(4-amino-4-(cyanomethyl)piperidin-1-yl)pyridin-2-yl)-6-(3-(trifluoromethyl)pyridin-2-yl)pyrazine-2-carboxamide | 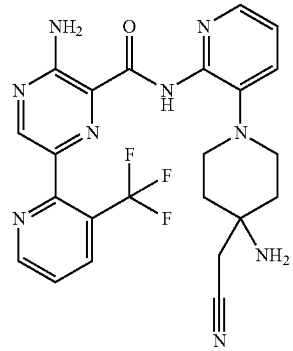 [SMILES: N#CCC1(N)CCN(c2cccnc2NC(=O)c2nc(-c3ncccc3C(F)(F)F)cnc2N)CC1] | Method 1 | 498.3 |

| | Compound Name | Structure | Synthetic Method | MS (M + H) |
|---|---|---|---|---|
| 106 | 3-amino-N-(3-(4-amino-3-fluoro-4-methylpiperidin-1-yl)pyridin-2-yl)-6-(3-(trifluoromethoxy)pyridin-2-yl)pyrazine-2-carboxamide | 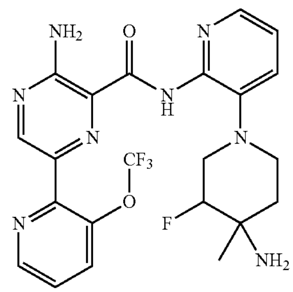 [SMILES: CC1(N)CCN(c2cccnc2NC(=O)c2nc(-c3ncccc3OC(F)(F)F)cnc2N)CC1F] | Method 1 | 507.2 |
| 107 | (R)-3-amino-N-(3-(4-amino-4-methylpiperidin-1-yl)pyridin-2-yl)-6-(6-(3-methylmorpholino)-3-(trifluoromethyl)pyridin-2-yl)pyrazine-2-carboxamide | 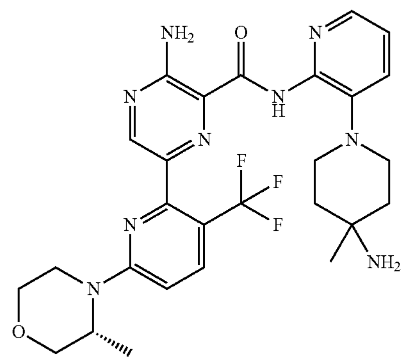 [SMILES: C[C@@H]1COCCN1c1ccc(C(F)(F)F)c(-c2cnc(N)c(C(=O)Nc3ncccc3N3CCC(C)(N)CC3)n2)n1] | Method 1 | 572.3 |
| 108 | (S)-3-amino-N-(3-(4-amino-4-methylpiperidin-1-yl)pyridin-2-yl)-6-(6-(3-methylmorpholino)-3-(trifluoromethyl)pyridin-2-yl)pyrazine-2-carboxamide | 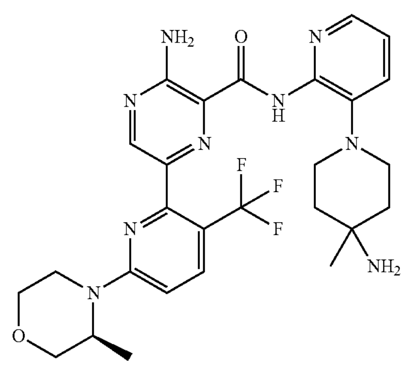 [SMILES: C[C@H]1COCCN1c1ccc(C(F)(F)F)c(-c2cnc(N)c(C(=O)Nc3ncccc3N3CCC(C)(N)CC3)n2)n1] | Method 1 | 572.3 |
| 109 | 6-(6-(3-oxa-8-azabicyclo[3.2.1]octan-8-yl)-3-(trifluoromethyl)pyridin-2-yl)-3-amino-N-(3-(4-amino-4-methylpiperidin-1-yl)pyridin-2-yl)pyrazine-2-carboxamide | 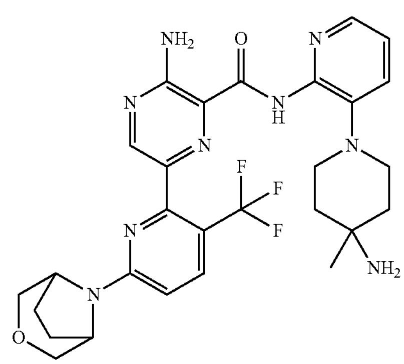 [SMILES: CC1(N)CCN(c2cccnc2NC(=O)c2nc(-c3nc(N4C5CCC4COC5)ccc3C(F)(F)F)cnc2N)CC1] | Method 4 | 584.3 |

| | Compound Name | Structure | Synthetic Method | MS (M + H) |
|---|---|---|---|---|
| 110 | 3-amino-N-(3-((3S,4R)-4-amino-3-fluoro-4-methylpiperidin-1-yl)pyridin-2-yl)-6-(3-(trifluoromethoxy)pyridin-2-yl)pyrazine-2-carboxamide | 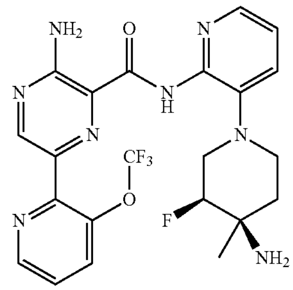 [SMILES: C[C@@]1(N)CCN(c2cccnc2NC(=O)c2nc(-c3ncccc3OC(F)(F)F)cnc2N)C[C@@H]1F] | Method 1 | 507.2 |
| 111 | 3-amino-N-(3-(4-amino-4-methylpiperidin-1-yl)pyridin-2-yl)-6-(3-cyano-4-ethoxypyridin-2-yl)pyrazine-2-carboxamide | 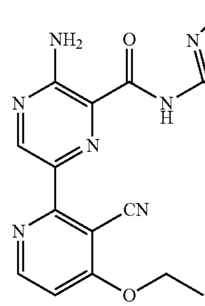 | Method 3 | 474.0 |
| 112 | 3-amino-N-(3-(4-amino-4-methylpiperidin-1-yl)pyridin-2-yl)-6-(6-(3-isopropylmorpholino)-3-(trifluoromethyl)pyridin-2-yl)pyrazine-2-carboxamide | 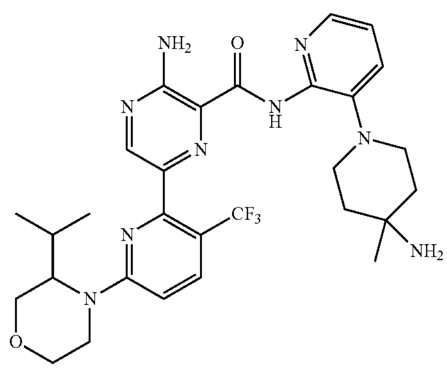 [SMILES: CC(C)C1COCCN1c1ccc(C(F)(F)F)c(-c2cnc(N)c(C(=O)Nc3ncccc3N3CCC(C)(N)CC3)n2)n1] | Method 3 | 600.3 |
| 113 | 3-amino-N-(3-(4-amino-3-fluoro-4-(2-hydroxyethyl)piperidin-1-yl)pyridin-2-yl)-6-(3-(trifluoromethyl)pyridin-2-yl)pyrazine-2-carboxamide | 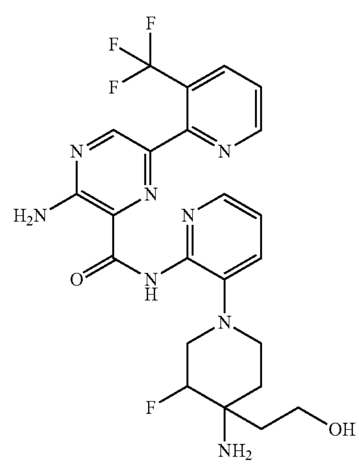 [SMILES: Nc1ncc(-c2ncccc2C(F)(F)F)nc1C(=O)Nc1ncccc1N1CCC(N)(CCO)C(F)C1] | Method 1 | 521.3 |

-continued

| | Compound Name | Structure | Synthetic Method | MS (M + H) |
|---|---|---|---|---|
| 114 | 3-amino-N-(3-(4-amino-4-(cyanomethyl)piperidin-1-yl)pyridin-2-yl)-6-(3-cyano-4-methoxypyridin-2-yl)pyrazine-2-carboxamide | 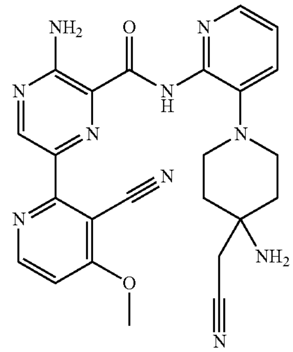 [SMILES: COc1ccnc(-c2cnc(N)c(C(=O)Nc3ncccc3N3CCC(N)(CC#N)CC3)n2)c1C#N] | Method 1 | 485.3 |
| 115 | (R)-3-amino-N-(3-(4-amino-4-methylpiperidin-1-yl)pyridin-2-yl)-6-(6-((1-hydroxypropan-2-yl)amino)-3-(trifluoromethyl)pyridin-2-yl)pyrazine-2-carboxamide | 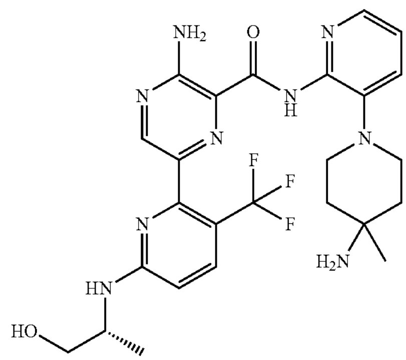 [SMILES: C[C@H](CO)Nc1ccc(C(F)(F)F)c(-c2cnc(N)c(C(=O)Nc3ncccc3N3CCC(C)(N)CC3)n2)n1] | Method 4 | 546.2 |
| 116 | (S)-3-amino-N-(3-(4-amino-4-methylpiperidin-1-yl)pyridin-2-yl)-6-(6-((1-hydroxypropan-2-yl)amino)-3-(trifluoromethyl)pyridin-2-yl)pyrazine-2-carboxamide | 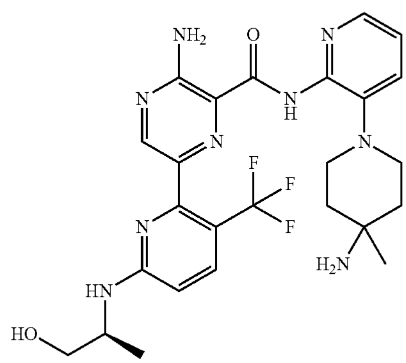 [SMILES: C[C@@H](CO)Nc1ccc(C(F)(F)F)c(-c2cnc(N)c(C(=O)Nc3ncccc3N3CCC(C)(N)CC3)n2)n1] | Method 4 | 546.2 |
| 117 | 3-amino-N-(3-(4-amino-4-methylpiperidin-1-yl)pyridin-2-yl)-6-(6-((2-hydroxyethyl)amino)-3-(trifluoromethyl)pyridin-2-yl)pyrazine-2-carboxamide | 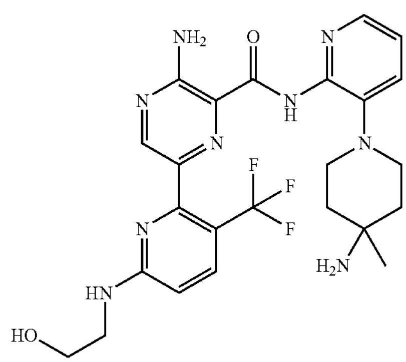 [SMILES: CC1(N)CCN(c2cccnc2NC(=O)c2nc(-c3nc(NCCO)ccc3C(F)(F)F)cnc2N)CC1] | Method 4 | 532.2 |

| | Compound Name | Structure | Synthetic Method | MS (M + H) |
|---|---|---|---|---|
| 118 | 3-amino-N-(3-(4-amino-4-methylpiperidin-1-yl)pyridin-2-yl)-6-(6-(2-hydroxyethoxy)-3-(trifluoromethyl)pyridin-2-yl)pyrazine-2-carboxamide | 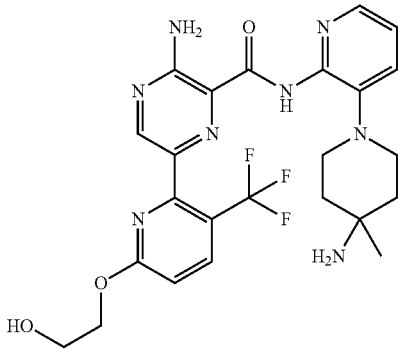 [SMILES: CC1(N)CCN(c2cccnc2NC(=O)c2nc(-c3nc(OCCO)ccc3C(F)(F)F)cnc2N)CC1] | Method 4 | 533.2 |
| 119 | 3-amino-N-(3-(4-amino-4-methylpiperidin-1-yl)pyridin-2-yl)-6-(6-(3-methoxyazetidin-1-yl)-3-(trifluoromethyl)pyridin-2-yl)pyrazine-2-carboxamide | 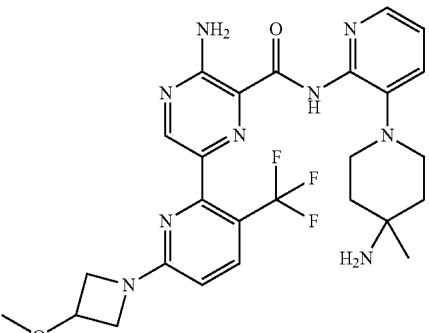 | Method 4 | 558.2 |

Example 110

Synthesis of tert-butyl (3-fluoro-4-methyl-1-(2-nitropyridin-3-yl)piperidin-4-yl)carbamate (Intermediate)

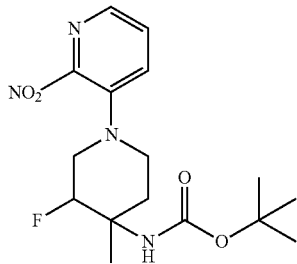

Step 1. Synthesis of 3-fluoro-1-(2-nitropyridin-3-yl)piperidin-4-one

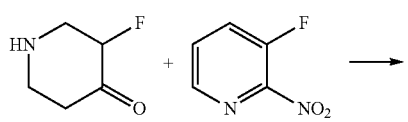 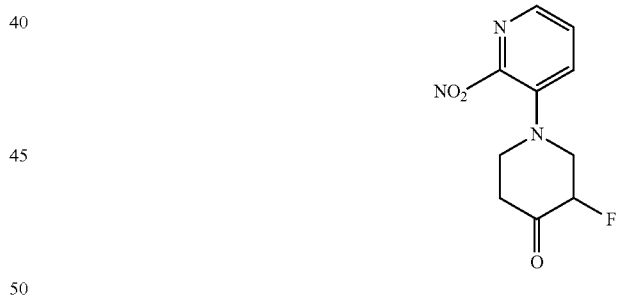

To a 100 mL round-bottom flask equipped with a magnetic stirrer and a nitrogen inlet, was added dioxane (10 mL), DMF (6 mL), 3-fluoropiperidin-4-one (550 mg, 3.58 mmol), 3-fluoro-2-nitropyridine (509 mg, 3.58 mmol) and diisopropylethylamine (1.876 ml, 10.74 mmol). The homogenous solution was stirred at 70° C. in an oil bath for 4 hours. The mixture was then partitioned between ethyl acetate (20 mL) and water (20 mL), and the organic extracts were washed with water (10 ml) twice and brine (10 ml), and then dried over $Na_2SO_4$. After evaporation of solvent, an amber oil was collected as crude product, 3-fluoro-1-(2-nitropyridin-3-yl)piperidin-4-one. Carried this crude product to the next step directly without further purification.

LC-MS (Acidic Method): ret.time=0.63 min, M+H=240.1

Step 2. Synthesis of (Z)-ethyl 2-(3-fluoro-1-(2-nitropyridin-3-yl)piperidin-4-ylidene)acetate

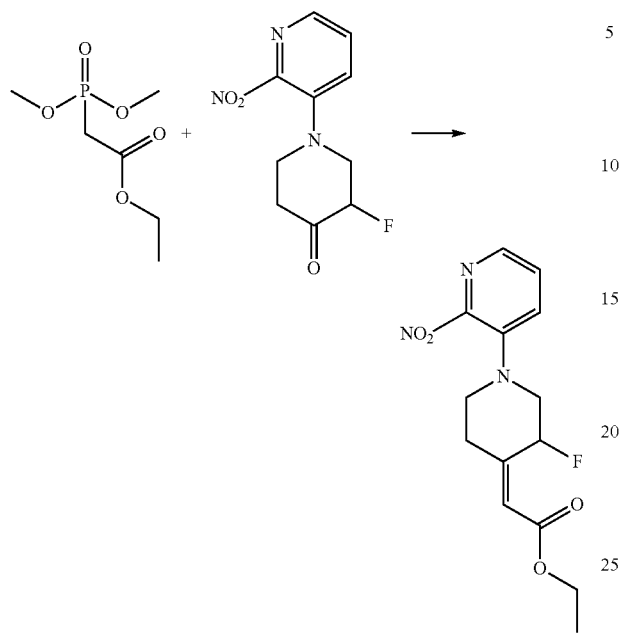

To a 100 mL round-bottom flask equipped with a magnetic stirrer and a nitrogen inlet, was added NaH (169 mg, 4.21 mmol) and THF (10 mL). The mixture was cooled to 0° C. and added ethyl 2-(dimethoxyphosphoryl)acetate (827 mg, 4.21 mmol) dropwise. The reaction was stirred at room temperature for 20 minutes then a solution of 3-fluoro-1-(2-nitropyridin-3-yl)piperidin-4-one (840 mg, 3.51 mmol) in THF (5 mL) was added. The mixture was stirred at room temperature for 3 hours and was quenched by addition of water (25 mL) at 0° C. The aqueous mixture was extracted with ethyl acetate (2×50 mL). The organic layer was washed with brine, dried over $Na_2SO_4$, filtered and concentrated. The crude material was purified by silica gel chromatography using ethyl acetate-heptane (Rf~0.5 at 50% of ethyl acetate in heptane). (Z)-ethyl 2-(3-fluoro-1-(2-nitropyridin-3-yl)piperidin-4-ylidene)acetate was obtained as light yellow solid.

LC-MS (Acidic Method): ret.time=1.44 min, M+H=310.2

Step 3. Synthesis of ethyl 2-(4-amino-3-fluoro-1-(2-nitropyridin-3-yl)piperidin-4-yl)acetate

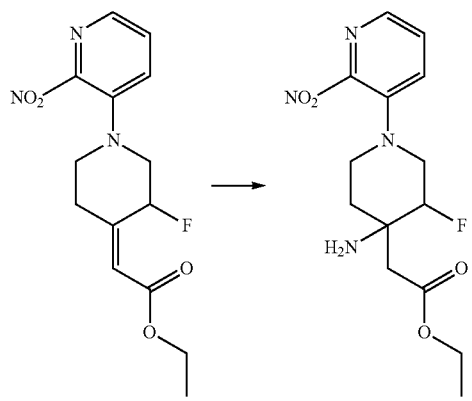

(Z)-ethyl 2-(3-fluoro-1-(2-nitropyridin-3-yl)piperidin-4-ylidene)acetate (4.02 g, 13 mmol) was dissolved in 10 mL of 7N $NH_3$ in MeOH in a pressure vessel. The vessel was sealed and heated at 80° C. for 12 hours. Evaporated the solvents and then applied to silica gel chromatography (Rf~0.4 at 5% MeOH (0.5% of $NH_4OH$) in DCM) to collect ethyl 2-(4-amino-3-fluoro-1-(2-nitropyridin-3-yl)piperidin-4-yl)acetate with >80% purity.

LC-MS (Acidic Method): ret.time=0.68 min, M+H=327.3

Step 4. Synthesis of ethyl 2-(4-((tert-butoxycarbonyl)amino)-3-fluoro-1-(2-nitropyridin-3-yl)piperidin-4-yl)acetate

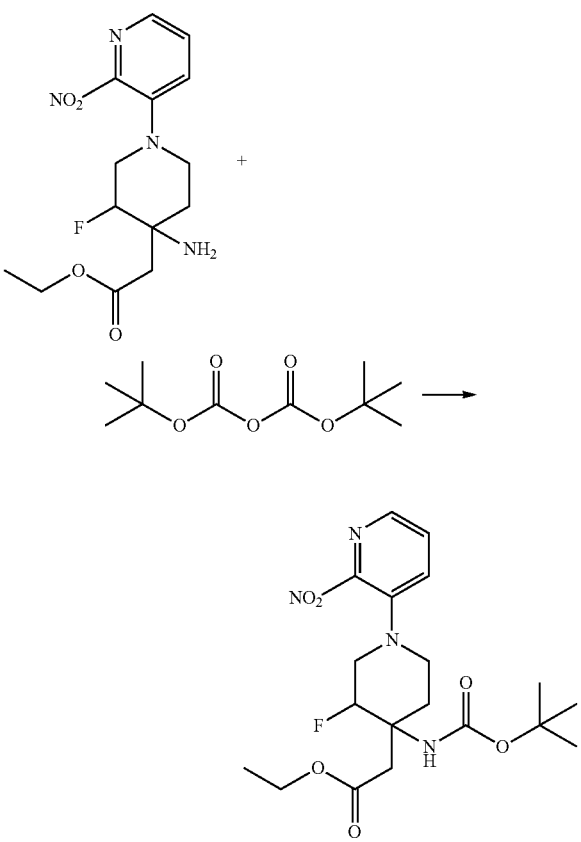

To a 100 mL flask was added a magnetic stirrer and ethyl 2-(4-amino-3-fluoro-1-(2-nitropyridin-3-yl)piperidin-4-yl) acetate (3 g, 9.19 mmol) and BOC Anhydride (2.006 g, 9.19 mmol) in THF (Volume: 33 mL, Ratio: 1.000), Water (Volume: 33.0 mL, Ratio: 1.000) and THF (Volume: 8.0 mL, Ratio: 1.000). Added DIPEA (1.606 mL, 9.19 mmol). The mixture was heated at 85° C. for 4 hours. The mixture cooled down to room temperature and yellow precipitate was observed. The mixture was filtered and the solid was rinsed with water. The solid was purified by silica gel chromatography (Rf~0.7 at 70% of ethyl acetate in heptane) to collect ethyl 2-(4-((tert-butoxycarbonyl)amino)-3-fluoro-1-(2-nitropyridin-3-yl)piperidin-4-yl)acetate.

LC-MS (Acidic Method): ret.time=1.51 min, M+H=427.2

Step 5. Synthesis of 2-(4-((tert-butoxycarbonyl)amino)-3-fluoro-1-(2-nitropyridin-3-yl)piperidin-4-yl)acetic acid

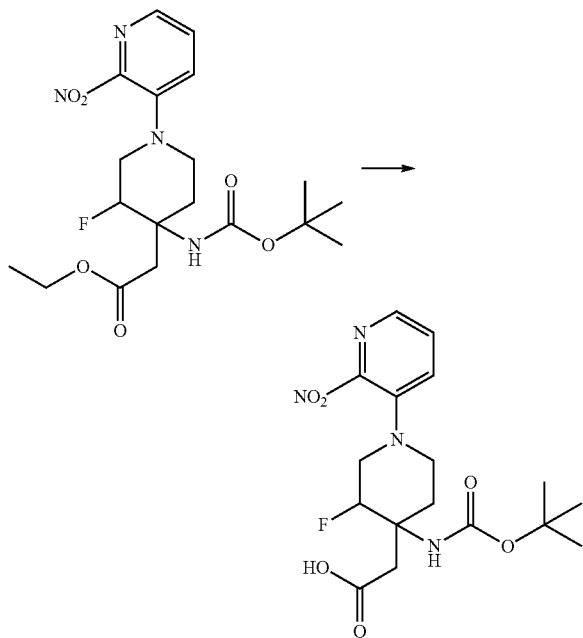

To a 100 mL flask was added a magnetic stirrer and ethyl 2-(4-((tert-butoxycarbonyl)amino)-3-fluoro-1-(2-nitropyridin-3-yl)piperidin-4-yl)acetate (2.4 g, 5.82 mmol) in MeOH (6 mL) and THF (3 mL). An aqueous solution of 3M NaOH (9.7 mL) was added and the reaction was heated at 55° C. for 2 hours. Diluted the reaction mixture with water (10 mL) and washed with Et₂O (20 mL). The aqueous layer was acidified with 1N HCl slowly to pH~6 and then extracted with ethyl acetate (2×50 mL); combine the ethyl acetate layers dried over Na₂SO₄, filtered and concentrated down. Purified by silica gel chromatography (Rf~0.3 at 70% of ethyl acetate in heptane) to collect 2-(4-((tert-butoxycarbonyl)amino)-3-fluoro-1-(2-nitropyridin-3-yl)piperidin-4-yl) acetic acid as yellow solid. $^1$H NMR (400 MHz, Chloroform-d) δ 8.15 (d, J=4.3 Hz, 1H), 7.67 (d, J=8.1 Hz, 1H), 7.51 (dd, J=8.2, 4.4 Hz, 1H), 5.02 (s, 1H), 4.92 (s, 1H), 3.36 (dd, J=26.9, 16.7 Hz, 2H), 3.10 (dt, J=22.4, 11.5 Hz, 2H), 2.91 (d, J=17.1 Hz, 2H), 1.89 (s, 1H), 1.46 (s, 9H), 0.87 (s, 1H).

LC-MS (Acidic Method): ret.time=1.05 min, M−56+H=343.1

Step 6. Synthesis of tert-butyl (3-fluoro-4-methyl-1-(2-nitropyridin-3-yl)piperidin-4-yl)carbamate

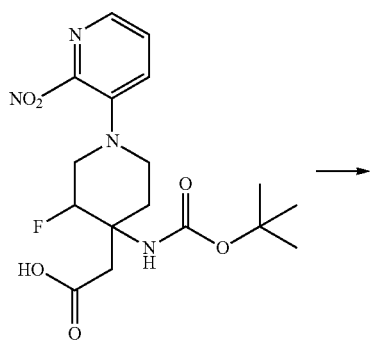

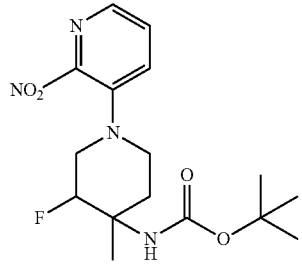 [SMILES: CC(C)(C)OC(=O)NC1(C)CCN(c2cccnc2[N+](=O)[O-])CC1F]

To the mixture of 2-(4-((tert-butoxycarbonyl)amino)-3-fluoro-1-(2-nitropyridin-3-yl)piperidin-4-yl)acetic acid (1 g, 2.51 mmol) and HOTT (1.118 g, 3.01 mmol) in acetonitrile (15 mL), added triethylamine (1.399 mL, 10.04 mmol) in THF (5 mL), isolated the reaction vial from light by aluminum foil. Added DMAP (0.031 g, 0.251 mmol) and kept the reaction stirred at room temperature for 2 hours. To the reaction mixture was added tert-dodecyl mercaptan (2.363 mL, 10.04 mmol) in acetonitrile (5 mL) and the reaction was brought to reflux for 18 hrs. The reaction mixture was concentrated and diluted with water (50 mL) and extracted with ethyl acetate. Collected ethyl acetate layer and dried over Na₂SO₄; filtered and evaporated. Purified by silica gel chromatography with DCM/MeOH (0-7%) to collected the desired product as yellow solid with >50% purity.

LC-MS (Basic Method): ret.time=1.38 min, M+H=355.1
This intermediate was then used as described in Method 3.
Biological Activity

PIM Kinase Inhibition Activity

For comparison between certain PKC inhibitors of the present application and structurally comparable PIM kinase inhibitors, the activity of PIM2 was measured using an in vitro Caliper kinase assay. Liquid handling and incubation steps were done on an Innovadyne Nanodrop Express equipped with a robotic arm (Thermo CatX, Caliper Twister II) and an incubator (Liconic STX40, Thermo Cytomat 2C450). The 384 well microtiter assay plates were prepared by addition of 50 nl per well of compound solution in 90% DMSO. The kinase reactions were started by stepwise addition of 4.5 µl per well of peptide/ATP-solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 1 mM MgCl2, 25 uM ATP, and 2 uM S6 peptide) and 4.5 µl per well of enzyme solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 1 mM MgCl2, and 0.6 nM PIM2 enzyme).

Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated S6 peptide (product) and unphosphorylated S6 peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Compounds of the foregoing examples were tested by the Pim2 kinase assay and found to exhibit an IC50 values as shown in Table 4. IC50, the half maximal inhibitory concentration, represents the concentration of a test compound of the invention that is required for 50% inhibition of its target in vitro.

GSKbeta Assay

Types of GSK-3 assay used to test the selectivity/off target potential compounds of the invention with respect to PKC α/θ inhibition activity includes the following: Type 1: The GSK-3 specific peptide used in this assay was derived from the phosphorylation site of glycogen synthase and its sequence is: YRRAAVPPSPSLSRHSSPHQ(S)EDEEE (S) is pre-phosphorylated as is glycogen synthase in vivo and the three consensus sites for GSK-3 specific phosphorylation are underlined. The buffer used to make up the glycogen synthase peptide and [γ-$^{33}$P] ATP consisted of MOPS 25 mM, EDTA 0.2 mM, magnesium acetate 10 mM, Tween-20 0.01% and mercaptoethanol 7.5 mM at pH 7.00. The compounds were dissolved in dimethyl sulphoxide (DMSO) to a final concentration of 100 mM. Various concentrations were made up in DMSO and mixed with the substrate (GSK-3 peptide) solution (to a final concentration 20 µM) described in the above section along with rabbit or human GSK-3α and GSK-3β (final concentration 0.5 µM/mL enzyme). The reactions were initiated with the addition of [γ-$^{33}$P] ATP (500 cpm/pmole) spiked into a mixture of ATP (final concentration of 10 µM). After 30 minutes at room temperature the reaction was terminated by the addition of 10 µL of $H_3PO_4$/ O.OP/0 Tween-20 (2.5%). A volume (10 µL) of the mixture was spotted onto P-30 phosphocellulose paper (Wallac & Berthold, EG&G Instruments Ltd, Milton Keynes). The paper was washed four times in $H_3PO_4$ (0.5%), 2 minutes for each wash, air dried and the radioactive phosphate incorporated into the synthetic glycogen synthase peptide, which binds to the P-30 phosphocellulose paper, was counted in a Wallac microbeta scintillation counter. Analysis of Data: Values for $IC_{50}$ for each inhibitor were calculated by fitting a four-parameter logistic curve to the model: cpm=lower+ (upper-lower)/(1+(concentration $IC_{50})^{slo\ e}$).
Type 2: This protocol is based on the ability of the kinase to phosphorylate a biotinylated peptide, sequence of which derived from the phosphorylation site of glycogen synthase and its sequence is: Biot-KYR-RAAVPPSPSLSRHSSPHQ(S)EDEEE. (S) is a pre-phosphorylated serine as is glycogen synthase in vivo and the three consensus sites for GSK-3 specific phosphorylation are underlined. The phosphorylated biotinylated peptide is then captured onto streptavidin coated SPA beads (Amersham Technology), where the signal from the $^{33}$P is amplified via the scintillant contained in the beads. The kinase was assayed at a concentration of 10 nM final in 25 mM MOPS buffer, pH 7.0 containing 0.01/o Tween-20, 7.5 mM 2-mercaptoethanol, 10 mM magnesium acetate, and 10 µM [γ-$^{33}$P]-ATP. After 60 minutes incubation at room temperature, the reaction was stopped by addition of 50 mM EDTA solution containing the Streptavidin coated SPA beads to give a final 0.5 mg of beads per assay well in a 384 microtiter plate format. 10 mM stock solutions of the compounds of the invention in 100% DMSO are generated as a first step in the screening process. The second step involves the creation of dose response plates where these compounds are diluted across the plate where the final low and high concentrations are to be 0.008 and 10 µM final in the kinase assay. The third step involves the creation of the assay plates. This is achieved by transferring the compounds from four 96 dose response plates to one 384 assay plate on the Robocon Robolab system. The fourth step is to perform the assay as described and count the resulting plates in the Trilux (Wallac 1450 microbeta liquid scintillation and luminescence counter). The final step is data acquisition and analysis where $IC_{50}$ values are generated for each compound in duplicate by fitting a four parameter logistic curve to the model·cpm==lower+(upper-lower)/(1+(concentration/ $IC_{50})^{s*oP^e}$) in a batch manner. The most potent PKC compounds of the present invention show GSKbeta$IC_{50}$ values in the range of from between 100 to 100,000 nM.

In Vitro PKCα/θ Inhibition Activity

The compounds of formula I were tested for their activity on different PKC isoforms according to a published method (D. Geiges et al. Biochem. Pharmacol. 1997; 53:865-875) The assay is performed in a 96-well polypropylene microtiterplate (Costar 3794) that has been previously siliconized with Sigmacote (Sigma SL-2). The reaction mixture (50 µL) contains 10 µL of the relevant PKC isozyme together with 25 µL of the PKC inhibitor compound and 15 µL of a mix solution that contains 200 µg/mL protamine sulfate, 10 mM $Mg(NO_3)_2$, 10 µM ATP (Boehringer 519987) and 3750 Bq of $^{33}$P-ATP (Hartmann Analytic SFC301, 110 TBq/mmol) in 20 mM Tris-buffer pH 7.4+0.1% BSA. Incubation was performed for 15 minutes at 32° C. in a microtiterplate shaking incubator (Biolabo Scientific Instruments). Reaction was stopped by adding 10 µl of 0.5 M $Na_2EDTA$, pH 7.4. 50 µl of mixture are pipetted onto a pre-wetted phosphocellulose paper (Whatmann 3698-915) under gentle pressure. Non-incorporated ATP is washed away with 100 µL bi-dist $H_2O$. The paper is washed twice in 0.5% $H_3PO_4$ for 15 minutes followed by 5 minutes in EtOH. Thereafter the paper is dryed and placed in an omnifilter (Packard 6005219), and overlayed with 10 µL/well of Microscint-O (Packard 6013611) before counting in a Topcount radioactivity counter (Packard). $IC_{50}$ measurement is performed on a routine basis by incubating a serial dilution of inhibitor at concentrations ranging between 1-1000 µM according to the procedures described above. $IC_{50}$ values are calculated from the graph by sigmoidal curve fitting.

2. Protein Kinase C α Assay

Human recombinant PKCα is used under the assay conditions as described above. In this assay, compounds of formula I inhibit PKC α with an $IC_{50}≤1$ µM. Compound of Examples 2, 9 75 and 76 inhibits PKCα in this assay with an $IC_{50}<10$ nM.

3. Protein Kinase C θ Assay

Human recombinant PKCθ was obtained from Oxford Biomedical Research and is used under the assay conditions as described under Section A.1 above: compounds of formula I inhibit PKC α with an $IC_{50}≤1$ µM. Compound of Examples 2, 9, 75 and 76 inhibits PKCθ in this assay with an $IC_{50}<10$ nM.

Cellular Assays

To assess the ability of compounds of the invention to inhibit PKC activity in cellular assays, compounds were evaluated for their ability to selectively inhibit the proliferation of 92.1 uveal melanoma cells and TMD8 B cell lymphoma cells, relative to SK-MEL-28 cells. 92.1 uveal melanoma cells are dependent on the expression of a mutant form of the G protein alpha subunit, GNAQ, which signals via PKC to enable growth and proliferation. TMD8 cells are dependent on the expression of a mutant form of CD79 which signals via PKC to enable growth and proliferation. SK-MEL-28 cells are dependent on the expression of a mutant form of B-Raf which does not signal via PKC to enable growth and proliferation. Therefore PKC inhibitors are expected to have anti-proliferative activity against 92.1 and/or TMD8 cells but not SK-MEL-28 cells. 92.1 cells (GNAQ mutant) were obtained from Martine Jager (Leiden University Medical Center, 2300 RC Leiden, The Netherlands). SK-MEL-28 cells can be obtained from the American Type Culture Collection (ATCC). Cells were maintained in RPMI 1640 media (Lonza) and 10% FBS (Lonza).

Proliferation Assay

For each cell line, the cell density may be adjusted to 40 000 cells/ml and 50 ul (2000 cells) added per well of a 384 well assay plate. Test compounds are re-suspended in DMSO at a concentration of 10 mM. A serial three-fold dilution of each compound with DMSO was performed in 384-well plates using the Janus Liquid Dispenser (PerkinElmer). 50 nL of each compound dilution was transferred to the assay plate containing cells for final assay concentrations of 10 µM, 3.33 µM, 1.11 µM, 0.37 µM, 0.12 µM, 0.041 µM, 0.014 µM, 0.0046 µM, 0.0015 µM, 0.00051 µM.

Cells may be incubated at 37 degrees celsius in a humidified environment with 5% carbon dioxide for 72 hours. ATPlite (Perkin Elmer) was prepared according to the manufacturer's instructions and 25 µL added to each well of the assay plate. Plates are incubated for 10 minutes and the luminescence detected on an EnVision Multimode plate reader (Perkin Elmer). The degree of luminescence correlates with the number of viable cells in each well. The effect of each inhibitor concentration was calculated and $IC_{50}$ values can be generated.

The PKCisoform alpha and theta $IC_{50}$ values for PKC inhibitors (Examples 1-29) are summarized in Table 2. The data presented herein represents the average of at least two replicates

TABLE 2

Selected PKC α/θ inhibition $IC_{50}$ data for Examples 1-29.

| | Compound | PKC Alpha (nM) | PKC Theta (nM) |
|---|---|---|---|
| 1 | 3-amino-N-(3-(4-aminopiperidin-1-yl)pyridin-2-yl)-6-(3-(trifluoromethyl)pyridin-2-yl)pyrazine-2-carboxamide | 1.3 | 2.8 |
| 2 | 3-amino-N-(3-(4-aminopiperidin-1-yl)pyridin-2-yl)-6-(3-(trifluoromethoxy)pyridin-2-yl)pyrazine-2-carboxamide | 0.25 | 1.3 |
| 3 | 3-amino-N-(3-(4-amino-4-(methoxymethyl)piperidin-1-yl)pyridin-2-yl)-6-(3-(trifluoromethyl)pyridin-2-yl)pyrazine-2-carboxamide | 7.4 | 1.3 |
| 4 | 3-amino-N-(3-(4-amino-4-methylpiperidin-1-yl)pyridin-2-yl)-6-(3 morpholinoisoquinolin-1-yl)pyrazine-2-carboxamide | 0.13 | 0.3 |
| 5 | 3-amino-N-(3-(4-amino-4-(hydroxymethyl)piperidin-1-yl)pyridin-2-yl)-6-(3-(trifluoromethyl)pyridin-2-yl)pyrazine-2-carboxamide | 5.9 | 2 |
| 6 | 3-amino-N-(3-(4-amino-4-(hydroxymethyl)piperidin-1-yl)pyridin-2-yl)-6-(3-(trifluoromethoxy)pyridin-2-yl)pyrazine-2-carboxamide | 0.22 | 2.1 |
| 7 | 3-amino-N-(3-(4-aminopiperidin-1-yl)pyridin-2-yl)-6-(6-morpholino-3-(trifluoromethyl)pyridin-2-yl)pyrazine-2-carboxamide | 0.13 | 0.27 |
| 8 | 3-amino-N-(3-(4-aminopiperidin-1-yl)pyridin-2-yl)-6-(2-morpholino thiazol-4-yl)pyrazine-2-carboxamide | 1 | 16 |
| 9 | 3-amino-N-(3-(4-amino-4-methylpiperidin-1-yl)pyridin-2-yl)-6-(3-(trifluoromethyl)pyridin-2-yl)pyrazine-2-carboxamide | 1.9 | 0.4 |
| 10 | 3-amino-N-(3-(4-amino-4-methylpiperidin-1-yl)pyridin-2-yl)-6-(3-(trifluoromethoxy)pyridin-2-yl)pyrazine-2-carboxamide | 0.9 | 2.8 |
| 11 | 3-amino-N-(3-(4-amino-4-methylpiperidin-1-yl)pyridin-2-yl)-6-(2-morpholino-5-(trifluoromethyl)pyrimidin-4-yl)pyrazine-2-carboxamide | 0.3 | 3.1 |
| 12 | 3-amino-N-(3-(4-amino-4-methylpiperidin-1-yl)pyridin-2-yl)-6-(6-fluoro-2-methylquinazolin-4-yl)pyrazine-2-carboxamide | 0.9 | 1.8 |
| 13 | 3-amino-N-(3-(4-amino-4-methylpiperidin-1-yl)pyridin-2-yl)-6-(4-methoxy-3-(trifluoromethyl)pyridin-2-yl)pyrazine-2-carboxamide | 1.3 | 0.45 |
| 14 | 3-amino-N-(3-(4-amino-4-methylpiperidin-1-yl)pyridin-2-yl)-6-(6-(3,3-difluoroazetidin-1-yl)-3-(trifluoromethyl)pyridin-2-yl)pyrazine-2-carboxamide | 0.68 | 1.2 |
| 15 | 3-amino-N-(3-(4-amino-4-methylpiperidin-1-yl)pyridin-2-yl)-6-(6-cyclopropyl-3-(trifluoromethyl)pyridin-2-yl)pyrazine-2-carboxamide | 0.4 | 2.1 |
| 16 | 3-amino-N-(3-(4-amino-4-methylpiperidin-1-yl)pyridin-2-yl)-6-(6-methoxy-3-(trifluoromethyl)pyridin-2-yl)pyrazine-2-carboxamide | 0.63 | 0.69 |
| 17 | 3-amino-N-(3-(4-amino-4-ethylpiperidin-1-yl)pyridin-2-yl)-6-(3-(trifluoromethyl)pyridin-2-yl)pyrazine-2-carboxamide | 2.1 | 1.1 |
| 18 | Synthesis of 3-amino-N-(3-(4-amino-4-methylpiperidin-1-yl)pyridin-2-yl)-6-(3-chloropyridin-2-yl)pyrazine-2-carboxamide | 0.7 | 0.9 |
| 19 | 3-amino-N-(3-(4-amino-4-methylpiperidin-1-yl)pyridin-2-yl)-6-(3-fluoropyridin-2-yl)pyrazine-2-carboxamide | 1.7 | 3.6 |
| 20 | 3-amino-N-(3-((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide | 0.5 | 3.6 |
| 21 | 3-amino-N-(3-(4-amino-4-methylpiperidin-1-yl)pyridin-2-yl)-6-(3-fluoro-4-methoxypyridin-2-yl)pyrazine-2-carboxamide | 0.55 | 1.2 |
| 22 | 3-amino-N-(3-(4-amino-4-(methoxymethyl)piperidin-1-yl)pyridin-2-yl)-6-(3-fluoropyridin-2-yl)pyrazine-2-carboxamide | 0.86 | 1.2 |
| 23 | 3-amino-N-(3-(4-amino-4-methylpiperidin-1-yl)pyridin-2-yl)-6-(6-cyano-3-fluoropyridin-2-yl)pyrazine-2-carboxamide | 1.9 | 3.9 |

TABLE 2-continued

Selected PKC α/θ inhibition IC$_{50}$ data for Examples 1-29.

| Compound | PKC Alpha (nM) | PKC Theta (nM) |
|---|---|---|
| 24 3-amino-N-(3-(4-amino-4-methylpiperidin-1-yl)pyridin-2-yl)-6-(3-cyanopyridin-2-yl)pyrazine-2-carboxamide | 0.4 | 1.2 |
| 25 3-amino-N-(3-(4-amino-4-ethylpiperidin-1-yl)pyridin-2-yl)-6-(3-(trifluoromethoxy)pyridin-2-yl)pyrazine-2-carboxamide | 0.6 | 2.1 |
| 26 3-amino-N-(3-(4-amino-4-methylpiperidin-1-yl)pyridin-2-yl)-6-(3-cyano-4-methoxypyridin-2-yl)pyrazine-2-carboxamide | 1 | 4.7 |
| 27 3-amino-N-(3-(4-amino-4-(methoxymethyl)piperidin-1-yl)pyridin-2-yl)-6-(3-(trifluoromethoxy)pyridin-2-yl)pyrazine-2-carboxamide | 3.4 | 12 |
| 28 3-amino-N-(3-(4-amino-4-(2-hydroxyethyl)piperidin-1-yl)pyridin-2-yl)-6-(3-(trifluoromethyl)pyridin-2-yl)pyrazine-2-carboxamide | 1.9 | 1.3 |
| 29 3-amino-N-(3-((1S,5R,8S)-8-amino-6-oxa-3-azabicyclo[3.2.1]octan-3-yl)pyridin-2-yl)-6-(6-morpholino-3-(trifluoromethyl)pyridin-2-yl)pyrazine-2-carboxamide | 0.24 | 6 |

The PKC isoform alpha and theta IC$_{50}$ values for PKC inhibitors (Examples 30-123) are summarized in Table 3

TABLE 3

Selected PKC α/θ inhibition IC$_{50}$ data for Examples 30-119.

| Ex. | Compound | PKC Alpha (nM) | PKC Theta (nM) |
|---|---|---|---|
| 30 | 3-amino-N-(3-(4-aminopiperidin-1-yl)pyridin-2-yl)-6-(5,6,7,8-tetrahydroquinazolin-4-yl)pyrazine-2-carboxamide | 0.43 | 7.9 |
| 31 | 3-amino-N-(3-(4-aminopiperidin-1-yl)pyridin-2-yl)-6-(thieno[2,3-d]pyrimidin-4-yl)pyrazine-2-carboxamide | 0.84 | 7.4 |
| 32 | 3-amino-N-(3-(4-amino-4-(2-hydroxyethyl)piperidin-1-yl)pyridin-2-yl)-6-(3-fluoropyridin-2-yl)pyrazine-2-carboxamide | 0.88 | 4 |
| 33 | 3-amino-N-(3-(4-amino-4-methylpiperidin-1-yl)pyridin-2-yl)-6-(6-(dimethylamino)-3-(trifluoromethyl)pyridin-2-yl)pyrazine-2-carboxamide | 0.55 | 3.8 |
| 34 | 3-amino-N-(3-((1R,5S,8s)-8-amino-3-azabicyclo[3.2.1]octan-3-yl)pyridin-2-yl)-6-(6-morpholino-3-(trifluoromethyl)pyridin-2-yl)pyrazine-2-carboxamide | 0.50 | 3.6 |
| 35 | 3-amino-N-(3-(4-amino-4-methylpiperidin-1-yl)pyridin-2-yl)-6-(4-cyano-3-fluoropyridin-2-yl)pyrazine-2-carboxamide | 0.99 | 3.4 |
| 36 | 3-amino-N-(3-(4-amino-4-(2-methoxyethyl) piperidin-1-yl)pyridin-2-yl)-6-(3-(trifluoromethyl)pyridin-2-yl)pyrazine-2-carboxamide | 9.3 | 29 |
| 37 | 3-amino-N-(3-(4-amino-4-methylpiperidin-1-yl)pyridin-2-yl)-6-(6-morpholino-3-(trifluoromethyl)pyridin-2-yl)pyrazine-2-carboxamide | 0.57 | 2.9 |
| 38 | 3-amino-N-(3-(4-amino-4-methylpiperidin-1-yl)pyridin-2-yl)-6-(6-fluoroquinazolin-4-yl)pyrazine-2-carboxamide | 1.5 | 2.9 |
| 39 | 3-amino-N-(3-(4-aminopiperidin-1-yl)pyridin-2-yl)-6-(5-fluoro-7H-pyrrolo[2,3-d]pyrimidin-4-yl)pyrazine-2-carboxamide | 0.33 | 2.9 |
| 40 | 3-amino-N-(3-(4-aminopiperidin-1-yl)pyridin-2-yl)-6-(3-morpholinophenyl)pyrazine-2-carboxamide | 0.13 | 2.8 |
| 41 | 3-amino-N-(3-(4-aminopiperidin-1-yl)pyridin-2-yl)-6-(3,6-bis(trifluoromethyl)pyridin-2-yl)pyrazine-2-carboxamide | 0.46 | 2.7 |
| 42 | 3-amino-N-(3-(4-amino-4-methylpiperidin-1-yl)pyridin-2-yl)-6-(5-morpholino-2-(trifluoromethyl)phenyl)pyrazine-2-carboxamide | 0.17 | 2.7 |
| 43 | (±) 3-amino-N-(3-((cis)-4-amino-3-fluoropiperidin-1-yl)pyridin-2-yl)-6-(3-(trifluoromethoxy)pyridin-2-yl)pyrazine-2-carboxamide | 0.30 | 2.2 |
| 44 | 3-amino-N-(3-(4-aminopiperidin-1-yl)pyridin-2-yl)-6-(2-morpholinopyrimidin-4-yl)pyrazine-2-carboxamide | 0.29 | 2.2 |
| 45 | 3-amino-N-(3-(4-amino-4-methylpiperidin-1-yl)pyridin-2-yl)-6-(2-(3,6-dihydro-2H-pyran-4-yl)-5-(trifluoromethyl) pyrimidin-4-yl)pyrazine-2-carboxamide | 0.13 | 2.1 |
| 46 | 3-amino-N-(3-(4-amino-4-methylpiperidin-1-yl)pyridin-2-yl)-6-(2-morpholinoquinazolin-4-yl)pyrazine-2-carboxamide | 0.13 | 1.7 |
| 47 | 3-amino-N-(3-(4-aminopiperidin-1-yl)pyridin-2-yl)-6-(1-methyl-1H-indazol-4-yl)pyrazine-2-carboxamide | 0.27 | 1.6 |
| 48 | 3-amino-N-(3-(4-amino-4-methylpiperidin-1-yl)pyridin-2-yl)-6-(7-fluoroisoquinolin-1-yl)pyrazine-2-carboxamide | 2.3 | 1.5 |
| 49 | 3-amino-N-(3-(4-aminopiperidin-1-yl)pyridin-2-yl)-6-(3-fluoropyridin-2-yl)pyrazine-2-carboxamide | 0.33 | 1.5 |
| 50 | 3-amino-N-(3-(4-aminopiperidin-1-yl)pyridin-2-yl)-6-(6-morpholinopyridin-2-yl)pyrazine-2-carboxamide | 0.19 | 1.5 |
| 51 | 3-amino-N-(3-(4-aminopiperidin-1-yl)pyridin-2-yl)-6-(3-morpholinophenyl)pyrazine-2-carboxamide | 0.20 | 1.5 |

TABLE 3-continued

Selected PKC α/θ inhibition IC$_{50}$ data for Examples 30-119.

| Ex. | Compound | PKC Alpha (nM) | PKC Theta (nM) |
|---|---|---|---|
| 52 | 3-amino-N-(3-(4-amino-4-methylpiperidin-1-yl)pyridin-2-yl)-6-(7-chloroisoquinolin-1-yl)pyrazine-2-carboxamide | 1.8 | 1.3 |
| 53 | 3-amino-N-(3-(4-aminopiperidin-1-yl)pyridin-2-yl)-6-(6-(azetidin-1-yl)-3-(trifluoromethyl)pyridin-2-yl)pyrazine-2-carboxamide | 0.20 | 1.3 |
| 54 | 3-amino-N-(3-((3S,4R)-4-amino-3-fluoropiperidin-1-yl)pyridin-2-yl)-6-(3-(trifluoromethoxy)pyridin-2-yl)pyrazine-2-carboxamide | 0.25 | 1.2 |
| 55 | 3-amino-N-(3-(4-aminopiperidin-1-yl)pyridin-2-yl)-6-(2-(trifluoromethyl)-1H-indol-4-yl)pyrazine-2-carboxamide | 0.13 | 0.99 |
| 56 | 3-amino-N-(3-(4-aminopiperidin-1-yl)pyridin-2-yl)-6-(5-morpholino-2-(trifluoromethyl)phenyl)pyrazine-2-carboxamide | 0.13 | 0.88 |
| 57 | 3-amino-N-(3-(4-aminopiperidin-1-yl)pyridin-2-yl)-6-(6-(dimethylamino)-3-(trifluoromethyl)pyridin-2-yl)pyrazine-2-carboxamide | 0.13 | 0.87 |
| 58 | 3-amino-N-(3-(4-amino-4-methylpiperidin-1-yl)pyridin-2-yl)-6-(2-(4,4-difluoropiperidin-1-yl)-5-fluoropyrimidin-4-yl)pyrazine-2-carboxamide | 0.13 | 0.85 |
| 59 | 3-amino-N-(3-(4-amino-4-ethylpiperidin-1-yl)pyridin-2-yl)-6-(3-fluoropyridin-2-yl)pyrazine-2-carboxamide | 0.86 | 0.71 |
| 60 | 3-amino-N-(3-(4-amino-4-methylpiperidin-1-yl)pyridin-2-yl)-6-(5-fluoro-2-morpholinopyrimidin-4-yl)pyrazine-2-carboxamide | 0.14 | 0.68 |
| 61 | 3-amino-N-(3-(4-aminopiperidin-1-yl)pyridin-2-yl)-6-(1-methyl-1H-indol-4-yl)pyrazine-2-carboxamide | 0.13 | 0.68 |
| 62 | 3-amino-N-(3-(4-aminopiperidin-1-yl)pyridin-2-yl)-6-(1H-indazol-4-yl)pyrazine-2-carboxamide | 0.13 | 0.67 |
| 63 | 3-amino-N-(3-(4-amino-4-methylpiperidin-1-yl)pyridin-2-yl)-6-(4-cyano-3-(trifluoromethyl)pyridin-2-yl)pyrazine-2-carboxamide | 0.8 | 0.63 |
| 64 | 3-amino-N-(3-(4-aminopiperidin-1-yl)pyridin-2-yl)-6-(6-fluoro-2-morpholinoquinazolin-4-yl)pyrazine-2-carboxamide | 0.13 | 0.43 |
| 65 | 3-amino-N-(3-(4-aminopiperidin-1-yl)pyridin-2-yl)-6-(2-methyl-1H-indol-4-yl)pyrazine-2-carboxamide | 0.13 | 0.36 |
| 66 | 3-amino-N-(3-(4-aminopiperidin-1-yl)pyridin-2-yl)-6-(6-morpholino-3-(trifluoromethyl)pyridin-2-yl)pyrazine-2-carboxamide | 0.13 | 0.36 |
| 67 | 3-amino-N-(3-(4-amino-4-methylpiperidin-1-yl)pyridin-2-yl)-6-(4-ethoxy-3-(trifluoromethyl)pyridin-2-yl)pyrazine-2-carboxamide | 1.3 | 0.33 |
| 68 | 4-(5-amino-6-((3-(4-amino-4-methylpiperidin-1-yl)pyridin-2-yl)carbamoyl)pyrazin-2-yl)-5-fluoropyrimidine-2-carboxamide | 0.4 | 0.27 |
| 69 | 3-amino-N-(3-(4-amino-4-methylpiperidin-1-yl)pyridin-2-yl)-6-(2-cyano-5-(trifluoromethyl)pyrimidin-4-yl)pyrazine-2-carboxamide | 0.48 | 1.9 |
| 70 | 3-amino-N-(3-(4-amino-4-methylpiperidin-1-yl)pyridin-2-yl)-6-(2-amino-5-chloropyrimidin-4-yl)pyrazine-2-carboxamide | 0.35 | 0.24 |
| 71 | 3-amino-N-(3-(4-aminopiperidin-1-yl)pyridin-2-yl)-6-(1H-indol-4-yl)pyrazine-2-carboxamide | 0.13 | 0.23 |
| 72 | 3-amino-N-(3-(4-aminopiperidin-1-yl)pyridin-2-yl)-6-(3-morpholinoisoquinolin-1-yl)pyrazine-2-carboxamide | 0.13 | 0.2 |
| 73 | 3-amino-N-(3-(4-aminopiperidin-1-yl)pyridin-2-yl)-6-(3-morpholino-5-(trifluoromethyl)phenyl)pyrazine-2-carboxamide | 0.13 | 0.16 |
| 74 | 3-amino-N-(3-(4-amino-4-methylpiperidin-1-yl)pyridin-2-yl)-6-(4-chloro-3-(trifluoromethyl)pyridin-2-yl)pyrazine-2-carboxamide | 0.5 | 0.13 |
| 75 | 3-amino-N-(3-(4-aminopiperidin-1-yl)pyridin-2-yl)-6-(3-(trifluoromethoxy)pyridin-2-yl)pyrazine-2-carboxamide | 0.97 | 4.7 |
| 76 | 3-amino-N-(3-(4-amino-4-methylpiperidin-1-yl)pyridin-2-yl)-6-(3-cyano-4-methoxypyridin-2-yl)pyrazine-2-carboxamide | 0.13 | 0.88 |
| 77 | 3-amino-N-(3-(4-aminopiperidin-1-yl)pyridin-2-yl)-6-(5-morpholino-2-(trifluoromethyl)phenyl)pyrazine-2-carboxamide | 0.13 | 0.36 |
| 78 | 3-amino-N-(3-(4-aminopiperidin-1-yl)pyridin-2-yl)-6-(6-morpholino-3-(trifluoromethyl)pyridin-2-yl)pyrazine-2-carboxamide | 0.13 | 0.2 |
| 79 | 3-amino-N-(3-(4-aminopiperidin-1-yl)-6-methylpyridin-2-yl)-6-(3-(trifluoromethoxy)pyridin-2-yl)pyrazine-2-carboxamide | 4.9 | 26 |
| 80 | 3-amino-N-(3-(4-aminopiperidin-1-yl)-6-methylpyridin-2-yl)-6-(3-(trifluoromethyl)pyridin-2-yl)pyrazine-2-carboxamide | 32 | 51 |
| 81 | (±) 3-amino-N-(3-(trans 4-amino-3-methoxypiperidin-1-yl)pyridin-2-yl)-6-(3-(trifluoromethoxy)pyridin-2-yl)pyrazine-2-carboxamide | 0.36 | 19 |
| 82 | 3-amino-N-(3-(4-amino-4-methylpiperidin-1-yl)pyridin-2-yl)-6-(3-fluoro-4-methylpyridin-2-yl)pyrazine-2-carboxamide | 4.9 | 4.6 |
| 83 | 3-amino-N-(3-(4-amino-4-methylpiperidin-1-yl)pyridin-2-yl)-6-(4-ethoxy-3-fluoropyridin-2-yl)pyrazine-2-carboxamide | 1.1 | 5.3 |
| 84 | 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide | 19 | 2.9 |
| 85 | 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide | 13 | 2.6 |
| 86 | 3-amino-N-(3-(4-amino-4-methylpiperidin-1-yl)pyridin-2-yl)-6-(6-cyano-3-fluoropyridin-2-yl)pyrazine-2-carboxamide | 1.9 | 3.9 |
| 87 | 3-amino-N-(3-(4-amino-4-methylpiperidin-1-yl)pyridin-2-yl)-6-(6-(2-methylmorpholino)-3-(trifluoromethyl)pyridin-2-yl)pyrazine-2-carboxamide | 0.51 | 2 |
| 88 | 3-amino-N-(3-(4-amino-4-(ethoxymethyl)piperidin-1-yl)pyridin-2-yl)-6-(3-(trifluoromethyl)pyridin-2-yl)pyrazine-2-carboxamide | 6.3 | 0.79 |

TABLE 3-continued

Selected PKC α/θ inhibition IC$_{50}$ data for Examples 30-119.

| Ex. | Compound | PKC Alpha (nM) | PKC Theta (nM) |
|---|---|---|---|
| 89 | 3-amino-N-(3-(4-amino-4-(ethoxymethyl)piperidin-1-yl)pyridin-2-yl)-6-(3-(trifluoromethoxy)pyridin-2-yl)pyrazine-2-carboxamide | 0.16 | 0.29 |
| 90 | 3-amino-N-(3-(4-amino-4-((difluoromethoxy)methyl)piperidin-1-yl)pyridin-2-yl)-6-(3-(trifluoromethyl)pyridin-2-yl)pyrazine-2-carboxamide | 11 | 3.6 |
| 91 | 3-amino-N-(3-(4-amino-4-((difluoromethoxy)methyl)piperidin-1-yl)pyridin-2-yl)-6-(3-(trifluoromethoxy)pyridin-2-yl)pyrazine-2-carboxamide | 4.2 | 15 |
| 92 | 3-amino-N-(3-(4-amino-4-(hydroxymethyl)piperidin-1-yl)pyridin-2-yl)-6-(1-morpholinoisoquinolin-3-yl)pyrazine-2-carboxamide | 0.25 | 3.1 |
| 93 | 3-amino-N-(3-(4-amino-4-(hydroxymethyl)piperidin-1-yl)pyridin-2-yl)-6-(6-morpholino-3-(trifluoromethyl)pyridin-2-yl)pyrazine-2-carboxamide | 0.13 | 0.13 |
| 94 | 3-amino-N-(3-(4-amino-4-methylpiperidin-1-yl)pyridin-2-yl)-6-(3-cyano-4-isopropoxypyridin-2-yl)pyrazine-2-carboxamide | 1.8 | 0.86 |
| 95 | 3-amino-N-(3-(4-amino-4-methylpiperidin-1-yl)pyridin-2-yl)-6-(3-cyano-4-cyclopropoxypyridin-2-yl)pyrazine-2-carboxamide | 1 | 32 |
| 96 | 3-amino-N-(3-(4-amino-4-methylpiperidin-1-yl)pyridin-2-yl)-6-(4-(trifluoromethoxy)pyridin-2-yl)pyrazine-2-carboxamide | N/A | N/A |
| 97 | 3-amino-N-(3-(4-amino-4-(hydroxymethyl)piperidin-1-yl)pyridin-2-yl)-6-(3-cyano-4-methoxypyridin-2-yl)pyrazine-2-carboxamide | 1.3 | 8.6 |
| 98 | 3-amino-N-(3-(4-amino-4-(hydroxymethyl)piperidin-1-yl)pyridin-2-yl)-6-(3-cyanopyridin-2-yl)pyrazine-2-carboxamide | 0.85 | 3.6 |
| 99 | 3-amino-N-(3-(4-amino-4-methylpiperidin-1-yl)pyridin-2-yl)-6-(3-cyano-4-(trifluoromethoxy)pyridin-2-yl)pyrazine-2-carboxamide | 0.6 | 1.8 |
| 100 | 3-amino-N-(3-(4-amino-4-methylpiperidin-1-yl)pyridin-2-yl)-6-(3-cyano-4-phenoxypyridin-2-yl)pyrazine-2-carboxamide | 23 | 100 |
| 101 | 3-amino-N-(3-(4-amino-4-methylpiperidin-1-yl)pyridin-2-yl)-6-(5-methoxy-3-(trifluoromethyl)pyridin-2-yl)pyrazine-2-carboxamide | 5.1 | 6.6 |
| 102 | 3-amino-N-(3-(4-amino-3-fluoro-4-methylpiperidin-1-yl)pyridin-2-yl)-6-(3-(trifluoromethyl)pyridin-2-yl)pyrazine-2-carboxamide | 37 | 14 |
| 103 | 3-amino-N-(3-(4-amino-4-methylpiperidin-1-yl)pyridin-2-yl)-6-(6-(3-hydroxyazetidin-1-yl)-3-(trifluoromethyl)pyridin-2-yl)pyrazine-2-carboxamide | 5.2 | 29 |
| 104 | 3-amino-N-(3-(4-amino-4-(cyanomethyl)piperidin-1-yl)pyridin-2-yl)-6-(3-(trifluoromethoxy)pyridin-2-yl)pyrazine-2-carboxamide | 4.4 | 66 |
| 105 | 3-amino-N-(3-(4-amino-4-(cyanomethyl)piperidin-1-yl)pyridin-2-yl)-6-(3-(trifluoromethyl)pyridin-2-yl)pyrazine-2-carboxamide | 12 | 27 |
| 106 | 3-amino-N-(3-(4-amino-3-fluoro-4-methylpiperidin-1-yl)pyridin-2-yl)-6-(3-(trifluoromethoxy)pyridin-2-yl)pyrazine-2-carboxamide | 2.7 | 57 |
| 107 | (R)-3-amino-N-(3-(4-amino-4-methylpiperidin-1-yl)pyridin-2-yl)-6-(6-(3-methylmorpholino)-3-(trifluoromethyl)pyridin-2-yl)pyrazine-2-carboxamide | 0.89 | 7.7 |
| 108 | (S)-3-amino-N-(3-(4-amino-4-methylpiperidin-1-yl)pyridin-2-yl)-6-(6-(3-methylmorpholino)-3-(trifluoromethyl)pyridin-2-yl)pyrazine-2-carboxamide | 0.32 | 3.8 |
| 109 | 6-(6-(3-oxa-8-azabicyclo[3.2.1]octan-8-yl)-3-(trifluoromethyl)pyridin-2-yl)-3-amino-N-(3-(4-amino-4-methylpiperidin-1-yl)pyridin-2-yl)pyrazine-2-carboxamide | 0.94 | 4.8 |
| 110 | 3-amino-N-(3-((3S,4R)-4-amino-3-fluoro-4-methylpiperidin-1-yl)pyridin-2-yl)-6-(3-(trifluoromethoxy)pyridin-2-yl)pyrazine-2-carboxamide | 14 | 66 |
| 111 | 3-amino-N-(3-(4-amino-4-methylpiperidin-1-yl)pyridin-2-yl)-6-(3-cyano-4-ethoxypyridin-2-yl)pyrazine-2-carboxamide | 3.6 | 16 |
| 112 | 3-amino-N-(3-(4-amino-4-methylpiperidin-1-yl)pyridin-2-yl)-6-(6-(3-isopropylmorpholino)-3-(trifluoromethyl)pyridin-2-yl)pyrazine-2-carboxamide | N/A | N/A |
| 113 | 3-amino-N-(3-(4-amino-3-fluoro-4-(2-hydroxyethyl)piperidin-1-yl)pyridin-2-yl)-6-(3-(trifluoromethyl)pyridin-2-yl)pyrazine-2-carboxamide | 21 | 30 |
| 114 | 3-amino-N-(3-(4-amino-4-(cyanomethyl)piperidin-1-yl)pyridin-2-yl)-6-(3-cyano-4-methoxypyridin-2-yl)pyrazine-2-carboxamide | 0.53 | 4.1 |
| 115 | (R)-3-amino-N-(3-(4-amino-4-methylpiperidin-1-yl)pyridin-2-yl)-6-(6-((1-hydroxypropan-2-yl)amino)-3-(trifluoromethyl)pyridin-2-yl)pyrazine-2-carboxamide | 0.26 | 3.9 |
| 116 | (S)-3-amino-N-(3-(4-amino-4-methylpiperidin-1-yl)pyridin-2-yl)-6-(6-((1-hydroxypropan-2-yl)amino)-3-(trifluoromethyl)pyridin-2-yl)pyrazine-2-carboxamide | 2 | 18 |
| 117 | 3-amino-N-(3-(4-amino-4-methylpiperidin-1-yl)pyridin-2-yl)-6-(6-((2-hydroxyethyl)amino)-3-(trifluoromethyl)pyridin-2-yl)pyrazine-2-carboxamide | 0.84 | 2 |
| 118 | 3-amino-N-(3-(4-amino-4-methylpiperidin-1-yl)pyridin-2-yl)-6-(6-(2-hydroxyethoxy)-3-(trifluoromethyl)pyridin-2-yl)pyrazine-2-carboxamide | 2.3 | 28 |
| 119 | 3-amino-N-(3-(4-amino-4-methylpiperidin-1-yl)pyridin-2-yl)-6-(6-(3-methoxyazetidin-1-yl)-3-(trifluoromethyl)pyridin-2-yl)pyrazine-2-carboxamide | 4.8 | 21 |

Table 4 presents comparative PKCα/θ inhibition activity data as well as other kinase activity data for Example 1, a PKC inhibitor from this application, and various PIM kinase inhibitors
TABLE 4
Selected kinase IC$_{50}$ data comparison between a PIM kinase inhibitor and various PKC inhibitors
| Compound | PKCα (nM) | PKCθ (nM) | GSK3β (nM) | PIM 2 (nM) | 92.1 Cell (nM) | SKMEL Cell (nM) |
|---|---|---|---|---|---|---|
| 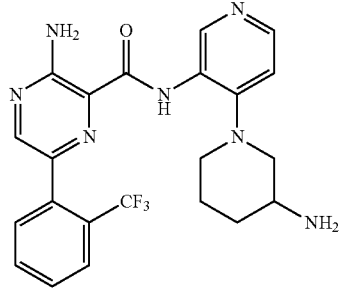 [SMILES: Nc1ncc(-c2ccccc2C(F)(F)F)nc1C(=O)Nc1cnccc1N1CCCC(N)C1] | 50 | 590 | 97 | 490 | 6,150 | >10,000 |
| 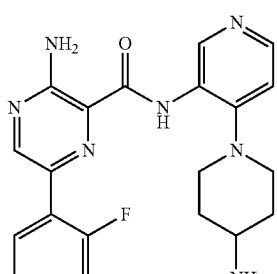 | 0.13 | 0.33 | 0.1 | 1.4 | 116 | 143 |
| 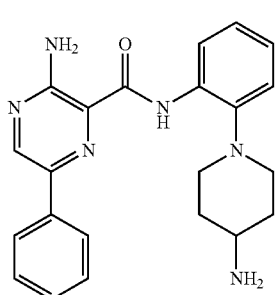 | 0.15 | 0.25 | 1 | 770 | 361 | 1860 |
| 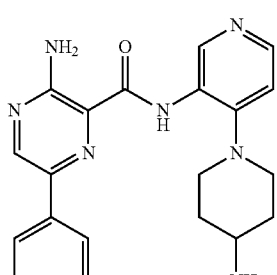 | 0.13 | 0.84 | 0.2 | 10 | 370 | 190 |

TABLE 4-continued

Selected kinase IC$_{50}$ data comparison between a PIM kinase inhibitor and various PKC inhibitors

| Compound | PKCα (nM) | PKCθ (nM) | GSK3β (nM) | PIM 2 (nM) | 92.1 Cell (nM) | SKMEL Cell (nM) |
|---|---|---|---|---|---|---|
| [structure] | 0.19 | 1.5 | 0.2 | 13 | 680 | 975 |
| [structure] | 0.8 | 6 | 0.2 | 78 | 360 | 140 |
| [structure] Example 1 | 1.3 | 2.8 | 5,500 | >10,000 | 141 | >10,000 |

Table 4 presents a direct comparison of the kinase assay data for various PIM kinase inhibitors disclosed in WO2008/160692 and Example 1, an exemplary PKC inhibitor disclosed in this application. These data reveal that Example 1 is unexpectedly selective with regards to off target GSK3β and unexpectedly potent in suppressing 92.1 (uveal melanoma) cell proliferation, as compared to the exemplary PIM inhibitors. This increased selectivity is likely the result of the pyridin-3-yl hinge portion attached to the piperdin-4-yl moiety which is present in Example 1. The pyridine-3-yl hinge portion is found in all of the PKC inhibitor compounds of this application. None of the exemplary PIM kinase inhibitors in Table 4 posess the pyridin-3-yl hinge portion and as shown in Table 4 the PIM kinase inhibitors are relatively non-selective. Accordingly, structurally similar PIM kinase inhibitors disclosed in WO2008/160692 do not or would not be expected to have the selectivity of the PKC inhibitors disclosed herein. In addition, the data in Table 4 shows that Example 1 has little to no PIM2 activity, which further differentiates the PKC inhibitor compounds of this application from known PIM kinase inhibitors.

Representative on target and off target kinase IC$_{50}$ data for additional exemplary PKC inhibitors of the invention are summarized in Table 5

TABLE 5

Kinase Inhibition IC$_{50}$ data for PKC inhibitors of the present application.

| Ex. | PKC Alpha (nM) | PKCtheta (nM) | GSK3 Beta (nM) | TMD8 Cell (nM) | 92.1 Cell (nM) | SKMEL Cell (nM) |
|---|---|---|---|---|---|---|
| 1 | 1.3 | 2.8 | 5500 | ND | 141 | >10,000 |
| 2 | 0.25 | 1.3 | 2,400 | 245 | 110 | >10,000 |
| 4 | 0.13 | 0.3 | 3,100 | 147 | 71 | >10,000 |
| 6 | 0.22 | 2.1 | 1,300 | 151 | 261 | >10,000 |
| 8 | 1 | 16 | 210 | 240 | 40 | 3860 |
| 9 | 1.9 | 0.4 | 3,100 | 900 | 184 | >10,000 |
| 10 | 0.9 | 2.8 | 2,100 | 385 | 228 | >10,000 |
| 13 | 1.3 | 0.45 | 2,100 | 763 | 67 | >10,000 |
| 20 | 0.5 | 3.6 | 10,000 | 410 | 387 | >10,000 |
| 21 | 0.25 | 1.2 | 2,100 | 176 | 12 | >10,000 |
| 30 | 0.6 | 2.1 | 1,500 | 227 | 188 | >10,000 |
| 75 | 0.97 | 4.7 | 2,400 | 146 | 108 | >10,000 |
| 76 | 0.13 | 0.88 | 6,500 | 77 | 34 | >10,000 |
| 77 | 0.13 | 0.36 | >10,000 | 72 | 14 | 4430 |
| 78 | 0.13 | 0.2 | 3,400 | 41 | 22 | 7015 |

In Vivo Efficacy Models—92.1 Uveal Melanoma Xenograft Studies of Selected PKC Inhibitors Mice were implanted with 92.1 GNAQ mutant uveal melanoma cells to test the in vivo efficacy of PKC inhibitors. Each mouse was injected subcutaneously (axillary region) with 5×10$^6$ cells mixed in 50 Ll Matrigel and 50 uL PBS. Tumor growth was monitored until tumors reached a volume of 150-250 mm$^3$ Tumor size, in mm$^3$, was calculated from: Tumor Volume=(w$^2$×1)/2 where w=width and l=length, in mm, of the tumor. When tumors reached the required size, test compounds were administered with the required doses and schedules at a dosing volume of 10 ml/kg. Animals were weighed twice per week and dosing volumes adjusted accordingly. Tumor volume was measured twice a week using caliper measurements and tumor volumes calculated as Length×width$^2$/2. The in-vivo data was generated for certain potent and selective PKC inhibitors (Examples 2, 9) and compared with AEB071. The invented PKC inhibitors achieved tumor regression as compared to tumor statsis for AEB071 at doses lower than those for AEB071 that only achieved stasis in the model.

Figure 3:
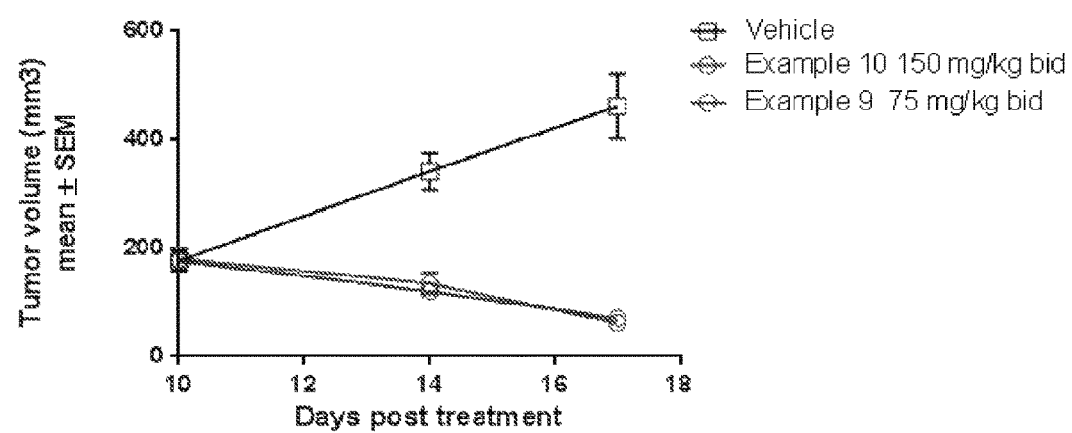
FIG. 3 depicts the reduction in tumor volume over time post-administration of Example 10 and Example 9, as compared to vehicle.

Example 2 decreases tumor proliferation in a 92.1 uveal melanoma xenografts in a dose dependent manner, as compared to sotrastaurin (FIG. 1). Further, Example 2 shows a significant reduction in dose to achieve improved efficacy (regression) vs. sotrastaurin (stasis). Based on the data presented herein the compounds disclosed in this application either do or would be expected to selectively induce tumor regression in a uveal melanoma model harboring GNAQ mutations, as well as achieve improved efficacy (regression) vs. sotrastaurin (stasis), as shown in FIG. 1. For example, as seen in FIG. 3, Example 9 and Example 10 also show improved efficacy (regression) in a 92.1 uveal melanoma xenograft model as compared to vehicle. Accordingly it is expected that the compounds disclosed herein do or would be expected to selectively induce tumor regression in vivo.

A comparison of in-vivo mouse and rat pharmacokinetic data for Example 2 and sotrastaurin (Tables 6 and 7) shows that Example 2 has improved PK versus sotrastaurin.

TABLE 6

In vivo Mouse Pharmacokinetic Data Comparison (C57BL/6)
Dose IV: 1 mg/kg PO: 10 mg/kg

|  | Example 2 | AEB071 |
|---|---|---|
| CL (ml/min · kg) | 14 | 28 |
| Vss (l/kg) | 0.4 | 1.9 |
| t$_{1/2}$ (h) | 0.5 | 1.2 |
| AUC (nmol · h/l) i.v. | 2455 | 1209 |
| AUC (nmol · h/l) p.o. | 1377 | 2151 |
| C$_{max}$ (nM) p.o. | 946 | 688 |
| T$_{max}$ p.o. (h) | 0.3 | 1.7 |
| Oral BA (% F) | 6 | 19 |

TABLE 7

In vivo Rat Pharmacokinetic Data Comparison
(Non-cannulated Wistar-Han)
Dose 0.3 mg/kg PO: 3 mg/kg

|  | Example 2 | AEB071 |
|---|---|---|
| CL (ml/min · kg) | 28 | 18 |
| Vss (l/kg) | 1.1 | 2.3 |
| t$_{1/2}$ (h) | 0.7 | 1.7 |
| AUC (nmol · h/l) i.v. | 380 | 609 |
| AUC (nmol · h/l) p.o. | 2765 | 620 |
| C$_{max}$ (nM) p.o. | 756 | 158 |
| T$_{max}$ p.o. (h) | 1.5 | 0.5 |
| Oral BA (% F) | 72 | 10 |

The compounds of this application represent an improved class of selective, small molecule PKC inhibitors with proven in-vivo anti-tumor activity and selectivity as compared to sotrastaurin. Moreover the PKC inhibitors of the this application generally exhibit improved potency, PK profile, absorption, gastrointestinal tolerance and kinase selectivity as compared to known PKC inhibitors.

The invention claimed is:

1. A method for treating a cancer selected from melanoma, uveal melanoma, lymphoma, diffused large B-cell lymphoma, ibrutinib resistant cancers and non-small cell lung cancer in a human subject in recognized need of such treatment, comprising administering to the subject a therapeutically effective daily dose of from 0.001 to 1000 mg/kg of subject body weight of a compound formula II:

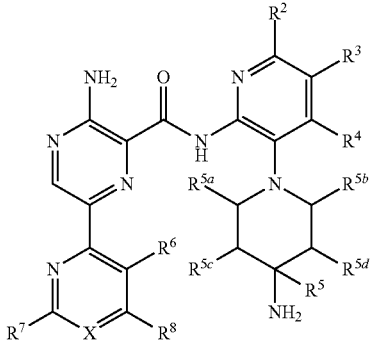

(II)

or a pharmaceutically acceptable salt thereof, wherein:

X is N or CR;

R, $R^2$, $R^3$ and $R^4$ are each independently H, $^2$H, halo, hydroxy (—OH), $C_{1-3}$ alkoxy, $C_{1-3}$ haloalkyl or $C_{1-3}$ alkyl, said $C_{1-3}$ alkyl optionally substituted with hydroxyl, halo, $C_{1-3}$ alkoxy or $C_{1-3}$ haloalkoxy;

$R^5$ is independently H, $^2$H, $CH_3$, $CH_2F$, $CHF_2$, $CF_3$, $CH_2OH$, or $C_{1-3}$ alkyl, said $C_{1-3}$ alkyl optionally substituted with F, OH, $C_{1-3}$ alkoxy or $C_{1-3}$ haloalkoxy;

$R^{5a}$ and $R^{5b}$ are each independently H, $^2$H, $C_{1-3}$ alkyl, said $C_{1-3}$ alkyl optionally substituted with F, OH or $C_{1-3}$ alkoxy, or $R^{5a}$ and $R^{5b}$ are joined together forming a methylene or ethylene bridging group;

$R^{5c}$ and $R^{5d}$ are each independently H, $^2$H, F, —OH, $C_{1-3}$ alkoxy, $C_{1-3}$ alkyl, said $C_{1-3}$ alkyl optionally substituted with F, OH or $C_{1-3}$ alkoxy, or $R^{5c}$ and $R^{5d}$ are joined together forming a methylene, ethylene or —$CH_2$—O— bridging group;

$R^6$, $R^7$ and $R^8$ are each independently selected from H, $^2$H, halo, $C_{1-3}$ alkyl, $C_{1-3}$ haloalkyl, $C_{1-3}$ alkoxy, $C_{1-3}$ haloalkoxy, $C_{3-7}$ cycloalkyl and 4-7 membered heterocyclyl having 1 to 3 heteroatoms selected from N, O and S, said $C_{1-3}$ alkyl optionally substituted with F, OH, $C_{1-3}$ alkoxy or $C_{1-3}$ haloalkoxy.

2. The method according to claim 1 wherein the cancer is non-small cell lung cancer.

3. The method according to claim 2, wherein the compound of formula II is selected from:
- 3-amino-N-(3-(4-aminopiperidin-1-yl)pyridin-2-yl)-6-(3-(trifluoromethyl)pyridin-2-yl)pyrazine-2-carboxamide;
- 3-amino-N-(3-(4-aminopiperidin-1-yl)pyridin-2-yl)-6-(3-(trifluoromethoxy)pyridin-2-yl)pyrazine-2-carboxamide;
- 3-amino-N-(3-(4-amino-4-(methoxymethyl)piperidin-1-yl)pyridin-2-yl)-6-(3-(trifluoromethyl)pyridin-2-yl)pyrazine-2-carboxamide;
- 3-amino-N-(3-(4-amino-4-(hydroxymethyl)piperidin-1-yl)pyridin-2-yl)-6-(3-(trifluoromethyl)pyridin-2-yl)pyrazine-2-carboxamide;
- 3-amino-N-(3-(4-amino-4-(hydroxymethyl)piperidin-1-yl)pyridin-2-yl)-6-(3-(trifluoromethoxy)pyridin-2-yl)pyrazine-2-carboxamide;
- 3-amino-N-(3-(4-amino-4-methylpiperidin-1-yl)pyridin-2-yl)-6-(3-(trifluoromethyl)pyridin-2-yl)pyrazine-2-carboxamide;
- 3-amino-N-(3-(4-amino-4-methylpiperidin-1-yl)pyridin-2-yl)-6-(3-(trifluoromethoxy)pyridin-2-yl)pyrazine-2-carboxamide;
- 3-amino-N-(3-(4-amino-4-methylpiperidin-1-yl)pyridin-2-yl)-6-(4-methoxy-3-(trifluoromethyl)pyridin-2-yl)pyrazine-2-carboxamide;
- 3-amino-N-(3-(4-amino-4-ethylpiperidin-1-yl)pyridin-2-yl)-6-(3-(trifluoromethyl)pyridin-2-yl) pyrazine-2-carboxamide;
- 3-amino-N-(3-(4-amino-4-methylpiperidin-1-yl)pyridin-2-yl)-6-(3-chloropyridin-2-yl)pyrazine-2-carboxamide;
- 3-amino-N-(3-(4-amino-4-methylpiperidin-1-yl)pyridin-2-yl)-6-(3-fluoropyridin-2-yl)pyrazine-2-carboxamide;
- 3-amino-N-(3-(4-amino-4-methylpiperidin-1-yl)pyridin-2-yl)-6-(3-fluoro-4-methoxypyridin-2-yl)pyrazine-2-carboxamide;
- 3-amino-N-(3-(4-amino-4-(methoxymethyl)piperidin-1-yl)pyridin-2-yl)-6-(3-fluoropyridin-2-yl)pyrazine-2-carboxamide;
- 3-amino-N-(3-(4-amino-4-methylpiperidin-1-yl)pyridin-2-yl)-6-(3-cyanopyridin-2-yl)pyrazine-2-carboxamide;
- 3-amino-N-(3-(4-amino-4-ethylpiperidin-1-yl)pyridin-2-yl)-6-(3-(trifluoromethoxy)pyridin-2-yl)pyrazine-2-carboxamide;
- 3-amino-N-(3-(4-amino-4-methylpiperidin-1-yl)pyridin-2-yl)-6-(3-cyano-4-methoxypyridin-2-yl)pyrazine-2-carboxamide;
- 3-amino-N-(3-(4-amino-4-(methoxymethyl)piperidin-1-yl)pyridin-2-yl)-6-(3-(trifluoromethoxy)pyridin-2-yl)pyrazine-2-carboxamide;
- 3-amino-N-(3-(4-amino-4-(2-hydroxyethyl)piperidin-1-yl)pyridin-2-yl)-6-(3-(trifluoromethyl)pyridin-2-yl)pyrazine-2-carboxamide;
- 3-amino-N-(3-(4-amino-4-(2-hydroxyethyl)piperidin-1-yl)pyridin-2-yl)-6-(3-fluoropyridin-2-yl)pyrazine-2-carboxamide;
- 3-amino-N-(3-(4-amino-4-methylpiperidin-1-yl)pyridin-2-yl)-6-(4-cyano-3-fluoropyridin-2-yl)pyrazine-2-carboxamide;
- 3-amino-N-(3-(4-amino-4-(2-methoxyethyl)piperidin-1-yl)pyridin-2-yl)-6-(3-(trifluoromethyl)pyridin-2-yl)pyrazine-2-carboxamide;
- (+)3-amino-N-(3-((cis)-4-amino-3-fluoropiperidin-1-yl)pyridin-2-yl)-6-(3-(trifluoromethoxy)pyridin-2-yl)pyrazine-2-carboxamide;
- 3-amino-N-(3-(4-aminopiperidin-1-yl)pyridin-2-yl)-6-(3-fluoropyridin-2-yl)pyrazine-2-carboxamide;
- 3-amino-N-(3-((3 S,4R)-4-amino-3-fluoropiperidin-1-yl)pyridin-2-yl)-6-(3-(trifluoromethoxy)pyridin-2-yl)pyrazine-2-carboxamide;
- 3-amino-N-(3-(4-amino-4-ethylpiperidin-1-yl)pyridin-2-yl)-6-(3-fluoropyridin-2-yl)pyrazine-2-carboxamide;
- 3-amino-N-(3-(4-amino-4-methylpiperidin-1-yl)pyridin-2-yl)-6-(4-cyano-3-(trifluoromethyl)pyridin-2-yl)pyrazine-2-carboxamide;
- 3-amino-N-(3-(4-amino-4-methylpiperidin-1-yl)pyridin-2-yl)-6-(4-ethoxy-3-(trifluoromethyl)pyridin-2-yl)pyrazine-2-carboxamide;
- 3-amino-N-(3-(4-amino-4-methylpiperidin-1-yl)pyridin-2-yl)-6-(4-chloro-3-(trifluoromethyl)pyridin-2-yl)pyrazine-2-carboxamide;
- 3-amino-N-(3-(4-amino-4-methylpiperidin-1-yl)pyridin-2-yl)-6-(3-cyano-4-methoxypyridin-2-yl)pyrazine-2-carboxamide;
- 3-amino-N-(3-(4-aminopiperidin-1-yl)-6-methylpyridin-2-yl)-6-(3-(trifluoromethoxy)pyridin-2-yl)pyrazine-2-carboxamide;
- 3-amino-N-(3-(4-aminopiperidin-1-yl)-6-methylpyridin-2-yl)-6-(3-(trifluoromethyl)pyridin-2-yl)pyrazine-2-carboxamide;
- 3-amino-N-(3-(4-amino-3-methoxypiperidin-1-yl)pyridin-2-yl)-6-(3-(trifluoromethoxy)pyridin-2-yl)pyrazine-2-carboxamide;
- 3-amino-N-(3-(4-amino-4-methylpiperidin-1-yl)pyridin-2-yl)-6-(3-fluoro-4-methylpyridin-2-yl)pyrazine-2-carboxamide;
- 3-amino-N-(3-(4-amino-4-methylpiperidin-1-yl)pyridin-2-yl)-6-(4-ethoxy-3-fluoropyridin-2-yl)pyrazine-2-carboxamide;
- 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide; and
- 3-amino-N-(3-(4-amino-4-methylpiperidin-1-yl)pyridin-2-yl)-6-(4-(methoxymethyl)-3-(trifluoromethyl)pyridin-2-yl)pyrazine-2-carboxamide;

or a pharmaceutically acceptable salt thereof.

4. The method according to claim 2, wherein the compound of formula II is selected from:
- 3-amino-N-(3-(4-amino-4-(ethoxymethyl)piperidin-1-yl)pyridin-2-yl)-6-(3-(trifluoromethyl)pyridin-2-yl)pyrazine-2-carboxamide;
- 3-amino-N-(3-(4-amino-4-(ethoxymethyl)piperidin-1-yl)pyridin-2-yl)-6-(3-(trifluoromethoxy)pyridin-2-yl)pyrazine-2-carboxamide;
- 3-amino-N-(3-(4-amino-4-((difluoromethoxy)methyl)piperidin-1-yl)pyridin-2-yl)-6-(3-(trifluoromethyl)pyridin-2-yl)pyrazine-2-carboxamide;
- 3-amino-N-(3-(4-amino-4-methylpiperidin-1-yl)pyridin-2-yl)-6-(3-cyano-4-isopropoxypyridin-2-yl)pyrazine-2-carboxamide;
- 3-amino-N-(3-(4-amino-4-methylpiperidin-1-yl)pyridin-2-yl)-6-(3-cyano-4-cyclopropoxypyridin-2-yl)pyrazine-2-carboxamide;
- 3-amino-N-(3-(4-amino-4-methylpiperidin-1-yl)pyridin-2-yl)-6-(4-(trifluoromethoxy)pyridin-2-yl)pyrazine-2-carboxamide;
- 3-amino-N-(3-(4-amino-4-(hydroxymethyl)piperidin-1-yl)pyridin-2-yl)-6-(3-cyano-4-methoxypyridin-2-yl)pyrazine-2-carboxamide;
- 3-amino-N-(3-(4-amino-4-(hydroxymethyl)piperidin-1-yl)pyridin-2-yl)-6-(3-cyanopyridin-2-yl)pyrazine-2-carboxamide;

3-amino-N-(3-(4-amino-4-methylpiperidin-1-yl)pyridin-2-yl)-6-(3-cyano-4-(trifluoromethoxy)pyridin-2-yl)pyrazine-2-carboxamide;

3-amino-N-(3-(4-amino-4-methylpiperidin-1-yl)pyridin-2-yl)-6-(3-cyano-4-phenoxypyridin-2-yl)pyrazine-2-carboxamide;

3-amino-N-(3-(4-amino-4-methylpiperidin-1-yl)pyridin-2-yl)-6-(5-methoxy-3-(trifluoromethyl)pyridin-2-yl)pyrazine-2-carboxamide;

3-amino-N-(3-(4-amino-3-fluoro-4-methylpiperidin-1-yl)pyridin-2-yl)-6-(3-(trifluoromethyl)pyridin-2-yl)pyrazine-2-carboxamide;

3-amino-N-(3-(4-amino-4-(cyanomethyl)piperidin-1-yl)pyridin-2-yl)-6-(3-(trifluoromethoxy)pyridin-2-yl)pyrazine-2-carboxamide;

3-amino-N-(3-(4-amino-4-(cyanomethyl)piperidin-1-yl)pyridin-2-yl)-6-(3-(trifluoromethyl)pyridin-2-yl)pyrazine-2-carboxamide;

3-amino-N-(3-(4-amino-3-fluoro-4-methylpiperidin-1-yl)pyridin-2-yl)-6-(3-(trifluoromethoxy)pyridin-2-yl)pyrazine-2-carboxamide;

3-amino-N-(3-((3S,4R)-4-amino-3-fluoro-4-methylpiperidin-1-yl)pyridin-2-yl)-6-(3-(trifluoromethoxy)pyridin-2-yl)pyrazine-2-carboxamide;

3-amino-N-(3-(4-amino-4-methylpiperidin-1-yl)pyridin-2-yl)-6-(3-cyano-4-ethoxypyridin-2-yl)pyrazine-2-carboxamide;

3-amino-N-(3-(4-amino-3-fluoro-4-(2-hydroxyethyl)piperidin-1-yl)pyridin-2-yl)-6-(3-(trifluoromethyl)pyridin-2-yl)pyrazine-2-carboxamide; and 3-amino-N-(3-(4-amino-4-(cyanomethyl)piperidin-1-yl)pyridin-2-yl)-6-(3-cyano-4-methoxypyridin-2-yl)pyrazine-2-carboxamide;

or a pharmaceutically acceptable salt thereof.

5. The method according to claim 2, wherein the compound of formula II is selected from:

3-amino-N-(3-(4-aminopiperidin-1-yl)pyridin-2-yl)-6-(3-(trifluoromethyl)pyridin-2-yl)pyrazine-2-carboxamide;

3-amino-N-(3-(4-aminopiperidin-1-yl)pyridin-2-yl)-6-(3-(trifluoromethoxy)pyridin-2-yl)pyrazine-2-carboxamide;

3-amino-N-(3-(4-amino-4-(methoxymethyl)piperidin-1-yl)pyridin-2-yl)-6-(3-(trifluoromethyl)pyridin-2-yl)pyrazine-2-carboxamide;

3-amino-N-(3-(4-amino-4-(hydroxymethyl)piperidin-1-yl)pyridin-2-yl)-6-(3-(trifluoromethyl)pyridin-2-yl)pyrazine-2-carboxamide;

3-amino-N-(3-(4-amino-4-(hydroxymethyl)piperidin-1-yl)pyridin-2-yl)-6-(3-(trifluoromethoxy)pyridin-2-yl)pyrazine-2-carboxamide;

3-amino-N-(3-(4-amino-4-methylpiperidin-1-yl)pyridin-2-yl)-6-(3-(trifluoromethyl)pyridin-2-yl)pyrazine-2-carboxamide;

3-amino-N-(3-(4-amino-4-methylpiperidin-1-yl)pyridin-2-yl)-6-(3-(trifluoromethoxy)pyridin-2-yl)pyrazine-2-carboxamide; and 3-amino-N-(3-(4-amino-4-methylpiperidin-1-yl)pyridin-2-yl)-6-(4-methoxy-3-(trifluoromethyl)pyridin-2-yl)pyrazine-2-carboxamide;

or a pharmaceutically acceptable salt thereof.

6. The method according to claim 2, wherein the compound is selected from:

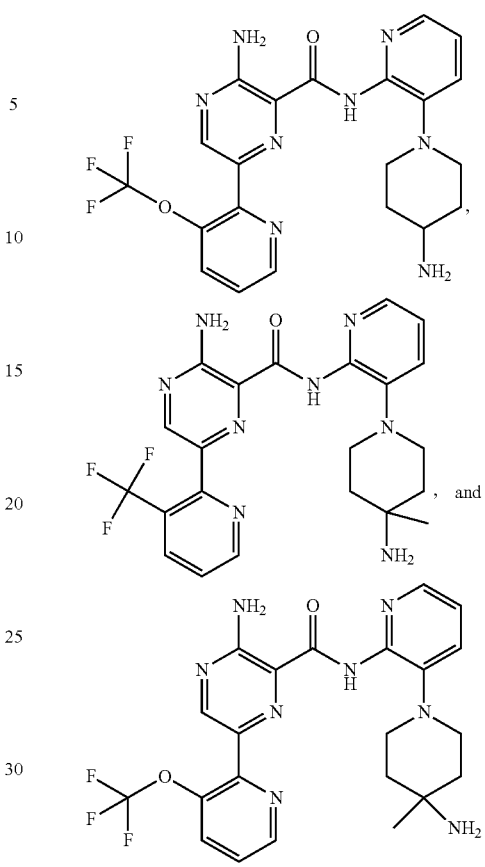

or a pharmaceutically acceptable salt thereof.

7. The method according to claim 2, wherein the compound of formula (II) is:

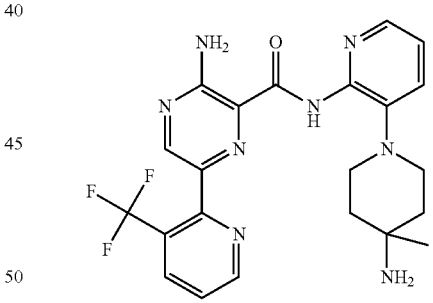

or a pharmaceutically acceptable salt thereof.

8. The method according to claim 2, wherein the compound or pharmaceutically acceptable salt thereof is administered in combination with at least one additional anticancer agent.

9. The method according to claim 7, wherein the compound or pharmaceutically acceptable salt thereof is administered in combination with at least one additional anticancer agent.

10. The method according to claim 8 wherein the anticancer agent is an EGFR inhibitor.

11. The method according to claim 9 wherein the anticancer agent is an EGFR inhibitor.

12. The method according to claim 10 wherein the EGFR inhibitor is gefitinib or erlotinib.

13. The method according to claim 11 wherein the EGFR inhibitor is gefitinib or erlotinib.

14. The method of claim 1 wherein the compound of formula (II) is a PKC inhibitor that is pan active to conventional and novel PKC isoforms.

15. The method of claim 2 wherein the compound of formula (II) is a PKC inhibitor that is pan active to conventional and novel PKC isoforms.

16. The method of claim 7 wherein the compound of formula (II) is a PKC inhibitor that is pan active to conventional and novel PKC isoforms.

17. The method of claim 8 wherein the compound of formula (II) is a PKC inhibitor that is pan active to conventional and novel PKC isoforms.

18. The method claim 9 wherein the compound of formula (II) is a PKC inhibitor that is pan active to conventional and novel PKC isoforms.

19. The method claim 10 wherein the compound of formula (II) is a PKC inhibitor that is pan active to conventional and novel PKC isoforms.

20. The method claim 11 wherein the compound of formula (II) is a PKC inhibitor that is pan active to conventional and novel PKC isoforms.

21. The method claim 12 wherein the compound of formula (II) is a PKC inhibitor that is pan active to conventional and novel PKC isoforms.

22. The method claim 13 wherein the compound of formula (II) is a PKC inhibitor that is pan active to conventional and novel PKC isoforms.

23. The method of claim 1 wherein the daily dose is administered as multiple divided doses.

\* \* \* \* \*